(12) United States Patent
Swinnen et al.

(10) Patent No.: US 9,688,702 B2
(45) Date of Patent: Jun. 27, 2017

(54) ALPHA-AMINO BORONIC ACID DERIVATIVES, SELECTIVE IMMUNOPROTEASOME INHIBITORS

(71) Applicant: Ares Trading S.A, Aubonne (CH)

(72) Inventors: Dominique Swinnen, Braine l'Alleud (BE); Stefano Crosignani, Nivelles (BE); Jeyaprakashnarayanan Seenisamy, Bangalore (IN); Federica Morandi, Cambridge, MA (US)

(73) Assignee: Ares Trading, Aubonne (CH)

( * ) Notice: Subject to any disclaimer, the term of this patent is extended or adjusted under 35 U.S.C. 154(b) by 140 days.

(21) Appl. No.: 14/366,949

(22) PCT Filed: Dec. 21, 2012

(86) PCT No.: PCT/EP2012/076595
§ 371 (c)(1),
(2) Date: Jun. 19, 2014

(87) PCT Pub. No.: WO2013/092979
PCT Pub. Date: Jun. 27, 2013

(65) Prior Publication Data
US 2014/0364396 A1  Dec. 11, 2014

Related U.S. Application Data

(60) Provisional application No. 61/579,076, filed on Dec. 22, 2011.

(30) Foreign Application Priority Data

Dec. 22, 2011 (EP) ..................................... 11195107

(51) Int. Cl.
C07F 5/02 (2006.01)
A61K 45/06 (2006.01)
A61K 31/69 (2006.01)

(52) U.S. Cl.
CPC .............. *C07F 5/025* (2013.01); *A61K 31/69* (2013.01); *A61K 45/06* (2013.01); *C07F 5/02* (2013.01); *A61K 2201/094* (2013.01)

(58) Field of Classification Search
CPC .................................. C07F 5/02; C07F 5/025
See application file for complete search history.

(56) References Cited

U.S. PATENT DOCUMENTS

| 7,271,186 B1 | 9/2007 | Shoichet et al. |
| 2006/0003459 A1 | 1/2006 | Anslyn et al. |

FOREIGN PATENT DOCUMENTS

| WO | 9509634 A1 | 4/1995 |
| WO | 2005097809 A2 | 10/2005 |
| WO | 2008060488 A1 | 5/2008 |
| WO | 2009051581 A1 | 4/2009 |
| WO | 2009064413 A1 | 5/2009 |
| WO | 2009064414 A1 | 5/2009 |
| WO | 2010036357 A1 | 4/2010 |
| WO | 2011123502 A1 | 10/2011 |
| WO | 2011137049 A1 | 11/2011 |

OTHER PUBLICATIONS

Matteson et al. "Synthesis of 1-amino-2-phenylethane-1-boronic acid derivatives" Organometallics, 1984, vol. 3, pp. 614-618.*
Morandi et al. "Nanomolar Inhibitors of AmpC β-Lactamase" Journal of the American Chemical Society, 2003, vol. 125, pp. 685-695.*
Kilbourn "Thiophenes as phenyl bio-isosteres: Application in radiopharmaceutical design—I. Dopamine uptake antagonists" International Journal of Radiation Applications and Instrumentation. Part B. Nuclear Medicine and Biology, 1989, vol. 16, pp. 681-686.*
Matteson et al. "R-1-Acetamido-2-phenylethaneboronic acid. A specific transition-state analog for chymotrypsin" Journal of the American Chemical Society, 1981, vol. 103, pp. 5241-5242.*
Ahmed et al., Suppression of pain and joint destruction by inhibition of the proteasome system in experimental osteoarthritis, PAIN, 2012, 153:18-26.
Allen et al., Juxtaposition of the Two Distal CX3C Motifs via Intrachain Disulfide Bonding Is Essential for the Folding of Tim10, J. Biol. Chem., 2003, 278:38505-38513.
Altun et al., Effects of PS-341 on the Activity and Composition of Proteasomes in Multiple Myeloma Cells, Cancer Res, 2005, 65:7896-7901.
Anan et al., Proteasome inhibition attenuates hepatic injury in the bile duct-ligated mouse, Am J Physiol Gastrointest Liver Physiol, 2006, 291:G709-G716.
Arastu-Kapur et al.,Nonproteasomal Targets of the Proteasome Inhibitors Bortezomib and Carfilzomib: a Link to Clinical Adverse Events, Clin Cancer Res, 2011,17:2734-2743.
Basler et al., Prevention of Experimental Colitis by a Selective Inhibitor of the Immunoproteasome, J. Immunol, 2010, 185:634-641.
Bontscho et al., Myeloperoxidase-Specific Plasma Cell Depletion by Bortezomib Protects from Anti-Neutrophil Cytoplasmic Autoantibodies—Induced Glomerulonephritis, J Am Soc Nephrol, 2011, 22:336-348.

(Continued)

*Primary Examiner* — Joseph Kosack
(74) *Attorney, Agent, or Firm* — Dwight D. Kim; EMD Serono Research and Development Institute

(57) ABSTRACT

The present invention provides compounds of Formula (I) as inhibitors of LMP7 for the treatment of autoimmune and inflammatory diseases.

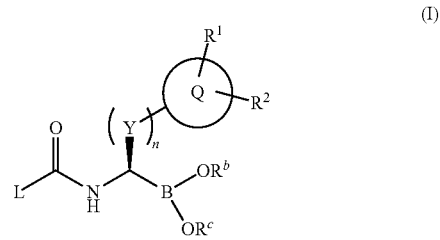

16 Claims, No Drawings

(56) References Cited

OTHER PUBLICATIONS

Chen et al., Bortezomib as the First Proteasome Inhibitor Anticancer Drug: Current Status and Future Perspectives, CURR Cancer Drug Targets, 2011,11(3):239-253.
Coppo et al., Is progression of IgA nephropathy conditioned by genes regulating atherosclerotic damage?, Nephrol Dial Transplant, 2009, 24:3573-3575.
Egerer et al., Tissue-Specific Up-Regulation of the Proteasome Subunit B5i (LMP7) in Sjogren's Syndrome, Arthritis & Rheumatism, 2006, 54(5):1501-1508.
Elliott et al., Proteasome inhibition: a new anti-inflammatory strategy, J Mol Med, 2003, 81:235-245.
Etienne et al., Local induction of heat shock protein 70 (Hsp70) by proteasome inhibition confers chondroprotection during surgically induced osteoarthritis in the rat knee, Bio-Medical Materials and Engineering, 2008, 18:253-260.
Feng et al., Preventive Effect of a Proteasome Inhibitor on the Formation of Accelerated Atherosclerosis in Rabbits With Uremia, J Cardiovasc Pharmacol, 2010, 55(2):129-138.
Fineschi et al., Proteasome blockade exerts an antifibrotic activity by coordinately down-regulating type I collagen and tissue inhibitor of metalloproteinase-1 and up-regulating metalloproteinase-1 production in human dermal fibroblasts, The FASEB Journal, 2006, pp. 1-23.
Fissolo et al., Dual inhibition of proteasomal and lysosomal proteolysis ameliorates autoimmune central nervous system inflammation, Eur J. Immunol., 2008, 38:2401-2411.
Goldberg et al., Proteolysis, proteasomes and antigen presentation, Nature, 1992, 357:375-379.
Gomez et al., Proteasome Inhibition with Bortezomib Depletes Plasma Cells and Autoantibodies in Experimental Autoimmune Myasthenia Gravis, J Immunol, 2011, 186:2503-2513.
Greene Theodora W. and Wuts Peter G. M., "Protective Groups in Organic Synthesis", Wiley Interscience, 3rd Edition 1999.
Hosseini et al., Protection against experimental autoimmune encephalomyelitis by a proteasome modulator, Journal of Neuroimmunology, 2001, 118:233-244.
Houben-Weyl, Methoden der organischen Chemie [Methods of Organic Chemistry], Georg-Thieme-Verlag, Stuttgart.
Ichikawa et al., Beneficial Effect of Novel Proteasome Inhibitors in Murine Lupus via Dual Inhibition of Type I Interferon and Autoantibody-Secreting Cells, Arthritis & Rheumatism, 2012, 64(2):493-503.
Inoue et al., the effect of proteasome inhibitor MG132 on experimental inflammatory bowel disease, British Society for Immunology, Clinical and Experimental Immunology, 2009, 156:172-182.
Jin et al., Identification of the first fluorescent alpha-amidoboronic acids that change fluorescent properties upon sugar binding, Bioorganic & Medicinal Chemistry Letters, 2009, 19:1596-1599.
Koca et al., Proteasome Inhibition Prevents Development of Experimental Dermal Fibrosis, Inflammation, 2012, 35(3):810-817.
Kocienski, Phillip J., "Protecting Groups", Georg Thieme Verlag Stuttgart, New York, 1994.
Kramer et al., Strong associations of psoriasis with antigen processing LMP and transport genes TAP differ by gender and phenotype, Genes and Immunity, 2007, 8:513-517.
Lang et al., The Early Marginal Zone B Cell-Initiated T-Independent Type 2 Response Resists the Proteasome Inhibitor Bortezomib, J Immunol, 2010,185:5637-5647.
Ma et al., MG132 treatment attenuates cardiac remodeling and dysfunction following aortic banding in rats via the NF-kappaB/TGFβ1 pathway, Biochemical Pharmacology, 2011, 81:1228-1236.
Matteson et al., Cesium Alkyltrifluoroborates from Asymmetric Boronic Esters, SYNLETT, 2006, 20:3501-3503.
Matteson et al., Hydrolysis of Substituted 1,3,2-Dioxaborolanes and an Asymmetric Synthesis of a Differentially Protected syn,syn-3-Methyl-2,4-hexanediol, J. Org. Chem., 1996, 61:6047-6051.
Matteson et al., Synthesis of 1-Amino-2-phenylethane-I-boronic Acid Derivatives, Organometallics, 1984, 3:614-618.
Matteson et al., (R)-1-Acetamido-2-phenylethaneboronic Acid. A Specific Transition-State Analogue for Chymotrypsin, J. Am. Chem. Soc., 1981, 103:5241-5242.
Mutlu et al., Proteasomal inhibition after injury prevents fibrosis by modulating TGF-β1 signalling, Thorax., 2012, 67(2):139-146.
Neubert et al., The proteasome inhibitor bortezomib depletes plasma cells and protects mice with lupus-like disease from nephritis, Nature Medicine, 2008, 14(7):748-755.
Orlowski, Marian, The Multicatalytic Proteinase Complex, a Major Extralysosomal Proteolytic System, Biochemistry. 1990, 29(45):10289-10297.
Puttaparthi et al., Non-neuronal induction of immunoproteasome subunits in an ALS model: Possible mediation by cytokines, Experimental Neurology, 2005, 196:441-451.
Rivett, Jennifer A., The Multicatalytic Proteinase of Mammalian Cells, Archives of Biochemistry and Biophysics, 1989, 268(1):1-8.
Sakairi et al., TGF-beta1 reduces Wilms' tumor suppressor gene expression in podocytes, Nephrol Dial Transplant, 2011, 26:2746-2752.
Schmidt et al., Targeting the proteasome: partial inhibition of the proteasome by bortezomib or deletion of the immunosubunit LMP7 attenuates experimental colitis, Gut, 2010, 59:896-906.
Singh et al., PR-924, a selective inhibitor of the immunoproteasome subunit LMP-7, blocks multiple myeloma cell growth both in vitro and in vivo, British Journal of Haematology, 2010, 152:155-163.
Tyle, Praveen, Iontophoretic Devices for Drug Delivery, Pharmaceutical Research, 1986, 3(6):318-326.
Van Der Heijden et al., The proteasome inhibitor bortezomib inhibits the release of NFκB-inducible cytokines and induces apoptosis of activated T cells from rheumatoid arthritis patients, Clinical and Experimental Rheumatology, 2009, 27:92-98.
Vanderlugt et al., Treatment of Established Relapsing Experimental Autoimmune Encephalomyelitis with the Proteasome Inhibitor PS-519, Journal of Autoimmunity, 2000,14:205-211.
Waiser et al., Comparison between bortezomib and rituximab in the treatment of antibody-mediated renal allograft rejection, Nephrol Dial Transplant, 2012, 27:1246-1251.
Yoshida et al., Study of biodegradable copoly (L-lactic acid/glycolic acid) formulations with controlled release of Z-100 for application in radiation therapy, Int. J. Pharm., 1995, 115:61-67.
International Search Report, dated Feb. 5, 2013.
Niewerth et al., Biochemical Pharmacology 89 (2014) 43-51.
Boronic Acids, Edited by Dennis G. Hall, Wiley-VCH Verlag, 2005, ISBN 3-527-30991-8.
Ness et al., Biochemistry, 2000, 39(18): 5312-5321.
Jin et al., Bioorganic & Medicinal Chemistry, 2010,18(4): 1449-1455.
Ohmura et al., Chemistry Letters, 2009, 38(7): 664-665.
Thomson et al., Journal of Biological Chemistry, 2006, 281(36): 26734-26744.
Ohmura et al., Journal of Biological Chemistry, 2010, 132(38): 13191-13193.
Martichonok et al., Journal of the American Chemical Society, 1996, 118(5): 950-958.
Caselli et al., Organic Letters, 2003, 5(25): 4863-4866.
Drawz et al., Protein Science, 2011, 20(6): 941-958.
Morandi et al., Tetrahedron Asymmetry, 2005, 16(17): 2918-2926.
Martin et al., Tetrahedron Letters, 1995, 36(46): 8399-402.
Sylvia et al., Biochimica et Biophysica Acta, 1993, 1163: 321-334.

* cited by examiner

ALPHA-AMINO BORONIC ACID DERIVATIVES, SELECTIVE IMMUNOPROTEASOME INHIBITORS

RELATED APPLICATIONS

This application is a U.S. national stage application of PCT international application PCT/EP2012/076595, filed on Dec. 21, 2012, which claims the benefit of U.S. provisional Application No. 61/579,076, filed on Dec. 22, 2011 and European Application Number 11195107.5, filed on Dec. 22, 2011. The entire contents of the aforementioned applications are hereby incorporated by reference.

The present invention provides α-Amino boronic acid derivatives and their use in the treatment of inflammatory and autoimmune diseases, neurodegenerative diseases, and proliferative diseases. In particular, the compounds of the present invention are selective imunoproteasome inhibitors.

The proteasome (also known as macropain, the multicatalytic protease, and 20S protease) is a high molecular weight, multisubunit protease which has been identified in every examined species from an archaebacterium to human. The enzyme has a native molecular weight of approximately 650,000 and, as revealed by electron microscopy, a distinctive cylinder-shaped morphology (Rivett, (1989) Arch. Biochem. Biophys. 268:1-8; and Orlowski, (1990) Biochemistry 29:10289-10297). The proteasome subunits range in molecular weight from 20,000 to 35,000 (3-5), and are homologous to one another but not to any other known protease.

The 20S proteasome is a 700 kDa cylindrical-shaped multicatalytic protease complex comprised of 28 subunits, classified as a- and β-type, that are arranged in 4 stacked heptameric rings. In yeast and other eukaryotes, 7 different a subunits form the outer rings and 7 different β subunits comprise the inner rings. The a subunits serve as binding sites for the 19S (PA700) and 1 IS (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome.

Cleavage of amino-terminal prosequences of β subunits during particle formation expose amino-terminal threonine residues, which serve as the catalytic nucleophiles. The subunits responsible for catalytic activity in proteasome thus possess an amino terminal nucleophilic residue, and these subunits belong to the family of N-terminal nucleophile (Ntn) ATTY REF: 26500-0023WO1 hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-γ-inducible β subunits (LMP7, LMP2 and MECLI), which replace their normal counterparts, β5, β1 and β2, respectively. When all three IFN-γ-inducible subunits are present, the proteasome is referred to as an "immunoproteasome". Thus, eukaryotic cells can possess two forms of proteasomes in varying ratios.

Through the use of different peptide substrates, three major proteolytic activities have been defined for the eukaryote 20S proteasomes: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. Although both forms of the proteasome possess all five enzymatic activities, differences in the extent of the activities between the forms have been described based on specific substrates. For both forms of the proteasome, the major proteasome proteolytic activities appear to be contributed by different catalytic sites within the 20S core.

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis and cell viability, antigen processing, NF-κB activation, and transduction of pro-inflammatory signals.

Proteasome activity is high in muscle wasting diseases that involve protein breakdown such as muscular dystrophy, cancer and AIDS. Evidence also suggests a possible role for the proteasome in the processing of antigens for the class I MHC molecules (Goldberg, et al. (1992) Nature 357:375-379).

Proteasomes are involved in neurodegenerative diseases and disorders such as Amyotrophic Lateral Sclerosis (ALS), (J Biol Chem 2003, Allen S et al., Exp Neurol 2005, Puttaparthi k et al.), Sjogren Syndrome (Arthritis & Rheumatism, 2006, Egerer T et al.), systemic lupus erythematoses and lupus nephritis (SLE/LN), (Arthritis & rheuma 2011, Ichikawa et al., J Immunol, 2010, Lang V R et al., Nat Med, 2008, Neubert K et al), glomerulonephritis (J Am Soc nephrol 2011, Bontscho et al.), Rheumatoid Arthritis (Clin Exp Rheumatol, 2009, Van der Heiden J W et al.), Inflammatory bowel disease (IBD), ulcerative colitis, crohn's diseases, (Gut 2010, Schmidt N et al., J Immunol 2010, Basler M et al., Clin Exp Immunol, 2009, Inoue S et al.), multiple sclerosis (Eur J Immunol 2008, Fissolo N et al., J Mol Med 2003, Elliott P J et al., J Neuroimmunol 2001, Hosseini et al., J Autoimmun 2000, Vanderlugt C L et al.), Amyotrophic lateral sclerosis (ALS), (Exp Neurol 2005, Puttaparthi k et al., J Biol Chem 2003, Allen S et al.), osteoarthritis (Pain 2011, Ahmed s et al., Biomed Mater Eng 2008, Etienne S et al.), Atherosclerosis (J Cardiovasc Pharmacol 2010, Feng B et al., Psoriasis (Genes & Immunity, 2007, Kramer U et al.), Myasthenia Gravis (J Immunol, 2011, Gomez A M et al.), Dermal fibrosis (Thorax 2011, Mutlu G M et al., Inflammation 2011, Koca S S et al., Faseb J 2006, Fineschi S et al.), renal fibrosis (Nephrology 2011 Sakairi T et al.), cardiac fibrosis (Biochem Pharmacol 2011, Ma y et al.,) Liver fibrosis (Am J Physiol gastrointest Liver Physiol 2006, Anan A et al.), Lung fibrosis (Faseb J 2006, Fineschi S et al et al.), Imunoglobuline A nephropathy (IGa nephropathy), (Kidney Int, 2009, Coppo R et al.), Vasculitis (J Am Soc nephrol 2011, Bontscho et al.), Transplant rejection (Nephrol Dial transplant 2011, Waiser J et al.), Hematological malignancies (Br J Haematol 2011, singh A V et al., Curr Cancer Drug Target 2011, Chen D et al.) and asthma.

Yet, it should be noted that commercially available proteasome inhibitors inhibit both the constitutive and immuno-forms of the proteasome. Even bortezomib, the FDA-approved proteasome inhibitor for the treatment of relapsed multiple myeloma patients, does not distinguish between the two forms (Altun et al, Cancer Res 65:7896, 2005). Furthermore, the use of Bortezomib is associated with a treatment-emergent, painful peripheral neuropathy (PN), this bortezomib-induced neurodegeneration in vitro occurs via a proteasome-independent mechanism and that bortezomib inhibits several nonproteasomal targets in vitro and in vivo (Clin. Cancer Res, 17(9), May 1, 2011).

In addition to conventional proteasome inhibitors, a novel approach may be to specifically target the hematological-specific immunoproteasome, thereby increasing overall effectiveness and reducing negative off-target effects. It has been shown that immunoproteasome-specific inhibitor, could display enhanced efficiency on cells from a hematologic origin (m).

Thus there is a need to provide new proteasome inhibitors that are selective of one specific form of the proteasome.

In another aspect, the present invention relates to a pharmaceutical preparation containing at least one of the compounds according to Formula (I) and related Formulae.

Such pharmaceutical preparation may also contain additional active agents. The additional active agents may be selected from immunosuppressors, anti-inflammatory agent or interferon.

In another aspect, the present invention relates to a process for making the compounds according to Formula (I) and related Formulae.

The present invention further relates to a set or a kit consisting of separate packs of (a) an effective amount of a compound according to Formula (I) or related Formulae and/or pharmaceutically usable derivatives, tautomers, salts, solvates and stereoisomers thereof, including mixtures thereof in all ratios, and (b) an effective amount of a further medicament active ingredient, The present invention encompasses compounds of Formula (I) and related Formulae either alone or in combination with one or several metabolites thereof.

DETAILED DESCRIPTION

Compounds of the present invention are inhibitors of the immunoproteasome subunit LMP7. They preferably show selectivity on LMP7 over Beta5.

The present invention provides compounds of Formula (I):

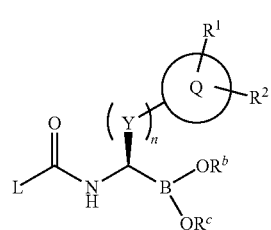

Wherein
$R^b$ and $R^c$ are independently selected from one another from H or $C_1$-$C_6$-alkyl; whereby $R^b$ and $R^c$ may be linked to form a 5 or 6 membered-ring containing the oxygen atoms to which they are bond.

Q denotes Ar, Het or cycloalkyl;
$R^1$, $R^2$ independently from each other denote H, $OR^a$, preferably methoxy, Hal, $C_1$-$C_6$-alkyl wherein 1 to 5H atoms may be independently replaced by OH or Hal;
Y denotes $CR^3R^4$, preferably $CH_2$ or $C(CH_3)_2$;
$R^3$, $R^4$ independently of one another denote H or $C_1$-$C_6$-alkyl, such as methyl;
L denotes $L_1$ or $L_2$, or alkyl, preferably methyl;
n is an integer selected from 0, 2 or 3 and is preferably 1;
$L_1$ is

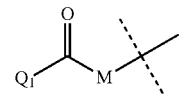

wherein
$Q_1$ is Ar or Het, preferably phenyl, naphthyl or pyridine, optionally substituted with 1 to 5 groups independently selected from $OR^a$, Hal, phenyl, and $C_1$-$C_6$-alkyl wherein 1 to 5H atoms may be independently replaced by OH or Hal;
$L_2$ is

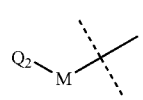

wherein
$Q_2$ is a fused bicyclic system containing 1 nitrogen atom and 1 to 3 additional groups independently selected from O, S, N, or CO, and wherein at least one of the ring is aromatic whereby the fused bicyclic system is optionally substituted with 1 to 5 groups independently selected from $OR^a$, Hal, phenyl, and $C_1$-$C_6$-alkyl wherein 1 to 5H atoms may be independently replaced by OH or Hal; or
$Q_2$ is unsaturated or aromatic 5 membered-ring system containing 1 to 3 heteroatoms selected from N, O, S and CO, and optionally substituted with a phenyl ring or pyridine ring whereby phenyl ring and pyridine ring are optionally substituted with 1 to 4 groups independently selected from $OR^a$, Hal, phenyl, and $C_1$-$C_6$-alkyl wherein 1 to 5H atoms may be independently replaced by OH or Hal;
M is a linear or branched alkylen having 1 to 5 carbon atoms wherein 1 or 2H atoms may be replaced by $OR^a$ or a phenyl ring optionally substituted with 1 to 5 groups independently selected from Hal, OR', and $C_1$-$C_6$-alkyl optionally substituted with 1 to 5 groups independently selected from OH, and Hal; or
M denotes a cycloalkylen having 3 to 7 carbon atoms; or
M denotes a thiazolidinyl group.
$R^a$ is H or $C_1$-$C_6$-alkyl wherein 1 to 5H atom may be independently replaced by OH or Hal;
Ar denotes a 6 membered-aromatic carbocyclic ring optionally fused with another carbocyclic saturated, unsaturated or aromatic ring having 5 to 8 carbon atoms;
Het denotes a 5- or 6-membered saturated, unsaturated or aromatic heterocyclic ring having 1 to 3 heteroatoms independently selected from N, $N^+O^-$, O, S, SO, and $SO_2$, and optionally fused with another saturated, unsaturated or aromatic ring having 5 to 8 atoms and optionally containing 1 to 3 heteroatoms selected from N, O, and S;
Hal denotes Cl, Br, I of F; preferably Cl or F,
As well as enantiomers, diastereoisomers, and mixture thereof, and pharmaceutically acceptable salts thereof;

In case L contains 1 or several chiral centers, Formula (I) encompasses any isolated enantiomer and diastereoisomers as well as mixtures thereof in all ratios.

In a specific embodiment, the present invention provides compounds of Formula (I) and related Formulae, wherein L denotes L1, whereby M is a cycloalkylen having 3 to 7 carbon atoms. Preferably, M is selected from a 5- or 6-membered cycloalkylen. Examples of such cycloalkylen groups are the followings:

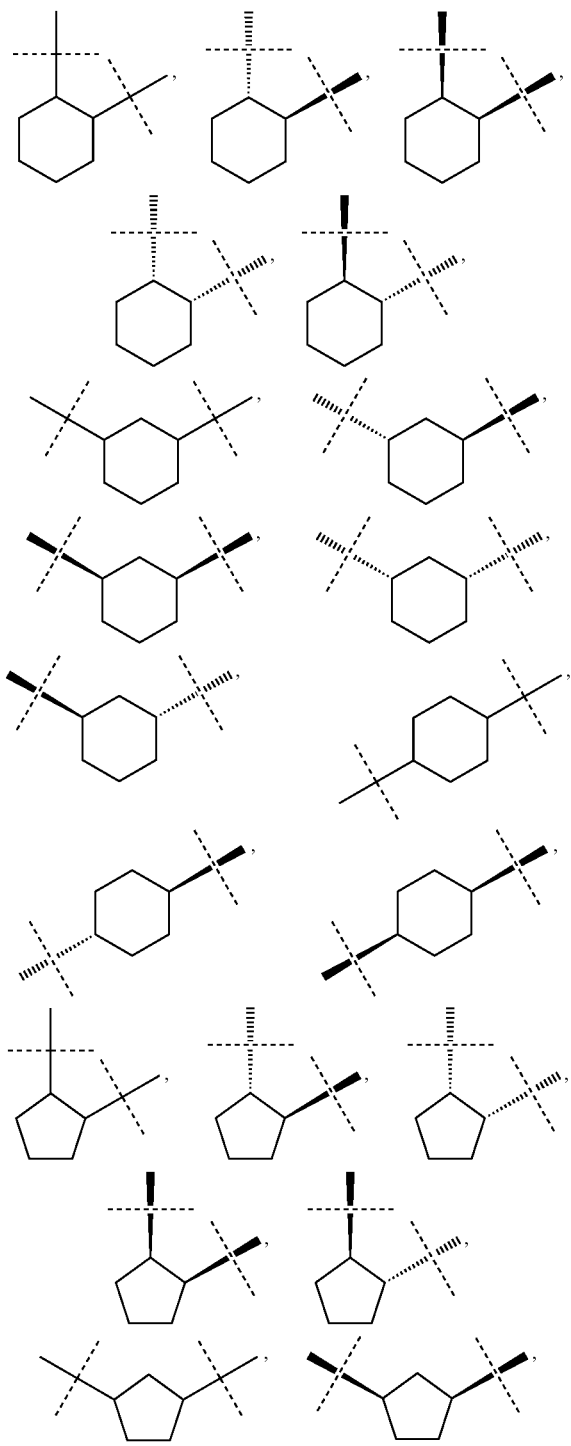

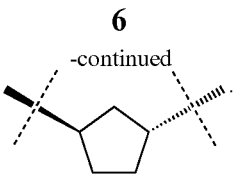

In another specific embodiment, the present invention provides compounds of Formula (I) and related Formulae, wherein L denotes L1 whereby M is a linear or branched alkylen having 1 to 5 carbon atoms wherein 1 or 2H atoms may be replaced by $OR^a$ or a phenyl ring optionally substituted with 1 to 5 groups independently selected from Hal, $OR^a$, and $C_1$-$C_6$-alkyl optionally substituted with 1 to 5 groups independently selected from OH, and Hal.

In another specific embodiment, the present invention provides compounds of Formula (I) and related Formulae, wherein L is L2 whereby M denotes a linear or branched alkylen having 1 to 5 carbon atoms wherein 1 or 2H atoms may be replaced by $OR^a$ or a phenyl ring optionally substituted with 1 to 5 groups independently selected from Hal, $OR^a$, and $C_1$-$C_6$-alkyl optionally substituted with 1 to 5 groups independently selected from OH, and Hal.

Preferably M in L2 is a non-substituted linear alkylen having 1 to 5 carbon atoms.

In another specific embodiment, the present invention provides compounds of Formula (I) and related Formulae, wherein L is $L_1$. $L_1$ is preferably selected from the following groups:

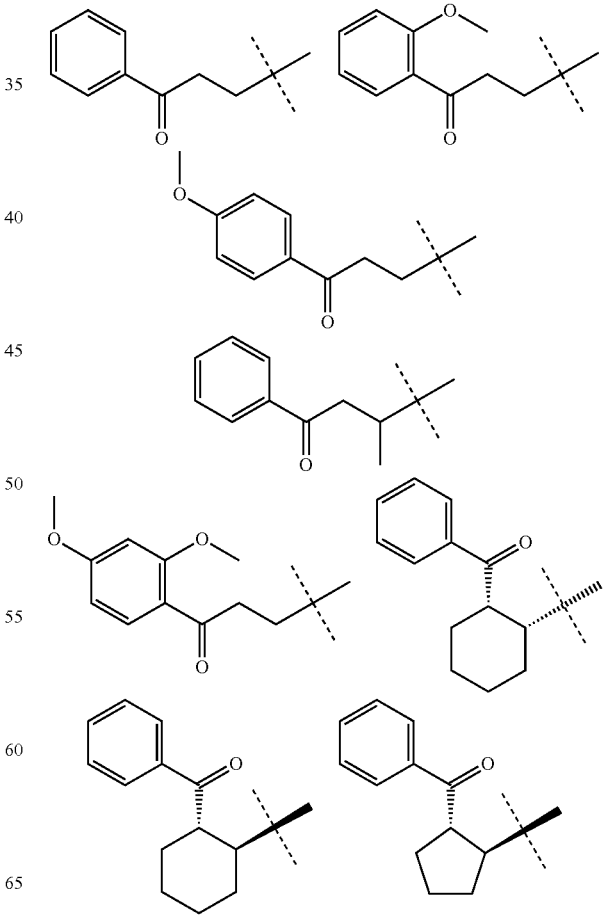

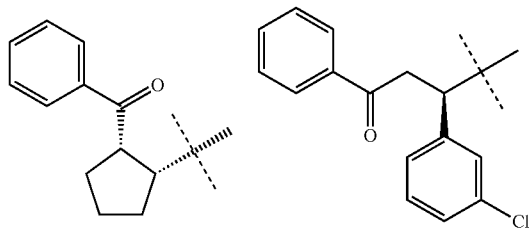
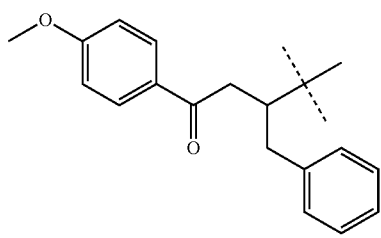
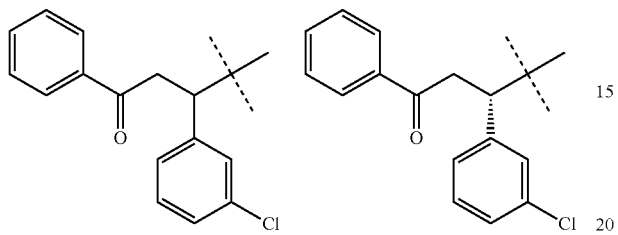
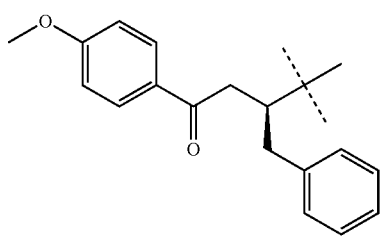
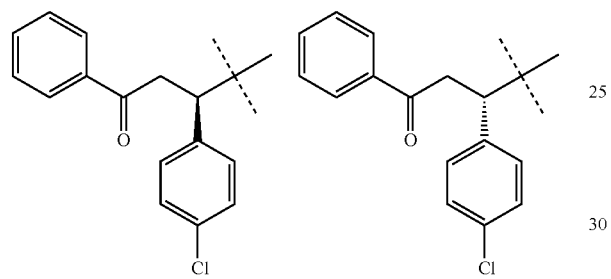
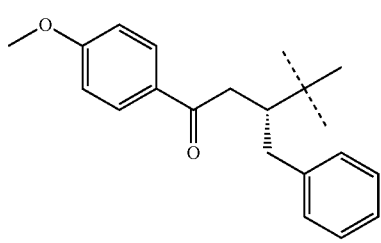
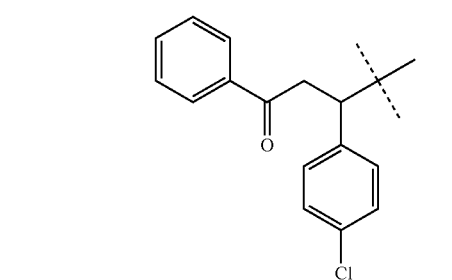
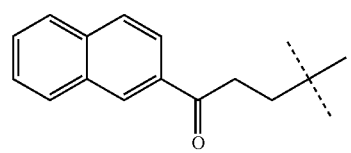
In another specific embodiment, the present invention provides compounds of Formula (I) and related Formulae, wherein L is $L_2$. $L_2$ is preferably selected from the following groups:
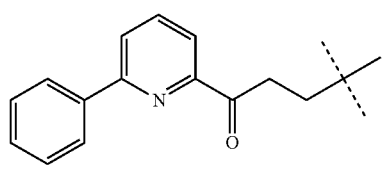
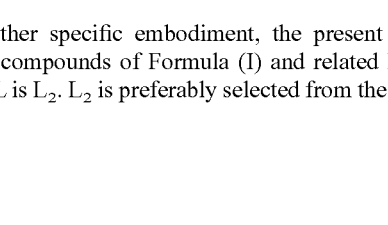
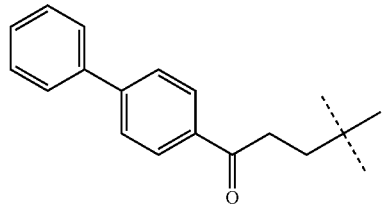
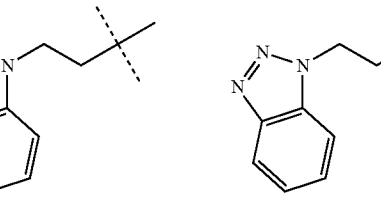
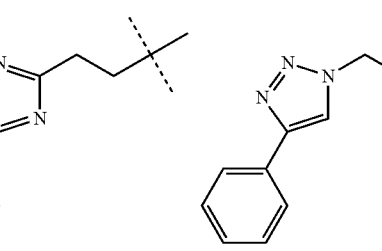

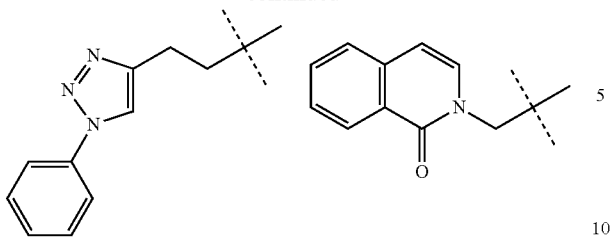

In another specific embodiment, the present invention provides compounds of Formula (I) and related Formulae wherein the group

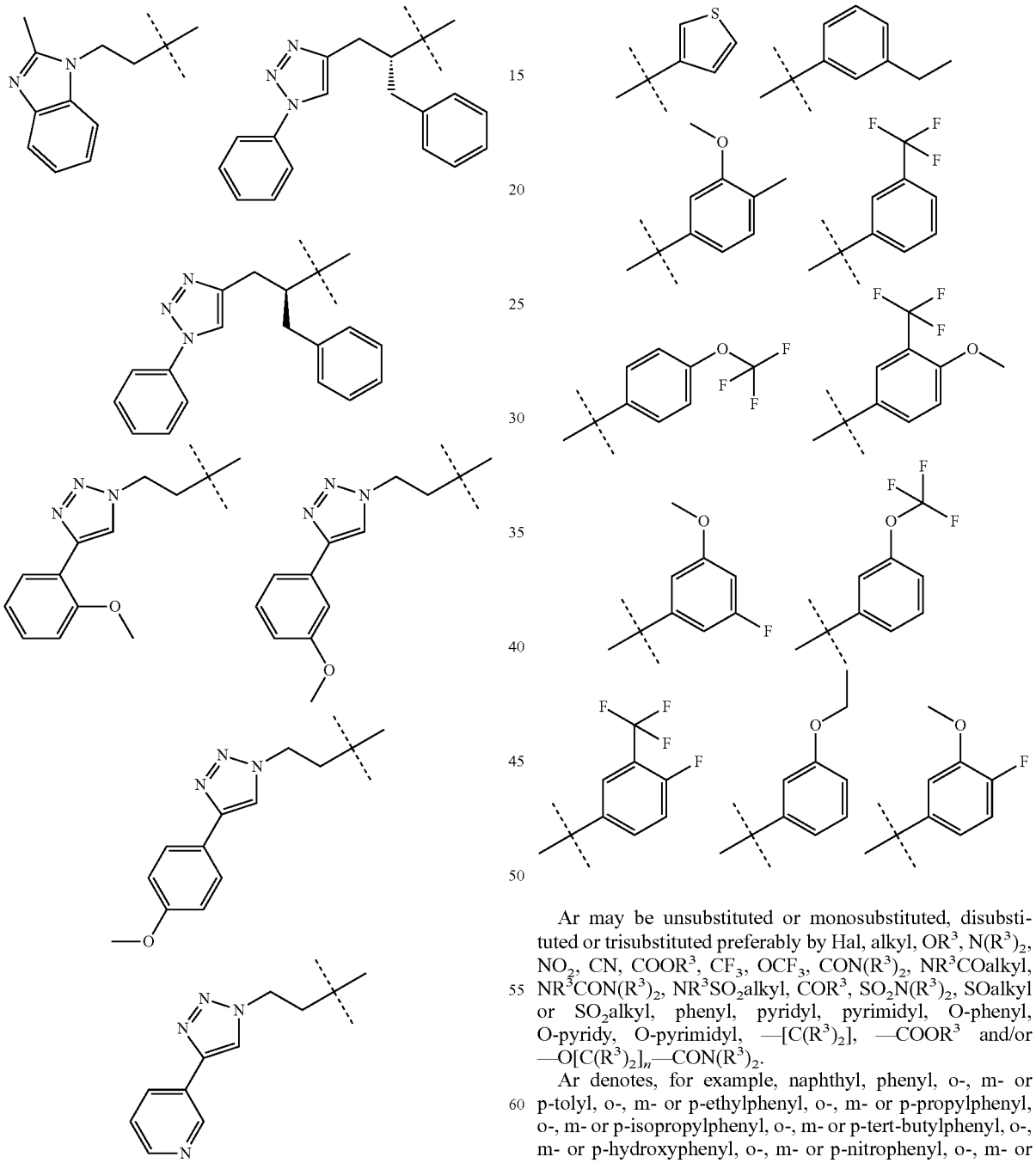

is selected from the following groups:

Ar may be unsubstituted or monosubstituted, disubstituted or trisubstituted preferably by Hal, alkyl, $OR^3$, $N(R^3)_2$, $NO_2$, CN, $COOR^3$, $CF_3$, $OCF_3$, $CON(R^3)_2$, $NR^3COalkyl$, $NR^3CON(R^3)_2$, $NR^3SO_2alkyl$, $COR^3$, $SO_2N(R^3)_2$, SOalkyl or $SO_2alkyl$, phenyl, pyridyl, pyrimidyl, O-phenyl, O-pyridy, O-pyrimidyl, $—[C(R^3)_2]$, $—COOR^3$ and/or $—O[C(R^3)_2]_n—CON(R^3)_2$.

Ar denotes, for example, naphthyl, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamido-phenyl, o-, m- or p-methoxyphenyl, o-, m- or p-ethoxyphenyl, o-, m- or p-ethoxycarbonyl-phenyl, o-, m- or p-(N,N-dimethylamino)phenyl, o-, m- or p-(N,N-dimethyl-aminocarbonyl)phenyl, o-, m- or p-(N-ethylamino) phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o, m or p-amino-sulfanyl-phenyl, o-, m- or p-phenoxyphenyl, further preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chloro-phenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxy-phenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar particularly preferably denotes, for example, phenyl which is unsubstituted or monosubstituted or disubstituted preferably monosubstituted, by F, OCH$_3$, CH$_3$, CF$_3$, phenyl and/or pyridyl, such as, for example, 2'-methoxy-phenyl-, 2'-trifluoromethyl-phenyl- (aryl bearing at least a 2' substituent), 2'-chloro-phenyl, 2',6'-dimethyl-phenyl- or 2'-alkyl-phenyl-, preferably 2'-methyl-phenyl.

Het is for example, 2- or 3-furyl, benzofuryl, 2- or 3-thienyl, benzothienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benz-oxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothia-diazol-4- or -5-yl or 2,1,3-benzoxadiazol-5-yl.

The heterocyclic radicals in Het may also be partially or fully hydrogenated.

Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoro-methylenedioxy)phenyl, 2,3-dihydrobenzofuran-5- or -6-yl, 2,3-(2-oxomethylenedioxy)-phenyl or also 3,4-dihydro-2H-1,5-benzodioxepin-6- or -7-yl, furthermore preferably 2,3-dihydrobenzofuranyl or 2,3-dihydro-2-oxofuranyl.

Het may be unsubstituted or monosubstituted, disubstituted or trisubstituted by Hal, alkyl, —[C(R$^3$)$_2$]$_n$—Ar, —[C(R$^3$)$_2$]$_n$-cycloalkyl, OR$^3$, CF$_3$, OCF$_3$, N(R$^3$)$_2$, NR$^3$CON(R$^3$)$_2$, NO$_2$, CN, —[C(R$^3$)$_2$]$_n$—COOR$^3$, —[C(R$^3$)$_2$]$_n$—CON(R$^3$)$_2$, NR$^3$COalkyl, NR$^3$SO$_2$alkyl, COR$^3$, SO$_2$N(R$^3$)$_2$, SOalkyl, O-phenyl, O-pyridy, O-pyrimidyl, phenyl, pyridyl and/or SO$_2$alkyl.

Alkyl is unbranched (linear) or branched, and has 1, 2, 3, 4, 5, 6, 7, 8, 9, 10, 11 or 12 carbon atoms. Alkyl preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

Alkyl very particularly preferably denotes alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl, 1,1,1-trifluoroethyl. In a preferred embodiment alkyl is perfluorated.

Cycloalkyl preferably denotes cyclopropyl, cyclobutyl, cyclopentyl, cyclohexyl or cycloheptyl. Cycloalkyl may be substituted preferably by alkyl, OH, O-alkyl, Hal.

In another specific embodiment, the compounds of the present invention are selected from the following group:

| Ex | Formula |
|---|---|
| 1 |  |
| 2 |  |
| 3 |  |

-continued

| Ex | Formula |
|----|---------|
| 4 | |
| 5 | |
| 6 | |
| 7 | |
| 8 | |
| 9 | |
| 10 | |
| 11 | |
| 12 | |
| 13 | |
| 14 | |

-continued
| Ex | Formula |
|---|---|
| 15 | 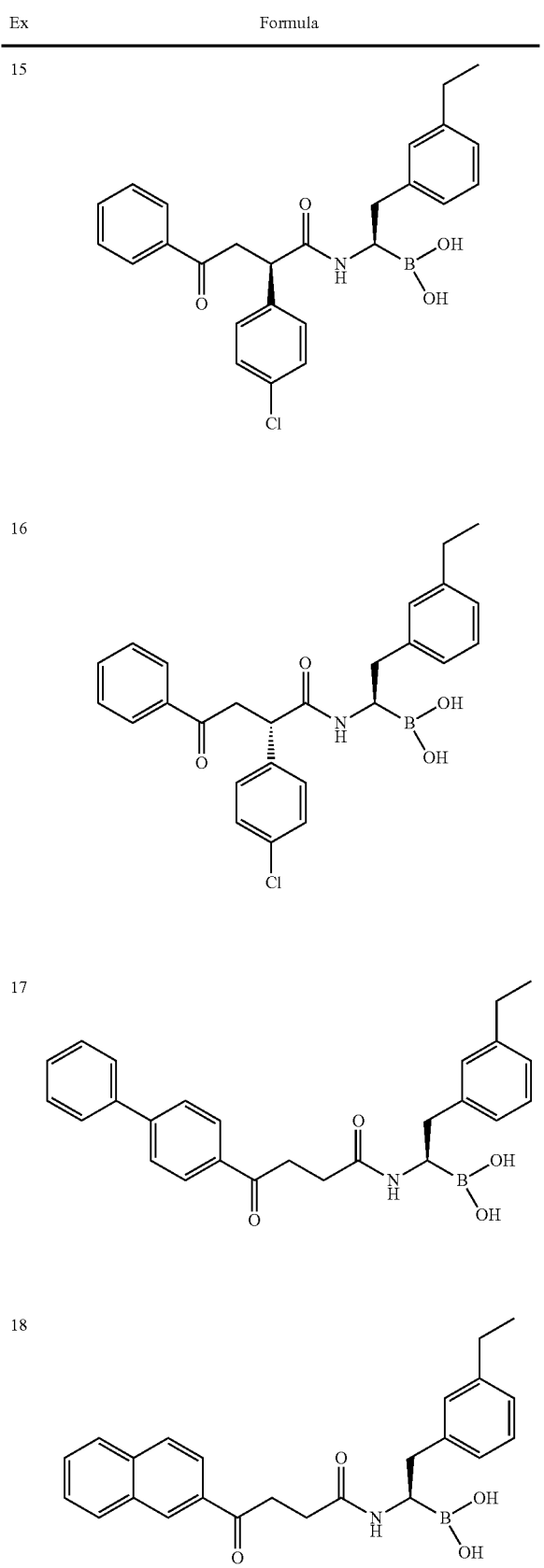 |
| 16 | |
| 17 | |
| 18 | |
-continued
| Ex | Formula |
|---|---|
| 19 | 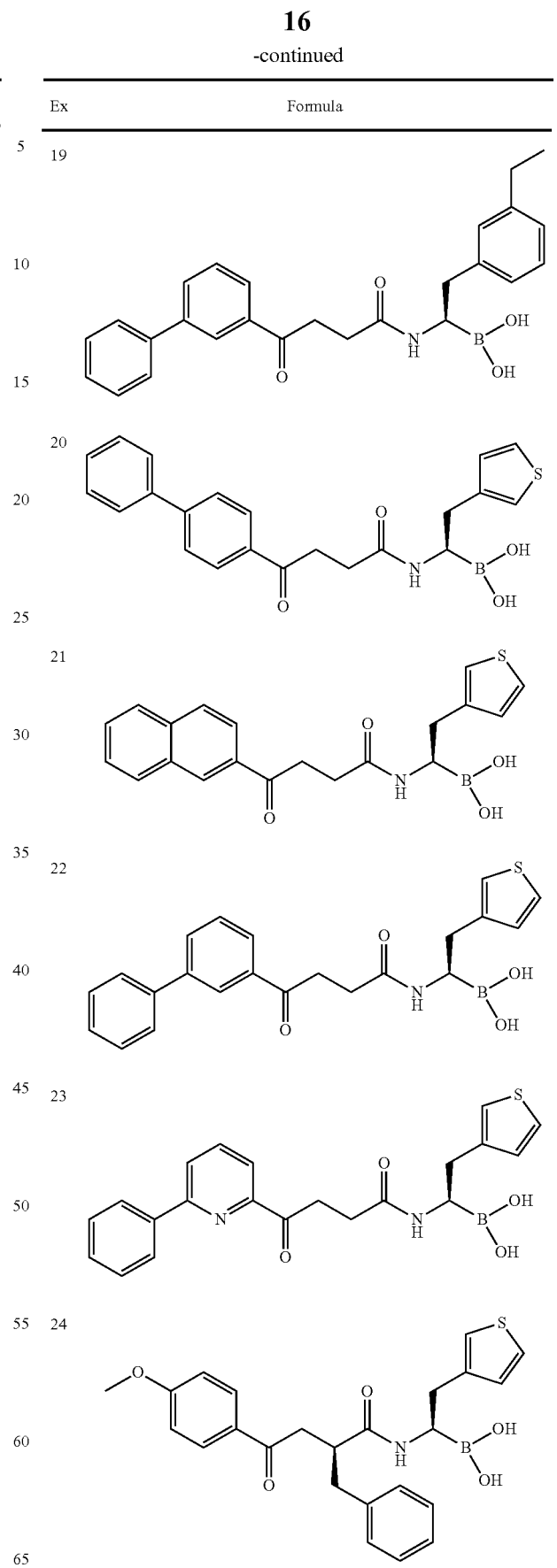 |
| 20 | |
| 21 | |
| 22 | |
| 23 | |
| 24 | |

| Ex | Formula |
|---|---|
| 25 | 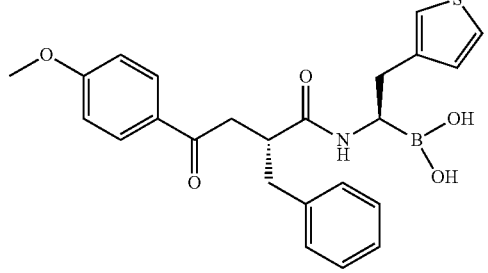 |
| 26 | 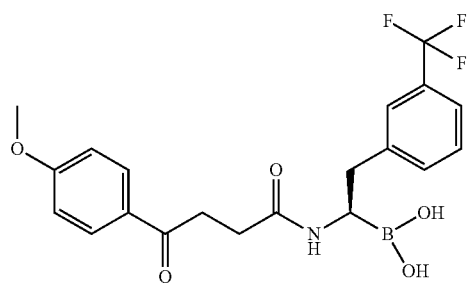 [SMILES: COc1ccc(C(=O)CCC(=O)N[C@@H](Cc2cccc(C(F)(F)F)c2)B(O)O)cc1] |
| 27 | 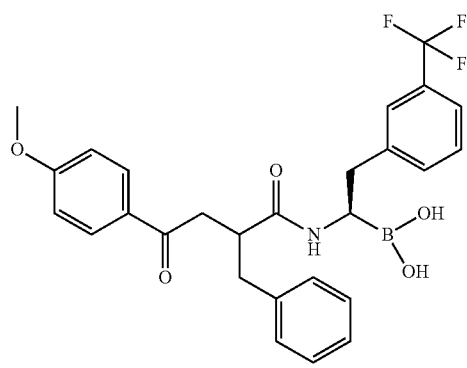 [SMILES: COc1ccc(C(=O)CC(Cc2ccccc2)C(=O)N[C@@H](Cc2cccc(C(F)(F)F)c2)B(O)O)cc1] |
| 28 | 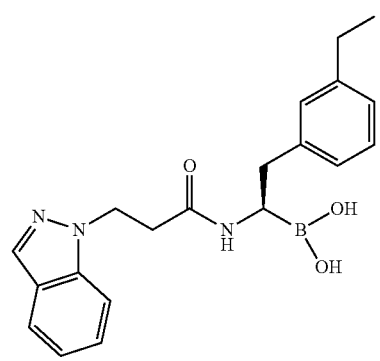 [SMILES: CCc1cccc(C[C@H](NC(=O)CCn2ncc3ccccc32)B(O)O)c1] |
| 29 | 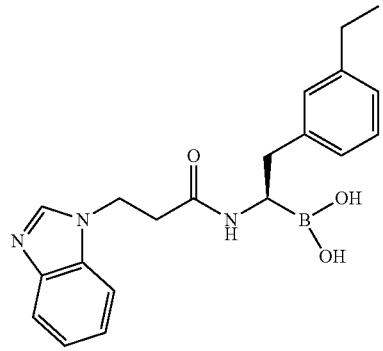 [SMILES: CCc1cccc(C[C@H](NC(=O)CCn2cnc3ccccc32)B(O)O)c1] |
| 30 | 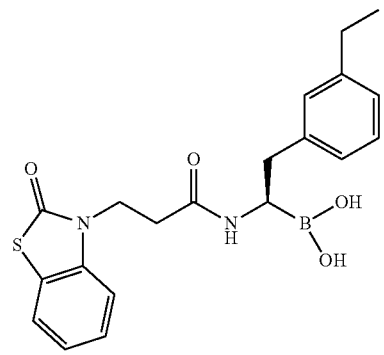 [SMILES: CCc1cccc(C[C@H](NC(=O)CCn2c(=O)sc3ccccc32)B(O)O)c1] |
| 31 | 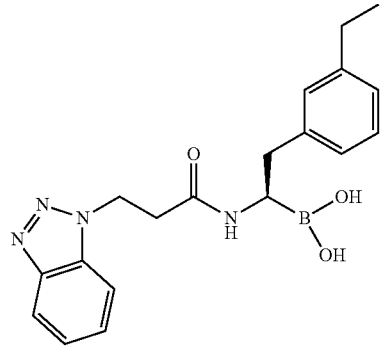 [SMILES: CCc1cccc(C[C@H](NC(=O)CCn2nnc3ccccc32)B(O)O)c1] |
| 32 | 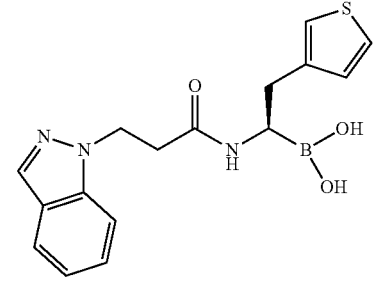 [SMILES: O=C(CCn1ncc2ccccc21)N[C@@H](Cc1ccsc1)B(O)O] |

-continued
| Ex | Formula |
|---|---|
| 33 | 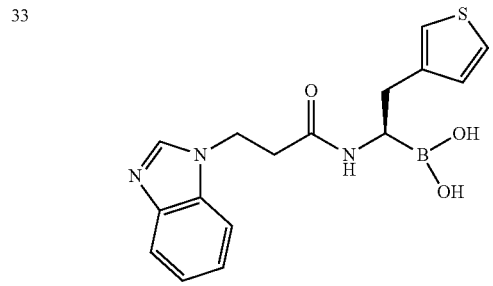 |
| 34 | 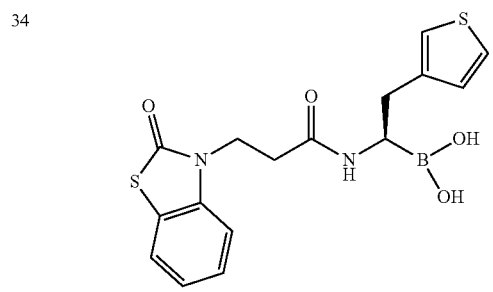 |
| 35 | 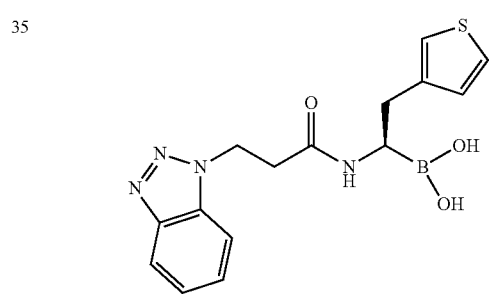 |
| 36 | 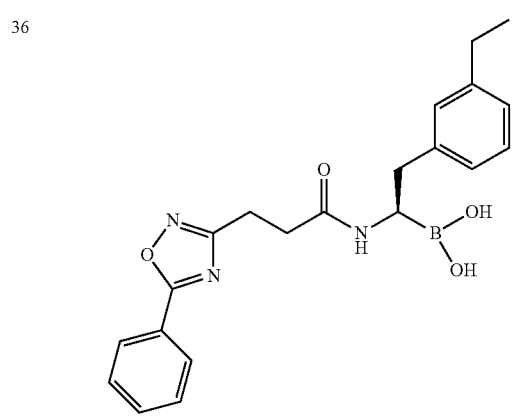 |
-continued
| Ex | Formula |
|---|---|
| 37 | 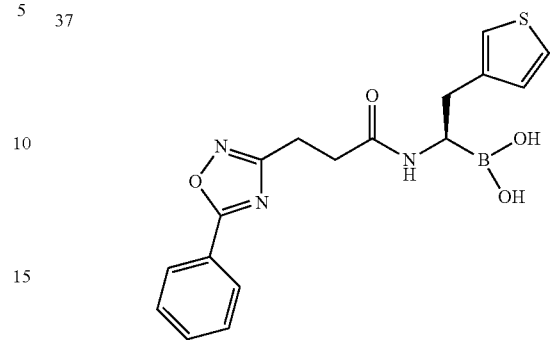 |
| 38 | 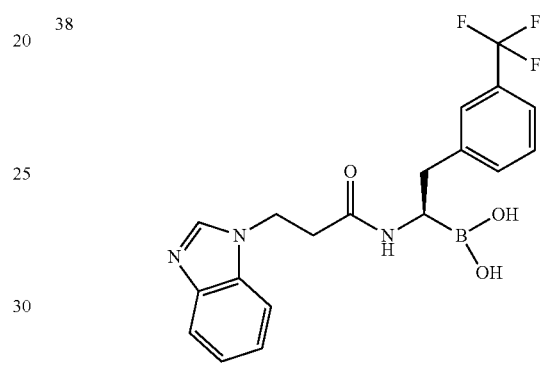 |
| 39 | 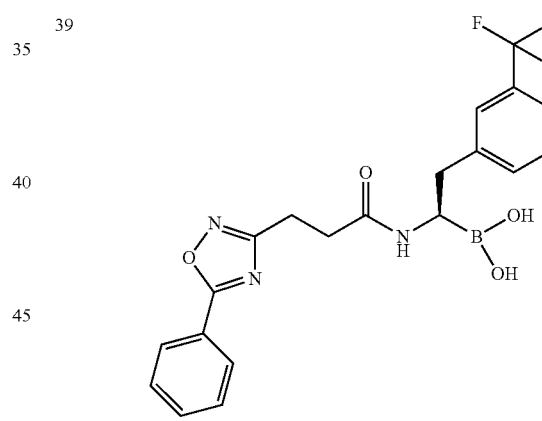 |
| 40 | 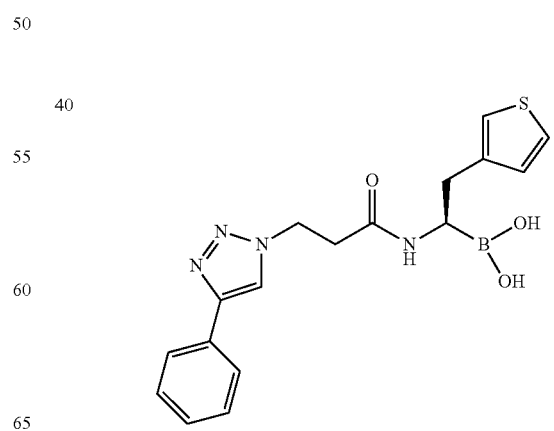 |

| Ex | Formula |
|---|---|
| 41 | 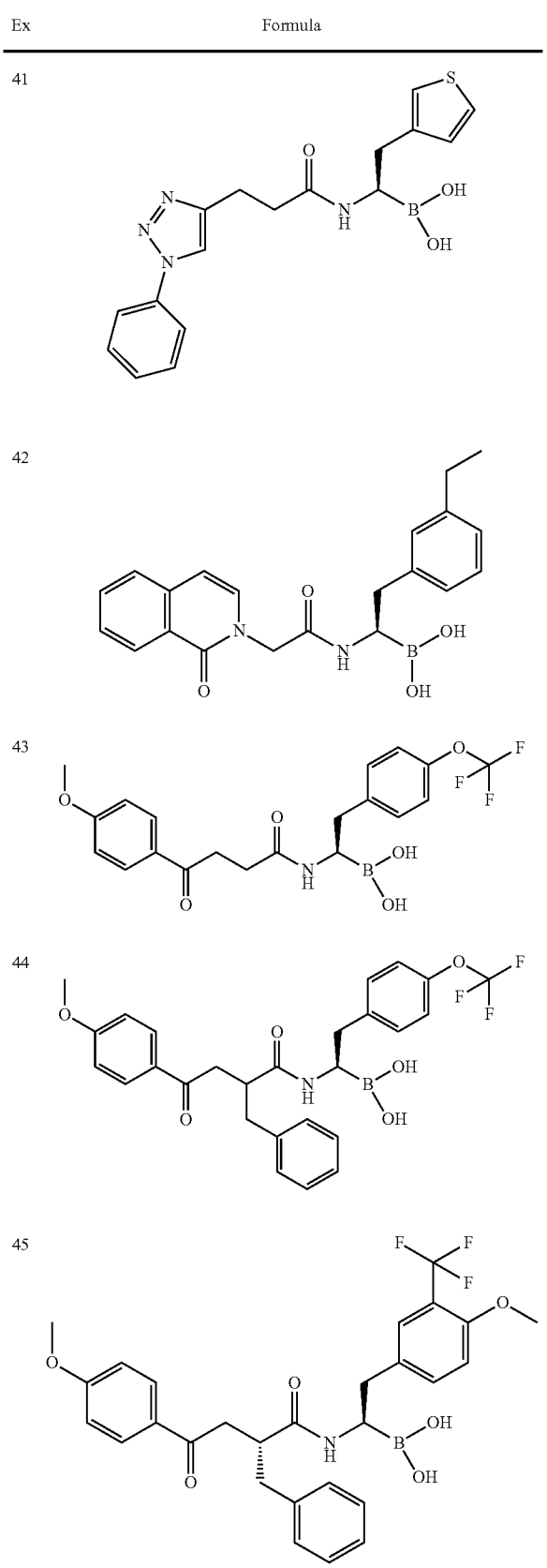 |
| 42 | |
| 43 | |
| 44 | |
| 45 | |
| Ex | Formula |
|---|---|
| 46 | 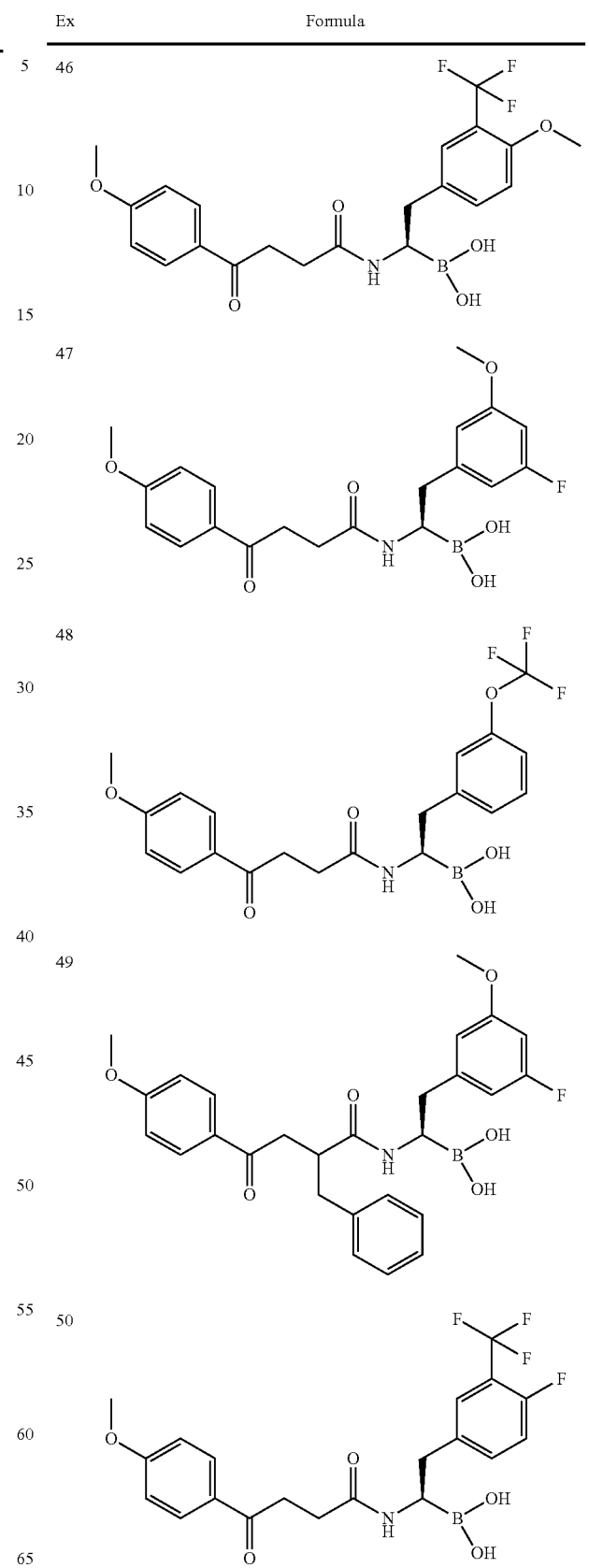 |
| 47 | |
| 48 | |
| 49 | |
| 50 | |

-continued
| Ex | Formula |
|---|---|
| 51 | |
| 52 | |
| 53 | |
| 54 | |
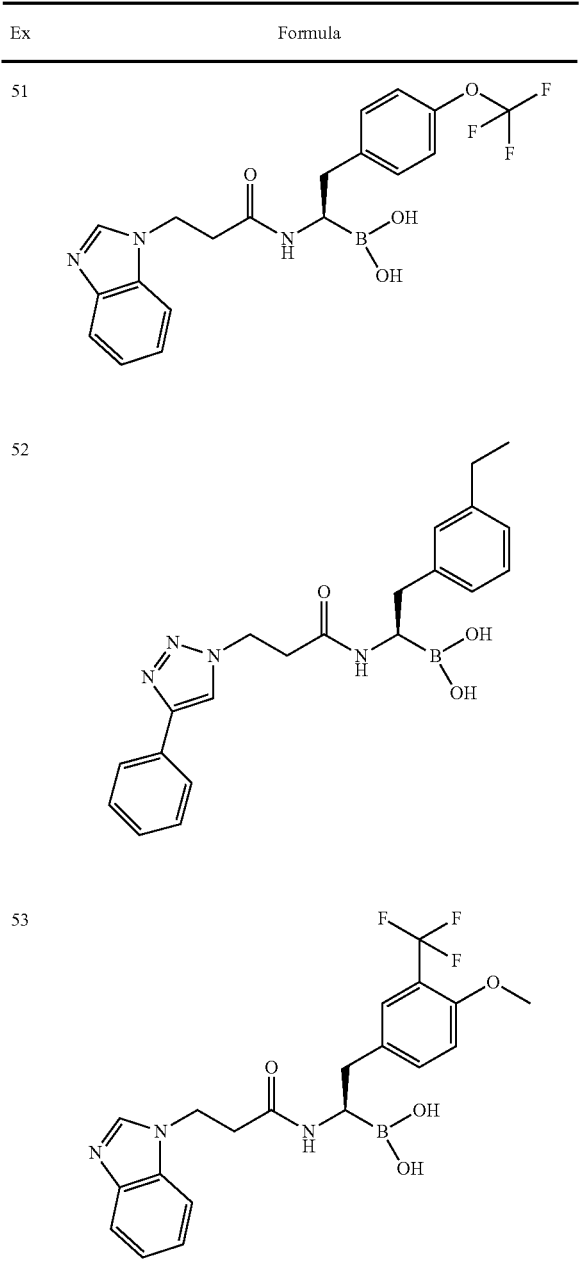
-continued
| Ex | Formula |
|---|---|
| 55 | |
| 56 | |
| 57 | |
| 58 | |
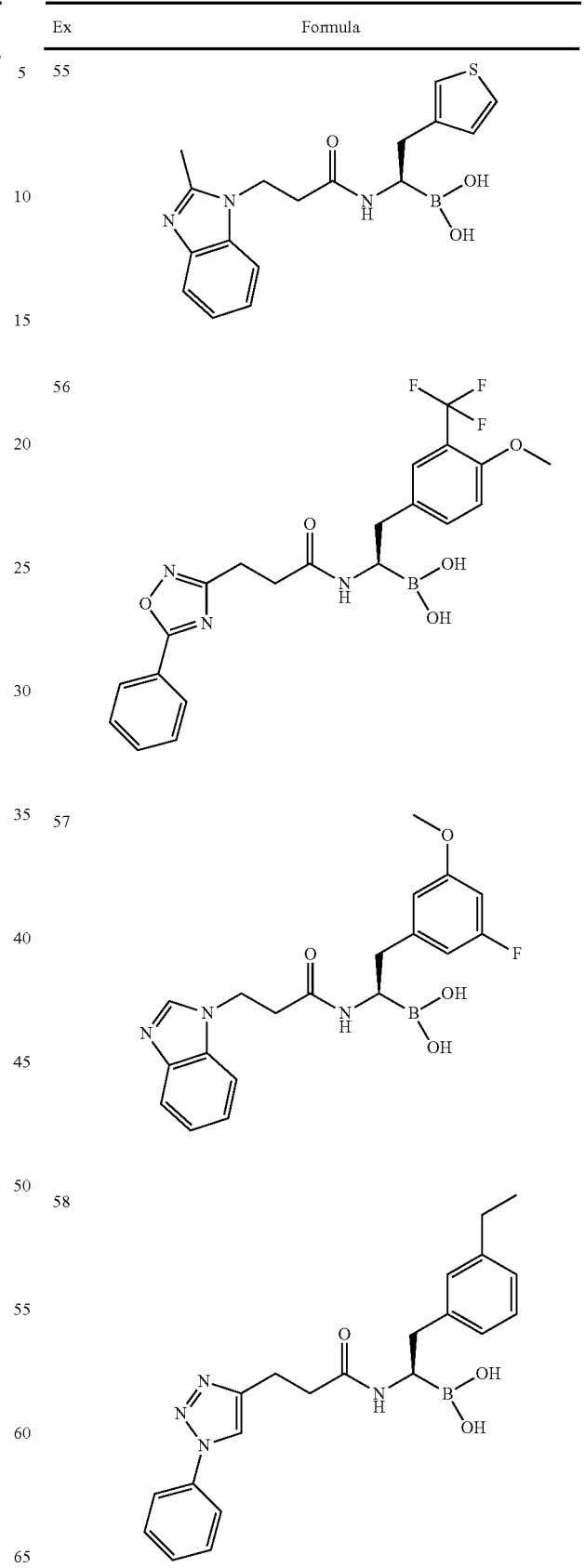

-continued
| Ex | Formula |
|---|---|
| 59 | 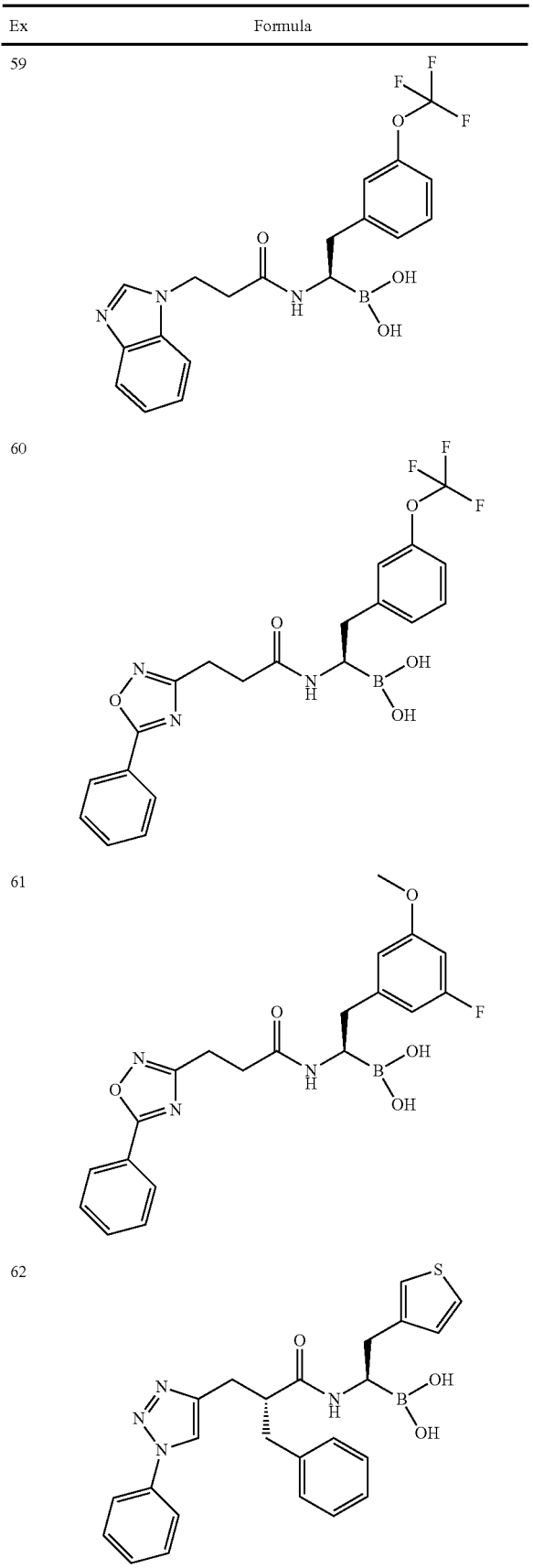 |
| 60 | |
| 61 | |
| 62 | |
-continued
| Ex | Formula |
|---|---|
| 63 | 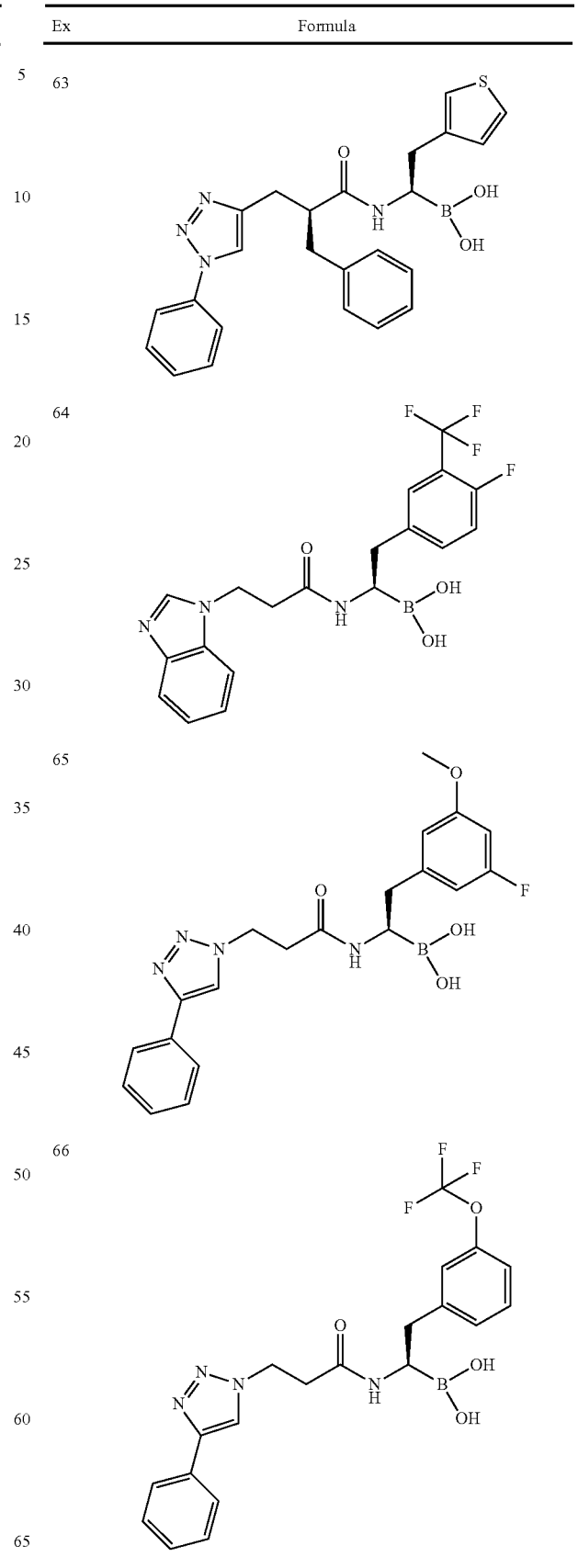 |
| 64 | |
| 65 | |
| 66 | |

27
-continued
| Ex | Formula |
|---|---|
| 67 | |
| 68 | |
| 69 | |
| 70 | |
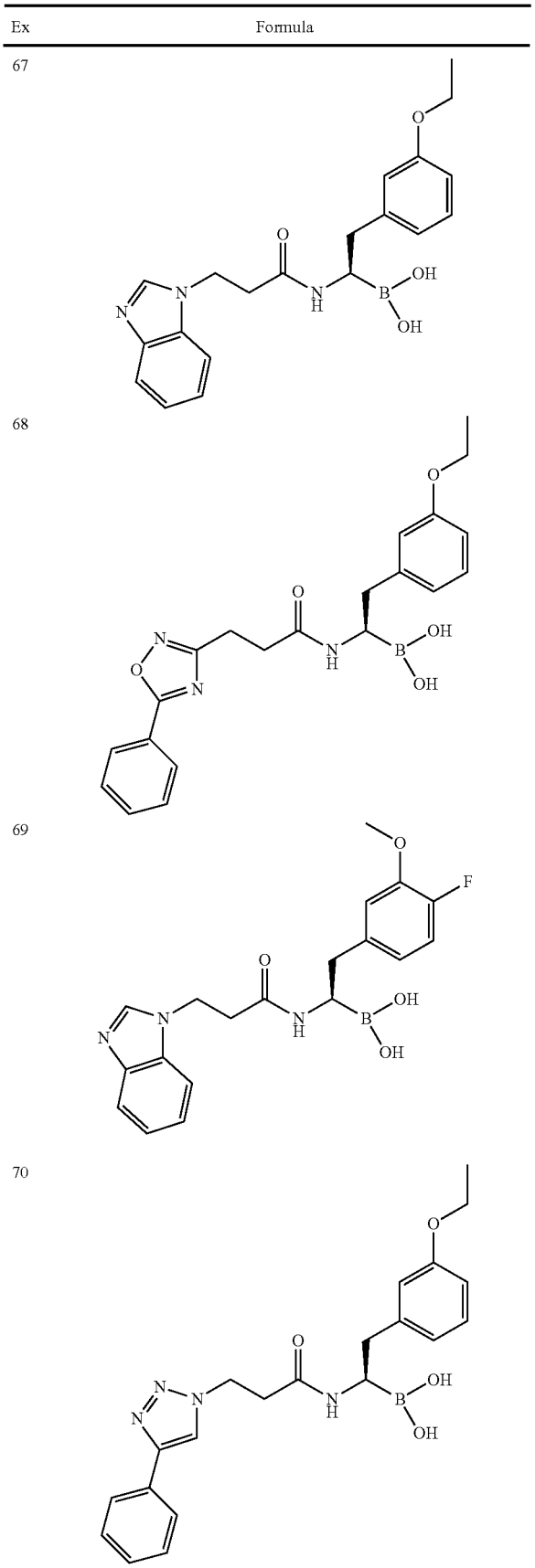
28
-continued
| Ex | Formula |
|---|---|
| 71 | |
| 72 | |
| 73 | |
| 74 | |
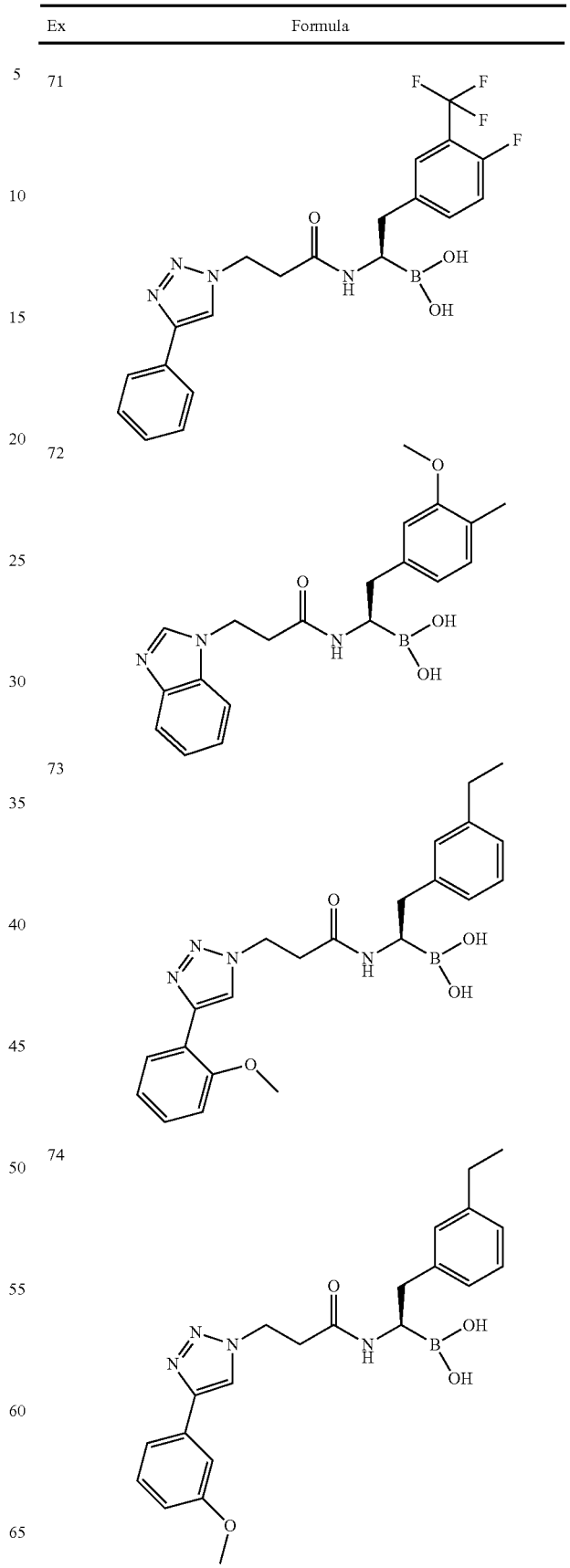

-continued
| Ex | Formula |
|---|---|
| 75 | 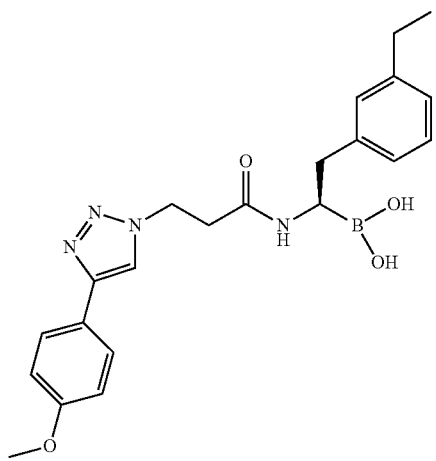 [SMILES: CCc1cccc(C[C@H](NC(=O)CCn2cc(-c3ccc(OC)cc3)nn2)B(O)O)c1] |
| 76 | 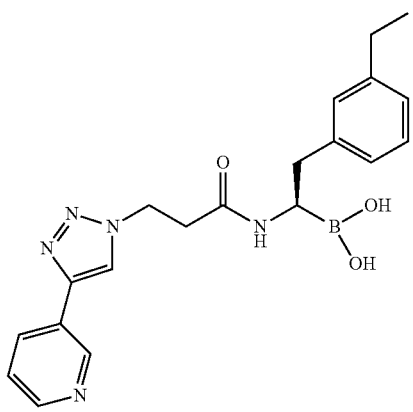 [SMILES: CCc1cccc(C[C@H](NC(=O)CCn2cc(-c3cccnc3)nn2)B(O)O)c1] |
| 77 | 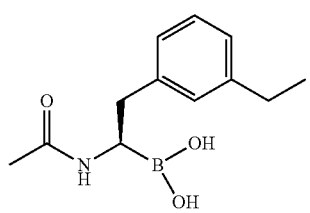 [SMILES: CCc1cccc(C[C@H](NC(C)=O)B(O)O)c1] |
| 78 | 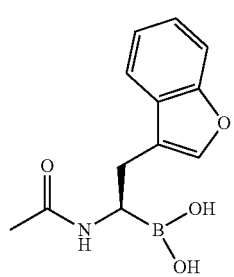 [SMILES: CC(=O)N[C@@H](Cc1coc2ccccc12)B(O)O] |
-continued
| Ex | Formula |
|---|---|
| 79 | 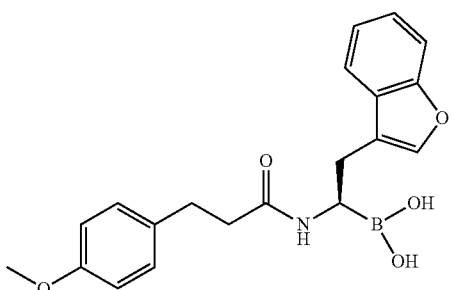 |
| 80 | 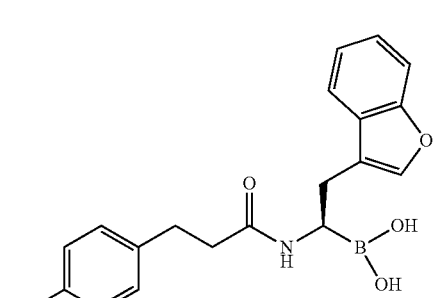 |
| 81 | 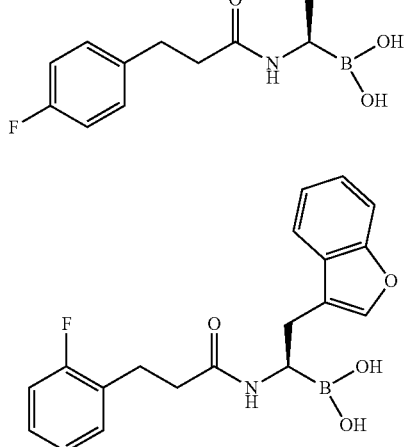 |
| 82 | 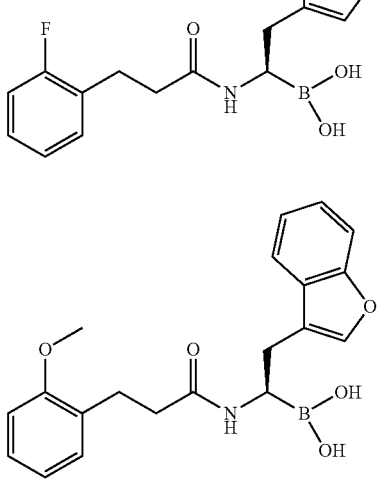 |
| 83 | 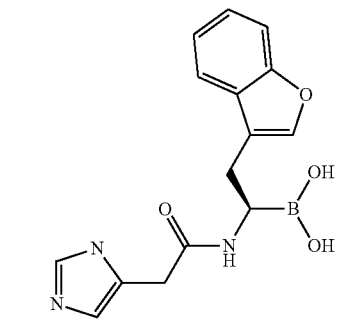 [SMILES: O=C(Cc1cnc[nH]1)N[C@@H](Cc1coc2ccccc12)B(O)O] |

| Ex | Formula |
|---|---|
| 84 | 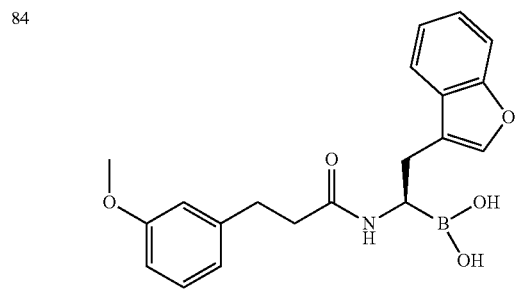 |
| 85 | 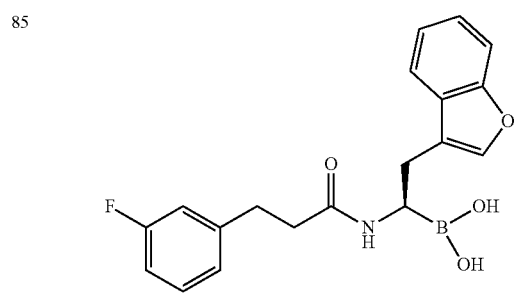 |
| 86 | 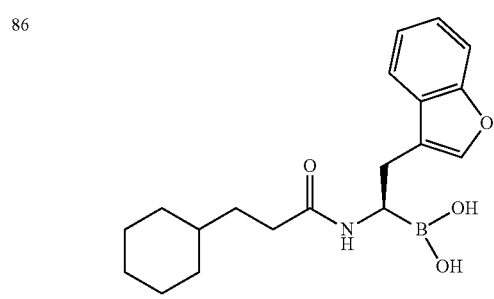 |
| 87 | 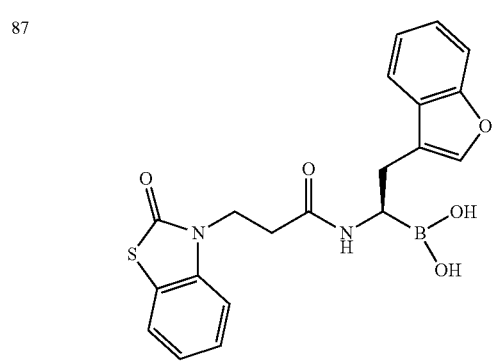 |
| 88 | 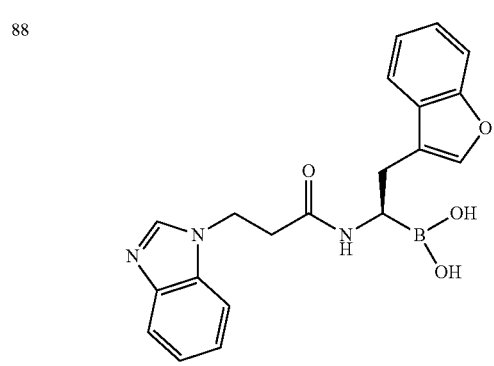 |
| 89 | 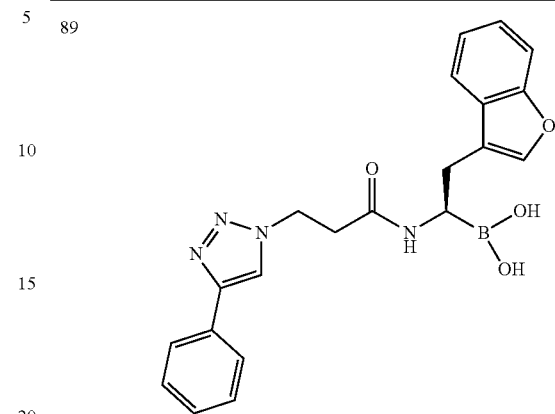 |
| 90 | 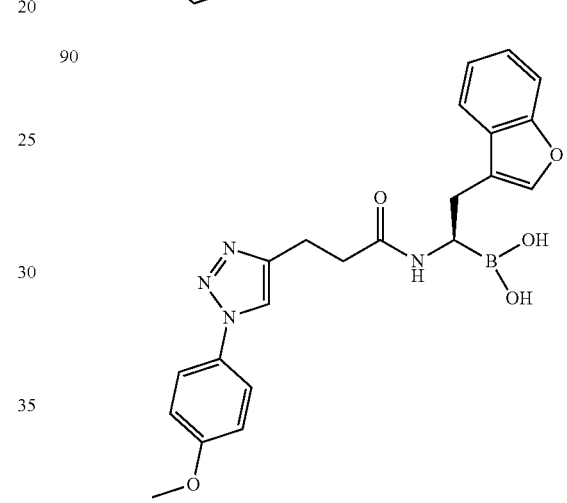 |
| 91 | 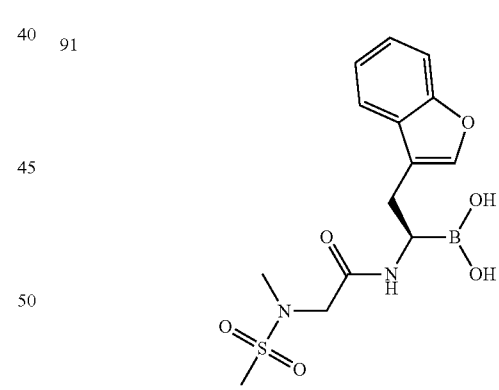 |
| 92 | 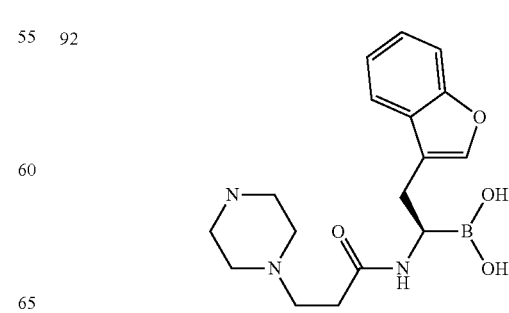 |

33
-continued
| Ex | Formula |
|---|---|
| 93 | 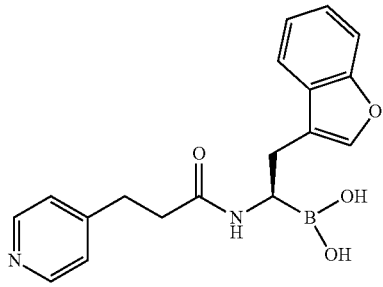 [SMILES: O=C(CCc1ccncc1)N[C@@H](Cc1coc2ccccc12)B(O)O] |
| 94 | 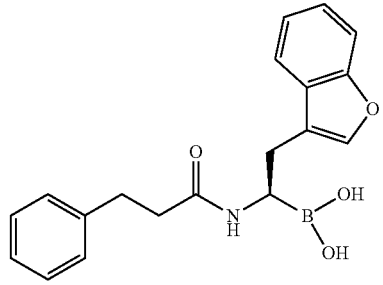 [SMILES: O=C(CCc1ccccc1)N[C@@H](Cc1coc2ccccc12)B(O)O] |
| 95 | 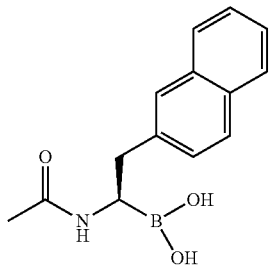 [SMILES: CC(=O)N[C@@H](Cc1ccc2ccccc2c1)B(O)O] |
| 96 | 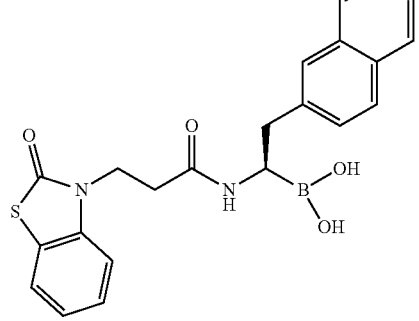 |
| 97 | 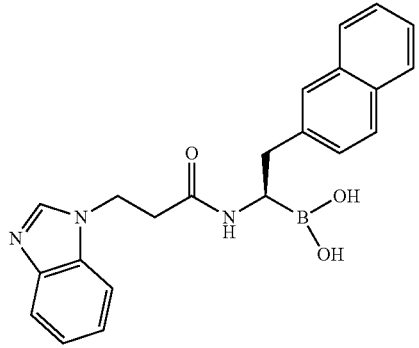 [SMILES: O=C(CCn1cnc2ccccc21)N[C@@H](Cc1ccc2ccccc2c1)B(O)O] |
34
-continued
| Ex | Formula |
|---|---|
| 98 | 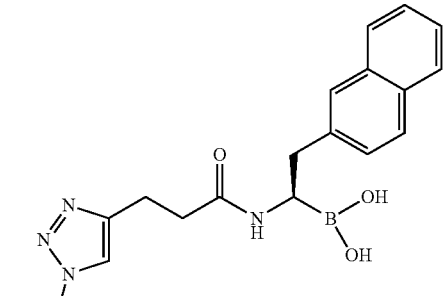 |
| 99 |  |
| 100 |  |

TABLE-continued
| Ex | Formula |
|---|---|
| 101 | 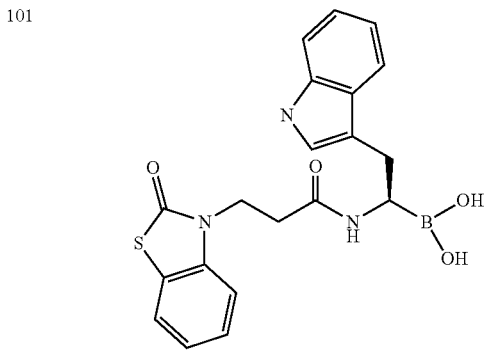 |
| 102 | 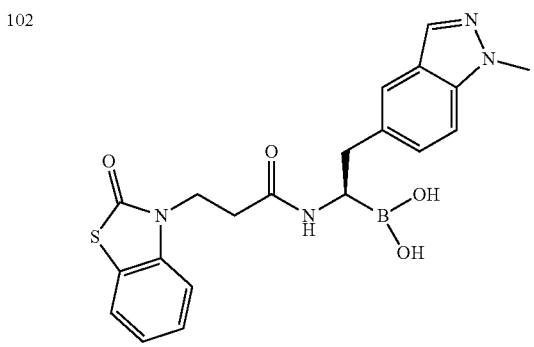 |
| 103 | 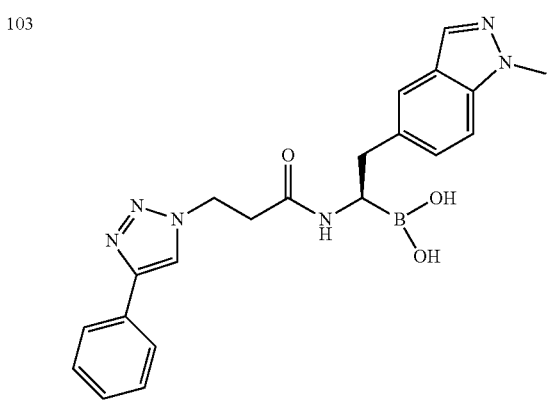 |
| 104 | 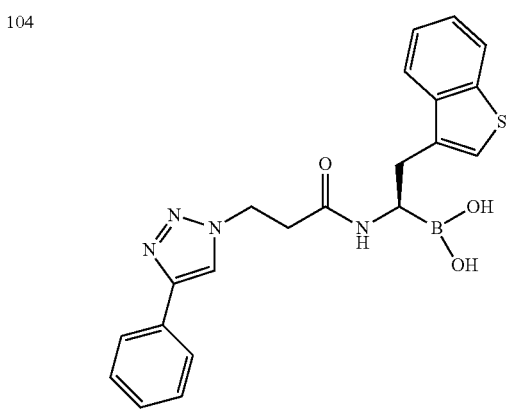 |
| 105 | 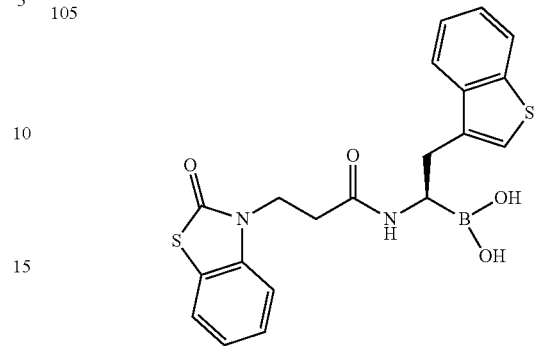 |
| 106 | 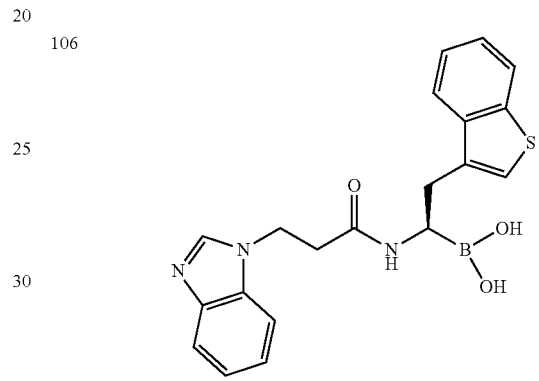 |
| 107 | 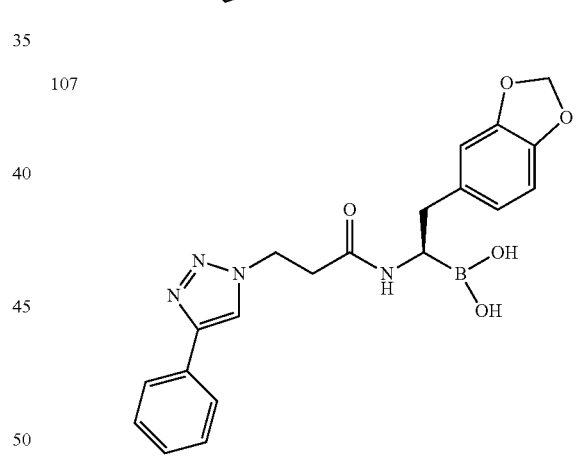 |
| 108 | 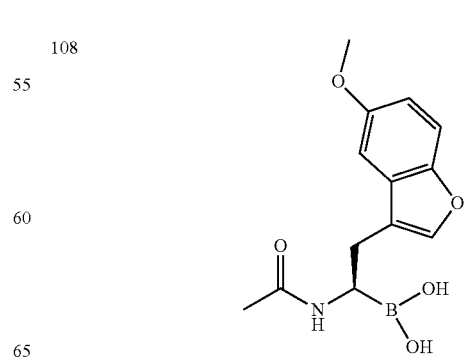 |

| Ex | Formula |
|---|---|
| 109 | 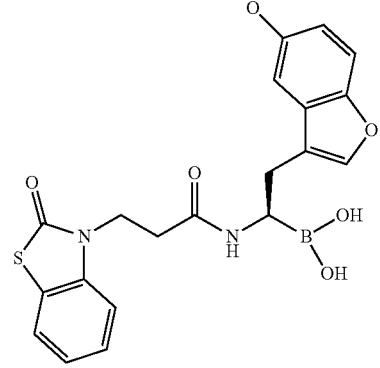 |
| 110 | 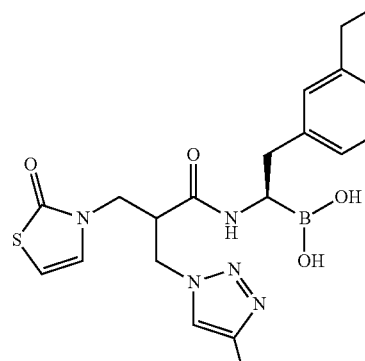 |

The following abbreviations refer to the abbreviations used below:

AcOH (acetic acid), BINAP (2,2'-bis(disphenylphosphino)-1,1'-binaphthalene), dba (dibenzylidene acetone), tBu (tert-Butyl), tBuOK (potassium tert-butoxide), CDI (1,1'-Carbonyldiimidazole), DBU (1,8-dizabicyclo[5.4.0]undec-7-ene), DCC (dicyclohexylcarbodiimide), DCM (dichloromethane), DIAD (diisobutylazodicarboxylate), DIC (diisopropilcarbodiimide), DIEA (di-isopropyl ethylamine), DMA (dimethyl acetamide), DMAP (4-dimethylaminopyridine), DMSO (dimethyl sulfoxide), DMF (N,N-dimethylformamide), EDC.HCl (1-ethyl-3-(3-dimethylaminopropyl) carbodiimide hydrochloride), EtOAc (ethyl acetate), EtOH (ethanol), g (gram), cHex (cyclohexane), HATU (dimethyl-amino-([1,2,3]triazolo[4,5-b]pyridin-3-yloxy)-methylene]-dimethyl-ammonium hexafluorophosphate), HOBt (N-hydroxybenzotriazole), HPLC (high performance liquid chromatography), hr (hour), MHz (Megahertz), MeOH (methanol), min (minute), mL (milliliter), mmol (millimole), mM (millimolar), mp (melting point), MS (mass spectrometry), MW (microwave), NMM (N-methyl morpholine), NMR (Nuclear Magnetic Resonance), NBS (N-bromo succinimide), PBS (phosphate buffered saline), PMB (para-methoxybenzyl), PyBOP (benzotriazol-1-yl-oxytripyrrolidinophosphonium hexafluorophosphate), RT (room temperature), TBAF (tetra-butylammonium fluoride), TBTU (N,N,N',N'-tetramethyl-O-(benzotriazol-1-Auronium tetrafluoroborate), T3P (propane phosphonic acid anhydride), TEA (triethyl amine), TFA (trifluoroacetic acid), THF (tetrahydrofuran), PetEther (petroleum ether), TBME (tert-butyl methyl ether), TLC (thin layer chromatography), TMS (trimethylsilyl), TMSI (trimethylsilyl iodide), UV (ultraviolet).

Generally, compounds of Formula (I), wherein $R^1$, n, $R^b$, $R^c$, L and Q are defined as above, can be obtained from a compound of Formula (II) as outlined in Scheme 1.

The first step consists in the reaction of a compound of Formula (II), wherein L is defined as above, with a compound of Formula (III), wherein $R^1$, n, $R^a$, $R^b$, $R^c$ and Q are defined as above. The reaction is performed using conditions and methods well known to those skilled in the art for the preparation of amides from a carboxylic acid with standard coupling agents, such as but not limited to HATU, TBTU, polymer-supported 1-alkyl-2-chloropyridinium salt (polymer-supported Mukaiyama's reagent), 1-methyl-2-chloropyridinium iodide (Mukaiyama's reagent), a carbodiimide (such as DCC, DIC, EDC) and HOBt, PyBOP® and other such reagents well known to those skilled in the art, preferably TBTU, in the presence or absence of bases such as TEA, DIEA, NMM, polymer-supported morpholine, preferably DIEA, in a suitable solvent such as DCM, THF or DMF, at a temperature between −10° C. to 50° C., preferably at 0° C., for a few hours, e.g. one hour to 24 h. Alternatively, the compounds of Formula (II) could be converted to carboxylic acid derivatives such as acyl halides or anhydrides, by methods well known to those skilled in the art, such as but not limited to treatment with $SOCl_2$, $POCl_3$, $PCl_5$, $(COCl)_2$, in the presence or absence of catalytic amounts of DMF, in the presence or absence of a suitable solvent such as toluene, DCM, THF, at a temperature rising from 20° C. to 100° C., preferably at 50° C., for a few hours, e.g. one hour to 24 h. Conversion of the carboxylic acid derivatives to compounds of Formula (I), can be achieved using conditions and methods well known to those skilled in the art for the preparation of amides from a carboxylic acid derivative (e.g. acyl chloride) with alkyl amines, in the presence of bases such as TEA, DIEA, NMM in a suitable solvent such as DCM, THF or DMF, at a temperature rising from 20° C. to 100° C., preferably at 50° C., for a few hours, e.g. one hour to 24 h.

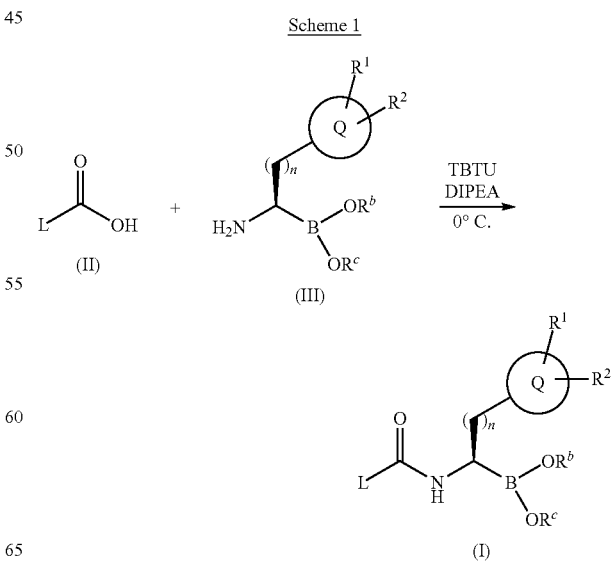

Scheme 1

Compounds of Formula (Ia), wherein $R^1$, n, L and Q are defined as above and wherein $R^b$ and $R^c$ are H, can be prepared starting from compounds of Formula (Ib), wherein $R^1$, n, L and Q are defined as above and wherein $R^b$ and $R^c$ are $C_1$-$C_6$-alkyl; whereby $R^b$ and $R^c$ may be linked to form a 5 or 6 membered-ring containing the oxygen atoms to which they are bond, using methods well known to those skilled in the art for the hydrolysis of boronic esters, such as but not limited to treatment with HCl, HBr, HI, TFA, in the presence or absence of an excess of a small molecular weight boronic acid, such as but not limited to i-BuB(OH)$_2$ (Scheme 2).

Scheme 2

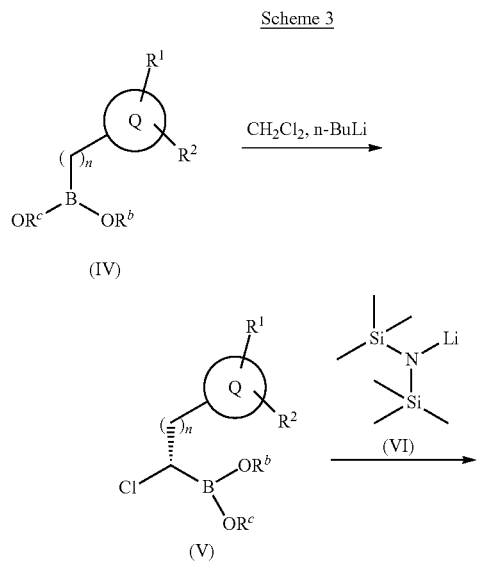

Compounds of Formula (III) can be prepared as outlined in Scheme 3.

Scheme 3

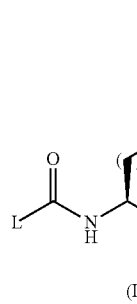

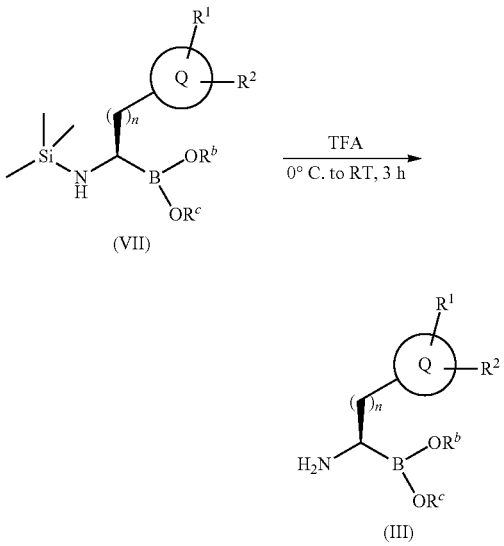

Conversion of compounds of Formula (IV), wherein $R^1$, n, $R^b$, $R^c$ and Q are defined as above, with the proviso that $R^b$, $R^c$ do not represent H, to give compounds of Formula (V), wherein $R^1$, n, $R^b$, $R^c$ and Q are defined as above, with the proviso that $R^b$, $R^c$ do not represent H, can be achieved by treatment with DCM, in the presence of strong bases such as nBuLi, tBuLi, MeLi, LDA, LiHMDS, preferably nBuLi, in a suitable solvent such as THF or dioxane, preferably THF, at a temperature rising from −100° C. to room temperature, for a few hours, e.g. one hour to 24 h. The reaction can give rise to enantiomerically enriched products when $R^b$ and $R^c$ are suitably selected. For example, when $R^b$ and $R^c$ together represent (1S,2S,3R,5S)-(+)-pinanediol, the product with (S) configuration is preferentially formed. (Matteson, D. S.; Sadhu, K. M. J. Am. Chem. Soc. 1981, 103, 5241-5242)

Conversion of compounds of Formula (V), wherein $R^1$, n, $R^b$, $R^c$, L and Q are defined as above, with the proviso that $R^b$, $R^c$ do not represent H, to give compounds of Formula (VII), wherein $R^1$, n, $R^b$, $R^c$ and Q are defined as above, with the proviso that $R^b$, $R^c$ do not represent H, can be achieved by reaction with a compound of Formula (VI), in a suitable solvent such as THF or dioxane, preferably THF, at a temperature rising from −100° C. to room temperature, for a few hours, e.g. one hour to 24 h. The reaction generally proceeds with inversion of configuration, thereby if the compound of Formula (V) had an (S) configuration, a compound of Formula (VII) with (R) configuration would be obtained. (Matteson, D. S.; Sadhu, K. M. J. Am. Chem. Soc. 1981, 103, 5241-5242)

Finally, conversion of the compounds of Formula (VII) into compounds of Formula (II) can be achieved by treatment with a suitable acid, such as HCl or TFA, preferably TFA, in the presence of a suitable solvent such as DCM, diethyl ether, diisopropyl ether, or THF, preferably diethylether, at a temperature between −30° C. to 30° C., preferably at −10° C., for a few hours, e.g. one hour to 48 h.

Alternatively, compounds of Formula (IIIa), wherein $R^1$, n, $R^b$, $R^c$ and Q are defined as above and $R^a$ represents H, can be prepared as outlined in Scheme 4.

Scheme 4

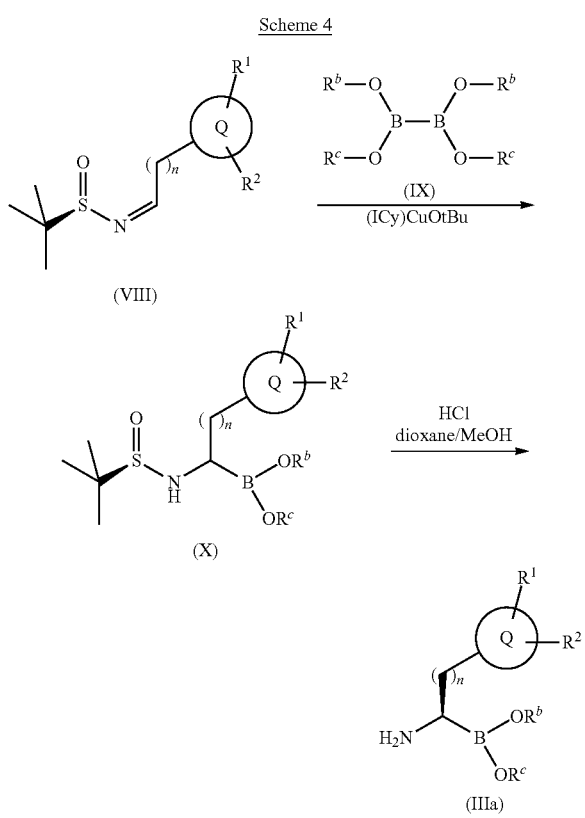

Compounds of Formula (VIII), wherein $R^1$ and Q are defined as above, can be converted into compounds of Formula (X), wherein $R^1$, n, $R^b$, $R^c$ and Q are defined as above, by reaction with a compound of Formula (IX), wherein $R^b$ and $R^c$ are defined as above, in the presence of a suitable catalyst, such as but not limited to (1,3-dicyclohexylimidazol-2-ylidene)copper(I) tert-butoxide ((ICy)CuOtBu), in a suitable solvent such as benzene, toluene, dioxane, THF, at at a temperature between room temperature and 80° C., for a few hours, e.g. one hour to 48 h.

Deprotection of the compounds of Formula (X) to give the compounds of Formula (IIIa) can be performed using an acid like HCl or TFA, preferably HCl, in the presence of a suitable solvent such as DCM, diethyl ether, diisopropyl ether, THF, dioxane or methanol, preferably a mixture of dioxane and methanol, at a temperature between −10° C. to 40° C., preferably at room temperature, for a few hours, e.g. one hour to 48 h.

If the above set of general synthetic methods is not applicable to obtain compounds according to Formula (I) and/or necessary intermediates for the synthesis of compounds of Formula (I), suitable methods of preparation known by a person skilled in the art should be used.

In general, the synthesis pathways for any individual compounds of formula (I) will depend on the specific substitutents of each molecule and upon the ready availability of Intermediates necessary; again such factors being appreciated by those of ordinary skill in the art. For all the protection and de-protection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compounds of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I), but contain corresponding protected amino and/or hydroxyl groups instead of one or more free amino and/or hydroxyl groups, preferably those which carry an amino-protecting group instead of an H atom bound to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxylprotecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr.

Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The term "solvates of the compounds" is taken to mean adductions of inert solvent molecules onto the compounds which form owing to their mutual attractive force. Solvates are, for example, mono- or dihydrates or alcoholates.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as DCM, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (RT).

The BOC, OBut and Mtr groups can, for example, preferably be cleaved off using TFA in DCM or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or DCM; alcohols, such as methanol, ethanol, isopropanol, n-propanol, n-butanol or tert-butanol; ethers, such as diethyl ether, diisopropyl ether, tetrahydrofurane (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Esters can be saponified, for example, using LiOH, NaOH or KOH in water, water/THF, water/THF/ethanol or water/dioxane, at temperatures between 0 and 100° C. Furthermore, ester can be hydrolysed, for example, using acetic acid, TFA or HCL.

Free amino groups can furthermore be acylated in a conventional manner using an acyl chloride or anhydride or alkylated using an unsubstituted or substituted alkyl halide or reacted with CH3-C(=NH)—OEt, advantageously in an inert solvent, such as DCM or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1 6 carbon atoms (preferably methylsulfonyloxy or trifluoromethylsulfonyloxy) or arylsulfonyloxy having 6 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N hydroxysuccinimide.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

Pharmaceutical Salts and Other Forms

The said compounds of the formula (I) can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide and sodium hydroxide; alkaline earth metal hydroxides, such as magnesium hydroxide and calcium hydroxide; and various organic bases, such as piperidine, diethanolamine and N-methylglucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. In the case of certain compounds of the formula I, which contain a basic center, acid-addition salts can be formed by treating these compounds with pharmaceutically acceptable organic and inorganic acids, for example hydrogen halides, such as hydrogen chloride or hydrogen bromide, other mineral acids and corresponding salts thereof, such as sulfate, nitrate or phosphate and the like, and alkyl- and monoaryl-sulfonates, such as methanesulfonate, ethanesulfonate, toluenesulfonate and benzene-sulfonate, and other organic acids and corresponding salts thereof, such as carbonate, acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, aspartate, benzoate, benzene-sulfonate (besylate), bisulfate, bisulfite, bromide, camphorate, camphor-sulfonate, caprate, caprylate, chloride, chlorobenzoate, citrate, cyclamate, cinnamate, digluconate, dihydrogen-phosphate, dinitrobenzoate, dodecyl-sulfate, ethanesulfonate, formate, glycolate, fumarate, galacterate (from mucic acid), galacturonate, glucoheptanoate, gluco-nate, glutamate, glycerophosphate, hemi-succinate, hemisulfate, heptanoate, hexanoate, hippurate, hydro-chloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, monohydrogen-phosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I include aluminium, ammonium, calcium, copper, iron (III), iron(II), lithium, magnesium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula I of the present invention which contain basic N2-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, mandelic acid, malic acid, lactic acid, suitable N-protected amino acids (for example N-benzoylproline or N-benzenesulfonyl-proline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula I, and related formulae in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41 g, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like.

Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for exam-ple, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compounds of formula (I). The present invention preferably relates to a method, wherein the sphingosine 1-phosphate-1 associated disorder is an autoimmune disorder or condition associated with an overactive immune response.

The present invention furthermore relates to a method of treating a subject suffering from an immunerogulatory abnomality, comprising administering to said subject a compounds of formula (I) in an amount that is effective for treating said immunoregulatory abnormality. The present invention preferably relates to a method wherein the immunoregulatory abnormality is an autoimmune or chronic inflammatory disease.

EXPERIMENTAL

The HPLC data provided in the examples described below were obtained as followed.

Condition A: Column Waters Xbridge™ $C_8$ 50 mm×4.6 mm at a flow of 2 mL/min; 8 min gradient from 0.1% TFA in $H_2O$ to 0.07% TFA in $CH_3CN$.

Condition B: Column: XTERRA RP18 (250×4.6 mm, 5 □m). at a flow of 1 mL/min; 20 min gradient from 95% (10 mM $K_2HPO_4$ in $H_2O$)/5% $CH_3CN$ to 100% $CH_3CN$. Column temperature 55° C.

Chiral HPLC: Column CHIRALPAK AD-H (250×4.6) mm, 5 μm at a flow of 1 mL/min; mobile phase: 0.1% TFA in hexane: isopropyl alcohol (80:20).

UV detection (maxplot) for all conditions.

The MS data provided in the examples described below were obtained as followed: Mass spectrum: LC/MS Waters ZMD (ESI) or a Waters Acquity SQD (ESI)

The NMR data provided in the examples described below were obtained as followed: $^1$H-NMR: Bruker DPX 400 MHz. All NMR of final compounds were obtained using $d_6$-DMSO, with the addition of a few drops of $D_2O$. Spectra were recorded 15-120 minutes after sample preparation.

The compounds of invention have been named according to the standards used in the program "ACD/Name Batch" from Advanced Chemistry Development Inc., ACD/Labs (7.00 Release). Product version: 7.10, build: 15 Sep. 2003

Intermediate 1: [(1R)-1-amino-2-(3-thienyl)ethyl] boronic acid acid (+)-pinanediol ester trifluroacetate

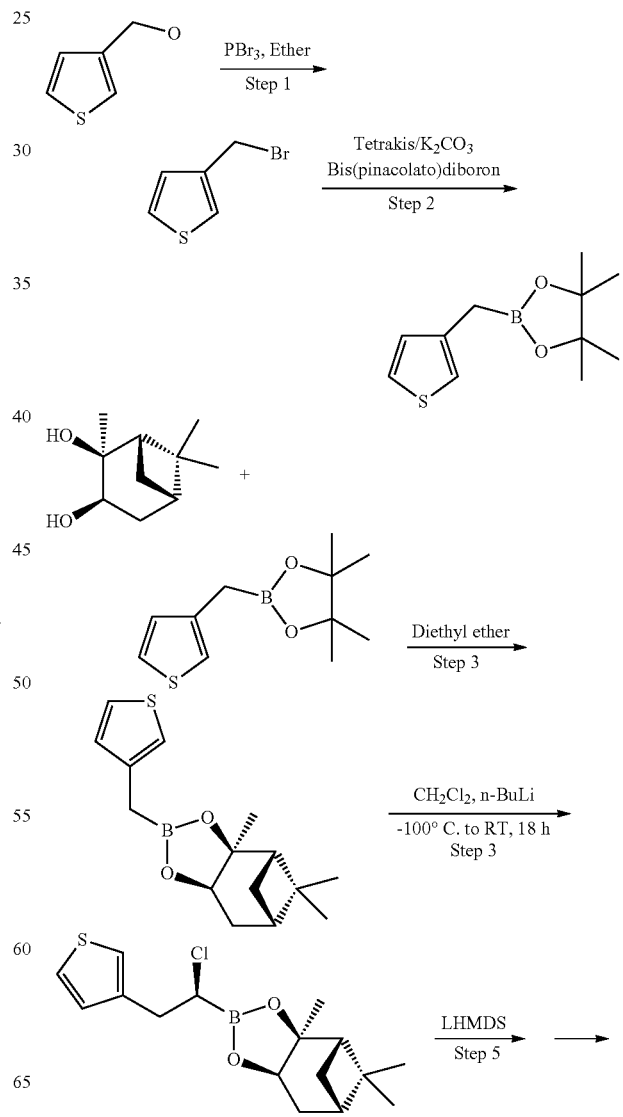

-continued

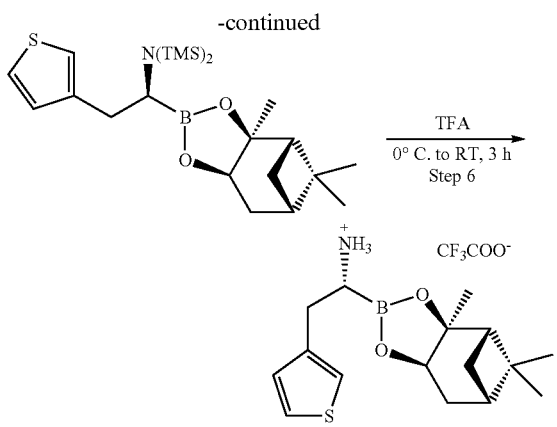

Step 1: 3-(bromomethyl)thiophene

A cooled (0° C.) solution of 3-thiophenemethanol (5.00 g, 43.7 mmol) in diethyl ether (40 mL) was treated with phosphorus tribromide (1.35 mL, 14.4 mmol) and the reaction mixture was stirred at 0° C. for 30 min. The reaction mixture was then poured into ice and extracted with diethyl ether. The organic layer was dried over sodium sulfate and concentrated to afford the title compound (5.23 g, 67%), which was used without further purification. $^1$H NMR (400 MHz, CDCl$_3$) δ 7.32-7.30 (m, 2H), 7.14 (d, J=4.6 Hz, 2H), 4.54 (s, 1H).

Step 2: 4,4,5,5-tetramethyl-2-(3-thienylmethyl)-1,3,2-dioxaborolane

A solution of 3-(bromomethyl)thiophene (5.23 g, 29.7 mmol) in degassed 1,4-dioxane (90 ml) was treated with bis(pinacolato)diboron (9.0 g, 36 mmol), potassium carbonate (12.3 g, 89.1 mmol) and tetrakis(triphenyl phosphine) palladium (1.72 g, 1.48 mmol) and the reaction mixture was heated at 100° C. for 12 h. The mixture was cooled to room temperature and filtered through a Celite bed. The filtrate was concentrated and the crude was purified by column chromatography on silica, eluting with 5-10% of ethyl acetate in petroleum ether to afford the title compound (3.55 g, 55%) as a yellow oil.
$^1$H NMR (400 MHz, CDCl$_3$) δ 7.22-7.20 (m, 1H), 6.96-6.93 (m, 2H), 2.28 (s, 2H), 1.24 (s, 12H).

Step 3: (3-thienylmethyl)boronic acid (+)-pinanediol ester

A solution of 4,4,5,5-tetramethyl-2-(3-thienylmethyl)-1,3,2-dioxaborolane (3.55 g, 15.8 mmol) in diethyl ether (40 ml) was treated with (1S,2S,3R,5S)-(+)-pinanediol (3.1 g, 18 mmol). The reaction mixture was stirred at room temperature for 2 days. The reaction mass was washed with water (2×15 ml), brine and dried over anhydrous sodium sulphate and concentrated to get a crude product which was purified by column chromatography on silica gel, eluting with 5% of ethyl acetate in petroleum ether, to afford the title compound (4.0 g, 90%)
$^1$H NMR (400 MHz, CDCl$_3$) δ 7.23 (dd, J=7.8, 3.2 Hz, 1H), 6.97-6.95 (m, 2H), 4.31 (dd, J=8.8, 2.0 Hz, 1H), 2.36-2.30 (m, 3H), 2.2-2.18 (m, 1H), 2.07 (t, J=5.2 Hz, 1H), 1.92-1.90 (m, 1H), 1.87-1.84 (m, 1H) 1.40 (s, 3H), 1.32 (s, 3H), 1.10 (d, J=10.9 Hz, 1H), 0.84 (s, 3H).

Step 4: [(1S)-1-chloro-2-(3-thienyl)ethyl]boronic acid acid (+)-pinanediol ester To a cooled (−100° C.) solution of dichloromethane (1.42 ml, 21.7 mmol) and tetrahydrofuran (10 ml) was added n-butyl lithium (2.5 M in THF; 3.18 ml; 7.96 mmol) over 10 min. After stirring for 20 min. a solution of (3-thienylmethyl)boronic acid (+)-pinanediol ester (2.00 g, 7.24 mmol) in THF (9 ml) was added over 10 min, keeping the temperature at −100° C. Then a solution of zinc chloride (0.5M in THF; 13 mL, 6.5 mmol) was added at −100° C. over 30 min. The mixture was allowed to reach room temperature and stirred for 18 h and concentrated. To the resulting oil was added diethyl ether and saturated ammonium chloride (50 ml each) and stirred vigorously. The aqueous layer was extracted with diethyl ether three times and the combined organic layers were dried over anhydrous sodium sulphate and concentrated in vacuo to afford the title compound (2.1 g, 89%), which was used as such for the next step without further purification.
$^1$H NMR (400 MHz, CDCl$_3$) δ 7.26 (dd, J=8.3 Hz, 1H), 7.11 (m, 1H), 7.03 (dd, J=6.1, 1.1 Hz, 1H), 4.36 (dd, J=10.7, 2 Hz, 1H), 3.75 (m, 1H), 3.21 (m, 1H), 2.34 (m, 1H), 2.19 (m, 1H), 2.07 (t, J=5.2, Hz, 2H), 1.91-1.84 (m, 2H), 1.35 (s, 3H), 1.28 (s, 3H), 1.05 (d, J=11 Hz, 1H), 0.84 (s, 3H).

Step 5: [(1R)-1-[bis(trimethylsilyl)amino]-2-(3-thienyl)ethyl]boronic acid

To a cooled (−78° C.) solution of [(1S)-1-chloro-2-(3-thienyl)ethyl]boronic acid acid (+)-pinanediol ester (2.30 g, 7.09 mmol) in 10 ml of anhydrous THF was added Lithium bis(trimethylsilyl) amide (1 M in THF, 10.6 ml, 10.6 mmol). The mixture was allowed to room temperature, stirred for 18 h and concentrated to dryness. To the resulting residue was added hexane, and then the precipitated solid was filtered off. The filtrate was concentrated to give the title compound (1.72 g, 53%), which was used as such for the next step without further purification.
$^1$H NMR (400 MHz, CDCl$_3$) δ 7.19-7.17 (m, 1H), 7.01-6.99 (m, 2H), 4.29-4.27 (m, 1H), 3.07-3.05 (m, 1H), 2.79 (m, 1H), 2.68 (m, 1H), 2.3 (m, 1H), 2.15 (m, 1H), 2.02 (t, J=5.2 Hz, 1H), 1.87-1.86 (m, 1H), 1.79 (m, 1H), 1.36 (s, 3H), 1.25 (s, 3H), 0.94 (m, 1H), 0.85 (s, 3H), 0.08 (s, 18H).

Step 6: [(1R)-1-amino-2-(3-thienyl)ethyl]boronic acid acid (+)-pinanediol ester trifluroacetate To a cooled (0° C.) solution [(1R)-1-[bis(trimethylsilyl) amino]-2-(3-thienyl)ethyl]boronic acid (1.72 g, 3.82 mmol) in diethyl ether (25 ml) was added trifluoroacetic acid (0.88 ml, 11.48 mmol) dropwise. Reaction was stirred for 3 h at room temperature. The reaction mixture was cooled with ice-methanol to −10° C. and the white solid formed was filtered, washed with ether and dried, to give the title compound.
$^1$H NMR (400 MHz, CDCl$_3$) δ 7.8 (bs, 3H), 7.33-7.27 (m, 1H), 7.23 (m, 1H), 7.01-6.99 (dd, J=5.0 hz, 1.2 Hz, 1H), 4.35-4.32 (m, 1H), 3.18-3.10 (m, 3H), 2.28-2.15 (m, 3H), 1.99 (m, 1H), 1.90 (m, 1H), 1.85 (t, J=5.2 Hz, 1H), 1.80 (m, 1H), 1.34 (s, 3H), 1.29 (s, 3H), 1.04-1.02 (m, 1H), 0.81 (s, 3H).

Intermediate 2: [(1R)-1-amino-2-(3-ethylphenyl)ethyl]boronic acid (+)-pinanediol ester trifluoroacetate

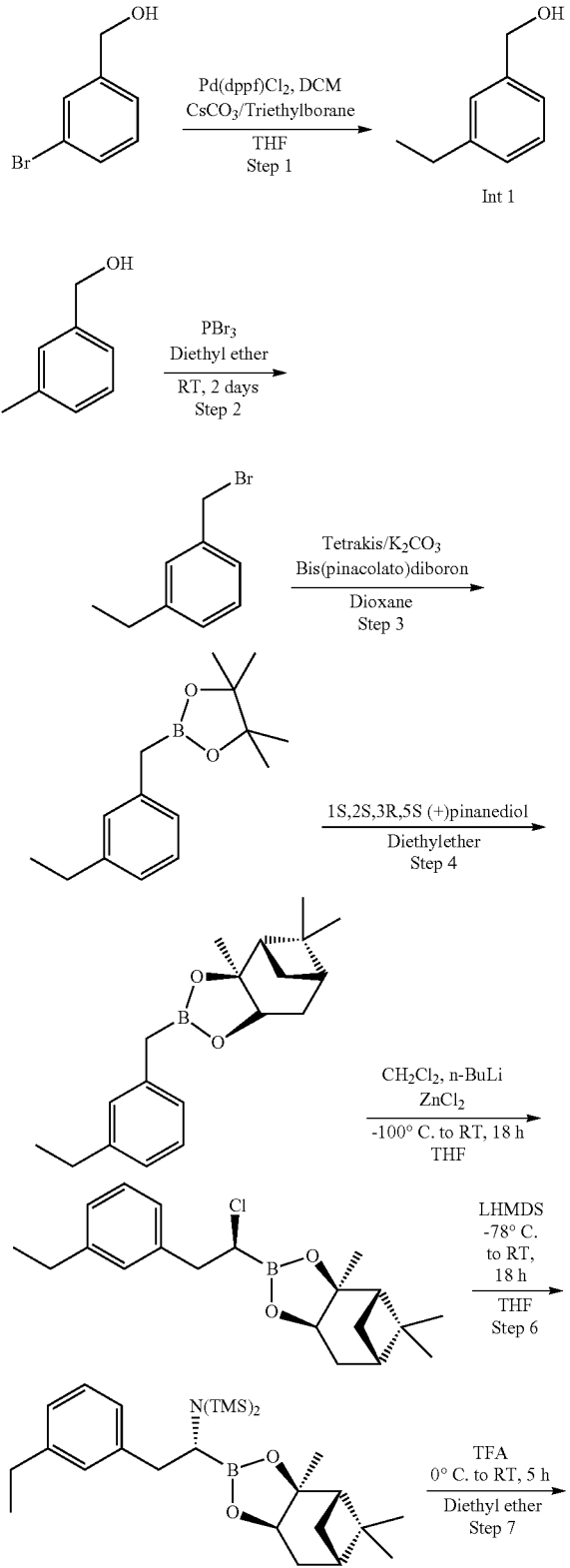

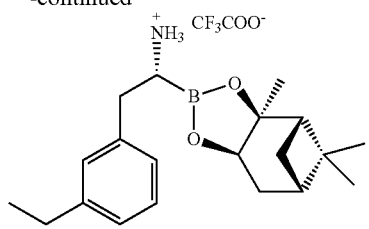

Step 1: (3-ethyl phenyl)methanol

A solution of 3-bromo benzyl alcohol (5.00 g, 26.7 mmol) in degassed tetrahydrofuran (50 ml) was placed in a pressure bottle and treated with cesium carbonate (26.0 g, 80.2 mmol), 1,1'-bis(diphenylphosphino)ferrocenedichloro palladium(1:1) complex with DCM (40 mg, 0.54 mmol). Triethylborane (1.0 M in THF, 80 mL, 80 mmol) was added and the reaction mixture was heated at 70° C. for 5 h. The contents of the pressure bottle were cooled to 0° C. and quenched by an aqueous (10%) NaOH solution and an aqueous (30%) $H_2O_2$ solution. The reaction mixture was stirred for 30 min. at room temperature, acidified with dilute aqueous HCl and extracted with diethyl ether. The organic layer was dried ($Na_2SO_4$) and concentrated. The crude was purified by flash chromatography on silica gel, eluting with 5-10% of ethyl acetate in petroleum ether to get the required product (3.5 g, 90%) as pale yellow liquid.

$^1$H NMR (400 MHz, $CDCl_3$) δ 7.31-7.27 (m, 1H), 7.22-7.14 (m, 3H), 4.68 (s, 2H) 2.70-2.64 (m, 2H), 1.27-1.24 (t, J=7.6, 3H).

Step 2: 1-(bromomethyl)-3-ethylbenzene

A cold (0° C.) solution of (3-ethylphenyl)methanol (3.50 g, 25.7 mmol) in diethyl ether (40 mL) was treated with phosphorus tribromide (0.8 mL, 8.5 mmol) and the reaction mixture was stirred at 0° C. for 30 min. The reaction mixture was then poured into ice and extracted with ether. The organic layer was dried over sodium sulfate and concentrated. The crude (3.1 g, 60%) was taken as such for next step without further purification.

$^1$H NMR (400 MHz, $CDCl_3$) δ 7.29-7.15 (m, 3H), 7.15-7.14 (m, 1H), 4.50 (s, 2H) 2.69-2.63 (m, 2H), 1.27-1.23 (t, J=7.6, 3H).

Step 3: 2-(3-ethylbenzyl)-4,4,5,5-tetramethyl-1,3,2-dioxaborolane

A solution of 1-(bromomethyl)-3-ethylbenzene (1.7 g, 8.59 mmol) in degassed 1, 4-dioxane (40 ml) was treated with bis(pinacolato)diboron (2.61 g, 10.3 mmol), potassium carbonate (3.56 g, 25.8 mmol), tetrakis(triphenylphosphine)palladium(0) (0.497 g, 0.429 mmol) and the mixture heated at 100° C. for 12 h The contents of the flask were cooled to room temperature and filtered through a celite bed. Filtrate was concentrated and the crude was purified by column chromatography on silica gel, eluting with 5-10% of ethylacetate in petroleum ether to get the title compound (1.4 g, 66%) as yellow oil.

$^1$H NMR (400 MHz, $CDCl_3$) δ 7.18-7.14 (m, 3H), 7.03-6.96 (m, 3H), 2.64-2.58 (m, 2H), 2.28 (s, 2H), 1.24-1.21 (m, 15H).

Step 4: (3-ethylbenzyl)boronic acid (+)-pinanediol ester

A solution of 2-(3-ethylbenzyl)-4,4,5,5-tetramethyl-1,3,2-dioxaborolane (1.4 g, 5.68 mmol) in diethyl ether (30 ml) was treated with (1S,2S,3R,5S)-(+)-pinanediol (1.45 g, 8.53 mmol). The reaction mixture was stirred at room temperature for 12 h then the mixture was washed with water twice, then with brine and dried over anhydrous sodium sulphate, then concentrated. The crude product was purified by column chromatography on silica gel, eluting with 5% of ethyl acetate in petroleum ether, to afford the title compound (1.43 g, 84%).

$^1$H NMR (400 MHz, CDCl$_3$) δ 7.19-7.15 (m, 1H), 7.04-7.01 (m, 2H), 6.98-6.96 (m, 1H), 4.29-4.27 (m, 1H), 2.64-2.58 (m, 2H), 2.34-2.28 (m, 3H), 2.20-2.19 (m, 1H), 2.07-2.04 (m, 1H), 1.89-1.81 (m, 2H), 1.29 (s, 3H), 1.25-1.21 (m, 3H), 1.1-1.08 (m, 1H), 0.84 (s, 3H).
GCMS: m/z: 298

Step 5: [(1S)-1-chloro-2-(3-ethylphenyl)ethyl]boronic acid (+)-pinanediol ester To a cooled (−100° C.) mixture of dichloromethane (0.89 ml, 13.7 mmol) and anhydrous tetrahydrofuran (6 ml) was added n-butyl lithium (2.5 M in hexanes, 2.0 ml, (3.7 mmol) over 10 min. After stirring for 20 min. at −100° C., a solution of (3-ethylbenzyl)boronic acid (+)-pinanediol ester (1.36 g, 4.56 mmol) in anhydrous THF (4 ml) was added over 10 min. Then a solution of zinc chloride (0.5 M in THF, 8.2 mL, 4.1 mmol) was added at −100° C. over 30 min. The mixture was allowed to reach room temperature and stirred for 18 h and concentrated. To the resulting oil was added diethyl ether and saturated ammonium chloride (25 ml each) and stirred vigorously. The aqueous layer was extracted with diethyl ether three times and the combined organic layers were dried over anhydrous sodium sulphate and concentrated in vacuo. The residue (1.5 g, 94%) was taken as such for the next step.
GCMS: m/z: 346

Step 6: [(1R)-1-[bis(trimethylsilyl)amino]-2-(3-ethylphenyl)ethyl]boronic acid (+)-pinanediol ester To a cooled (−78° C.) solution of [(1S)-1-chloro-2-(3-ethylphenyl)ethyl]boronic acid (+)-pinanediol ester (1.5 g, 4.32 mmol) in 15 ml of anhydrous tetrahydrofuran was added lithium bis(trimethylsilyl)amide (1 M in THF, 6.5 ml, 6.5 mmol). The mixture was allowed to room temperature, stirred for 18 h and concentrated to dryness. To the resulting residue was added hexane, and then the precipitated solid was filtered off. The filtrate was concentrated to give the required crude product (1.2 g, 58%) which was taken as such for the next step without further purification.

Step 7: [(1R)-1-amino-2-(3-ethylphenyl)ethyl]boronic acid (+)-pinanediol ester trifluroacetate A cooled (0° C.) solution of [(1R)-1-[bis(trimethylsilyl)amino]-2-(3-ethylphenyl)ethyl]boronic acid (+)-pinanediol ester (1.20 g, 2.54 mmol) in diethyl ether (20 ml) was treated with trifluoroacetic acid (0.87 ml, 7.6 mmol) dropwise. The reaction mixture was evaporated under reduced pressure at a temperature below 30° C. The crude was taken up in toluene and evaporated, and this sequence was repeated four times. The white solid obtained (1.0 g, 89%) was used without further purification for the next step.

$^1$H NMR (400 MHz, DMSO-d6): δ 7.22-7.26 (m, 1H), 7.09-7.11 (m, 3H), 4.31-4.33 (m, 1H), 3.00-3.19 (m, 3H), 2.59-2.65 (m, 2H), 2.18-2.23 (m, 2H), 1.90-1.98 (m, 1H), 1.80-1.89 (m, 1H), 1.33 (s, 3H), 1.20-1.26 (m, 6H), 1.06 (m, 1H), 0.80 (s, 3H)

Intermediate 3: [(1R)-1-amino-2-(3-trifluoromethyphenyl)ethyl]boronic acid (+)-pinanediol ester trifluroacetate

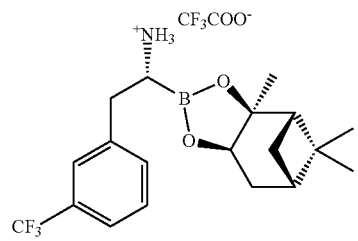

Step 1: 2-(3-trifluoromethylbenzyl)-4,4,5,5-tetramethyl-1,3,2-dioxaborolane

A solution of 3-(trifluoromethyl)benzyl bromide (5.00 g, 20.9 mmol) in degassed 1,4-dioxane (100 ml) was treated with bis(pinacolato)diboron (6.4 g, 25 mmol), potassium carbonate (20.9 g, 62.7 mmol), tetrakis(triphenylphosphine)palladium(0) (1.2 g, 1.0 mmol) and the mixture heated at 100° C. for 12 h The contents of the flask were cooled to room temperature and filtered through a celite bed. Filtrate was concentrated and the crude was purified by column chromatography on silica gel, eluting with 2% of ethylacetate in petroleum ether to get the title compound (5.1 g, 85%) as a colorless liquid.

$^1$H NMR (400 MHz, CDCl$_3$): δ 7.45 (s, 1H), 7.33-7.40 (m, 3H), 2.36 (s, 2H), 1.25 (s, 12H).
GCMS: m/z=286

Step 2: (3-trifluoromethylbenzyl)boronic acid (+)-pinanediol ester

A solution of 2-(3-trifluoromethylbenzyl)-4,4,5,5-tetramethyl-1,3,2-dioxaborolane (5.10 g, 17.8 mmol) in diethyl ether (50 ml) was treated with (1S,2S,3R,5S)-(+)-pinanediol (4.55 g, 26.7 mmol). The reaction mixture was stirred at room temperature for 12 h, then the mixture was washed with water twice, then with brine and dried over sodium sulphate, then concentrated. The crude product was purified by column chromatography on silica gel, eluting with 2% of ethyl acetate in petroleum ether to afford the title compound (6.0 g, 99%) as a colourless liquid.

$^1$H NMR (400 MHz, CDCl$_3$): δ 7.40 (s, 1H), 7.35-7.38 (m, 3H), 4.29 (dd, J=2.0, 8.8 Hz, 1H), 2.40 (s, 2H), 2.31-2.36 (m, 1H), 2.17-2.21 (m, 1H), 2.05 (t, J=5.8 Hz, 1H), 1.90-1.92 (m, 1H), 1.80-1.85 (m, 1H), 1.39 (s, 3H), 1.29 (s, 3H), 1.02-1.05 (m, 1H), 0.84 (s, 3H). GCMS: m/z=338

Step 3: (1S)-1-chloro-2-(3-trifluoromethylbenzyl)-ethylboronic acid (+)-pinanediol ester To a cooled (−100° C.) mixture of dichloromethane (1.70 mL, 26.6 mmol) and anhydrous tetrahydrofuran (17 ml) was added n-butyl lithium (1.6 M, 6.1 mL, 9.75 mmol) over 15 min. After stirring for 20 min. at −100° C., a solution of (3-trifluoromethylbenzyl)boronic acid (+)-pinanediol ester (3.0 g, 8.87 mmol) in anhydrous THF (12 ml) was added over 15 min. Then a solution of zinc chloride (0.5 M in THF, 16.0 mL, 8.0 mmol) was added at −100° C. over 30 min. The mixture was allowed to reach room temperature and stirred for 18 h and concentrated. To the resulting oil was added diethyl ether and saturated ammonium chloride (25 ml each) and stirred vigorously. The aqueous layer was extracted with diethyl ether three times and the combined organic layers were dried over anhydrous sodium sulphate and concentrated in vacuo. The yellow liquid (3.4 g, 99%) was taken as such for the next step.

$^1$H NMR (400 MHz, CDCl$_3$): δ 7.27-7.54 (m, 4H), 4.36 (dd, J=1.6, 8.9 Hz, 1H), 3.63-3.69 (m, 1H), 3.24-3.26 (m, 1H), 3.17-3.19 (m, 1H), 2.32-2.40 (m, 1H), 2.17-2.19 (m, 1H), 2.05-2.08 (m, 1H), 1.84-1.91 (m, 2H), 1.36 (s, 3H), 1.28 (s, 3H), 0.99-1.02 (m, 1H), 0.84 (s, 3H).

GCMS: m/z=386

Step 4: [(1R)-1-[bis(trimethylsilyl)amino]-2-(3-trifluoromethylphenyl)ethyl]boronic acid (+)-pinanediol ester To a cooled (−78° C.) solution of [(1S)-1-chloro-2-(3-trifluoromethylphenyl)ethyl]boronic acid (+)-pinanediol ester (3.4 g, 8.8 mmol) in 25 ml of anhydrous tetrahydrofuran was added lithium bis(trimethylsilyl)amide (1M in THF, 15 ml, 15 mmol). The mixture was allowed to room temperature, stirred for 18 h and concentrated to dryness. To the resulting residue was added hexane, and then the precipitated solid was filtered off. The filtrate was concentrated to give the title compound as a crude product which was taken as such for the next step without further purification.

$^1$H NMR (400 MHz, CDCl$_3$): δ 7.27-7.53 (m, 4H), 4.22-4.25 (m, 1H), 3.06-3.07 (m, 1H), 2.91-2.93 (m, 1H), 2.22-2.32 (m, 3H), 2.02-2.03 (m, 1H), 1.87-1.88 (m, 2H), 1.37 (s, 3H), 1.27 (s, 3H), 0.94-0.96 (m, 1H), 0.83 (s, 3H), 0.17 (s, 12H), 0.06 (s, 6H)

Step 5: [(1R)-1-amino-2-(3-trifluoromethyphenyl)ethyl]boronic acid (+)-pinanediol ester trifluroacetate A cooled (0° C.) solution of [(1R)-1-[bis(trimethylsilyl)amino]-2-(3-trifluoromethylphenyl)ethyl]boronic acid (+)-pinanediol ester (1.5 g, 2.93 mmol) in diethyl ether (15 ml) and at 0° C. was treated with trifluoroacetic acid (0.67 ml, 8.8 mmol) dropwise. Reaction was stirred for 3 h at room temperature. The reaction mixture was evaporated under reduced pressure at a temperature below 30° C. The crude was taken up in toluene and evaporated, and this sequence was repeated four times. The crude product obtained (1.7 g) was used without further purification for the next step.

$^1$H NMR (400 MHz, CDCl$_3$): δ 7.27-7.54 (m, 4H), 4.33-4.35 (m, 1H), 3.10-3.39 (m, 2H), 2.15-2.35 (m, 2H), 2.01-2.08 (m, 2H), 1.89-1.95 (m, 2H), 1.37 (s, 3H), 1.27 (s, 3H), 0.94-0.97 (m, 1H), 0.83 (s, 3H)

Intermediate 4: 4-Biphenyl-3-yl-4-oxo-butyric acid

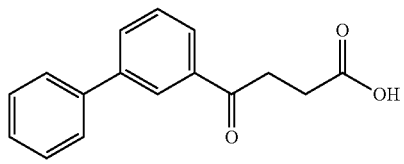 [SMILES: O=C(O)CCC(=O)c1cccc(-c2ccccc2)c1]

Step 1: 4-biphenyl-3-yl-4-oxo-butyric acid ethyl ester

A mixture of 4-(3-bromo-phenyl)-4-oxo-butyric acid ethyl ester (500 mg, 1.75 mmol), phenylboronic acid (340 mg, 2.62 mmol) and cesium fluoride (1.06 g, 7 mmol) in dioxane: water (2:1, 20 mL) was degassed with nitrogen for 15 min, then treated with bis(triphenylphosphine)dichloropalladium (II) (11 mg, 0.175 mmol) and the reaction mixture was irradiated in a microwave reactor at 90° C. for 1 h. The reaction mixture was then diluted with ethyl acetate, filtered through celite, and the solvents evaporated under reduced pressure. The crude was purified by flash chromatography on silica gel using ethyl acetate and petroleum ether as eluent, to give the Title compound (0.40 g, 83%).

MS (ESI+): 283.0, HPLC (Method A): Rt. 5.2 min, HPLC purity 95.3%

Step 2: 4-Biphenyl-3-yl-4-oxo-butyric acid

A solution of 4-biphenyl-3-yl-4-oxo-butyric acid ethyl ester (400 mg, 1.41 mmol) in tetrahydrofuran: water (4:1, 10 mL) was treated with LiOH.H$_2$O (170 mg, 4.23 mmol) and the reaction mixture was stirred at RT overnight. The reaction mixture was concentrated under reduced pressure, the residue was diluted with water and extracted with ethyl acetate thrice. The aqueous layer was acidified with an aqueous solution of HCl (1.5N) and extracted with dichloromethane. The organic layer was dried over Na$_2$SO$_4$ and concentrated to afford the title compound (0.3 g, 83%).

$^1$H NMR (400 MHz, DMSO-d6): δ 8.20 (s, 1H), 7.92-7.98 (m, 2H), 7.72-7.74 (m, 2H), 7.60-7.64 (m, 1H), 7.50-7.51 (m, 2H), 7.40-7.41 (m, 1H), 3.32-3.35 (m, 2H), 2.59-2.61 (m, 2H).

MS (ESI+): 255.0, HPLC Rt. 4.0 min, HPLC purity 99.7%.

Intermediate 5: 6-Phenyl-pyridine-2-carbaldehyde

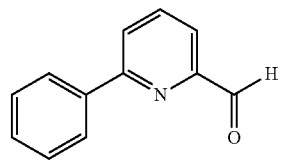 [SMILES: O=Cc1cccc(-c2ccccc2)n1]

A mixture of 6-bromo pyridine-2-carboxaldehyde (500 mg, 2.68 mmol), phenylboronic acid (870 mg, 6.7 mmol) and cesium fluoride (610 mg, 4.0 mmol) were taken in dioxane: water (2:1) 7.5 mL and degassed with nitrogen for 15 min. Then was added Bis(triphenylphosphine)dichloropalladium (II) (94 mg, 0.13 mmol) and the reaction mixture was irradiated in a microwave reactor at 90° C. for 2 h. The reaction mixture was then diluted with ethyl acetate, filtered through celite, and evaporated. The crude was purified by flash chromatography on silica gel using ethyl acetate and petroleum ether as eluent.

MS (ESI+): 184.0, HPLC (Method A) Rt. 3.3 min, HPLC purity 95.1%

Intermediate 6: 4-Oxo-4-(6-phenyl-pyridin-2-yl)-butyric acid

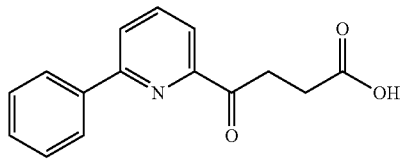 [SMILES: O=C(O)CCC(=O)c1cccc(-c2ccccc2)n1]

Step 1: 4-Oxo-4-(6-phenyl-pyridin-2-yl)-butyric acid methyl ester

A solution of 6-phenyl-pyridine-2-carbaldehyde (Intermediate 5; 800 mg, 4.37 mmol) in methanol was treated with methyl acrylate (0.54 mL, 5.2 mmol), 3-ethyl-5-(2-hydroxyethyl)-4-methyl-1,3-thiazonium bromide (220 mg, 0.87 mmol) and triethylamine (1.8 mL, 13 mmol). The reaction mixture was then refluxed at 70° C. for 1 h. The reaction mixture was cooled to RT, quenched with a saturated NH$_4$Cl solution in water and extracted with ethyl acetate. The organic layer was separated, washed with NaHCO$_3$, brine, dried over Na$_2$SO$_4$ and concentrated. The crude was purified by column chromatography on silica gel using ethyl acetate and petroleum ether as eluent (0.80 g; 68%).
MS (ESI+): 270.0

Step 2: 4-Oxo-4-(6-phenyl-pyridin-2-yl)-butyric acid

A solution of 4-oxo-4-(6-phenyl-pyridin-2-yl)-butyric acid methyl ester (600 mg, 2.2 mmol) in tetrahydrofuran:water (4:1, 10 mL) was treated with LiOH.H$_2$O (280 mg, 6.68 mmol) and the reaction mixture was stirred at RT for overnight. The solvent was removed and the residue was diluted with water and washed with dichloromethane. The aqueous layer was then neutralized with an aqueous solution of HCl (1.5 N) and extracted with dichloromethane. The organic layer was dried over Na$_2$SO$_4$ and concentrated. The solid obtained was further purified by preparative HPLC.
$^1$H NMR (400 MHz, DMSO-d6): δ 8.20-8.26 (m, 3H), 8.00-8.10 (m, 1H), 7.88-7.90 (m, 1H), 7.47-7.57 (m, 3H), 3.50-3.53 (m, 2H), 2.62-2.65 (m, 2H). HPLC (Method A) Rt. 3.9 min,
HPLC purity 99.5%

Intermediate 7: 3-(N-Hydroxycarbamimidoyl)-propionic acid methyl ester

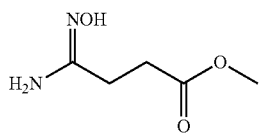

A mixture of 3-cyanopropionic acid methylester (2.00 g, 17.7 mmol), hydroxylamine hydrochloride (1.80 g, 26.5 mmol) and triethylamine (5 mL, 35 mmol) in ethanol was refluxed at 85° C. for 2 h. The reaction mixture was evaporated and azeotroped with toluene thrice and directly taken to next step without further purification (2.5 g, 96%).

Intermediate 8: 3-(5-Phenyl-[1,2,4]oxadiazol-3-yl)-propionic acid

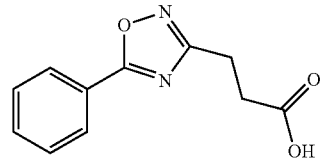 [SMILES: O=C(O)CCc1noc(-c2ccccc2)n1]

Step 1: 3-(5-Phenyl-[1,2,4]oxadiazol-3-yl)-propionic acid methyl ester

Benzoic acid (2.00 g, 16.4 mmol) and 1.1'-carbonyldiimidazole (3.8 g, 18 mmol) were stirred in dimethylformamide (25 mL) at RT for 2 h. Then 3-(N-Hydroxycarbamimidoyl)-propionic acid methyl ester (Intermediate 7; 2.5 g, 18 mmol) was added and the reaction mixture was stirred at RT overnight. The reaction mixture was then heated at 100° C. for 2 h. The reaction mixture was diluted with ethyl acetate and washed with brine. The organic layer was dried over Na$_2$SO$_4$ and concentrated. The crude was purified by column chromatography on silica gel using dichloromethane and methanol as eluent.
$^1$H NMR (400 MHz, DMSO-d6): δ 8.06-8.09 (m, 2H), 7.67-7.72 (m, 1H), 7.60-7.64 (m, 2H), 3.61 (s, 3H), 3.03-3.06 (m, 2H), 2.80-2.84 (m, 2H). MS (ESI+): 233.0, HPLC (Method A) Rt 3.9 min, HPLC purity 95.5%

Step 2: 3-(5-Phenyl-[1,2,4]oxadiazol-3-yl)-propionic acid

A solution of 3-(5-phenyl-[1,2,4]oxadiazol-3-yl)-propionic acid methyl ester (800 mg, 3.44 mmol) in tetrahydrofuran:water (4:1) was treated with LiOH.H$_2$O (400 mg, 10.3 mmol) and the reaction mixture was stirred at RT overnight. The solvent was removed under reduced pressure and the residue was diluted with water, washed with dichloromethane. The aqueous layer was then neutralized with an aqueous solution of HCl (1.5 N) and extracted with dichloromethane. The organic layer was dried over Na$_2$SO$_4$ and concentrated. The product was used without further purification in the next steps
$^1$H NMR (400 MHz, DMSO-d6): δ 8.07-8.10 (m, 2H), 7.60-7.72 (m, 3H), 2.98-3.01 (m, 2H), 2.71-2.74 (m, 2H). MS (ESI+): 219.0, HPLC (Method A) Rt 3.1 min, HPLC purity 99.6%

Intermediate 9: 3-azido-propionic acid

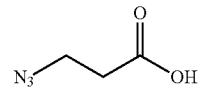

A solution of beta-alanine (15.0 g, 168 mmol) in anhydrous methanol was treated with potassium carbonate (46.3 g, 336 mmol), CuSO$_4$.5H$_2$O (0.83 g, 3.36 mmol) and imidazolium sulfonyl azide (35.0 g, 202 mmol) and the reaction mixture was stirred at RT for 16 hours. The reaction mixture was evaporated under reduced pressure at a temperature below 30° C. The residue was diluted with water; the pH was adjusted to 6 and extracted with ethyl acetate. The pH of the aqueous phase was finally adjusted to 3 and the aqueous layer extracted with ethyl acetate; the organic layer was separated, dried over Na$_2$SO$_4$ and concentrated to give crude 3-azido-propionic acid.

Intermediate 10:
3-(4-Phenyl-[1,2,3]triazol-1-yl)-propionic acid

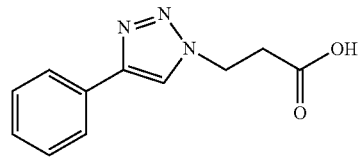 [SMILES: O=C(O)CCn1cc(-c2ccccc2)nn1]

A solution of phenyl acetylene (1.61 g, 15.8 mmol) and 3-azido-propionic acid (2.0 g, 17.4 mmol) in t-BuOH: H$_2$O (2:1, 45 mL) was treated with sodium ascorbate (469 mg, 2.37 mmol) and CuSO$_4$.5H$_2$O (196 mg, 0.79 mmol) and the reaction mixture was stirred at RT for 12 h. Ethyl acetate was added to the reaction mixture and extracted with water. Then the organic layer was washed with water followed by brine. The combined organic layers were concentrated, dried under vacuum to give the title compound as a white solid (1.6 g, 46%).
$^1$H NMR (400 MHz, DMSO-d$_6$): δ 12.58 (s, 1H), 8.55 (s, 1H), 7.82 (d, J=7.4 Hz, 2H), 7.44 (t, J=7.4 Hz, 2H), 7.32 (t, J=7.4 Hz, 1H), 4.60 (s, 2H), 3.01 (s, 2H). MS (ESI+): 218.0.
HPLC (Method A) RT 2.7 min, HPLC purity 99.7%.

Intermediate 11:
3-(1-Phenyl-1H-[1,2,3]triazol-4-yl)-propionic acid

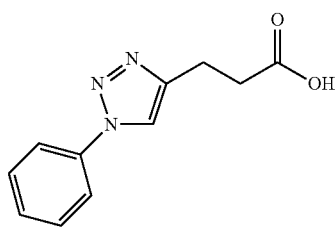 [SMILES: O=C(O)CCc1cn(-c2ccccc2)nn1]

This intermediate was prepared according to the protocol described for Intermediate 10.
$^1$H NMR (400 MHz, DMSO-d$_6$): δ 12.25 (s, 1H), 8.57 (s, 1H), 7.87-7.85 (m, 2H), 7.60-7.56 (m, 2H), 7.46 (t, J=7.4 Hz, 1H), 2.93 (t, J=7.4 Hz, 2H), 2.66 (t, J=7.4 Hz, 2H). MS (ESI+): 218.2. HPLC (Method A) RT 2.7 min, HPLC purity 99.8%.

Intermediate 11: (1-oxoisoquinolin-2(1H)-yl)acetic acid

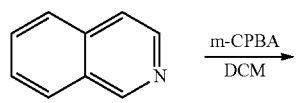

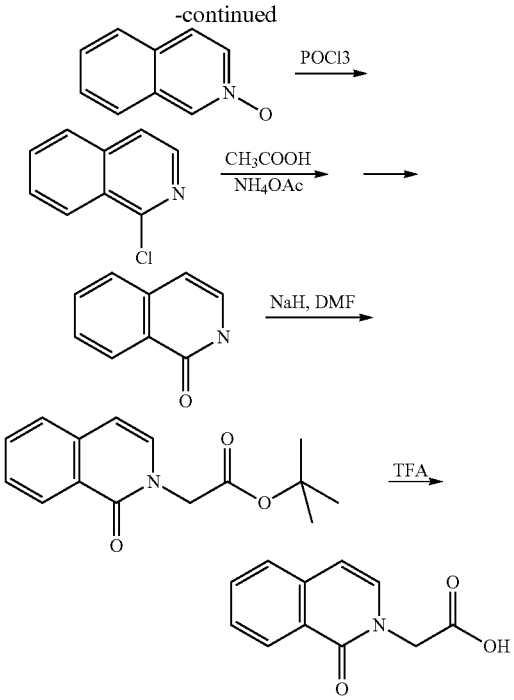

Step 1: isoquinolin-N-oxide

A solution of isoquinoline (20.0 g, 155 mmol) in dichloromethane (400 mL) was treated with m-chloroperbenzoic acid (40.0 g, 232 mmol) and the reaction mixture was stirred at room temperature overnight. The reaction mixture was filtered and the filtrate was evaporated and taken to next step without further purification (20.0 g, 89%).
MS (ESI+): M=146.3

Step 2: 1-chloroisoquinoline

Phosphorus oxychloride (200 mL) was added dropwise under ice-cold condition to isoquinolin-N-oxide (20.0 g). The reaction mixture was then heated to reflux at 105° C. overnight. Phosphorus oxychloride was evaporated under reduced pressure, then the residue was quenched with ice and extracted with dichloromethane. The organic layer was separated, dried over sodium sulfate and concentrated. The crude was purified by column chromatography on silica gel using ethylacetate and petroleum ether as eluent (21.0 g; 85%).
$^1$H NMR (400 MHz, DMSO-d6): δ 8.25-8.31 (m, 2H), 8.08 (d, J=8.0 Hz, 1H), 7.88-7.91 (m, 2H), 7.80-7.84 (m, 1H). MS (ESI+): 164.0, HPLC (Method A) Rt 8.29 min; HPLC purity 96.0%

Step 3: isoquinolin-1(2H)-one

A solution of 1-chloroisoquinoline (8.1 g) in glacial acetic acid (170 mL) was treated with ammonium acetate (25 g). The reaction mixture was then heated at 100° C. for 3 h. The reaction mixture was cooled to room temperature and the solvent was evaporated under reduced pressure. The residue was quenched with ice and the solid formed was filtered and dried on the filter (5.8 g, 80%).
$^1$H NMR (400 MHz, DMSO-d6): δ 11.24 (s, 1H), 8.18 (d, J=8.4 Hz, 1H), 7.63-7.71 (m, 2H), 7.45-7.49 (m, 1H), 7.15-7.18 (m, 1H), 6.55 (d, J=7.2 Hz, 1H). MS (ESI+): 146.0, HPLC (Method A) Rt 2.23 min; HPLC purity 98.2° A)

Step 4: tert-butyl (1-oxoisoquinolin-2(1H)-yl)acetate

A cold (0° C.) solution of isoquinolin-1(2H)-one 3 (1.0 g, 6.9 mmol) and tertiary butyl acetate (2.0 mL, 13.8 mmol) in dimethyl formamide (15 mL) was treated with sodium hydride (60% in mineral oil, 660 mg, 17.2 mmol). After 10 minutes the reaction mixture was quenched with ice and the solid formed was filtered and dried (1.2 g; 60%).

¹H NMR 400 MHz, CDCl3: δ 8.42-8.44 (m, 1H), 7.63-7.67 (m, 1H), 7.47-7.53 (m, 2H), 7.01 (d, J=8.0 Hz, 1H), 6.53 (d, J=8.0 Hz, 1H), 4.64 (s, 2H), 1.49 (s, 9H). MS (ESI+): 204.3, HPLC (Method A) Rt 4.08 min; HPLC purity 98.4° A)

Step 5: (1-oxoisoquinolin-2(1H)-yl)acetic acid

A cold solution of tert-butyl (1-oxoisoquinolin-2(1H)-yl) acetate (1.2 g, 4.6 mmol) in dichloromethane (20 mL) was treated with trifluoroacetic acid (10 mL) dropwise. The reaction mixture was then stirred at room temperature for 3 h. The solvent was evaporated and the residue was azeotroped with toluene. The solid formed was triturated with ether to afford the title compound.

¹H NMR (400 MHz, DMSO-d6): δ 10.76 (s, 1H), 8.18-8.20 (m, 1H), 7.64-7.73 (m, 2H), 7.42-7.52 (m, 2H), 6.62 (d, J=8.0 Hz, 1H), 4.67 (s, 2H). MS (ESI+): 204.3, HPLC (Method A) Rt 2.34 min; HPLC purity 99.3%

Intermediates 12 and 13: (+)-2-(3-chlorophenyl)-4-oxo-4-phenylbutanoic acid and (−)-2-(3-chlorophenyl)-4-oxo-4-phenylbutanoic acid

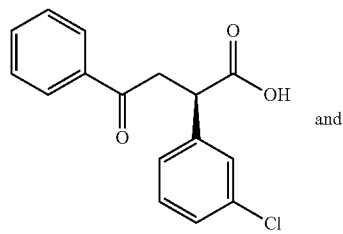
and

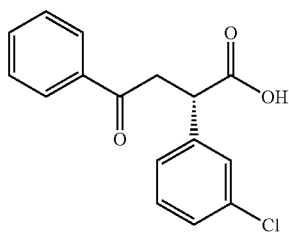

Racemic 2-(3-chlorophenyl)-4-oxo-4-phenylbutanoic acid was separated by chiral preparative HPLC on a CHIRALPAK IA (250×20) mm, 5 μm, Mobile Phase hexane: isopropyl alcohol (65:35), flow: 10 ml/min.

The two products elute at 13.7 min (Intermediate 12) and at 18.6 min (Intermediate 13).

The two products were analyzed using the following HPLC method:

Column: CHIRALPAK AD-H (250×4.6) mm, 5 μm

Mobile Phase: 0.1% TFA in hexane: isopropyl alcohol (80:20)

Flow: 1.0 ml/min

Intermediate 12: Rt-10.8 min (Purity 100%); αD +101.9°; ethanol, c=1.0 g/100 mL

Intermediate 13: Rt-14.9 min (Purity 99.2%)

Absolute assignment of the chiral centre as either (R) or (S) is arbitrary.

Intermediates 14 and 15: (+)-2-(4-chlorophenyl)-4-oxo-4-phenylbutanoic acid and (−)-2-(4-chlorophenyl)-4-oxo-4-phenylbutanoic acid

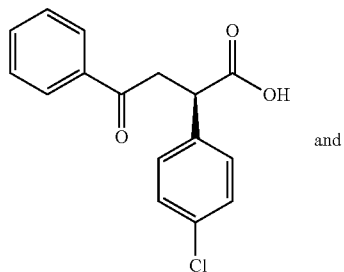
and

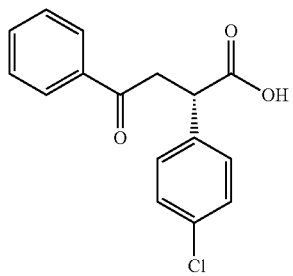

Racemic 2-(4-chlorophenyl)-4-oxo-4-phenylbutanoic acid was separated by chiral preparative HPLC on a CHIRALPAK IA (250×20) mm, 5 μm, Mobile Phase hexane: isopropyl alcohol (60:40), flow: 10 ml/min.

The two products elute at 14.2 min (Intermediate 14) and at 21.4 min (Intermediate 15).

The two products were analyzed using the following HPLC method: Column: CHIRALPAK AD-H (250×4.6) mm, 5 μm Mobile Phase: 0.1% TFA in hexane: isopropyl alcohol (80:20)

Flow: 1.0 ml/min

Intermediate 14: Rt-15.4 min (Purity 99.3%). αD +103.4°; ethanol, c=0.57 g/100 mL Intermediate 15: Rt-22.2 min (Purity 99.3%). αD −111.5°; ethanol, c=0.57 g/100 mL Absolute assignment of the chiral centre as either (R) or (S) is arbitrary.

Intermediates 16 and 17: (+)-2-benzyl-4-(4-methoxyphenyl)-4-oxo-butyric acid and (−)-2-benzyl-4-(4-methoxyphenyl)-4-oxo-butyric acid

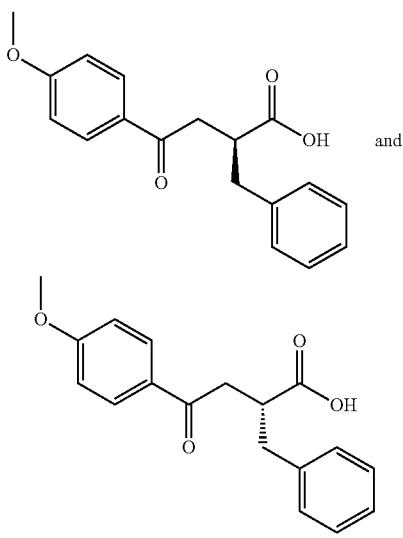

Racemic 2-benzyl-4-(4-methoxyphenyl)-4-oxo-butyric acid was separated by chiral preparative HPLC on a CHIRALCEL OJ-H (250×20) mm, 5 μm, Mobile Phase hexane: isopropyl alcohol (75:25), flow: 10 ml/min.

The two products elute at 15.5 min (Intermediate 16) and at 20.2 min (Intermediate 17).

The two products were analyzed using the following HPLC method:

Column: CHIRALCEL OJ (250×4.6) mm, 5 μm

Mobile Phase: 0.1% TFA in hexane: isopropyl alcohol (90:10)

Flow: 1.0 ml/min

Intermediate 16: Rt-22.3 min (Purity 98.7%). αD +21.1°; ethanol, c=1.0 g/100 mL

Intermediate 17: Rt-33.6 min (Purity 97.7%). αD −21.0°; ethanol, c=1.0 g/100 mL

Absolute assignment of the chiral centre as either (R) or (S) is arbitrary.

Intermediate 18: (1R)-2-(benzofuran-3-yl)-1-(3a,5,5-trimethylhexahydro-4,6-methanobenzo[d][1,3,2]dioxaborol-2-yl)ethanaminetrifluoroacetate

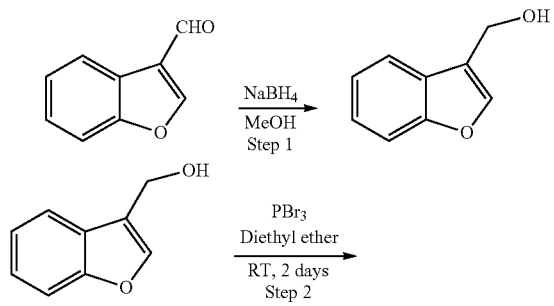

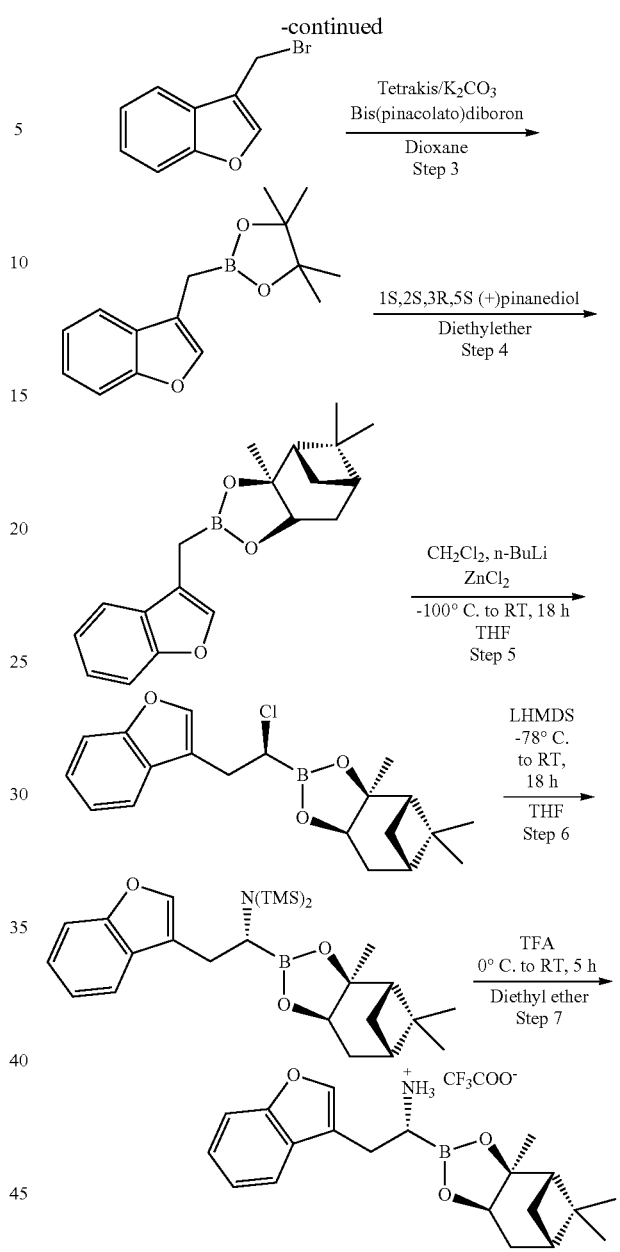

Step 1: benzofuran-3-ylmethanol

A solution of 1-Benzofuran-3-carbaldehyde (5 g, 34.2 mmol) in methanol (50 mL) was cooled with ice and sodium borohydride (1.9 g, 51.3 mmol) was added portionwise. The reaction mixture was stirred at room temperature for 1 h. The reaction mixture was concentrated and the residue was partitioned between saturated ammonium chloride and dichloromethane. The organic layer was separated, dried over sodium sulfate and concentrated. The crude (5.0 g, 98%) was taken as such for next step without further purification.

$^1$H NMR (400 MHz, CDCl$_3$): δ 7.68-7.70 (m, 1H), 7.62 (s, 1H), 7.50-7.52 (m, 1H), 7.26-7.36 (m, 2H), 4.86 (s, 2H).

Step 2: 3-(bromomethyl)benzofuran

A cold (0° C.) solution of benzofuran-3-ylmethanol (5.0 g, 33.7 mmol) in diethyl ether (50 mL) was treated with phosphorus tribromide (1.1 mL, 11.2 mmol) and the reaction mixture was stirred at 0° C. for 30 min. The reaction mixture was then poured into ice and extracted with ether. The organic layer was dried over sodium sulfate and concentrated. The crude (7.1 g, 100%) was taken as such for next step without further purification.

$^1$H NMR (400 MHz, CDCl$_3$): δ 7.71-7.74 (m, 2H), 7.53 (s, 1H), 7.31-7.39 (m, 2H), 4.65 (s, 2H).

Step 3: 2-(benzofuran-3-ylmethyl)-4,4,5,5-tetramethyl-1,3,2-dioxaborolane

A solution of 3-(bromomethyl)benzofuran (7.1 g, 33.8 mmol) in degassed 1, 4-dioxane (70 ml) was treated with bis(pinacolato)diboron (10.3 g, 40.5 mmol), potassium carbonate (13.9 g, 101.0 mmol), tetrakis(triphenylphosphine) palladium(0) (1.9 g, 1.7 mmol) and the mixture heated at 100° C. for 12 h The contents of the flask were cooled to room temperature and filtered through a celite bed. Filtrate was concentrated and the crude was purified by column chromatography on silica gel, eluting with 2-5% of ethylacetate in petroleum ether to get the title compound (6.1 g, 69%) as yellow oil.

$^1$H NMR (400 MHz, CDCl$_3$) δ 7.52-7.57 (m, 2H), 7.44-7.46 (m, 1H), 7.21-7.30 (m, 2H), 2.23 (s, 2H), 1.29 (s, 12H).

Step 4: 2-(benzofuran-3-ylmethyl)boronic acid (+)-pinanediol ester

A solution of 2-(benzofuran-3-ylmethyl)-4,4,5,5-tetramethyl-1,3,2-dioxaborolane (6.1 g, 23.6 mmol) in diethyl ether (60 ml) was treated with (1S,2S,3R,5S)-(+)-pinanediol (6.0 g, 35.4 mmol). The reaction mixture was stirred at room temperature for 12 h then the mixture was washed with water twice, then with brine and dried over anhydrous sodium sulphate, then concentrated. The crude product was purified by column chromatography on silica gel, eluting with 5% of ethyl acetate in petroleum ether, to afford the title compound (6.3 g, 82%).

$^1$H NMR (400 MHz, CDCl$_3$): δ 7.56-7.58 (m, 1H), 7.53-7.55 (m, 1H), 7.44-7.46 (m, 1H), 7.23-7.28 (m, 2H), 4.33 (dd, J=1.88, 8.76 Hz, 1H), 2.32-2.34 (m, 1H), 2.28 (s, 2H), 2.21-2.22 (m, 1H), 2.08 (t, J=5.88 Hz, 1H), 1.42 (s, 3H), 1.29 (s, 3H), 1.13 (d, J=10.92 Hz, 1H), 0.85 (s, 3H). GCMS: m/z: 310

Step 5: [(1S)-1-chloro-2-(benzofuran-3-ylmethyl) boronic acid (+)-pinanediol ester To a cooled (−100° C.) mixture of dichloromethane (6.3 ml, 60.9 mmol) and anhydrous tetrahydrofuran (36 ml) was added n-butyl lithium (1.6 M in hexanes, 14.0 ml, (22.3 mmol) over 20 min. After stirring for 20 min. at −100° C., a solution of 2-(benzofuran-3-ylmethyl)boronic acid (+)-pinanediol ester (6.3 g, 20.3 mmol) in anhydrous THF (22 ml) was added over 20 min. Then a solution of zinc chloride (0.5 M in THF, 36.5 mL, 18.2 mmol) was added at −100° C. over 30 min. The mixture was allowed to reach room temperature and stirred for 18 h and concentrated. To the resulting oil was added diethyl ether and saturated ammonium chloride (100 ml each) and stirred vigorously. The aqueous layer was extracted with diethyl ether three times and the combined organic layers were dried over anhydrous sodium sulphate and concentrated in vacuo. The residue (7.3 g, 99%) was taken as such for the next step.

$^1$H NMR (400 MHz, DMSO-d6): δ 7.57-7.60 (m, 2H), 7.47-7.49 (m, 1H), 7.25-7.31 (m, 2H), 4.34-4.36 (m, 1H), 3.29-3.31 (m, 1H), 3.22-3.24 (m, 1H), 2.31-2.35 (m, 1H), 2.12-2.14 (m, 1H), 2.06 (t, J=5.84 Hz, 1H), 1.86-1.90 (m, 2H), 1.42 (s, 3H), 1.04 (d, J. 11.04 Hz, 1H), 0.85 (s, 3H). GCMS: m/z: 358.2

Step 6: [(1R)-1-[bis(trimethylsilyl)amino]-2-(benzofuran-3-ylmethyl)boronic acid (+)-pinanediol ester To a cooled (−78° C.) solution of [(1S)-1-chloro-2-(benzofuran-3-ylmethyl)boronic acid (+)-pinanediol ester (7.3 g, 20.3 mmol) in 40 ml of anhydrous tetrahydrofuran was added lithium bis(trimethylsilyl)amide (1 M in THF, 25.5 ml, 25.5 mmol). The mixture was allowed to room temperature, stirred for 18 h and concentrated to dryness. To the resulting residue was added hexane, and then the precipitated solid was filtered off. The filtrate was concentrated to give the required crude product (6.7 g, 68%) which was taken as such for the next step without further purification.

$^1$H NMR (400 MHz, CDCl$_3$): δ 7.59-7.60 (m, 1H), 7.45-7.50 (m, 2H), 7.24-7.28 (m, 2H), 4.31 (dd, J=1.56, 8.70 Hz, 1H), 3.14-3.18 (m, 1H), 2.90-2.92 (m, 1H), 2.72-2.75 (m, 1H), 2.30-2.34 (m, 1H), 2.14-2.15 (m, 1H), 2.03 (t, J=5.68 Hz, 1H), 1.80-1.88 (m, 2H), 1.39 (s, 3H), 1.30 (s, 3H), 1.01 (d, J=10.88 Hz, 1H), 0.84 (s, 3H), 0.09 (s, 18H).

Step 7: [(1R)-1-amino-2-(benzofuran-3-ylmethyl) boronic acid (+)-pinanediol ester trifluroacetate A cooled (0° C.) solution of [(1R)-1-[bis(trimethylsilyl) amino]-2-(benzofuran-3-ylmethyl)boronic acid (+)-pinanediol ester (6.7 g, 13.9 mmol) in diethyl ether (30 ml) was treated with trifluoroacetic acid (3.2 ml, 41.7 mmol) dropwise. The reaction mixture was evaporated under reduced pressure at a temperature below 30° C. The crude was taken up in toluene and evaporated, and this sequence was repeated four times. The white solid obtained (2.3 g, 36%) was used without further purification for the next step.

$^1$H NMR (400 MHz, DMSO-d$_6$): δ 7.66 (s, 1H), 7.60-7.61 (m, 1H), 7.45-7.47 (m, 1H), 7.20-7.29 (m, 2H), 4.28-4.30 (m, 1H), 3.16-3.27 (m, 3H), 2.13-2.25 (m, 3H), 1.94 (t, J=5.56 Hz, 1H), 1.81-1.86 (m, 2H), 1.25 (s, 6H), 1.01 (d, J=8.00 Hz, 1H), 0.75 (s, 3H).

Example 1: [(1R)-1-[(4-oxo-4-phenylbutanoyl) amino]-2-(3-thienyl)ethyl]boronic acid

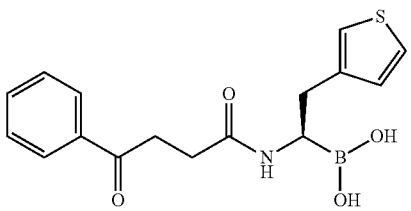 [SMILES: O=C(CCC(=O)c1ccccc1)N[C@@H](Cc1ccsc1)B(O)O]

Step 1: [(1R)-1-[(4-oxo-4-phenylbutanoyl)amino]-2-(3-thienyl)ethyl]boronic acid (+)-pinanediol ester A cooled (0° C.) solution of Intermediate 1 (100 mg, 0.24 mmol) anhydrous dichloromethane (15 ml) was treated with diisopropylethylamine (0.12 ml, 0.72 mmol) and 3-benzoyl propionic acid (42 mg, 0.24 mmol) and TBTU (91 mg, 0.29 mmol). The reaction mixture was stirred at 0° C. for 3 h. The reaction mixture was concentrated under reduced pressure keeping an external bath temperature below 30° C., and then 10 ml ethyl acetate were added. The organic layer was washed with brine, dried over sodium sulfate and concentrated. The desired product was isolated by purification by chromatography on silica gel, eluting with pet ether/ethyl acetate 1:1.

MS (ESI+): 466.3, HPLC (Method A): Rt 5.44 min 85.0%

Step 2: [(1R)-1-[(4-oxo-4-phenylbutanoyl)amino]-2-(3-thienyl)ethyl]boronic acid

A cooled (0° C.) solution of [(1R)-1-[(4-oxo-4-phenylbutanoyl)amino]-2-(3-thienyl)ethyl]boronic acid (+)-pinanediol ester (74 mg, 0.16 mmol) in methanol/pentane (1:1, 15 mL) was treated with 2-methylpropyl boronic acid (64 mg, 0.636 mmol) and an aqueous HCl solution (1.5 N, 0.4 mL) and the reaction mixture was stirred at room temperature for 15 h. The reaction mixture was then extracted with pentane thrice. The aqueous methanol layer was concentrated at temperature below 30° C. The residue was treated with ice and basified with an aqueous (2N) solution of NaOH and extracted with dichloromethane thrice. The aqueous layer was then acidified with an aqueous (1.5 N) HCl solution and extracted with dichloromethane twice. The DCM layer was dried over sodium sulfate, filtered and concentrated to give a solid residue, which was purified by flash chromatography on high performance silica gel to obtain the title compound as a white solid.

$^1$H NMR (400 MHz, DMSO-d6): δ 8.66 (s, 1H), 7.89-7.94 (m, 2H), 7.58-7.62 (m, 1H), 7.45-7.49 (m, 2H), 7.29-7.31 (m, 1H), 7.04 (s, 1H), 6.92-6.93 (m, 1H), 3.24-3.26 (m, 2H), 2.68-2.72 (m, 2H), 2.55-2.58 (m, 3H). MS (ESI+): 314.0 [M+H—H$_2$O], HPLC (Method A): Rt 2.89 min; HPLC purity 95.8%

The following compounds were synthesized using the same procedure followed for Example 1:

Example 2: [(1R)-1-({[(1RS,2RS)-2-benzoylcyclohexyl]carbonyl}amino)-2-(3-thienyl)ethyl]boronic acid

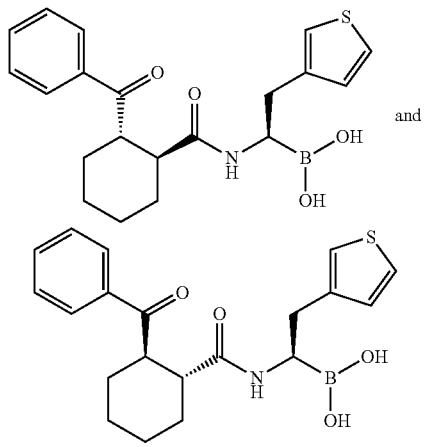

This Example is a mixture of diastereoisomers. The chiral centres on the cyclohexane ring have trans configuration. Prepared starting from trans-2-benzoylcyclohexane-1-carboxylic acid from Rielke Chemicals. Pale pink solid. $^1$H NMR (400 MHz, DMSO-d6): δ 8.14-8.84 (m, 1H), 7.82-7.91 (m, 2H), 7.25-7.58 (m, 4H), 6.77-6.88 (m, 2H), 3.60-3.63 (m, 1H), 2.63-2.69 (m, 1H), 2.43-2.49 (m, 1H), 2.13-2.28 (m, 1H), 1.86-1.89 (m, 1H), 1.66-1.76 (m, 3H), 1.30-1.40 (m, 2H), 1.18-1.23 (m, 3H), 1.06-1.08 (m, 2H). MS (ESI+): 368.0 [M+H—H$_2$O], HPLC (Method A): Rt 3.71 min; HPLC purity 50.6%+45.6%

Example 3: [(1R)-1-{[2-(RS)-(3-chlorophenyl)-4-oxo-4-phenylbutanoyl]amino}-2-(3-thienyl)ethyl]boronic acid

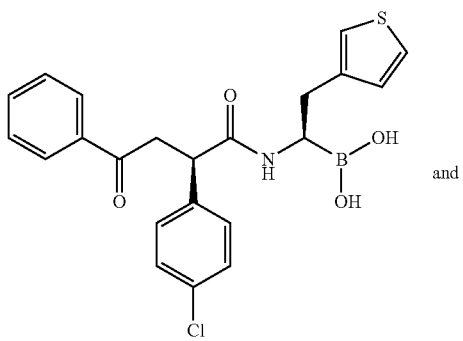

This Example is a mixture of diastereoisomers. Off-white solid. $^1$H NMR (400 MHz, DMSO-d6): δ 7.95-7.96 (m, 2H), 7.58-7.60 (m, 1H), 7.48-7.50 (m, 2H), 7.42-7.44 (m, 1H), 7.22-7.34 (m, 4H), 6.88-6.95 (m, 1H), 6.60-6.62 (m, 1H), 4.13 (t, J=5.1 Hz, 1H), 3.75-3.85 (m, 1H), 3.24-3.28 (m, 2H), 2.64-2.73 (m, 2H). MS (ESI+): 424.0 [M+H—H$_2$O], HPLC (Method A): Rt 8.57; 8.96 min; HPLC purity 28.7%+67.9%

Example 4: [(1R)-1-{[2-(RS)-(4-chlorophenyl)-4-oxo-4-phenylbutanoyl]amino}-2-(3-thienyl)ethyl]boronic acid

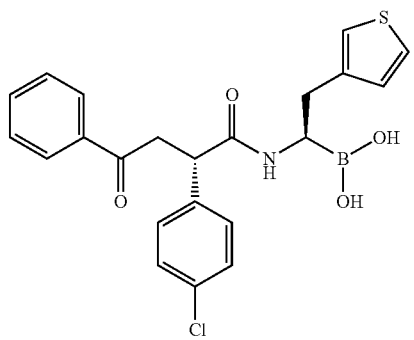

This Example is a mixture of diastereoisomers. White solid. ¹H NMR (400 MHz, DMSO-d6): δ 7.95-7.95 (m, 2H), 7.60-7.62 (m, 1H), 7.48-7.52 (m, 2H), 7.31-7.41 (m, 6H), 6.88-6.97 (m, 1H), 6.63-6.64 (m, 1H), 4.12-4.15 (m, 1H), 3.85-3.95 (m, 1H), 3.25-3.29 (m, 1H), 3.12-3.14 (m, 1H), 2.66-2.75 (m, 2H). MS (ESI+): 424.0 [M+H—H₂O], HPLC (Method A): Rt 8.56; 8.97 min; HPLC purity 40.0%+53.4%

Example 5: [1-({[(1RS,2SR)-2-benzoylcyclopentyl]carbonyl}amino)-2-(3-thienyl)ethyl]boronic acid

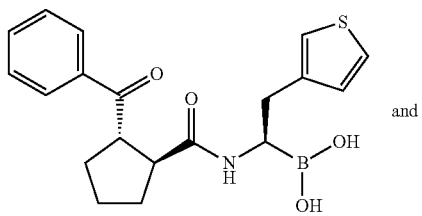

and

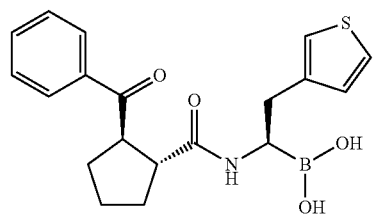

This Example is a mixture of diastereoisomers. The chiral centres on the cyclohexane ring have trans configuration. Prepared starting from trans-2-benzoylcyclopentane-1-carboxylic acid from Rielke Chemicals. Off-white solid. ¹H NMR (400 MHz, DMSO-d6): δ 7.91-7.93 (m, 1H), 7.82-7.84 (m, 1H), 7.59-7.61 (m, 1H), 7.55-7.57 (m, 1H), 7.33 (s, 1H), 7.25-7.26 (m, 1H), 6.87-6.92 (m, 1H), 6.78-6.86 (m, 1H), 4.01-4.02 (m, 1H), 3.00-3.15 (m, 2H), 2.66-2.68 (m, 2H), 2.00-2.03 (m, 1H), 1.85-1.92 (m, 1H), 1.56-1.68 (m, 4H). MS (ESI+): 354.3 [M+H—H₂O], HPLC (Method A): Rt 3.53 min; HPLC purity 92.0%

Example 9: [(1R)-1-{[4-(4-methoxyphenyl)-4-oxobutanoyl]amino}-2-(3-thienyl)ethyl]boronic acid

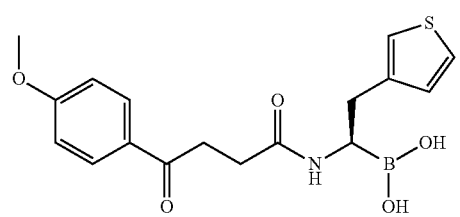 [SMILES: COc1ccc(C(=O)CCC(=O)N[C@@H](Cc2ccsc2)B(O)O)cc1]

Off-white solid. ¹H NMR (400 MHz, DMSO-d6): δ 8.65 (s, 1H), 7.87-7.92 (m, 2H), 7.30-7.35 (m, 1H), 7.04 (s, 1H), 6.95-6.98 (m, 2H), 6.92-6.93 (m, 1H), 3.81 (s, 3H), 3.18-3.20 (m, 2H), 2.65-2.74 (m, 2H), 2.52-2.55 (m, 3H). MS (ESI+): 344.3 [M+H—H₂O], HPLC (Method A): Rt 3.00 min; HPLC purity 96.2%

Example 10: [(1R)-1-[(2-(RS)-methyl-4-oxo-4-phenylbutanoyl)amino]-2-(3-thienyl)ethyl]boronic acid

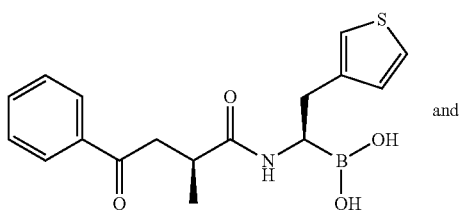

and

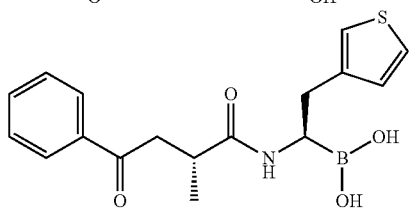

This Example is a mixture of diastereoisomers. The chiral centres on the cyclohexane ring have trans configuration. Prepared starting from 2-methyl-4-oxo-4-phenylbutyric acid from ABCR. Off-white solid. ¹H NMR (400 MHz, DMSO-d6): δ 8.56-8.61 (m, 1H), 7.87-7.91 (m, 2H), 7.57-7.59 (m, 1H), 7.46-7.51 (m, 2H), 7.26-7.28 (m, 1H), 7.09 (s, 1H), 6.93 (s, 1H), 3.20-3.30 (m, 1H), 3.04-3.09 (m, 1H), 2.93-2.96 (m, 1H), 2.65-2.74 (m, 2H), 2.48-2.50 (m, 1H), 1.02-1.05 (m, 3H). MS (ESI+): 328.3 [M+H—H₂O], HPLC (Method A): Rt 3.15 min; HPLC purity 87.0%

Example 12: [(1R)-1-{[4-(2-methoxyphenyl)-4-oxobutanoyl]amino}-2-(3-thienyl)ethyl]boronic acid

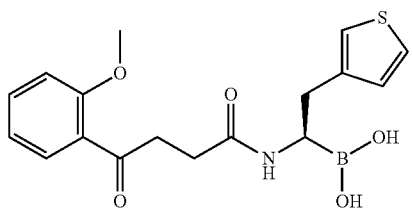 [SMILES: COc1ccccc1C(=O)CCC(=O)N[C@@H](Cc1ccsc1)B(O)O]

White solid. $^1$H NMR (400 MHz, DMSO-d6): δ 7.51-7.53 (m, 2H), 7.49 (s, 1H), 7.14 (d, J=8.1 Hz, 1H), 7.07 (s, 1H), 7.00-7.06 (m, 1H), 6.92-6.94 (m, 1H), 3.84 (s, 3H), 3.07-3.13 (m, 3H), 2.80-2.81 (m, 1H), 2.76-2.78 (m, 1H), 2.38 (t, J=7.0 Hz, 2H).

MS (ESI+): 344.0 [M+H—H$_2$O], HPLC (Method A): Rt 3.03; HPLC purity 93.2%

Example 13: [(1R)-1-{[4-(2,4-dimethoxyphenyl)-4-oxobutanoyl]amino}-2-(3-thienyl)ethyl]boronic acid

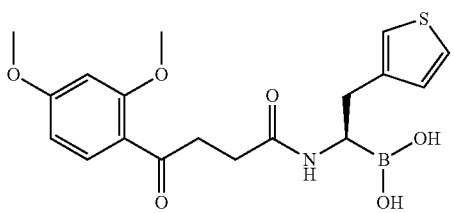 [SMILES: COc1ccc(C(=O)CCC(=O)N[C@@H](Cc2ccsc2)B(O)O)c(OC)c1]

White solid. $^1$H NMR (400 MHz, DMSO-d6): δ 7.63 (d, J=8.6 Hz, 1H), 7.34-7.36 (m, 1H), 7.06 (s, 1H), 6.94 (s, 1H), 6.57-6.60 (m, 2H), 3.85 (s, 3H), 3.80 (s, 3H), 3.04-3.10 (m, 3H), 2.75-2.80 (m, 1H), 2.65-2.71 (m, 1H), 2.34-2.35 (m, 2H).

MS (ESI+): 374.0 [M+H—H$_2$O], HPLC (Method A): Rt 3.13; 3.41 min; HPLC purity 99.0%

Example 6: {(1R)-2-(3-ethylphenyl)-1-[(4-oxo-4-phenylbutanoyl)amino]ethyl}boronic acid

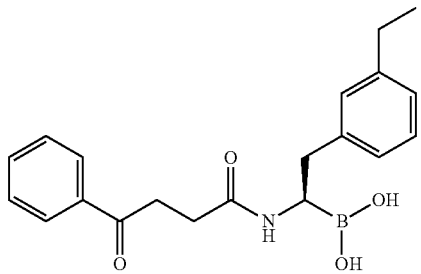 [SMILES: CCc1cccc(C[C@H](NC(=O)CCC(=O)c2ccccc2)B(O)O)c1]

Step 1: {(1R)-2-(3-ethylphenyl)-1-[(4-oxo-4-phenylbutanoyl)amino]ethyl}boronic acid (+)-pinanediol ester A cold (−10° C.) solution of Intermediate 2 (150 mg, 0.34 mmol) in anhydrous dimethylformamide (10 ml) was treated with diisopropylethylamine (0.17 ml, 1.0 mmol). 3-benzoyl propionic acid (60 mg, 0.340 mmol) and TBTU (130 mg, 0.41 mmol). The reaction mixture was stirred at −10° C. for 3 h then concentrated under reduced pressure keeping an external bath temperature below 30° C., and then 10 ml ethyl acetate was added. The organic layer was washed with brine, dried over sodium sulfate and concentrated. The desired product (120 mg; 72%) was isolated by purification through Flash chromatography on silica gel, eluting with pet ether/ethyl acetate 1:1. MS (ESI+): 488.3, HPLC (Method A): Rt 6.08 min; HPLC purity 91.0%

Step 2: {(1R)-2-(3-ethylphenyl)-1-[(4-oxo-4-phenylbutanoyl)amino]ethyl}boronic acid A cold (0° C.) solution of {(1R)-2-(3-ethylphenyl)-1-[(4-oxo-4-phenylbutanoyl)amino]ethyl}boronic acid (+)-pinanediol ester (120 mg, 0.25 mmol) in methanol/pentane (1:1, 15 mL) was treated with 2-methylpropyl boronic acid (99 mg, 0.99 mmol) and an aqueous solution of HCl (1.5 N, 0.5 mL) and the reaction mixture was stirred at room temperature for 15 h. The reaction mixture was then extracted with pentane thrice. The aqueous methanol layer was concentrated at temperature below 30° C. The residue was purified by flash chromatography on high performance silica gel to obtain a solid, which was triturated with pentane to afford the Title compound as an off-white solid.

$^1$H NMR (400 MHz, DMSO-d6): δ 7.91-7.92 (m, 2H), 7.70-7.72 (m, 1H), 7.60-7.62 (m, 2H), 7.10-7.14 (m, 1H), 6.94-6.98 (m, 3H), 3.12-3.18 (m, 3H), 2.73-2.76 (m, 1H), 2.64-2.67 (m, 1H), 2.51-2.55 (m, 2H), 2.40-2.43 (m, 2H), 1.13 (t, J=7.6 Hz, 3H). MS (ESI+): 336.0 [M+H—H$_2$O], HPLC (Method A): Rt 3.75 min; HPLC purity 96.8%

The following compounds were synthesized using the same procedure followed for Example 6:

Example 7: ((1R)-2-(3-ethylphenyl)-1-{[4-(4-methoxyphenyl)-4-oxobutanoyl]amino}ethyl)boronic acid

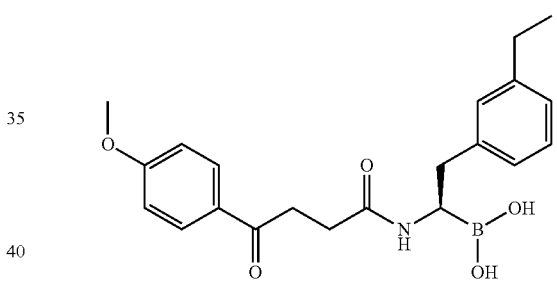

Off-white solid. $^1$H NMR (400 MHz, DMSO-d6): δ 7.85-7.90 (m, 2H), 6.91-7.13 (m, 6H), 3.81 (s, 3H), 3.52-3.54 (m, 1H), 3.09-3.18 (m, 2H), 2.65-2.68 (m, 2H), 2.52-2.54 (m, 2H), 2.46-2.48 (m, 1H), 2.37-2.40 (m, 1H), 1.06-1.15 (m, 3H). MS (ESI+): 366.3 [M+H—H$_2$O], HPLC (Method A): Rt 3.77 min; HPLC purity 96.4%

Example 8: ((1R)-2-(3-ethylphenyl)-1-{[4-(2-methoxyphenyl)-4-oxobutanoyl]amino}ethyl)boronic acid

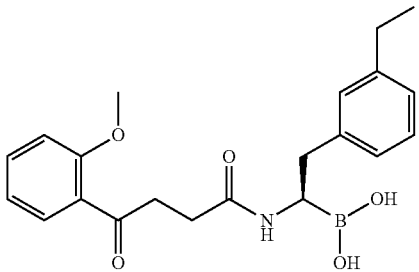 [SMILES: CCc1cccc(C[C@H](NC(=O)CCC(=O)c2ccccc2OC)B(O)O)c1]

Off-white solid. ¹H NMR (400 MHz, DMSO-d6): δ 7.49-7.53 (m, 2H), 7.10-7.15 (m, 2H), 6.93-7.02 (m, 4H), 3.84 (s, 3H), 3.05-3.14 (m, 3H), 2.76-2.78 (m, 1H), 2.73-2.74 (m, 1H), 2.48-2.49 (m, 2H), 2.33-2.37 (m, 2H), 1.08-1.14 (m, 3H). MS (ESI+): 366.3 [M+H—H₂O], HPLC (Method A): Rt 3.81 min; HPLC purity 90.1%

Example 11: [(1R)-1-{[4-(2,4-dimethoxyphenyl)-4-oxobutanoyl]amino}-2-(3-ethylphenyl)ethyl]boronic acid

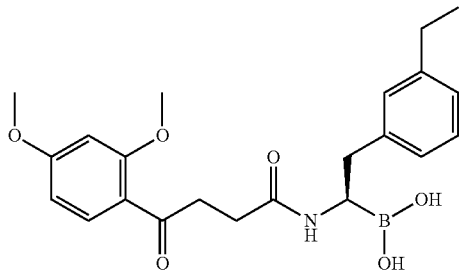 [SMILES: CCc1cccc(C[C@H](NC(=O)CCC(=O)c2ccc(OC)cc2OC)B(O)O)c1]

Off-white solid. ¹H NMR (400 MHz, DMSO-d6): δ 8.49 (s, 1H), 7.64 (d, J=8.7 Hz, 1H), 7.04-7.07 (m, 1H), 6.99 (s, 1H), 6.90-6.93 (m, 2H), 6.52-6.58 (m, 2H), 3.79 (s, 6H), 3.10-3.14 (m, 2H), 2.66-2.74 (m, 2H), 2.48-2.49 (m, 1H), 2.48 (m, 4H), 1.10 (t, J=7.6 Hz, 3H).
MS (ESI+): 396.2 [M+H—H₂O], HPLC (Method A): Rt 3.85 min; HPLC purity 97.7%

Example 14: [(1R)-1-{[(2R)-2-(3-chlorophenyl)-4-oxo-4-phenylbutanoyl]amino}-2-(3-ethylphenyl)ethyl]boronic acid

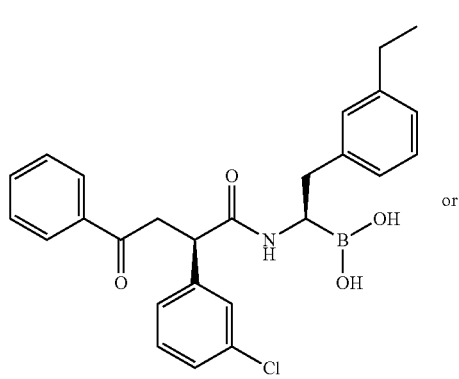

or

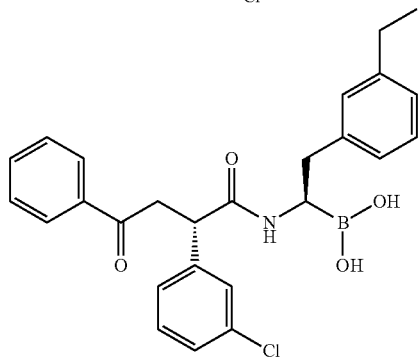

White solid. One diastereoisomer. The configuration at the chiral position most removed from the boronic acid group is arbitrarily assigned. This Example was prepared from Intermediate 12 (+)-2-(3-chlorophenyl)-4-oxo-4-phenylbutanoic acid (with αD +101.9°; ethanol, c=1.0 g/100 mL). ¹H NMR (400 MHz, DMSO-d6): δ 7.95 (d, J=8.0 Hz, 2H), 7.61-7.63 (m, 1H), 7.49-7.53 (m, 2H), 7.27-7.41 (m, 4H), 7.04-7.07 (m, 1H), 6.91-6.96 (m, 2H), 6.79-6.81 (m, 1H), 4.07-4.11 (m, 1H), 3.71-3.76 (m, 1H), 3.29-3.34 (m, 1H), 3.05-3.10 (m, 1H), 2.62-2.73 (m, 2H), 2.48-2.49 (m, 1H), 1.08 (t, J=8.0 Hz, 3H). MS (ESI+): 446.0 [M+H—H₂O], HPLC (Method A): Rt 5.02 min; HPLC purity 85.1%

Example 15: [(1R)-1-{[(2R)-2-(4-chlorophenyl)-4-oxo-4-phenylbutanoyl]amino}-2-(3-ethylphenyl)ethyl]boronic acid

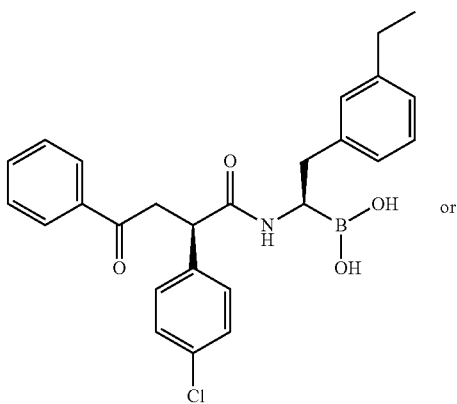

or

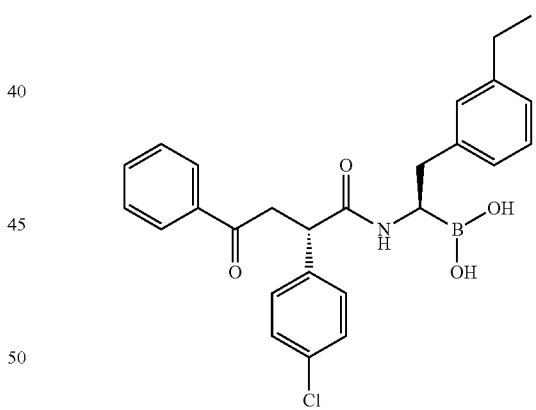

One diastereoisomer. The configuration at the chiral position most removed from the boronic acid group is arbitrarily assigned. This Example was prepared from Intermediate 14 (+)-2-(4-chlorophenyl)-4-oxo-4-phenylbutanoic acid (with αD +103.4°; ethanol, c=0.57 g/100 mL). Off-white solid. ¹H NMR (400 MHz, DMSO-d6): δ 8.50 (s, 1H), 7.93-7.95 (m, 2H), 7.60-7.63 (m, 1H), 7.46-7.49 (m, 2H), 7.14-7.19 (m, 3H), 7.00-7.04 (m, 1H), 6.90-6.92 (m, 1H), 6.78-6.80 (m, 2H), 4.15-4.18 (m, 1H), 3.75-3.82 (m, 1H), 3.32-3.34 (m, 1H), 2.59-2.62 (m, 1H), 2.38-2.44 (m, 2H), 2.21-2.26 (m, 1H), 1.07 (t, J=8.0 Hz, 3H). MS (ESI+): 446.3 [M+H—H₂O], HPLC (Method A): Rt 13.54 min; HPLC purity 97.1%, CHIRAL HPLC Rt 5.48 min (98.3%)

Example 16: [(1R)-1-{[(2R)-2-(4-chlorophenyl)-4-oxo-4-phenylbutanoyl]amino}-2-(3-ethylphenyl)ethyl]boronic acid

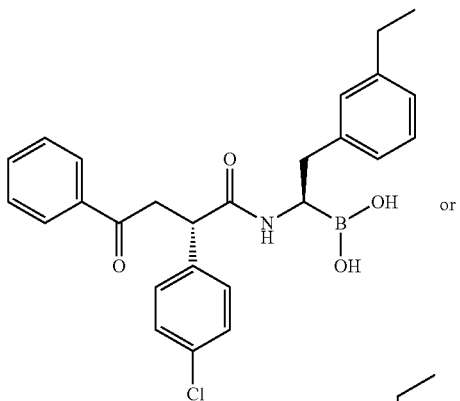 or

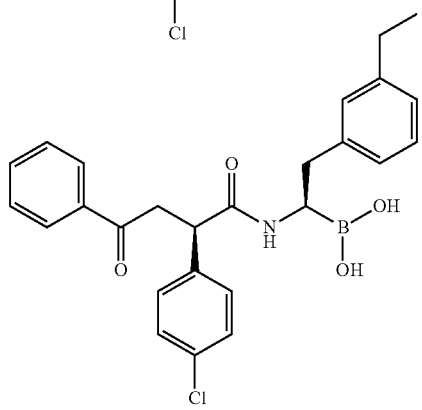

One diastereoisomer. The configuration at the chiral position most removed from the boronic acid group is arbitrarily assigned. This Example was prepared starting from Intermediate 15 (−)-2-(4-chlorophenyl)-4-oxo-4-phenylbutanoic acid (with αD −111.5°; ethanol, c=0.57 g/100 mL). Pale pink solid. $^1$H NMR (400 MHz, DMSO-d6): δ 8.75 (s, 1H), 7.85-7.87 (m, 2H), 7.55-7.59 (m, 1H), 7.41-7.43 (m, 2H), 7.30-7.39 (m, 2H), 7.21-7.23 (m, 2H), 7.00-7.04 (m, 1H), 6.89-6.91 (m, 1H), 6.83-6.85 (m, 1H), 4.17-4.21 (m, 1H), 3.67-3.74 (m, 1H), 3.39-3.40 (m, 2H), 2.63-2.67 (m, 1H), 2.57-2.59 (m, 1H), 2.45-2.48 (m, 2H), 1.10 (t, J=7.6 Hz, 3H). MS (ESI+): 446.3 [M+H—H$_2$O], HPLC (Method A): Rt 13.58 min; HPLC purity 97.1%, CHIRAL HPLC Rt 8.15 min (98.3%)

Example 17: [(1R)-1-[(4-biphenyl-4-yl-4-oxobutanoyl)amino]-2-(3-ethylphenyl)ethyl]boronic acid

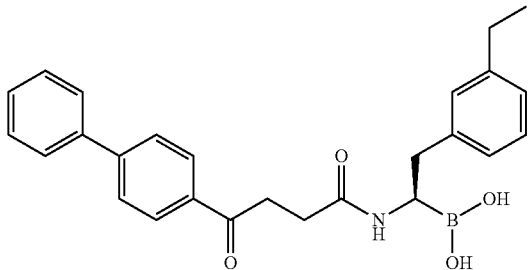 [SMILES: CCc1cccc(C[C@H](NC(=O)CCC(=O)c2ccc(-c3ccccc3)cc2)B(O)O)c1]

Step 1: [(1R)-1-[(4-biphenyl-4-yl-4-oxobutanoyl)amino]-2-(3-ethylphenyl)ethyl]boronic acid (+)-pinanediol ester A cold (−10° C.) solution of Intermediate 2 (300 mg, 0.68 mmol) in anhydrous N,N-dimethylformamide (25 mL) was treated with N,N-diisopropylethylamine (0.35 mL, 2.0 mmol), 3-(4-phenylbenzoyl)propionic acid (173 mg, 0.68 mmol) and TBTU (262 mg, 0.815 mmol). The reaction mixture was stirred at −10° C. for 3 h, then diluted with ethyl acetate and washed with brine repeatedly. The organic layer was separated, dried over sodium sulfate and concentrated. The crude was purified by flash chromatography on silica gel eluting with ethylacetate and petroleum ether (pale yellow gummy liquid).

MS (ESI+): 564.3; HPLC (Method A): Rt. 6.6 min; HPLC purity 97.7%; CHIRAL HPLC (Method A): Rt. 4.5 min; HPLC purity 98.5° A)

Step 2: [(1R)-1-[(4-biphenyl-4-yl-4-oxobutanoyl)amino]-2-(3-ethylphenyl)ethyl]boronic acid A cold (0° C.) solution of [(1R)-1-[(4-biphenyl-4-yl-4-oxobutanoyl)amino]-2-(3-ethylphenyl)ethyl]boronic acid (+)-pinanediol ester (167 mg, 0.296 mmol) in methanol/pentane (1:1, 30 mL) was treated with 2-methylpropyl boronic acid (120 mg, 1.18 mmol) and an aqueous solution of HCl (1.5 N, 0.8 mL). The reaction mixture was stirred at RT for 15 h, then evaporated under reduced pressure. The crude was purified by flash chromatography on silica gel eluting with dichloromethane and methanol to obtain the Title compound as an off-white solid.

$^1$H NMR (400 MHz, DMSO-d6): δ 7.95-7.94 (m, 2H), 7.67-7.73 (m, 4H), 7.41-7.49 (m, 3H), 7.05-7.09 (m, 1H), 6.91-7.09 (m, 3H), 3.27-3.38 (m, 3H), 2.72-2.77 (m, 2H), 2.57-2.62 (m, 2H), 2.46-2.50 (m, 2H), 1.07-1.11 (m, 3H). MS (ESI+): 412.0 [M+H—H$_2$O]. HPLC (Method B): Rt 13.1 min; HPLC purity 91.9%

The following products were prepared according to the same two-steps protocol described for Example 17:

Example 18: ((1R)-2-(3-ethylphenyl)-1-{[4-(2-naphthyl)-4-oxobutanoyl]amino}ethyl)boronic acid

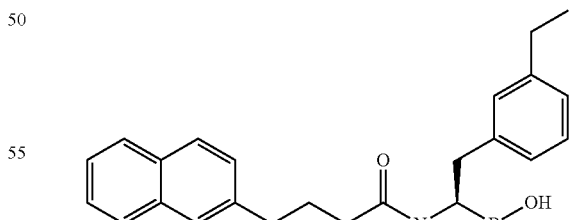

Off-white solid. $^1$H NMR (400 MHz, DMSO-d6): δ 8.59 (s, 1H), 8.04 (d, J=8.1 Hz, 1H), 7.89-7.95 (m, 3H), 7.55-7.66 (m, 2H), 6.94-7.05 (m, 3H), 6.87-6.89 (m, 1H), 3.40-3.42 (m, 2H), 2.73-2.76 (m, 2H), 2.64-2.66 (m, 2H), 2.40-2.50 (3H, m), 1.07 (t, J=7.5 Hz, 3H). MS (ESI+): 386.3 [M+H—H$_2$O]; HPLC (Method B): Rt 12.7 min, HPLC purity 96.1%

Example 19: [(1R)-1-[(4-biphenyl-3-yl-4-oxobutanoyl)amino]-2-(3-ethylphenyl)ethyl]boronic acid

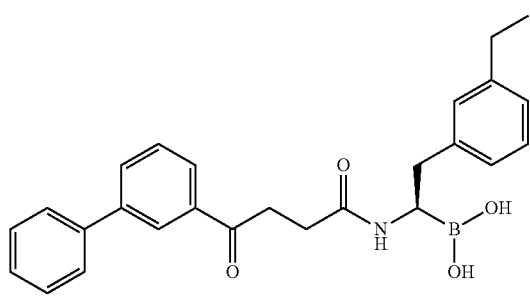 [SMILES: CCc1cccc(C[C@H](NC(=O)CCC(=O)c2cccc(-c3ccccc3)c2)B(O)O)c1]

Off-white solid. ¹H NMR (400 MHz, DMSO-d6): δ 8.13 (s, 1H), 7.88 (d, J=7.8 Hz, 2H), 7.78 (d, J=8.6 Hz, 2H), 7.52-7.56 (m, 1H), 7.42-7.48 (m, 2H), 7.36-7.39 (m, 1H), 7.01-7.03 (m, 1H), 6.93-6.98 (m, 2H), 6.87 (d, J=7.2 Hz, 1H), 3.31-0.00 (m, 2H), 2.70-2.80 (m, 2H), 2.48-2.62 (m, 5H), 1.05-1.09 (m, 3H). MS (ESI+): 412.0 [M+H—H₂O]; HPLC (Method A): Rt. 4.6 min, HPLC purity 96.4

Example 20: [(1R)-1-[(4-biphenyl-4-yl-4-oxobutanoyl)amino]-2-(3-thienyl)ethyl]boronic acid

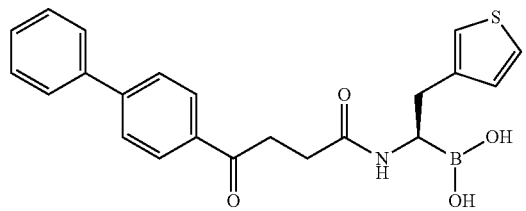 [SMILES: O=C(CCC(=O)c1ccc(-c2ccccc2)cc1)N[C@@H](Cc1ccsc1)B(O)O]

White solid. ¹H NMR (400 MHz, DMSO-d6): δ 7.98 (d, J=8.0 Hz, 2H), 7.68-7.76 (m, 4H), 7.46-7.52 (m, 2H), 7.39-7.41 (m, 1H), 7.30 (m, 1H), 7.05 (s, 1H), 6.94 (d, J=4.8 Hz, 1H), 3.29-3.31 (m, 2H), 2.70-2.72 (m, 2H), 2.54-2.59 (m, 3H). MS (ESI+): 390.0 [M+H—H₂O]. HPLC (Method A): Rt. 4.0 min, HPLC purity 97.8

Example 21: [(1R)-1-{[4-(2-naphthyl)-4-oxobutanoyl]amino}-2-(3-thienyl)ethyl]boronic acid

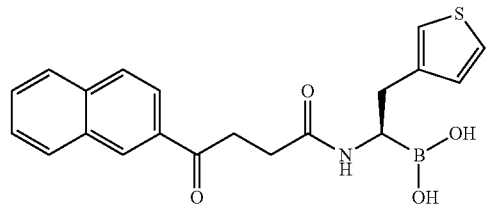 [SMILES: O=C(CCC(=O)c1ccc2ccccc2c1)N[C@@H](Cc1ccsc1)B(O)O]

White solid. ¹H NMR (400 MHz, DMSO-d6): δ 8.65 (s, 1H), 8.13 (d, J=8.0 Hz, 1H), 7.94-8.02 (m, 3H), 7.59-7.67 (m, 2H), 7.36-7.38 (m, 1H), 7.10 (s, 1H), 6.95-6.96 (m, 2H), 3.32-3.35 (m, 2H), 3.14-3.17 (m, 1H), 2.70-2.83 (m, 2H), 2.48-2.50 (m, 2H). MS (ESI+): 364.0 [M+H—H₂O]; HPLC (Method A): Rt. 3.6 min, HPLC purity 95.6

Example 22: [(1R)-1-[(4-biphenyl-3-yl-4-oxobutanoyl)amino]-2-(3-thienyl)ethyl]boronic acid

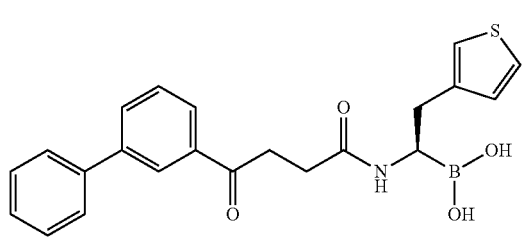 [SMILES: O=C(CCC(=O)c1cccc(-c2ccccc2)c1)N[C@@H](Cc1ccsc1)B(O)O]

White solid. ¹H NMR (400 MHz, DMSO-d6): δ 8.12 (s, 1H), 7.89-7.93 (m, 2H), 7.69 (d, J=7.6 Hz, 2H), 7.59-7.63 (m, 1H), 7.46-7.50 (m, 2H), 7.37-7.40 (m, 1H), 7.32-7.34 (m, 1H), 7.06 (s, 1H), 6.94 (d, J=4.4 Hz, 1H), 3.24-3.27 (m, 2H), 3.08-3.11 (m, 1H), 2.66-2.81 (m, 2H), 2.45-2.49 (m, 2H). MS (ESI+): 390.0 [M+H—H₂O]. HPLC (Method A): Rt. 4.0 min, HPLC purity 96.5

Example 23: [(1R)-1-{[4-oxo-4-(6-phenylpyridin-2-yl)butanoyl]amino}-2-(3-thienyl)ethyl]boronic acid

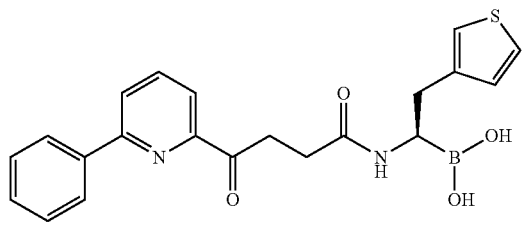 [SMILES: O=C(CCC(=O)c1cccc(-c2ccccc2)n1)N[C@@H](Cc1ccsc1)B(O)O]

Off-white solid. ¹H NMR (400 MHz, DMSO-d6): δ 8.17-8.23 (m, 3H), 8.07 (t, J=7.6 Hz, 1H), 7.89 (d, J=6.8 Hz, 1H), 7.46-7.56 (m, 3H), 7.35-7.37 (m, 1H), 7.09 (s, 1H), 6.95 (d, J=5.2 Hz, 1H), 3.47-3.49 (m, 2H), 3.15 (t, J=6.0 Hz, 1H), 2.63-2.83 (m, 3H). MS (ESI+): 413.3 [M+Na—H₂O]. HPLC (Method A): Rt. 3.8 min, HPLC purity 94.4%

Example 24: [(1R)-1-{[(2R)-2-benzyl-4-(4-methoxyphenyl)-4-oxobutanoyl]amino}-2-(3-thienyl)ethyl]boronic acid

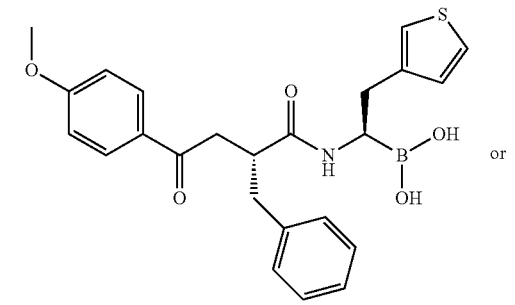

or

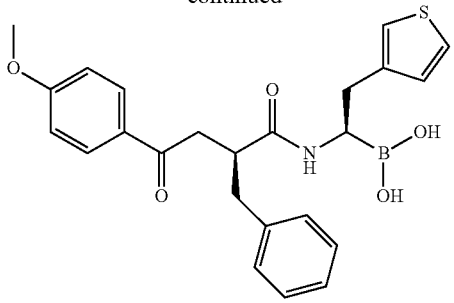

One diastereoisomer. The configuration at the chiral position most removed from the boronic acid group is arbitrarily assigned. This Example was prepared starting from Intermediate 17 (−)-2-benzyl-4-(4-methoxyphenyl)-4-oxo-butyric acid (with αD −21.0°; ethanol, c=1.0 g/100 mL). White solid.

$^1$H NMR (400 MHz, DMSO-d6): δ 7.86 (d, J=8.8 Hz, 2H), 7.32-7.34 (m, 1H), 7.20-7.26 (m, 4H), 7.14-7.18 (m, 1H), 7.00 (d, J=8.8 Hz, 2H), 6.95 (s, 1H), 6.87-6.89 (m, 1H), 3.81 (s, 3H), 3.24-3.28 (m, 1H), 3.09-3.13 (m, 2H), 2.85-2.90 (m, 1H), 2.56-2.75 (m, 4H). MS (ESI+): 434.2 [M+H—H$_2$O]. HPLC (Method A): Rt. 4.1 min, HPLC purity 95.9

Example 25: [(1R)-1-{[(2S)-2-benzyl-4-(4-methoxyphenyl)-4-oxobutanoyl]amino}-2-(3-thienyl)ethyl]boronic acid

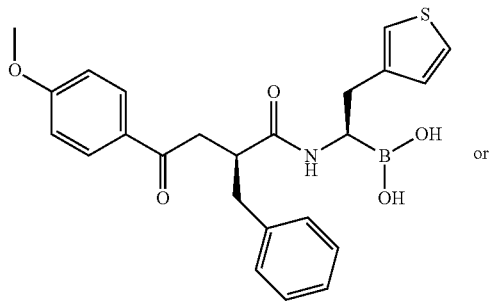

or

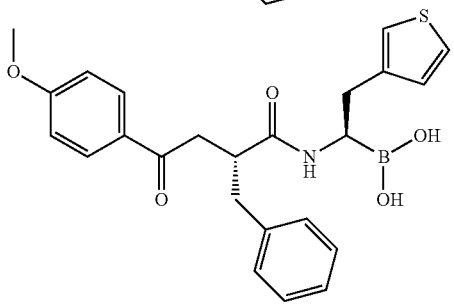

One diastereoisomer. The configuration at the chiral position most removed from the boronic acid group is arbitrarily assigned. This Example was prepared starting from Intermediate 16 (+)-2-benzyl-4-(4-methoxyphenyl)-4-oxo-butyric acid (with αD +21.1°; ethanol, c=1.0 g/100 mL). Off-white solid. $^1$H NMR (400 MHz, DMSO-d6): δ 7.86 (d, J=8.8 Hz, 2H), 7.30-7.32 (m, 1H), 7.14-7.26 (m, 5H), 6.99 (d, J=6.0 Hz, 2H), 6.79-6.83 (m, 2H), 3.80 (s, 3H), 3.16-3.27 (m, 2H), 3.04-3.00 (m, 1H), 2.75-2.83 (m, 2H), 2.48-2.69 (m, 3H). MS (ESI+): 434.2 [M+H—H$_2$O]. HPLC (Method A): Rt. 4.2 min, HPLC purity 92.7%

Example 26: {(1R)-1-{[4-(4-methoxyphenyl)-4-oxobutanoyl]amino}-2-[3-(trifluoromethyl)phenyl]ethyl}boronic acid

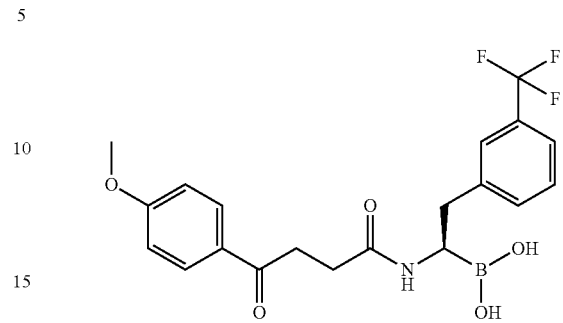

Pale brown solid. $^1$H NMR (400 MHz, DMSO-d$_6$): δ 7.89 (d, J=8.9 Hz, 2H), 7.45-7.49 (m, 4H), 7.02 (d, J=8.9 Hz, 2H), 3.81 (s, 3H), 3.12-3.16 (m, 1H), 3.06-3.08 (m, 2H), 2.85-2.90 (m, 1H), 2.70-2.76 (m, 1H), 2.35-2.39 (m, 2H). MS (ESI+): 406.0 [M+H—H$_2$O]. HPLC (Method A): Rt. 3.9 min, HPLC purity 97.3%

Example 27: {(1R)-1-{[2-(RS)-benzyl-4-(4-methoxyphenyl)-4-oxobutanoyl]amino}-2-[3-(trifluoromethyl)phenyl]ethyl}boronic acid

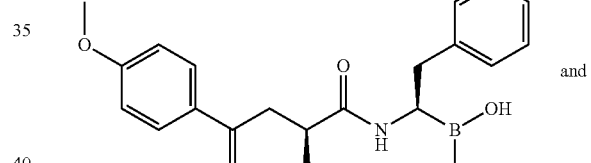

and

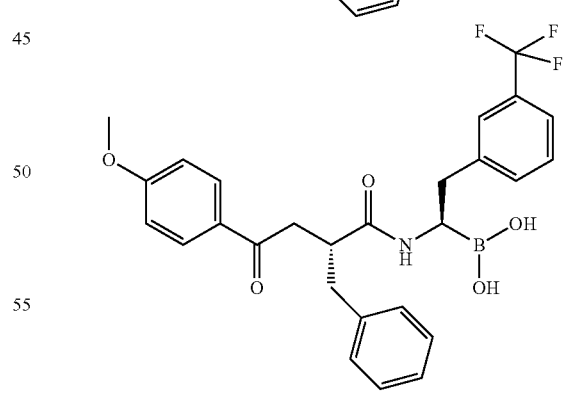

Mixture of diastereoisomers. Yellow solid. $^1$H NMR (400 MHz, DMSO-d$_6$): δ 7.82 (d, J=8.7 Hz, 1H), 7.37-7.46 (m, 3H), 7.30 (d, J=7.6 Hz, 1H), 7.13-7.25 (m, 5H), 6.98 (d, J=8.7 Hz, 2H), 3.81 (s, 3H), 3.37 (s, 1H), 3.21-3.23 (m, 1H), 3.17-3.19 (m, 1H), 3.06-3.10 (m, 1H), 2.97-3.00 (m, 1H), 2.74-2.83 (m, 3H), 2.56-2.67 (m, 2H). MS (ESI+): 496.2 [M+H—H$_2$O]. HPLC (Method A): Rt. 4.7 min, HPLC purity 73.9%+14.4%

The following compounds were prepared according to the same two-steps protocol described for Example 1:

Example 28: ((1R)-2-(3-ethylphenyl)-1-{[3-(1H-indazol-1-yl)propanoyl]amino}ethyl)boronic acid

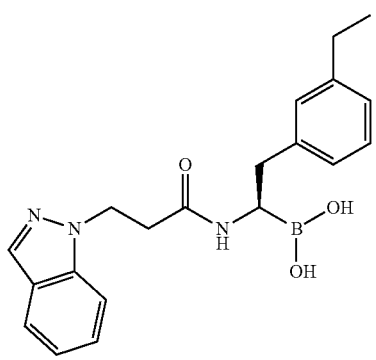 [SMILES: CCc1cccc(C[C@H](NC(=O)CCn2ncc3ccccc32)B(O)O)c1]

White solid. $^1$H NMR (400 MHz, DMSO-d6): δ 8.04 (s, 1H), 7.70-7.75 (m, 1H), 7.56-7.61 (m, 1H), 7.23-7.27 (m, 1H), 7.02-7.10 (m, 2H), 6.90-6.95 (m, 1H), 6.81-6.85 (m, 1H), 6.73-6.75 (m, 1H), 4.61 (t, J=6.80 Hz, 2H), 2.78-2.81 (m, 1H), 2.65-2.69 (m, 3H), 2.48-2.50 (m, 2H), 2.35-0.00 (m, 1H), 1.08-1.13 (m, 3H). MS (ESI+): 348.3 [M+H—$H_2O$]. HPLC (Method B): Rt 11.8 min, HPLC purity 87.9%

Example 29: [(1R)-1-{[3-(1H-benzimidazol-1-yl)propanoyl]amino}-2-(3-ethylphenyl)ethyl]boronic acid

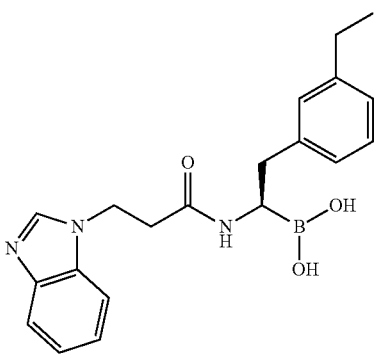 [SMILES: CCc1cccc(C[C@H](NC(=O)CCn2cnc3ccccc32)B(O)O)c1]

White solid. $^1$H NMR (400 MHz, DMSO-d6): δ 7.88 (s, 1H), 7.52-7.61 (m, 2H), 7.15-7.18 (m, 2H), 6.98-7.02 (m, 1H), 6.90 (m, 1H), 6.88 (s, 1H), 6.72-6.74 (m, 1H), 4.48-4.52 (m, 2H), 2.89-2.90 (m, 2H), 2.74 (m, 1H), 2.59-2.66 (m, 2H), 2.41-2.45 (m, 2H), 2.36-2.38 (m, 1H), 1.07 (m, 3H). MS (ESI+): 370.3 [M+Na—$H_2O$]. HPLC (Method A): Rt 2.8 min, HPLC purity 95.9%

Example 30: ((1R)-2-(3-ethylphenyl)-1-{[3-(2-oxo-1,3-benzothiazol-3(2H)-yl)propanoyl]amino}ethyl)boronic acid

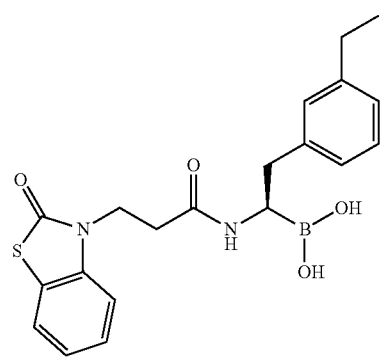 [SMILES: CCc1cccc(C[C@H](NC(=O)CCn2c(=O)sc3ccccc32)B(O)O)c1]

White solid. $^1$H NMR (400 MHz, DMSO-d6): δ 7.51-7.65 (m, 1H), 7.24-7.34 (m, 2H), 7.14-7.18 (m, 1H), 7.05-7.09 (m, 1H), 6.89-6.93 (m, 1H), 6.82-6.91 (m, 2H), 4.12-4.15 (m, 2H), 2.61-2.71 (m, 5H), 2.50-2.52 (m, 1H), 2.30-2.40 (m, 1H), 1.09-1.11 (m, 3H) MS (ESI+): 381.0 [M+H—$H_2O$]. HPLC (Method A): Rt 3.8 min, HPLC purity 95.7%

Example 31: [(1R)-1-{[3-(1H-1,2,3-benzotriazol-1-yl)propanoyl]amino}-2-(3-ethylphenyl)ethyl]boronic acid

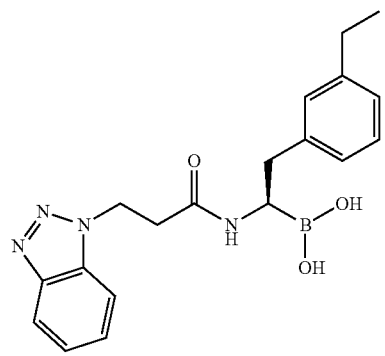 [SMILES: CCc1cccc(C[C@H](NC(=O)CCn2nnc3ccccc32)B(O)O)c1]

White solid. $^1$H NMR (400 MHz, DMSO-d6): δ 8.61-8.68 (m, 1H), 7.97-8.02 (m, 1H), 7.80-7.84 (m, 1H), 7.41-7.45 (m, 1H), 7.32-7.38 (m, 1H), 7.00-7.04 (m, 1H), 6.90-6.93 (m, 1H), 6.77 (s, 1H), 6.71 (d, J=7.6 Hz, 1H), 4.90-4.93 (m, 2H), 2.92-2.95 (m, 2H), 2.65-2.67 (m, 2H), 2.50-2.45 (m, 2H), 2.30-2.31 (m, 1H), 1.06-1.10 (m, 3H) MS (ESI+): 349.0 [M+H—$H_2O$]. HPLC (Method A): Rt 3.3 min, HPLC purity 96.4%

Example 32: [(1R)-1-{[3-(1H-indazol-1-yl)propanoyl]amino}-2-(3-thienyl)ethyl]boronic acid

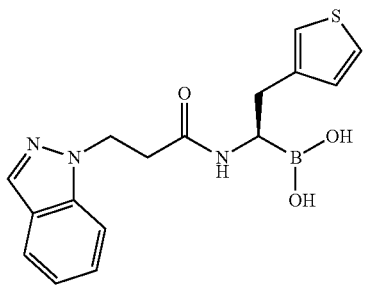 [SMILES: O=C(CCn1ncc2ccccc21)N[C@@H](Cc1ccsc1)B(O)O]

Off-white solid. ¹H NMR (400 MHz, DMSO-d6): δ 8.02 (s, 1H), 7.73 (d, J=8.4 Hz, 1H), 7.58 (d, J=8.8 Hz, 1H), 7.34-7.38 (m, 1H), 7.23-7.25 (m, 1H), 7.09-7.12 (m, 1H), 6.67-6.70 (m, 2H), 4.50-4.56 (m, 2H), 3.03-3.06 (m, 1H), 2.48-2.65 (m, 4H)

MS (ESI+): 326.0 [M+H—H₂O]; HPLC (Method A): Rt. 3.0 min, HPLC purity 95.4%

Example 33: [(1R)-1-{[3-(1H-benzimidazol-1-yl)propanoyl]amino}-2-(3-thienyl)ethyl]boronic acid

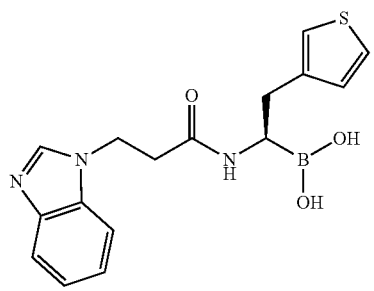 [SMILES: O=C(CCn1cnc2ccccc21)N[C@@H](Cc1ccsc1)B(O)O]

White solid. ¹H NMR (400 MHz, DMSO-d6): δ 8.09 (m, 1H), 7.56-7.63 (m, 2H), 7.18-7.26 (m, 3H), 6.72 (d, J=4.4 Hz, 2H), 4.39-4.43 (m, 2H), 3.11-3.14 (m, 1H), 2.59-2.72 (m, 4H).

MS (ESI+): 348.0 [M+Na—H₂O]. HPLC (Method A): Rt. 2.0 min, HPLC purity 96.6%

Example 34: [(1R)-1-{[3-(2-oxo-1,3-benzothiazol-3(2H)-yl)propanoyl]amino}-2-(3-thienyl)ethyl]boronic acid

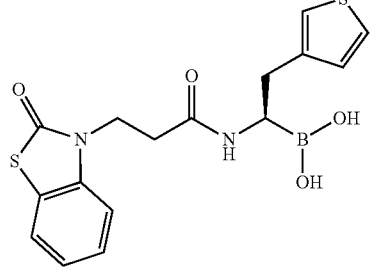

White solid. ¹H NMR (400 MHz, DMSO-d6): δ 7.60-7.62 (m, 1H), 7.30-7.37 (m, 3H), 7.15-7.20 (m, 1H), 6.79-6.84 (m, 2H), 4.08 (t, J=7.2 Hz, 2H), 3.11-3.15 (m, 1H), 2.61-2.73 (m, 2H), 2.42-2.48 (m, 2H). MS (ESI+): 359.0 [M+H—H₂O]. HPLC (Method A): Rt. 3.1 min, HPLC purity 98.9%

Example 35: [(1R)-1-{[3-(1H-1,2,3-benzotriazol-1-yl)propanoyl]amino}-2-(3-thienyl)ethyl]boronic acid

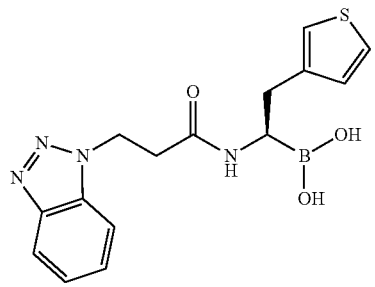 [SMILES: O=C(CCn1nnc2ccccc21)N[C@@H](Cc1ccsc1)B(O)O]

White solid. ¹H NMR (400 MHz, DMSO-d6): δ 8.01 (d, J=8.0 Hz, 1H), 7.83 (d, J=8.4 Hz, 1H), 7.51-7.54 (m, 1H), 7.36-7.40 (m, 1H), 7.26-7.28 (m, 1H), 6.72-6.74 (m, 2H), 4.80-4.90 (m, 2H), 3.11-3.15 (m, 1H), 2.76-2.80 (m, 2H), 2.57-2.71 (m, 2H). MS (ESI+): 327.0 [M+H—H₂O]. HPLC (Method A): Rt. 2.5 min, HPLC purity 86.4%

Example 38: {(1R)-1-{[3-(1H-benzimidazol-1-yl)propanoyl]amino}-2-[3-(trifluoromethyl)phenyl]ethyl}boronic acid

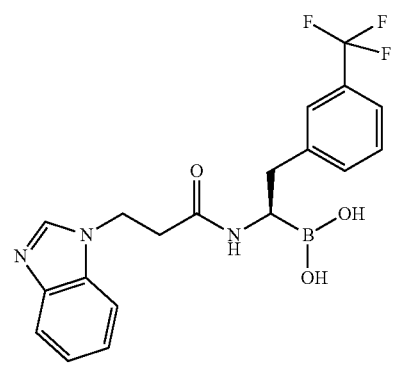 [SMILES: O=C(CCn1cnc2ccccc21)N[C@@H](Cc1cccc(C(F)(F)F)c1)B(O)O]

White solid. ¹H NMR (400 MHz, DMSO-d₆): δ 8.07 (s, 1H), 7.63 (d, J=7.5 Hz, 1H), 7.55 (d, J=7.5 Hz, 1H), 7.44 (d, J=7.9 Hz, 1H), 7.40 (s, 1H), 7.17-7.29 (m, 3H), 7.08 (d, J=7.8 Hz, 1H), 4.38 (t, J=6.7 Hz, 2H), 3.15-3.19 (m, 1H), 2.77-2.82 (m, 1H), 2.63-2.68 (m, 1H), 2.58 (t, J=6.8 Hz, 2H). MS (ESI+): 410.0 [M+Na—H₂O]. HPLC (Method A): Rt. 3.0 min, HPLC purity 95.3%

The following compounds were prepared according to the same two-steps protocol described for Example 6:

Example 36: ((1R)-2-(3-ethylphenyl)-1-{[3-(5-phenyl-1,2,4-oxadiazol-3-yl)propanoyl]amino}ethyl)boronic acid

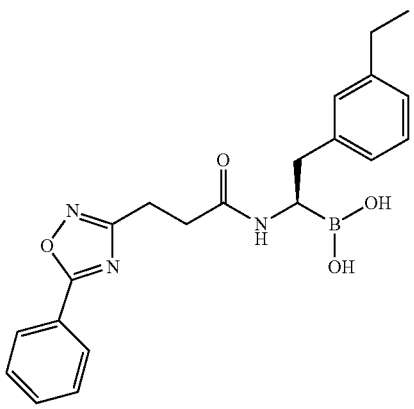 [SMILES: CCc1cccc(C[C@H](NC(=O)CCc2noc(-c3ccccc3)n2)B(O)O)c1]

Pale brown solid. $^1$H NMR (400 MHz, DMSO-d6): δ 8.06-8.08 (m, 2H), 7.67-7.71 (m, 1H), 7.59-7.63 (m, 2H), 7.07-7.10 (m, 1H), 6.90-6.97 (m, 3H), 3.17-3.20 (m, 1H), 2.93 (t, J=7.6 Hz, 2H), 2.65-2.79 (m, 2H), 2.48-2.54 (m, 4H), 1.13 (t, J=7.9 Hz, 3H). MS (ESI+): 376.3 [M+H—H$_2$O]. HPLC (Method A): Rt. 4.0 min, HPLC purity 97.0%

Example 37: [(1R)-1-{[3-(5-phenyl-1,2,4-oxadiazol-3-yl)propanoyl]amino}-2-(3-thienyl)ethyl]boronic acid

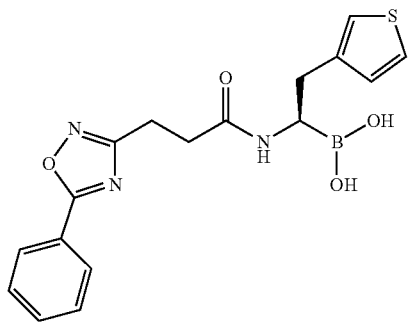 [SMILES: O=C(CCc1noc(-c2ccccc2)n1)N[C@@H](Cc1ccsc1)B(O)O]

White solid. $^1$H NMR (400 MHz, DMSO-d6): δ 8.06-8.09 (m, 2H), 7.67-7.71 (m, 1H), 7.59-7.63 (m, 2H), 7.31-7.33 (m, 1H), 7.03 (s, 1H), 6.89-6.91 (m, 1H), 3.15-3.19 (m, 1H), 2.93-2.97 (m, 2H), 2.68-2.83 (m, 2H), 2.55-2.57 (m, 2H). MS (ESI+): 354.0 [M+H—H$_2$O]. HPLC (Method A): Rt. 3.3 min, HPLC purity 97.8%

Example 39: {(1R)-1-{[3-(5-phenyl-1,2,4-oxadiazol-3-yl)propanoyl]amino}-2-[3-(trifluoromethyl)phenyl]ethyl}boronic acid

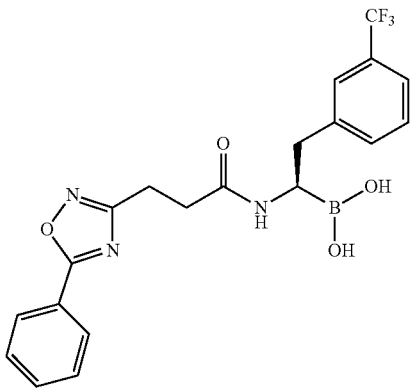 [SMILES: O=C(CCc1noc(-c2ccccc2)n1)N[C@@H](Cc1cccc(C(F)(F)F)c1)B(O)O]

Off-white solid. $^1$H NMR (400 MHz, DMSO-d$_6$): δ 8.04 (d, J=7.2 Hz, 2H), 7.66-7.69 (m, 1H), 7.58-7.62 (m, 2H), 7.40-7.45 (m, 4H), 3.17-3.20 (m, 1H), 2.85-2.91 (m, 3H), 2.70-2.76 (m, 1H), 2.49-2.51 (m, 2H). MS (ESI+): 416.2 [M+H—H$_2$O]. HPLC (Method B): Rt. 4.1 min, HPLC purity 96.9%

Example 40: [(1R)-1-{[3-(4-phenyl-1H-1,2,3-triazol-1-yl)propanoyl]amino}-2-(3-thienyl)ethyl]boronic acid

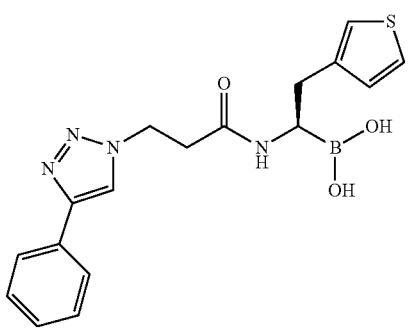 [SMILES: O=C(CCn1cc(-c2ccccc2)nn1)N[C@@H](Cc1ccsc1)B(O)O]

White solid. $^1$H NMR (400 MHz, DMSO-d$_6$): δ 8.37 (s, 1H), 7.79 (d, J=8.4 Hz, 2H), 7.42 (t, J=8.4 Hz, 2H), 7.30-7.33 (m, 1H), 7.24-7.26 (m, 1H), 6.90 (s, 1H), 6.80 (d, J=8.4 Hz, 2H), 4.53-4.62 (m, 2H), 3.12-3.16 (m, 1H), 2.63-2.77 (m, 4H). MS (ESI+): 353.0 [M+H—H$_2$O].

HPLC (Method A): Rt 3.0 min, HPLC purity 99.7%

Example 41: [(1R)-1-{[3-(1-phenyl-1H-1,2,3-triazol-4-yl)propanoyl]amino}-2-(3-thienyl)ethyl]boronic acid

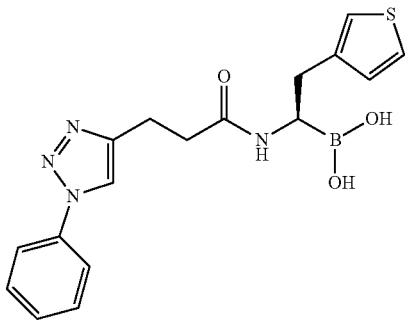 [SMILES: O=C(CCc1cn(-c2ccccc2)nn1)N[C@@H](Cc1ccsc1)B(O)O]

Off-white solid. $^1$H NMR (400 MHz, DMSO-d$_6$): δ 8.39 (s, 1H), 7.78-7.80 (m, 2H), 7.54-7.58 (m, 2H), 7.44-7.47 (m, 1H), 7.27-7.29 (m, 1H), 6.91 (s, 1H), 6.85 (d, J=4.8 Hz, 1H), 2.92-3.11 (m, 1H), 2.88-2.92 (m, 2H), 2.74-2.79 (m, 1H), 2.63-2.69 (m, 1H), 2.46-2.49 (m, 2H).

MS (ESI+): 353.0 [M+H—H$_2$O]. HPLC (Method A): Rt 2.9 min, HPLC purity 95.1%

Example 42: ((1R)-2-(3-ethylphenyl)-1-{[(1-oxoiso-quinolin-2(1H)-yl)acetyl]amino}ethyl)boronic acid

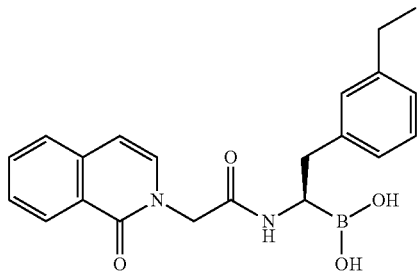 [SMILES: CCc1cccc(C[C@H](NC(=O)Cn2ccc3ccccc3c2=O)B(O)O)c1]

White solid. ¹H NMR (400 MHz, DMSO-d₆): δ 8.82 (s, 1H), 8.19 (d, J=8.0 Hz, 1H), 7.66-7.72 (m, 1H), 7.61-7.63 (m, 1H), 7.46-7.50 (m, 1H), 7.31 (d, J=8.0 Hz, 1H), 6.98-7.02 (m, 1H), 6.87-6.92 (m, 2H), 6.57 (d, J=8.0 Hz, 1H), 4.71-4.76 (m, 2H), 2.66-2.70 (m, 2H), 2.49-2.50 (m, 1H), 2.45-2.48 (m, 2H), 1.08 (t, J=8.0 Hz, 3H). MS (ESI+): 361.3 [M+H—H₂O].

The following compounds were prepared according to the same two-step protocol described for Example 17:

Example 43: (R)-(1-(4-(4-methoxyphenyl)-4-oxobu-tanamido)-2-(4-(trifluoromethoxy)phenyl)ethyl)bo-ronic acid

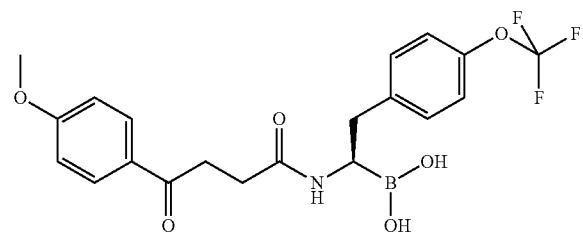 [SMILES: COc1ccc(C(=O)CCC(=O)N[C@@H](Cc2ccc(OC(F)(F)F)cc2)B(O)O)cc1]

Pale brown solid. ¹H NMR (400 MHz, DMSO-d₆): δ 7.90 (dd, J=1.92, 6.96 Hz, 2H), 7.26 (d, J=8.64 Hz, 2H), 7.18 (d, J=8.12 Hz, 2H), 7.00-7.03 (m, 2H), 3.80 (s, 3H), 3.08-3.12 (m, 3H), 2.78-2.83 (m, 1H), 2.65-2.70 (m, 1H), 2.39 (t, J=6.88 Hz, 2H). MS (ESI+): 422.2 [M+H—H₂O]. HPLC (Method A): Rt. 4.0 min, HPLC purity 97.3%

Example 44: ((1R)-1-(2-benzyl-4-(4-methoxyphe-nyl)-4-oxobutanamido)-2-(4-(trifluoromethoxy)phe-nyl)ethyl)boronic acid

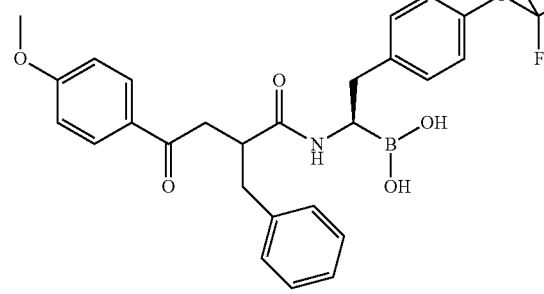

White solid. ¹H NMR (400 MHz, DMSO-d₆): δ 7.82 (d, J=8.88 Hz, 2H), 7.22-7.26 (m, 2H), 7.14-7.18 (m, 3H), 7.05-7.07 (m, 4H), 6.98 (d, J=8.92 Hz, 2H), 3.77 (s, 3H), 3.18-3.24 (m, 1H), 2.95-3.04 (m, 2H), 2.73-2.83 (m, 2H), 2.59-2.71 (m, 3H). MS (ESI+): 512.2 [M+H—H₂O]. HPLC (Method A): Rt. 4.9 min, HPLC purity 73.2%+19.5%

Example 45: ((R)-1-((R)-2-benzyl-4-(4-methoxy-phenyl)-4-oxobutanamido)-2-(4-methoxy-3-(trifluo-romethyl)phenyl)ethyl)boronic acid

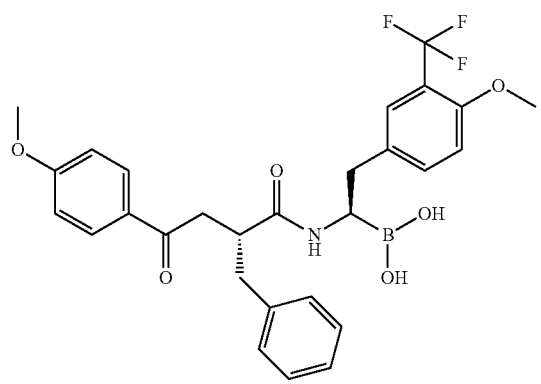 [SMILES: COc1ccc(C(=O)C[C@@H](Cc2ccccc2)C(=O)N[C@@H](Cc2ccc(OC)c(C(F)(F)F)c2)B(O)O)cc1]

White solid. ¹H NMR (400 MHz, DMSO-d₆): δ 7.82 (d, J=8.92 Hz, 2H), 7.32-7.32 (m, 1H), 7.21-7.26 (m, 3H), 7.13-7.18 (m, 3H), 6.97-6.99 (m, 3H), 3.81-3.83 (m, 3H), 3.74 (s, 3H), 3.14-3.16 (m, 1H), 2.98-3.07 (m, 2H), 2.68-2.84 (m, 3H), 2.53-2.60 (m, 2H). MS (ESI+): 526.2 [M+H—H₂O]. HPLC (Method A): Rt. 4.7 min, HPLC purity 95.8%

Example 46: (R)-(2-(4-methoxy-3-(trifluoromethyl)phenyl)-1-(4-(4-methoxyphenyl)-4-oxobutanamido)ethyl)boronic acid

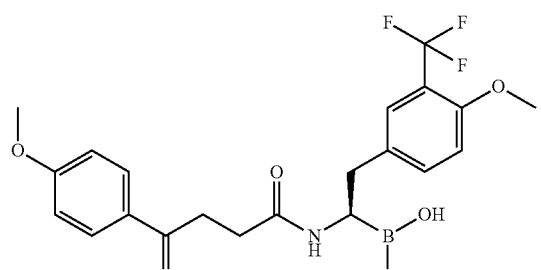

White solid. ¹H NMR (400 MHz, DMSO-d₆): δ 7.88-7.92 (m, 2H), 7.38-7.39 (m, 2H), 7.10 (d, J=8.84 Hz, 1H), 7.00-7.04 (m, 2H), 3.81 (s, 6H), 3.05-3.13 (m, 3H), 2.75-2.80 (m, 1H), 2.61-2.67 (m, 1H), 2.32-2.40 (m, 2H). MS (ESI+): 436.2 [M+H—H₂O]. HPLC (Method A): Rt. 3.9 min, HPLC purity 95.7%

Example 47: (R)-(2-(3-fluoro-5-methoxyphenyl)-1-(4-(4-methoxyphenyl)-4-oxobutanamido)ethyl)boronic acid

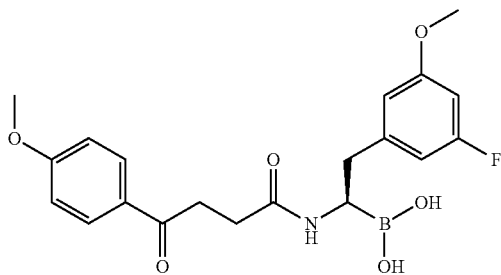 [SMILES: COc1ccc(C(=O)CCC(=O)N[C@@H](Cc2cc(F)cc(OC)c2)B(O)O)cc1]

White solid. ¹H NMR (400 MHz, DMSO-d₆): δ 7.91 (d, J=8.84 Hz, 2H), 7.02 (d, J=8.88 Hz, 2H), 6.55-6.59 (m, 3H), 3.81 (s, 3H), 3.71 (s, 3H), 3.09-3.13 (m, 3H), 2.73-2.78 (m, 1H), 2.60-2.66 (m, 1H), 2.49-2.50 (m, 2H), 2.38-2.40 (m, 1H). MS (ESI+): 386.2 [M+H—H₂O]. HPLC (Method A): Rt. 3.4 min, HPLC purity 99.3%

Example 48: (R)-(1-(4-(4-methoxyphenyl)-4-oxobutanamido)-2-(3-(trifluoromethoxy)phenyl)ethyl)boronic acid

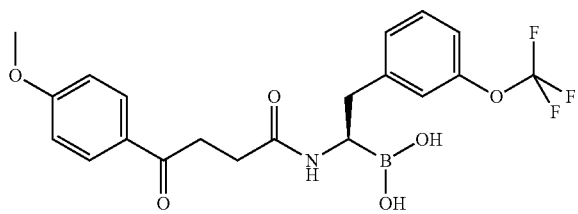 [SMILES: COc1ccc(C(=O)CCC(=O)N[C@@H](Cc2cccc(OC(F)(F)F)c2)B(O)O)cc1]

Off-white solid. ¹H NMR (400 MHz, DMSO-d₆): δ 7.89-7.92 (m, 2H), 7.34-7.38 (m, 1H), 7.18-7.20 (m, 1H), 7.13-7.14 (m, 2H), 7.00-7.04 (m, 2H), 3.82 (s, 3H), 3.08-3.17 (m, 3H), 2.82-2.87 (m, 1H), 2.70-2.73 (m, 1H), 2.39-2.40 (m, 2H). MS (ESI+): 422.2 [M+H—H₂O]. HPLC (Method A): Rt. 4.0 min, HPLC purity 99.0%

Example 49: ((1R)-1-(2-benzyl-4-(4-methoxyphenyl)-4-oxobutanamido)-2-(3-fluoro-5-methoxyphenyl)ethyl)boronic acid

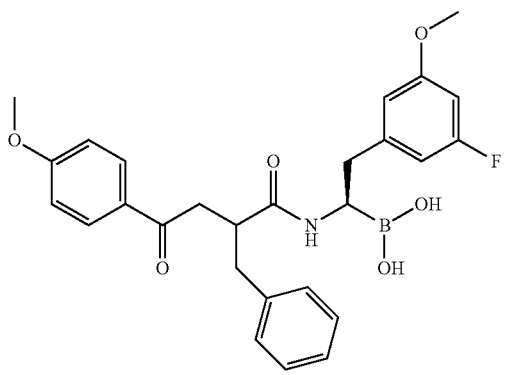 [SMILES: COc1ccc(C(=O)CC(Cc2ccccc2)C(=O)N[C@@H](Cc2cc(F)cc(OC)c2)B(O)O)cc1]

White solid. ¹H NMR (400 MHz, DMSO-d₆): δ 7.79-7.80 (m, 2H), 7.11-7.25 (m, 5H), 6.95-6.97 (m, 2H), 6.43-6.49 (m, 2H), 6.35 (d, J=9.36 Hz, 1H), 3.76 (s, 1H), 3.65 (s, 3H), 3.19-3.25 (m, 1H), 3.00-3.02 (m, 1H), 2.77-2.98 (m, 3H), 2.61-2.66 (m, 2H), 2.44-2.46 (m, 1H). MS (ESI+): 476.2 [M+H—H₂O]. HPLC (Method A): Rt. 4.4 min, HPLC purity 72.2%+23.0%

Example 50: (R)-(2-(4-fluoro-3-(trifluoromethyl)phenyl)-1-(4-(4-methoxyphenyl)-4-oxobutanamido)ethyl)boronic acid

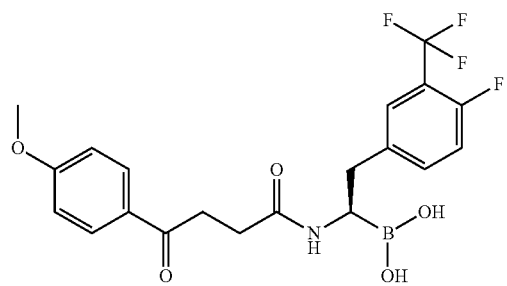 [SMILES: COc1ccc(C(=O)CCC(=O)N[C@@H](Cc2ccc(F)c(C(F)(F)F)c2)B(O)O)cc1]

White solid. ¹H NMR (400 MHz, DMSO-d₆): δ 7.89 (d, J=8.00 Hz, 2H), 7.48-7.52 (m, 2H), 7.29-7.34 (m, 1H), 7.01 (d, J=8.00 Hz, 2H), 3.80 (s, 3H), 3.07-3.12 (m, 3H), 2.81-2.86 (m, 1H), 2.66-2.72 (m, 1H), 2.50-2.51 (m, 2H), 2.35-2.39 (m, 2H). MS (ESI+): 424.2 [M+H—H₂O]. HPLC (Method A): Rt. 4.0 min, HPLC purity 98.6%

Example 58: (R)-(2-(3-ethylphenyl)-1-(3-(1-phenyl-1H-1,2,3-triazol-4-yl)propanamido)ethyl)boronic acid

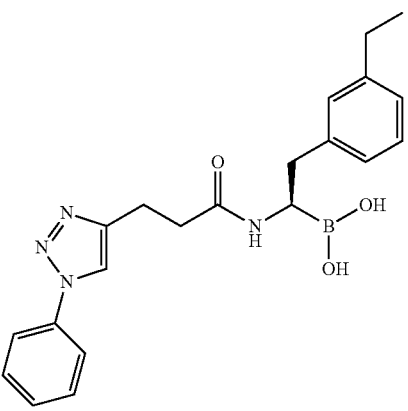 [SMILES: CCc1cccc(C[C@H](NC(=O)CCc2cn(-c3ccccc3)nn2)B(O)O)c1]

White solid. ¹H NMR (400 MHz, DMSO-d₆): δ 8.40 (s, 1H), 7.83-7.83 (m, 2H), 7.54-7.58 (m, 2H), 7.44-7.47 (m, 1H), 7.05-7.09 (m, 1H), 6.87-6.94 (m, 3H), 3.12-3.16 (m, 1H), 2.86-2.90 (m, 2H), 2.73-2.74 (m, 1H), 2.60-2.66 (m, 1H), 2.41-2.51 (m, 4H), 1.11 (t, J=7.60 Hz, 3H). MS (ESI+): 375.2 [M+H—H₂O]. HPLC (Method A): Rt. 3.6 min, HPLC purity 96.8%

95

Example 61: (R)-(2-(3-fluoro-5-methoxyphenyl)-1-(3-(5-phenyl-1,2,4-oxadiazol-3-yl)propanamido)ethyl)boronic acid

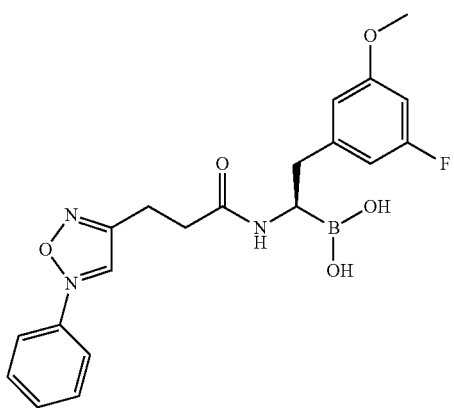

White solid. ¹H NMR (400 MHz, DMSO-d₆): δ 8.03-8.03 (m, 2H), 7.57-7.68 (m, 3H), 6.47-6.52 (m, 3H), 3.65 (s, 3H), 3.11-3.14 (m, 1H), 2.90-2.94 (m, 2H), 2.71-2.76 (m, 1H), 2.58-2.63 (m, 1H), 2.51-2.53 (m, 2H). MS (ESI+): 396.2 [M+H—H₂O]. HPLC (Method A): Rt. 3.6 min, HPLC purity 97.1%

The following compounds were prepared according to the same two-step protocol described for Example 1:

Example 51: (R)-(1-(3-(1H-benzo[d]imidazol-1-yl)propanamido)-2-(4-(trifluoromethoxy)phenyl)ethyl)boronic acid

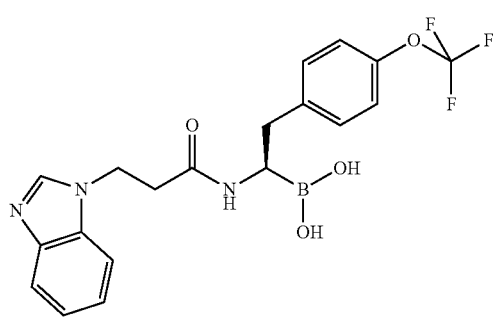 [SMILES: O=C(CCn1cnc2ccccc21)N[C@@H](Cc1ccc(OC(F)(F)F)cc1)B(O)O]

Off-white solid. ¹H NMR (400 MHz, DMSO-d₆): δ 8.09 (s, 1H), 7.64 (d, J=7.56 Hz, 1H), 7.57 (d, J=7.68 Hz, 1H), 7.19-7.28 (m, 2H), 6.96 (d, J=8.08 Hz, 2H), 6.85 (d, J=8.56 Hz, 2H), 4.40 (t, J=6.32 Hz, 2H), 3.07-3.10 (m, 1H), 2.49-2.70 (m, 4H). MS (ESI+): 426.0 [M+Na—H₂O]. HPLC (Method A): Rt. 3.2 min, HPLC purity 96.5%

96

Example 52: (R)-(2-(3-ethylphenyl)-1-(3-(4-phenyl-1H-1,2,3-triazol-1-yl)propanamido)ethyl)boronic acid

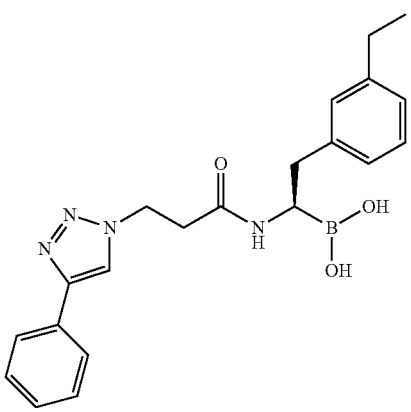

Off-white solid. ¹H NMR (400 MHz, DMSO-d₆): δ 8.30 (s, 1H), 7.77 (d, J=7.20 Hz, 2H), 7.41 (t, J=7.76 Hz, 3H), 7.29-7.33 (m, 1H), 7.00 (t, J=7.52 Hz, 1H), 6.88 (d, J=7.88 Hz, 1H), 6.81 (s, 1H), 6.75 (d, J=7.40 Hz, 1H), 3.07-3.11 (m, 1H), 2.66-2.70 (m, 3H), 2.55-2.57 (m, 1H), 2.39-2.44 (m, 2H), 1.03 (t, J=7.96 Hz, 3H). MS (ESI+): 397.2 [M+Na—H₂O]. HPLC (Method A): Rt. 3.7 min, HPLC purity 96.5%

Example 53: (R)-(1-(3-(1H-benzo[d]imidazol-1-yl)propanamido)-2-(4-methoxy-3-(trifluoromethyl)phenyl)ethyl)boronic acid

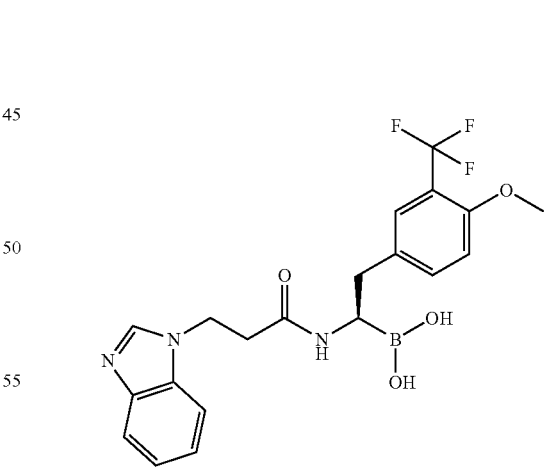

White solid. ¹H NMR (400 MHz, DMSO-d₆): δ 8.09 (s, 1H), 7.65 (d, J=8.24 Hz, 1H), 7.56 (d, J=7.40 Hz, 1H), 7.19-7.29 (m, 3H), 6.91 (dd, J=1.92, 8.54 Hz, 1H), 6.81 (d, J=8.56 Hz, 1H), 4.39 (t, J=6.76 Hz, 2H), 3.76 (s, 3H), 3.09-3.13 (m, 1H), 2.67-2.70 (m, 1H), 2.54-2.61 (m, 3H). MS (ESI+): 440.0 [M+Na—H₂O]. HPLC (Method A): Rt. 3.0 min, HPLC purity 94.5%

Example 54: (R)-(2-(3-ethylphenyl)-1-(3-(2-methyl-1H-benzo[d]imidazol-1-yl)propanamido)ethyl)boronic acid

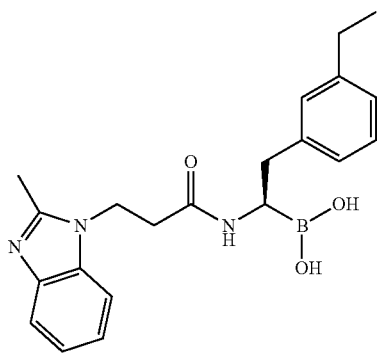 [SMILES: CCc1cccc(C[C@H](NC(=O)CCn2c(C)nc3ccccc32)B(O)O)c1]

White solid. ¹H NMR (400 MHz, DMSO-d₆): δ 7.43-7.50 (m, 2H), 7.13-7.17 (m, 2H), 6.89-6.99 (m, 2H), 6.77 (s, 1H), 6.59 (d, J=7.40 Hz, 1H), 4.28-4.32 (m, 2H), 3.10-3.13 (m, 1H), 2.52-2.62 (m, 4H), 2.40-2.44 (m, 2H), 1.07 (t, J=7.60 Hz, 3H).). MS (ESI+): 384.2 [M+Na—H₂O]. HPLC (Method A): Rt. 3.0 min, HPLC purity 98.7%

Example 55: (R)-(1-(3-(2-methyl-1H-benzo[d]imidazol-1-yl)propanamido)-2-(thiophen-3-yl)ethyl)boronic acid

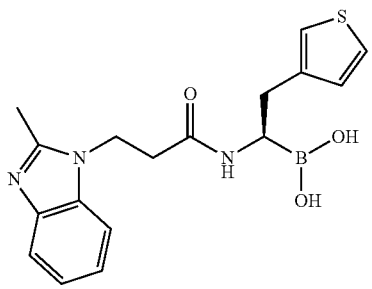

White solid. ¹H NMR (400 MHz, DMSO-d₆): δ 7.44-7.50 (m, 2H), 7.11-7.25 (m, 3H), 6.65-6.68 (m, 2H), 4.28-4.37 (m, 2H), 3.09-3.12 (m, 1H), 2.51-2.68 (m, 7H). MS (ESI+): 362.2 [M+Na—H₂O]. HPLC (Method A): Rt. 2.0 min, HPLC purity 93.7%

Example 56: (R)-(2-(4-methoxy-3-(trifluoromethyl)phenyl)-1-(3-(5-phenyl-1,2,4-oxadiazol-3-yl)propanamido)ethyl)boronic acid

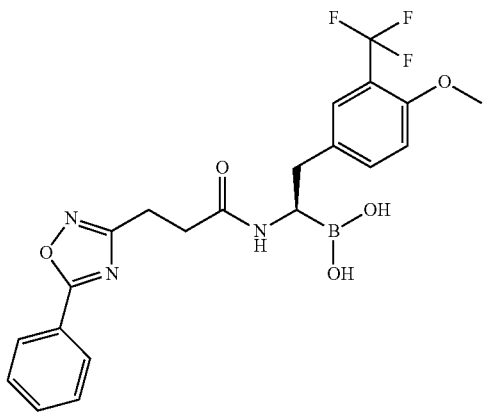 [SMILES: COc1ccc(C[C@H](NC(=O)CCc2noc(-c3ccccc3)n2)B(O)O)cc1C(F)(F)F]

White solid. ¹H NMR (400 MHz, DMSO-d₆): δ 8.06 (d, J=7.20 Hz, 2H), 7.59-7.70 (m, 3H), 7.31-7.35 (m, 2H), 7.04 (d, J=8.44 Hz, 1H), 3.76 (s, 3H), 3.14-3.17 (m, 1H), 2.90-2.94 (m, 2H), 2.76-2.81 (m, 1H), 2.63-2.68 (m, 1H), 2.48-249.00 (m, 2H). MS (ESI+): 446.2 [M+H—H₂O]. HPLC (Method A): Rt. 4.0 min, HPLC purity 97.7%

Example 57: (R)-(1-(3-(1H-benzo[d]imidazol-1-yl)propanamido)-2-(3-fluoro-5-methoxyphenyl)ethyl)boronic acid

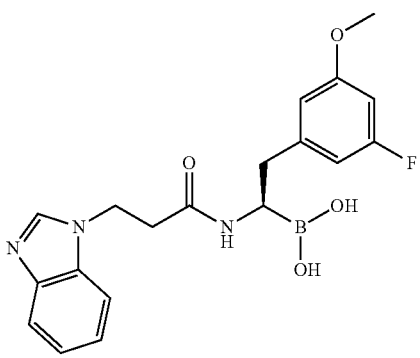 [SMILES: COc1cc(F)cc(C[C@H](NC(=O)CCn2cnc3ccccc32)B(O)O)c1]

White solid. ¹H NMR (400 MHz, DMSO-d₆): δ 8.07 (s, 1H), 7.54-7.62 (m, 2H), 7.17-7.26 (m, 2H), 6.51-6.54 (m, 1H), 6.50 (s, 1H), 6.37-6.45 (m, 1H), 4.36-4.40 (m, 2H), 3.64 (s, 3H), 3.11-3.14 (m, 1H), 2.53-2.69 (m, 4H). MS (ESI+): 390.2 [M+Na—H₂O]. HPLC (Method A): Rt. 2.5 min, HPLC purity 98.8%

Example 59: (R)-(1-(3-(1H-benzo[d]imidazol-1-yl)propanamido)-2-(3-(trifluoromethoxy)phenyl)ethyl)boronic acid

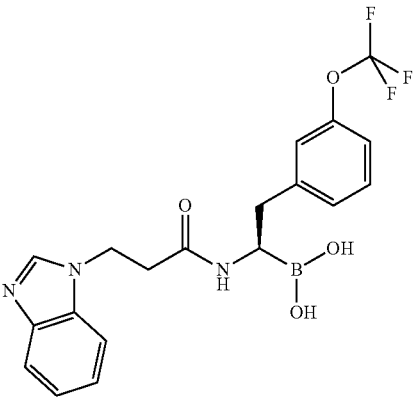 [SMILES: O=C(CCn1cnc2ccccc21)N[C@@H](Cc1cccc(OC(F)(F)F)c1)B(O)O]

White solid. ¹H NMR (400 MHz, DMSO-d₆): δ 8.08 (s, 1H), 7.55-7.57 (m, 1H), 7.61-7.63 (m, 1H), 7.15-7.26 (m, 3H), 7.05-7.07 (m, 1H), 7.00 (s, 1H), 6.81-6.83 (m, 1H), 4.39 (t, J=6.72 Hz, 2H), 3.15 (t, J=5.60 Hz, 1H), 2.73-2.78 (m, 1H), 2.57-2.65 (m, 3H). MS (ESI+): 426.2 [M+Na—H₂O]. HPLC (Method A): Rt. 3.1 min, HPLC purity 99.6%

Example 60: (R)-(1-(3-(5-phenyl-1,2,4-oxadiazol-3-yl)propanamido)-2-(3-(trifluoromethoxy)phenyl)ethyl)boronic acid Example 63: ((R)-1-((S)-2-benzyl-3-(1-phenyl-1H-1,2,3-triazol-4-yl)propanamido)-2-(thiophen-3-yl)ethyl)boronic acid

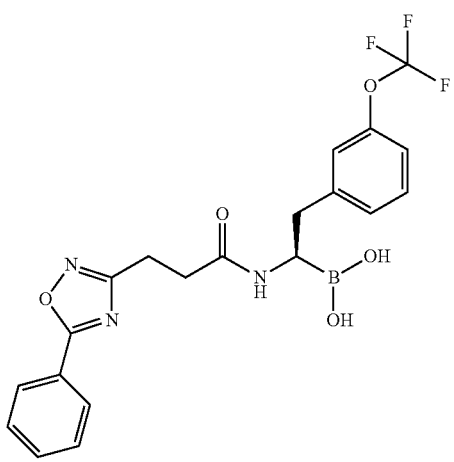 [SMILES: O=C(CCc1noc(-c2ccccc2)n1)N[C@@H](Cc1cccc(OC(F)(F)F)c1)B(O)O]

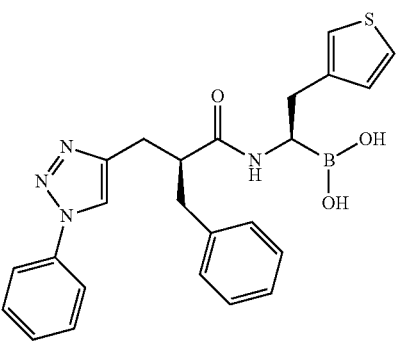

White solid. $^1$H NMR (400 MHz, DMSO-d$_6$): δ 8.04-8.05 (m, 2H), 7.58-7.70 (m, 3H), 7.29-7.33 (m, 1H), 7.08-7.29 (m, 3H), 3.17-3.21 (m, 1H), 2.82-2.93 (m, 3H), 2.67-2.73 (m, 1H), 2.49-2.51 (m, 2H). MS (ESI+): 432.0 [M+H—H$_2$O]. HPLC (Method A): Rt. 4.2 min, HPLC purity 98.3%

White solid. $^1$H NMR (400 MHz, DMSO-d$_6$): δ 8.39 (s, 1H), 7.75-7.77 (m, 2H), 7.52-7.56 (m, 2H), 7.44-7.45 (m, 1H), 7.23-7.27 (m, 2H), 7.15-7.19 (m, 4H), 6.61-6.64 (m, 2H), 2.84-2.95 (m, 4H), 2.63-2.70 (m, 3H), 2.52-2.54 (m, 1H). MS (ESI+): 443.2 [M+H—H$_2$O]. HPLC (Method A): Rt. 4.0 min, HPLC purity 99.6%

Example 62: ((R)-1-((R)-2-benzyl-3-(1-phenyl-1H-1,2,3-triazol-4-yl)propanamido)-2-(thiophen-3-yl)ethyl)boronic acid Example 64: (R)-(1-(3-(1H-benzo[d]imidazol-1-yl)propanamido)-2-(4-fluoro-3-(trifluoromethyl)phenyl)ethyl)boronic acid

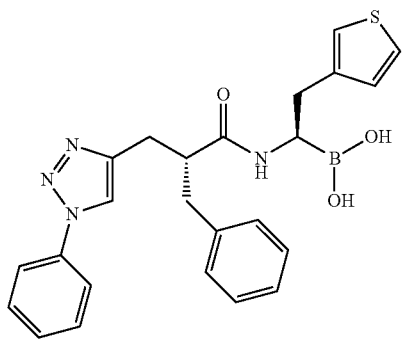 [SMILES: O=C(N[C@@H](Cc1ccsc1)B(O)O)[C@H](Cc1ccccc1)Cc1cn(-c2ccccc2)nn1]

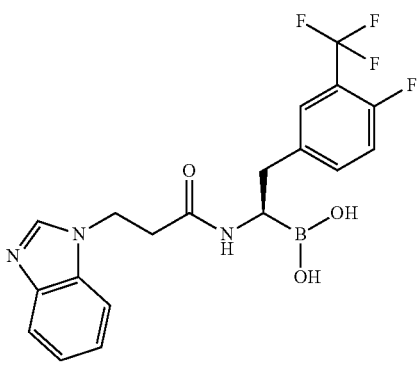 [SMILES: O=C(CCn1cnc2ccccc21)N[C@@H](Cc1ccc(F)c(C(F)(F)F)c1)B(O)O]

White solid. $^1$H NMR (400 MHz, DMSO-d$_6$): δ 8.39 (s, 1H), 7.76-7.78 (m, 2H), 7.53-7.57 (m, 2H), 7.44-7.46 (m, 1H), 7.23-7.27 (m, 3H), 7.16-7.18 (m, 3H), 6.62-6.67 (m, 2H), 3.07-3.10 (m, 1H), 2.81-2.94 (m, 3H), 2.71-2.75 (m, 1H), 2.56-2.66 (m, 3H). MS (ESI+): 443.2 [M+H—H$_2$O]. HPLC (Method A): Rt. 4.0 min, HPLC purity 97.7%

White solid. $^1$H NMR (400 MHz, DMSO-d$_6$): δ 8.07 (s, 1H), 7.63 (d, J=8.00 Hz, 1H), 7.54 (d, J=8.00 Hz, 1H), 7.39-7.41 (m, 1H), 7.18-7.27 (m, 2H), 7.04-7.10 (m, 2H), 4.38 (t, J=6.60 Hz, 2H), 3.08-3.12 (m, 1H), 2.71-2.76 (m, 1H), 2.56-2.62 (m, 3H). MS (ESI+): 428.0 [M+Na—H$_2$O]. HPLC (Method A): Rt. 3.1 min, HPLC purity 98.8%

Example 65: (R)-(2-(3-fluoro-5-methoxyphenyl)-1-(3-(4-phenyl-1H-1,2,3-triazol-1-yl)propanamido)ethyl)boronic acid

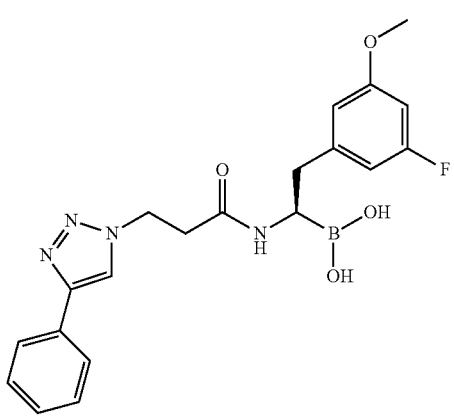 [SMILES: COc1cc(F)cc(C[C@H](NC(=O)CCn2cc(-c3ccccc3)nn2)B(O)O)c1]

White solid. $^1$H NMR (400 MHz, DMSO-$d_6$): δ 8.37 (s, 1H), 7.78 (d, J=8.00 Hz, 2H), 7.39-7.43 (m, 2H), 7.29-7.32 (m, 1H), 6.46-6.53 (m, 3H), 4.55 (t, J=6.80 Hz, 2H), 3.66 (s, 3H), 3.13-3.17 (m, 1H), 2.58-2.75 (m, 4H). MS (ESI+): 395.3 [M+H—H$_2$O]. HPLC (Method A): Rt. 3.4 min, HPLC purity 98.6%

Example 66: (R)-(1-(3-(4-phenyl-1H-1,2,3-triazol-1-yl)propanamido)-2-(3-(2,2,2-trifluoroethyl)phenyl)ethyl)boronic acid

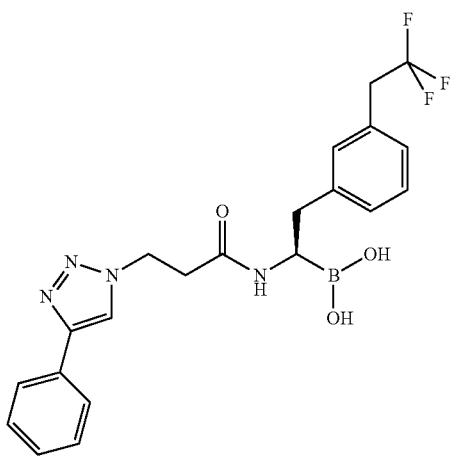 [SMILES: O=C(CCn1cc(-c2ccccc2)nn1)N[C@@H](Cc1cccc(CC(F)(F)F)c1)B(O)O]

White solid. $^1$H NMR (400 MHz, DMSO-$d_6$): δ 8.40 (s, 1H), 7.77-7.80 (m, 2H), 7.40-7.43 (m, 2H), 7.23-7.33 (m, 2H), 7.01-7.05 (m, 3H), 4.54 (t, J=6.80 Hz, 2H), 3.15-3.19 (m, 1H), 2.79-2.83 (m, 1H), 2.63-2.69 (m, 3H). MS (ESI+): 431.0 [M+H—H$_2$O]. HPLC (Method A): Rt. 4.0 min, HPLC purity 96.2%

Example 67: (R)-(1-(3-(1H-benzo[d]imidazol-1-yl)propanamido)-2-(3-ethoxyphenyl)ethyl)boronic acid

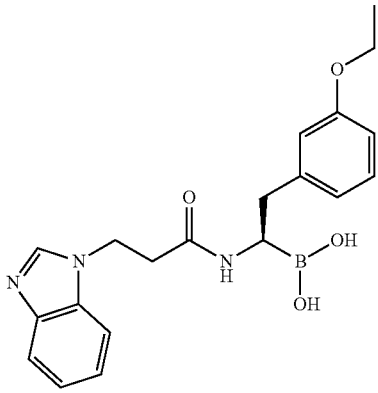 [SMILES: CCOc1cccc(C[C@H](NC(=O)CCn2cnc3ccccc32)B(O)O)c1]

White solid. $^1$H NMR (400 MHz, DMSO-$d_6$): δ 8.07 (s, 1H), 7.62 (d, J=7.60 Hz, 1H), 7.56 (d, J=7.60 Hz, 1H), 7.17-7.26 (m, 2H), 6.95 (t, J=8.00 Hz, 1H), 6.58-6.63 (m, 2H), 6.39 (d, J=8.00 Hz, 1H), 4.39 (t, J=6.40 Hz, 2H), 3.85-3.90 (m, 2H), 3.11-3.13 (m, 1H), 2.55-2.64 (m, 4H), 1.24 (t, J=6.80 Hz, 3H). MS (ESI+): 386.2 [M+Na—H$_2$O]. HPLC (Method A): Rt. 2.5 min, HPLC purity 98.5

Example 68: (R)-(2-(3-ethoxyphenyl)-1-(3-(5-phenyl-1,2,4-oxadiazol-3-yl)propanamido)ethyl)boronic acid

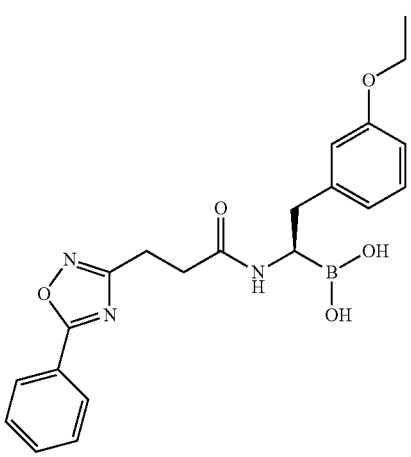 [SMILES: CCOc1cccc(C[C@H](NC(=O)CCc2noc(-c3ccccc3)n2)B(O)O)c1]

White solid. $^1$H NMR (400 MHz, DMSO-$d_6$): δ 8.05 (d, J=-8.00 Hz, 2H), 7.65-7.69 (m, 1H), 7.58-7.62 (m, 2H), 7.06 (t, J=7.60 Hz, 1H), 6.63-6.67 (m, 3H), 3.89-3.94 (m, 2H), 3.14-3.17 (m, 1H), 2.92 (t, J=7.60 Hz, 2H), 2.71-2.76 (m, 1H), 2.61-2.64 (m, 1H), 2.52-2.59 (m, 2H), 1.26-1.28 (m, 3H). MS (ESI+): 392.3 [M+H—H$_2$O]. HPLC (Method A): Rt. 3.7 min, HPLC purity 98.7%

Example 69: (R)-(1-(3-(1H-benzo[d]imidazol-1-yl)propanamido)-2-(4-fluoro-3-methoxyphenyl)ethyl)boronic acid

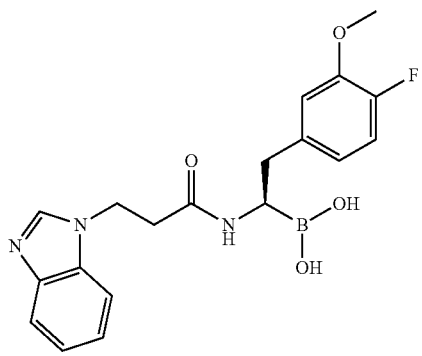 [SMILES: COc1cc(C[C@H](NC(=O)CCn2cnc3ccccc32)B(O)O)ccc1F]

White solid. $^1$H NMR (400 MHz, DMSO-$d_6$): δ 8.07 (s, 1H), 7.62 (d, J=8.00 Hz, 1H), 7.55 (d, J=8.00 Hz, 1H), 7.19-7.27 (m, 2H), 6.74-6.81 (m, 2H), 6.27-6.30 (m, 1H), 4.40 (t, J=6.40 Hz, 2H), 3.66 (s, 3H), 3.05-3.09 (m, 1H), 2.60-2.64 (m, 3H), 2.54-2.58 (m, 1H). MS (ESI+): 386.2 [M+H—H$_2$O]. HPLC (Method A): Rt. 2.4 min, HPLC purity 96.6%

Example 70: (2-(3-ethoxyphenyl)-1-(3-(4-phenyl-1H-1,2,3-triazol-1-yl)propanamido)ethyl)boronic acid

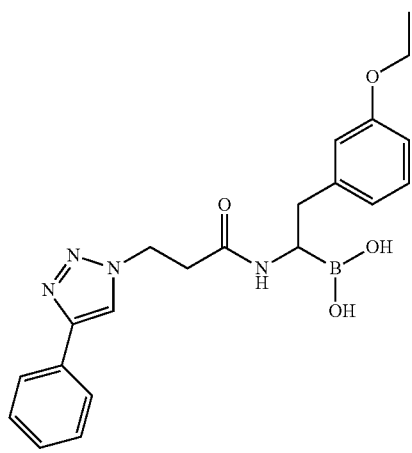 [SMILES: CCOc1cccc(CC(NC(=O)CCn2cc(-c3ccccc3)nn2)B(O)O)c1]

White solid. $^1$H NMR (400 MHz, DMSO-$d_6$): δ 8.34 (s, 1H), 7.78 (d, J=8.00 Hz, 2H), 7.42 (t, J=13.88 Hz, 2H), 7.29-7.33 (m, 1H), 6.99-7.03 (m, 1H), 6.59-6.62 (m, 2H), 6.55 (d, J=8.00 Hz, 1H), 4.55 (t, J=7.24 Hz, 2H), 3.85-3.91 (m, 2H), 3.12-3.15 (m, 1H), 2.66-2.71 (m, 3H), 2.58-2.61 (m, 1H), 1.24 (t, J=7.00 Hz, 3H). MS (ESI+): 413.3 [M+Na—H$_2$O]. HPLC (Method A): Rt. 3.4 min, HPLC purity 98.5%

Example 71: (R)-(2-(4-fluoro-3-(trifluoromethyl)phenyl)-1-(3-(4-phenyl-1H-1,2,3-triazol-1-yl)propanamido)ethyl)boronic acid

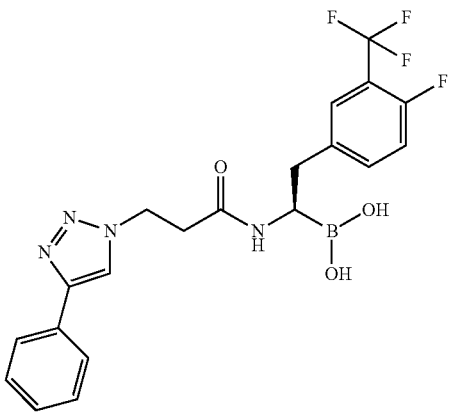 [SMILES: O=C(CCn1cc(-c2ccccc2)nn1)N[C@@H](Cc1ccc(F)c(C(F)(F)F)c1)B(O)O]

White solid. $^1$H NMR (400 MHz, DMSO-$d_6$): δ 8.35 (s, 1H), 7.76-7.78 (m, 2H), 7.39-7.45 (m, 3H), 7.29-7.32 (m, 2H), 7.15-7.20 (m, 1H), 4.53 (t, J=8.00 Hz, 2H), 3.11-3.14 (m, 1H), 2.77-2.82 (m, 1H), 2.62-2.69 (m, 3H). MS (ESI+): 433.3 [M+H—H$_2$O]. HPLC (Method A): Rt. 3.9 min, HPLC purity 98.1%

Example 72: (R)-(1-(3-(1H-benzo[d]imidazol-1-yl)propanamido)-2-(3-methoxy-4-methylphenyl)ethyl)boronic acid

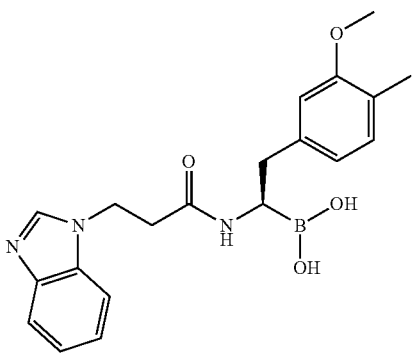 [SMILES: COc1cc(C[C@H](NC(=O)CCn2cnc3ccccc32)B(O)O)ccc1C]

White solid. $^1$H NMR (400 MHz, DMSO-$d_6$): δ 8.06 (s, 1H), 7.62 (d, J=8.00 Hz, 1H), 7.54 (d, J=8.00 Hz, 1H), 7.19-7.27 (m, 2H), 6.77 (d, J=8.00 Hz, 1H), 6.54 (s, 1H), 6.26 (d, J=8.00 Hz, 1H), 4.40 (t, J=6.40 Hz, 2H), 3.59 (s, 3H), 3.09 (t, J=7.20 Hz, 1H), 2.58-2.63 (m, 4H), 1.98 (s, 3H). MS (ESI+): 386.2 [M+Na—H$_2$O]. HPLC (Method A): Rt. 2.7 min, HPLC purity 97.1%

Example 73: (R)-(2-(3-ethylphenyl)-1-(3-(4-(2-methoxyphenyl)-1H-1,2,3-triazol-1-yl)propanamido)ethyl)boronic acid

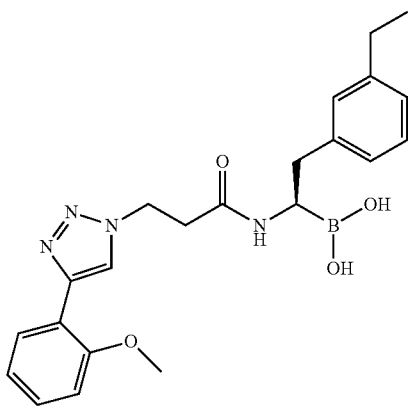 [SMILES: CCc1cccc(C[C@H](NC(=O)CCn2cc(-c3ccccc3OC)nn2)B(O)O)c1]

White solid. $^1$H NMR (400 MHz, DMSO-d$_6$): δ 8.25 (s, 1H), 8.07-8.09 (m, 1H), 7.28-7.32 (m, 1H), 6.97-7.09 (m, 3H), 6.87 (d, J=8.00 Hz, 1H), 6.82 (s, 1H), 6.77 (d, J=8.00 Hz, 1H), 4.56 (t, J=8.00 Hz, 2H), 3.85 (s, 3H), 3.13-3.17 (m, 1H), 2.59-2.71 (m, 4H), 2.37-2.43 (m, 2H), 1.03 (t, J=8.00 Hz, 3H). MS (ESI+): 427.2 [M+Na—H$_2$O]. HPLC (Method A): Rt. 3.8 min, HPLC purity 97.6%

Example 74: (R)-(2-(3-ethylphenyl)-1-(3-(4-(3-methoxyphenyl)-1H-1,2,3-triazol-1-yl)propanamido)ethyl)boronic acid

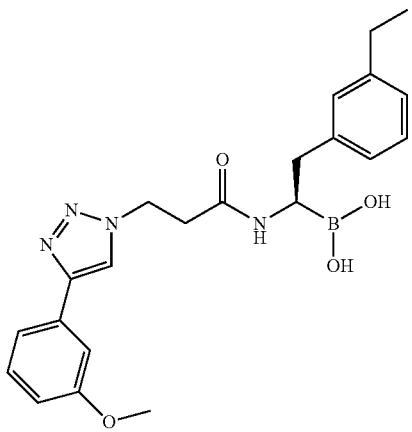 [SMILES: CCc1cccc(C[C@H](NC(=O)CCn2cc(-c3cccc(OC)c3)nn2)B(O)O)c1]

White solid. $^1$H NMR (400 MHz, DMSO-d$_6$): δ 8.37 (s, 1H), 7.33-7.35 (m, 3H), 6.99-7.03 (m, 1H), 6.84-6.90 (m, 3H), 6.78 (d, J=8.00 Hz, 1H), 4.55 (t, J=12.00 Hz, 2H), 3.79 (s, 3H), 3.10-3.14 (m, 1H), 2.65-2.69 (m, 3H), 2.58-2.60 (m, 1H), 2.41-2.46 (m, 2H), 1.06-1.08 (m, 3H). MS (ESI+): 427.2 [M+Na—H$_2$O]. HPLC (Method A): Rt. 3.7 min, HPLC purity 98.0%

Example 75: (R)-(2-(3-ethylphenyl)-1-(3-(4-(4-methoxyphenyl)-1H-1,2,3-triazol-1-yl)propanamido)ethyl)boronic acid

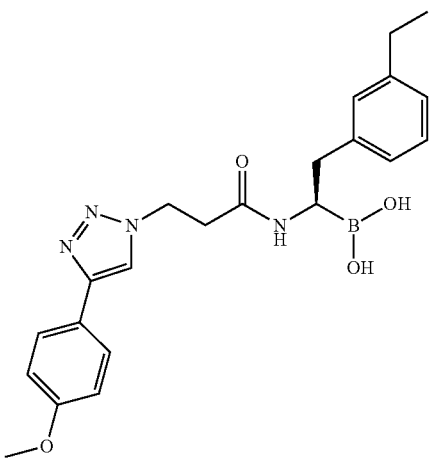 [SMILES: CCc1cccc(C[C@H](NC(=O)CCn2cc(-c3ccc(OC)cc3)nn2)B(O)O)c1]

White solid. $^1$H NMR (400 MHz, DMSO-d6): δ 8.23 (s, 1H), 7.71 (d, J=8.00 Hz, 2H), 6.96-7.04 (m, 4H), 6.85-6.91 (m, 1H), 6.79 (d, J=8.00 Hz, 1H), 4.53 (t, J=8.00 Hz, 2H), 3.11-3.15 (m, 1H), 2.54-2.73 (m, 4H), 2.42-2.45 (m, 2H), 1.05-1.09 (m, 3H). MS (ESI+): 427.2 [M+Na—H$_2$O]. HPLC (Method A): Rt. 3.6 min, HPLC purity 98.1%

Example 76: (R)-(2-(3-ethylphenyl)-1-(3-(4-(pyridin-3-yl)-1H-1,2,3-triazol-1-yl)propanamido)ethyl)boronic acid

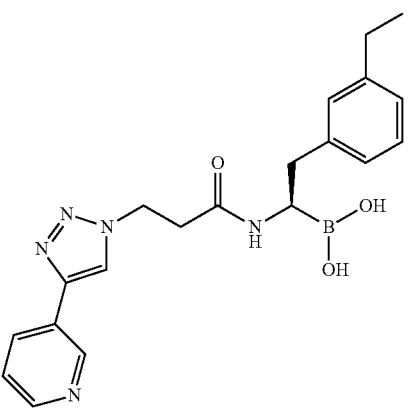 [SMILES: CCc1cccc(C[C@H](NC(=O)CCn2cc(-c3cccnc3)nn2)B(O)O)c1]

White solid. $^1$H NMR (400 MHz, DMSO-d6): δ 8.95 (s, 1H), 8.45-8.49 (m, 2H), 8.15-8.17 (m, 1H), 7.46-7.49 (m, 1H), 6.98-7.02 (m, 1H), 6.83-6.88 (m, 2H), 6.77 (d, J=8.00 Hz, 1H), 4.55-4.59 (m, 2H), 3.11-3.13 (m, 1H), 2.67-2.70 (m, 3H), 2.57-2.59 (m, 1H), 2.39-2.45 (m, 2H), 1.04 (t, J=8.00 Hz, 3H). MS (ESI+): 398.3 [M+Na—H$_2$O]. HPLC (Method A): Rt. 2.4 min, HPLC purity 97.9%

107

Example 78: (R)-(1-acetamido-2-(benzofuran-3-yl)ethyl)boronic acid

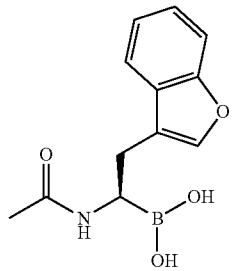 [SMILES: CC(=O)N[C@@H](Cc1coc2ccccc12)B(O)O]

Step 1: (R)-(1-acetamido-2-(benzofuran-3-yl)ethyl)boronic acid(+)-pinanediol ester A cooled (−10° C.) solution of Intermediate 18 (700 mg, 1.54 mmol) in anhydrous dichloromethane (20 ml) was treated with diisopropylethylamine (0.8 ml, 4.6 mmol) and acetyl chloride (0.09 ml, 1.54 mmol). The reaction mixture was stirred at −10° C. for 3 h. The reaction mixture was concentrated under reduced pressure keeping an external bath temperature below 30° C., and then 25 ml ethyl acetate were added. The organic layer was washed with brine, dried over sodium sulfate and concentrated. The desired product (520 mg, 88%) was isolated by purification by chromatography on silica gel, eluting with 2° A) methanol in dichloromethane.

MS (ESI+): 382.3

Step 2: (R)-(1-acetamido-2-(benzofuran-3-yl)ethyl)boronic acid

A cooled (0° C.) solution of (R)-(1-acetamido-2-(benzofuran-3-yl)ethyl)boronic acid(+)-pinanediol ester (520 mg, 1.35 mmol) in methanol/pentane (1:1, 30 mL) was treated with 2-methylpropyl boronic acid (545 mg, 5.4 mmol) and an aqueous HCl solution (1.5 N, 1 mL) and the reaction mixture was stirred at room temperature for 15 h. The reaction mixture was then extracted with pentane thrice. The aqueous methanol layer was concentrated at temperature below 30° C. The residue was treated with ice and basified with an aqueous (2N) solution of NaOH and extracted with dichloromethane thrice (discarded). The aqueous layer was then acidified with an aqueous (1.5 N) HCl solution and extracted with dichloromethane thrice. The DCM layer was dried over sodium sulfate, filtered and concentrated to give a solid residue, which was triturated with diethylether and lyophilized to obtain the title compound (42 mg, 26%) as a white solid.

$^1$H NMR: (400 MHz, DMSO-$d_6$): δ 7.64 (s, 1H), 7.58-7.60 (d, J=8.0 Hz, 1H), 7.48-7.50 (d, J=8.0 Hz, 1H), 7.19-7.28 (m, 2H), 3.09-3.13 (m, 1H), 2.81-2.86 (m, 1H), 2.69-2.75 (m, 1H), 1.77 (s, 3H).

MS (ESI+): 230.0 [M+H—H$_2$O], HPLC (Method A): Rt 2.0 min; HPLC purity 98.8%

The following compounds were synthesized using the same procedure followed for Example 78

108

Example 77: (R)-(1-acetamido-2-(3-ethylphenyl)ethyl)boronic acid

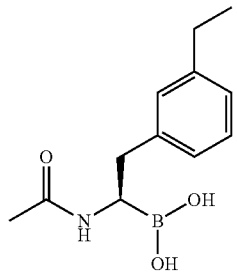 [SMILES: CCc1cccc(C[C@H](NC(C)=O)B(O)O)c1]

Pale pink solid. $^1$H NMR (400 MHz, DMSO-$d_6$): δ 7.11-7.15 (m, 1H), 6.93-6.98 (m, 3H), 2.98-3.01 (m, 1H), 2.71-2.76 (m, 1H), 2.49-2.54 (m, 3H), 1.77 (s, 3H), 1.10-1.14 (m, 3H). MS (ESI+): 218.0 [M+H—H$_2$O]. HPLC (Method A): Rt. 2.4 min, HPLC purity 98.0%

Example 95: (R)-(1-acetamido-2-(naphthalen-2-yl)ethyl)boronic acid

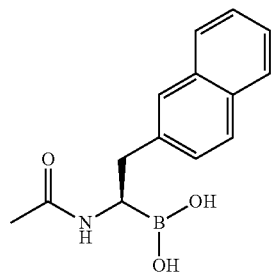 [SMILES: CC(=O)N[C@@H](Cc1ccc2ccccc2c1)B(O)O]

White solid. $^1$H NMR: (400 MHz, DMSO-$d_6$): δ 7.76-7.78 (m, 3H), 7.61 (s, 1H), 7.38-7.46 (m, 2H), 7.32-7.35 (m, 1H), 3.04-3.08 (m, 1H), 2.90-2.95 (m, 1H), 2.73-2.78 (m, 1H), 1.79 (s, 3H). MS (ESI+): 240.3 [M+H—H$_2$O]. HPLC (Method A): Rt. 2.6 min, HPLC purity 92.4%

Example 108: (R)-(1-acetamido-2-(5-methoxybenzofuran-3-yl)ethyl)boronic acid

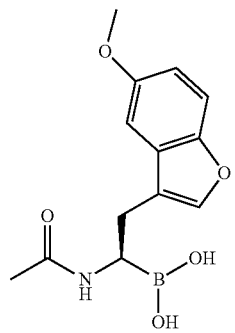 [SMILES: COc1ccc2occ(C[C@H](NC(C)=O)B(O)O)c2c1]

White solid. $^1$H NMR: (400 MHz, DMSO-$d_6$): δ 7.60 (s, 1H), 7.38 (d, J=8.88 Hz, 1H), 7.09-7.10 (m, 1H), 6.84 (dd, J=2.56, 8.92 Hz, 1H), 3.76 (s, 3H), 3.08-3.12 (m, 1H), 2.78-2.83 (m, 1H), 2.66-2.72 (m, 1H), 1.79 (s, 3H). MS (ESI+): 260.0 [M+H—H$_2$O]. HPLC (Method A): Rt. 2.2 min, HPLC purity 96.5%

Example 79: (R)-(2-(benzofuran-3-yl)-1-(3-(4-methoxyphenyl)propanamido)ethyl) boronic acid

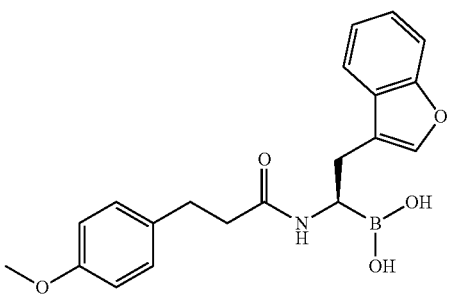 [SMILES: COc1ccc(CCC(=O)N[C@@H](Cc2coc3ccccc23)B(O)O)cc1]

Step 1: (R)-(2-(benzofuran-3-yl)-1-(3-(4-methoxyphenyl)propanamido)ethyl) boronic acid pinacol ester A cooled (−10° C.) solution of Intermediate 18 (170 mg, 0.37 mmol) in anhydrous N,N-dimethylformamide (20 ml) was treated with diisopropylethylamine (0.2 ml, 1.1 mmol) and 3-(4-methoxyphenyl)propionic acid (67 mg, 0.37 mmol) and TBTU (142 mg, 0.44 mmol). The reaction mixture was stirred at −10° C. for 3 h. The reaction mixture was concentrated under reduced pressure keeping an external bath temperature below 30° C., and then 25 ml ethyl acetate were added. The organic layer was washed with brine, dried over sodium sulfate and concentrated. The desired product (160 mg, 86%) was isolated by purification by chromatography on silica gel, eluting with 40% ethylacetate in petroleum ether.

MS (ESI+): 502.2

Step 2: (R)-(2-(benzofuran-3-yl)-1-(3-(4-methoxyphenyl)propanamido)ethyl) boronic acid A cooled (0° C.) solution of (R)-(2-(benzofuran-3-yl)-1-(3-(4-methoxyphenyl)propan amido)ethyl)boronicacid pinacol ester (160 mg, 0.32 mmol) in methanol/pentane (1:1, 20 mL) was treated with 2-methylpropyl boronic acid (129 mg, 1.3 mmol) and an aqueous HCl solution (1.5 N, 0.5 mL) and the reaction mixture was stirred at room temperature for 15 h. The reaction mixture was then extracted with pentane thrice. The aqueous methanol layer was concentrated at temperature below 30° C. The residue was treated with ice and basified with an aqueous (2N) solution of NaOH and extracted with dichloromethane thrice (discarded). The aqueous layer was then acidified with an aqueous (1.5 N) HCl solution and extracted with dichloromethane thrice. The DCM layer was dried over sodium sulfate, filtered and concentrated to give a solid residue, which was triturated with diethylether and lyophilized to obtain the title compound (25 mg, 21%) as a white solid.

$^1$H NMR: (400 MHz, DMSO-d$_6$): δ 7.57 (d, J=7.68 Hz, 1H), 7.49 (t, J=3.92 Hz, 2H), 7.21-7.26 (m, 2H), 7.06 (d, J=8.44 Hz, 2H), 6.77 (d, J=8.48 Hz, 2H), 3.67 (s, 3H), 3.15-3.17 (m, 1H), 2.65-2.81 (m, 5H), 2.30 (t, J=7.32 Hz, 2H). MS (ESI+): 350.3 [M+H—H$_2$O]. HPLC (Method A): Rt. 3.5 min, HPLC purity 93.8%

The following compounds were synthesized using the same procedure followed for Example 79

Example 80: (R)-(2-(benzofuran-3-yl)-1-(3-(4-fluorophenyl)propanamido)ethyl) boronic acid

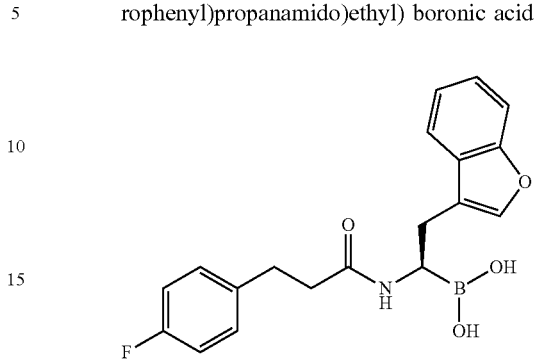

Off-white solid. $^1$H NMR (400 MHz, DMSO-d$_6$): 400 MHz, DMSO-d6: δ 7.57 (d, J=7.16 Hz, 1H), 7.48 (d, J=6.88 Hz, 1H), 7.15-7.28 (m, 4H), 6.99-7.04 (m, 2H), 3.18 (t, J=5.72 Hz, 1H), 2.80-2.81 (m, 1H), 2.71-2.75 (m, 3H), 2.32 (t, J=7.28 Hz, 2H). MS (ESI+): 338.3 [M+H—H$_2$O]. HPLC (Method A): Rt. 3.7 min, HPLC purity 99.0%

Example 81: (R)-(2-(benzofuran-3-yl)-1-(3-(2-fluorophenyl)propanamido)ethyl) boronic acid

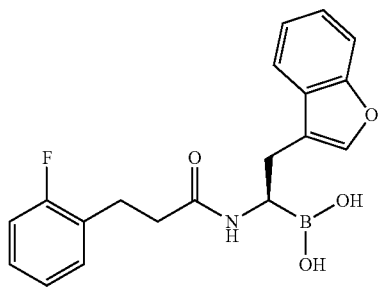 [SMILES: O=C(CCc1ccccc1F)N[C@@H](Cc1coc2ccccc12)B(O)O]

Off-white solid. $^1$H NMR: (400 MHz, DMSO-d$_6$): δ 7.57 (d, J=7.2 Hz, 1H), 7.50-7.52 (m, 2H), 7.18-7.28 (m, 4H), 7.02-7.12 (m, 2H), 3.18-3.21 (m, 1H), 2.73-2.82 (m, 4H), 2.34 (t, J=7.36 Hz, 2H). MS (ESI+): 338.3 [M+H—H$_2$O]. HPLC (Method A): Rt. 3.7 min, HPLC purity 97.9%

Example 82: (R)-(2-(benzofuran-3-yl)-1-(3-(2-methoxyphenyl)propanamido)ethyl boronic acid

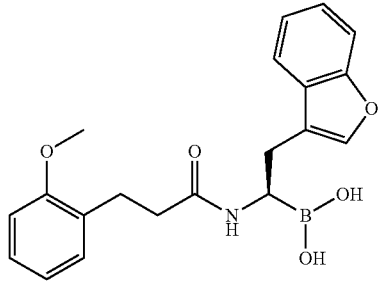 [SMILES: COc1ccccc1CCC(=O)N[C@@H](Cc1coc2ccccc12)B(O)O]

Pale pink solid. $^1$H NMR: (400 MHz, DMSO-d$_6$): δ 7.57 (d, J=7.00 Hz, 1H), 7.48 (d, J=7.36 Hz, 2H), 7.20-7.28 (m, 2H), 7.12-7.19 (m, 1H), 7.05-7.07 (m, 1H), 6.91 (d, J=7.80 Hz, 1H), 6.77-6.81 (m, 1H), 3.73 (s, 1H), 3.12-3.15 (m, 1H), 2.79-2.81 (m, 1H), 2.68-2.74 (m, 3H), 2.29 (t, J=7.20 Hz, 2H). MS (ESI+): 350.3 [M+H—$H_2O$]. HPLC (Method A): Rt. 3.7 min, HPLC purity 98.1%

Example 84: (R)-(2-(benzofuran-3-yl)-1-(3-(3-methoxyphenyl)propanamido)ethyl) boronic acid

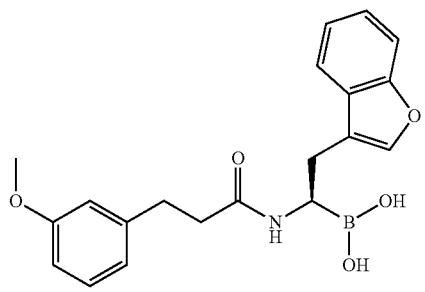 [SMILES: O=C(CCc1cccc(F)c1)N[C@@H](Cc1coc2ccccc12)B(O)O]

White solid. $^1$H NMR: (400 MHz, DMSO-$d_6$): δ 7.57 (d, J=7.08 Hz, 1H), 7.47-7.49 (m, 2H), 7.19-7.28 (m, 2H), 7.14 (t, J=7.96 Hz, 1H), 6.70-6.73 (m, 3H), 3.68 (s, 3H), 3.16-3.19 (m, 1H), 2.80-2.81 (m, 1H), 2.69-2.74 (m, 3H), 2.34 (t, J=7.32 Hz, 2H). MS (ESI+): 350.3 [M+H—$H_2O$]. HPLC (Method A): Rt. 3.6 min, HPLC purity 99.7%

Example 85: (R)-(2-(benzofuran-3-yl)-1-(3-(3-fluorophenyl)propanamido)ethyl) boronic acid

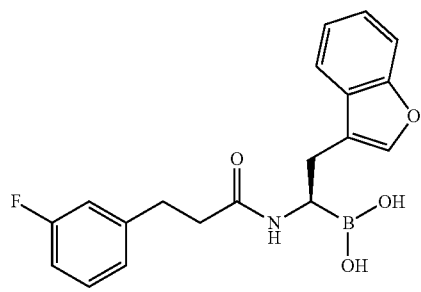

White solid. $^1$H NMR: (400 MHz, DMSO-$d_6$): δ 7.56-7.58 (m, 1H), 7.47-7.49 (m, 2H), 7.19-7.28 (m, 3H), 6.93-7.00 (m, 3H), 3.17-3.20 (m, 1H), 2.68-2.85 (m, 4H), 2.36 (t, J=7.36 Hz, 2H). MS (ESI+): 338.3 [M+H—$H_2O$]. HPLC (Method A): Rt. 3.7 min, HPLC purity 98.4%

Example 86: (R)-(2-(benzofuran-3-yl)-1-(3-cyclohexylpropanamido)ethyl)boronic acid

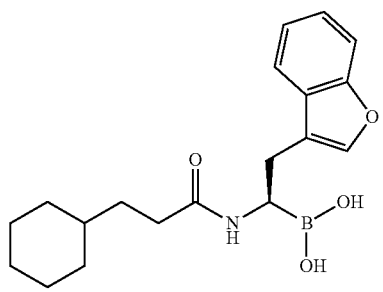 [SMILES: O=C(CCC1CCCCC1)N[C@@H](Cc1coc2ccccc12)B(O)O]

White solid. $^1$H NMR: (400 MHz, DMSO-$d_6$): δ 7.58-7.62 (m, 2H), 7.48 (d, J=7.92 Hz, 1H), 7.19-7.28 (m, 2H), 3.10-3.13 (m, 1H), 2.80-2.85 (m, 1H), 2.68-2.72 (m, 1H), 2.05 (t, J=7.92 Hz, 2H), 1.56-1.59 (m, 5H), 1.27-1.32 (m, 2H), 1.04-1.08 (m, 4H), 0.74-0.80 (m, 2H). MS (ESI+): 326.3 [M+H—$H_2O$]. HPLC (Method A): Rt. 4.2 min, HPLC purity 99.2%

Example 87: (R)-(2-(benzofuran-3-yl)-1-(3-(2-oxobenzo[d]thiazol-3(2H)-yl)propanamido)ethyl) boronic acid

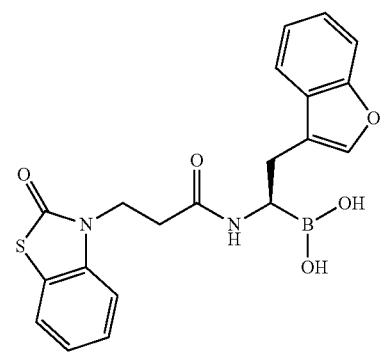 [SMILES: O=C(CCn1c(=O)sc2ccccc21)N[C@@H](Cc1coc2ccccc12)B(O)O]

White solid. $^1$H NMR: (400 MHz, DMSO-$d_6$): δ 7.57 (d, J=7.84 Hz, 1H), 7.52 (d, J=7.56 Hz, 1H), 7.46 (d, J=8.04 Hz, 1H), 7.41 (s, 1H), 7.13-7.34 (m, 5H), 4.05-4.09 (m, 2H), 3.14-3.84 (m, 1H), 2.75-2.80 (m, 1H), 2.64-2.70 (m, 1H), 2.43-2.49 (m, 2H). MS (ESI+): 393.0 [M+H—$H_2O$]. HPLC (Method A): Rt. 3.6 min, HPLC purity 98.8%

Example 88: (R)-(1-(3-(1H-benzo[d]imidazol-1-yl)propanamido)-2-(benzofuran-3-yl)ethyl)boronic acid

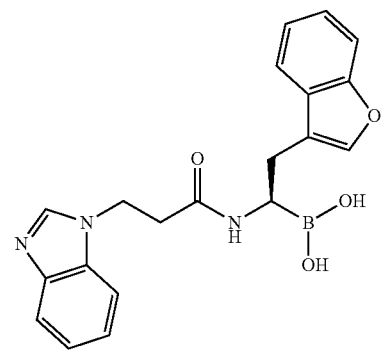 [SMILES: O=C(CCn1cnc2ccccc21)N[C@@H](Cc1coc2ccccc12)B(O)O]

White solid. $^1$H NMR: (400 MHz, DMSO-$d_6$): δ 8.09 (s, 1H), 7.61-7.63 (m, 1H), 7.56 (d, J=7.44 Hz, 1H), 7.43-7.46 (m, 2H), 7.18-7.27 (m, 4H), 7.09-7.13 (m, 1H), 4.39-4.43 (m, 2H), 3.13-3.17 (m, 1H), 2.72-2.86 (m, 1H), 2.50-2.66 (m, 3H). MS (ESI+): 382.3 [M+Na—$H_2O$]. HPLC (Method A): Rt. 2.6 min, HPLC purity 94.3%

Example 89: (R)-(2-(benzofuran-3-yl)-1-(3-(4-phenyl-1H-1,2,3-triazol-1-yl) propanamido)ethyl)boronic acid

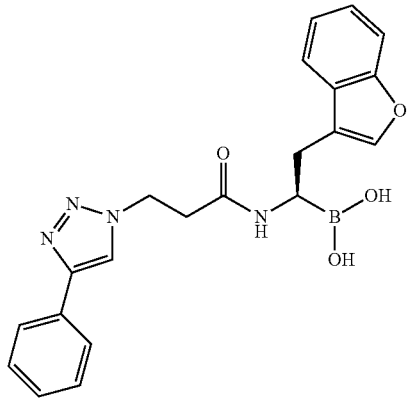 [SMILES: O=C(CCn1cc(-c2ccccc2)nn1)N[C@@H](Cc1coc2ccccc12)B(O)O]

White solid. ¹H NMR: (400 MHz, DMSO-d₆): δ 8.34 (s, 1H), 7.76 (d, J=7.48 Hz, 2H), 7.48 (d, J=7.28 Hz, 2H), 7.41 (t, J=7.52 Hz, 3H), 7.31 (t, J=7.40 Hz, 1H), 7.23 (t, J=7.52 Hz, 1H), 7.16 (t, J=7.16 Hz, 1H), 4.55-4.56 (m, 2H), 3.16-3.18 (m, 1H), 2.77-2.86 (m, 1H), 2.66-2.73 (m, 3H). MS (ESI+): 409.2 [M+Na—H₂O]. HPLC (Method A): Rt. 3.5 min, HPLC purity 94.8%

Example 90: (R)-(2-(benzofuran-3-yl)-1-(3-(1-(4-methoxyphenyl)-1H-1,2,3-triazol-4-yl)propanamido) ethyl)boronic acid

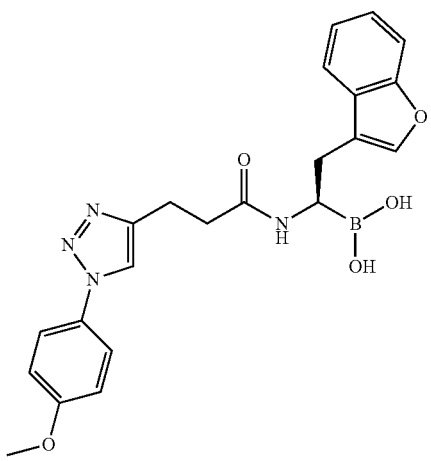 [SMILES: COc1ccc(-n2cc(CCC(=O)N[C@@H](Cc3coc4ccccc34)B(O)O)nn2)cc1]

White solid. ¹H NMR: (400 MHz, DMSO-d₆): δ 8.31 (s, 1H), 7.68 (d, J=8.92 Hz, 2H), 7.55-7.57 (m, 2H), 7.45 (d, J=7.96 Hz, 1H), 7.18-7.27 (m, 2H), 7.08 (d, J=9.00 Hz, 2H), 3.79 (s, 3H), 3.17-3.21 (m, 1H), 2.82-2.90 (m, 3H), 2.67-2.76 (m, 1H), 2.43-2.50 (m, 2H). MS (ESI+): 439.3 [M+Na—H₂O]. HPLC (Method A): Rt. 3.4 min, HPLC purity 95.0%

Example 91: (R)-(2-(benzofuran-3-yl)-1-(2-(N-methylmethylsulfonamido) acetamido)ethyl)boronic acid

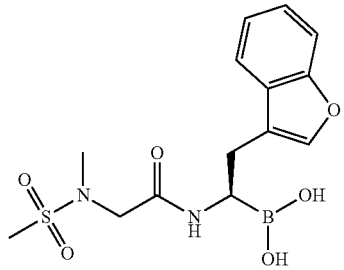 [SMILES: CN(CC(=O)N[C@@H](Cc1coc2ccccc12)B(O)O)S(C)(=O)=O]

White solid. ¹H NMR: (400 MHz, DMSO-d₆): δ 7.60-7.60 (m, 2H), 7.48 (d, J=7.84 Hz, 1H), 7.19-7.28 (m, 2H), 3.68 (d, J=8.12 Hz, 2H), 3.33-3.36 (m, 1H), 2.87-2.92 (m, 4H), 2.76-2.82 (m, 1H), 2.66 (s, 3H). MS (ESI+): 337.0 [M+H—H₂O]. HPLC (Method A): Rt. 2.8 min, HPLC purity 97.5%

Example 94: (R)-(2-(benzofuran-3-yl)-1-(3-phenyl-propanamido)ethyl)boronic acid

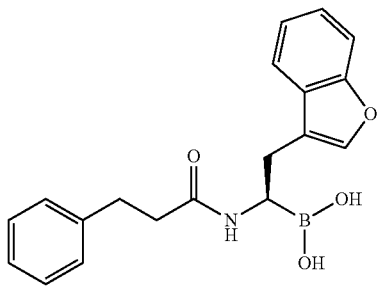 [SMILES: O=C(CCc1ccccc1)N[C@@H](Cc1coc2ccccc12)B(O)O]

White solid. ¹H NMR: (400 MHz, DMSO-d₆): δ 7.56 (d, J=7.68 Hz, 1H), 7.46-7.49 (m, 2H), 7.18-7.28 (m, 4H), 7.11-7.15 (m, 3H), 3.13-3.15 (m, 1H), 2.79-2.80 (m, 1H), 2.71-2.75 (m, 3H), 2.34 (t, J=7.32 Hz, 2H). MS (ESI+): 320.2 [M+H—H₂O]. HPLC (Method A): Rt. 3.6 min, HPLC purity 97.6%

Example 96: (R)-(2-(naphthalen-2-yl)-1-(3-(2-oxobenzo[d]thiazol-3(2H)-yl) propanamido)ethyl) boronic acid

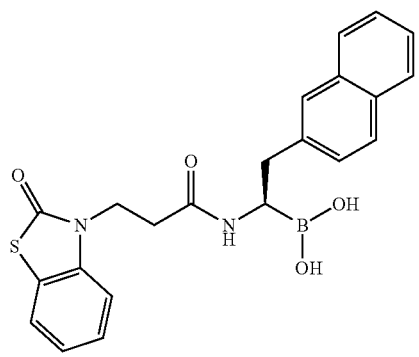 [SMILES: O=C(CCn1c(=O)sc2ccccc21)N[C@@H](Cc1ccc2ccccc2c1)B(O)O]

White solid. ¹H NMR: (400 MHz, DMSO-d₆): 400 MHz, DMSO-d6: δ 7.80 (d, J=8.32 Hz, 1H), 7.71 (d, J=8.48 Hz, 2H), 7.60 (d, J=7.76 Hz, 1H), 7.37-7.43 (m, 3H), 7.30-7.34 (m, 1H), 7.25 (d, J=8.00 Hz, 1H), 7.15-7.18 (m, 2H), 4.04 (t, J=6.96 Hz, 2H), 3.19-3.23 (m, 1H), 2.82-2.87 (m, 1H), 2.71-2.77 (m, 1H), 2.41 (t, J=7.00 Hz, 2H). MS (ESI+): 403.0 [M+H—H$_2$O]. HPLC (Method A): Rt. 3.9 min, HPLC purity 98.6%

Example 97: (R)-(1-(3-(1H-benzo[d]imidazol-1-yl) propanamido)-2-(naphthalen-2-yl)ethyl)boronic acid

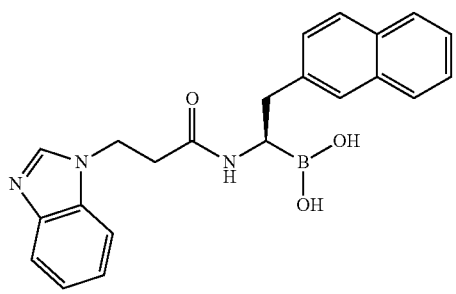 [SMILES: O=C(CCn1cnc2ccccc21)N[C@@H](Cc1ccc2ccccc2c1)B(O)O]

White solid. $^1$H NMR: (400 MHz, DMSO-d$_6$): δ 8.09 (s, 1H), 7.75-7.77 (m, 1H), 7.59-7.65 (m, 3H), 7.54 (dd, J=2.04, 6.80 Hz, 1H), 7.36-7.41 (m, 2H), 7.29 (s, 1H), 7.20-7.27 (m, 2H), 7.06 (dd, J=1.52, 8.40 Hz, 1H), 4.38-4.41 (m, 2H), 3.20 (d, J=2.32 Hz, 1H), 2.74-2.81 (m, 1H), 2.59-2.61 (m, 1H), 2.49-2.57 (m, 2H). MS (ESI+): 392.3 [M+Na—H$_2$O]. HPLC (Method A): Rt. 2.9 min, HPLC purity 96.5%

Example 98: (R)-(2-(naphthalen-2-yl)-1-(3-(1-phenyl-1H-1,2,3-triazol-4-yl) propanamido)ethyl)boronic acid

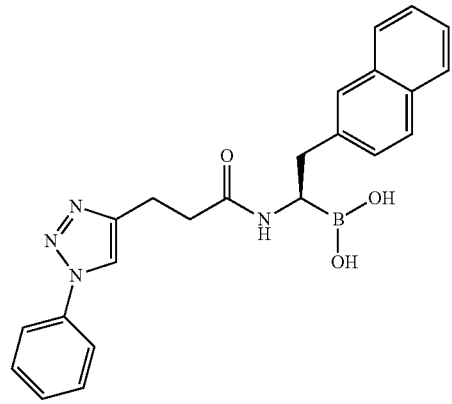 [SMILES: O=C(CCc1cn(-c2ccccc2)nn1)N[C@@H](Cc1ccc2ccccc2c1)B(O)O]

White solid. $^1$H NMR: (400 MHz, DMSO-d$_6$): δ 8.37 (s, 1H), 7.78-7.78 (m, 3H), 7.69-7.72 (m, 2H), 7.52-7.57 (m, 3H), 7.46 (d, J=7.40 Hz, 1H), 7.36-7.41 (m, 2H), 7.25 (dd, J=1.48, 8.44 Hz, 1H), 3.17-3.20 (m, 1H), 2.87-2.94 (m, 3H), 2.75-2.81 (m, 1H), 2.42-2.50 (m, 2H). MS (ESI+): 419.2 [M+Na—H$_2$O]. HPLC (Method A): Rt. 3.7 min, HPLC purity 96.7%

Example 99: (R)-(2-(naphthalen-2-yl)-1-(3-(1-(pyridin-3-yl)-1H-1,2,3-triazol-4-yl) propanamido)ethyl) boronic acid

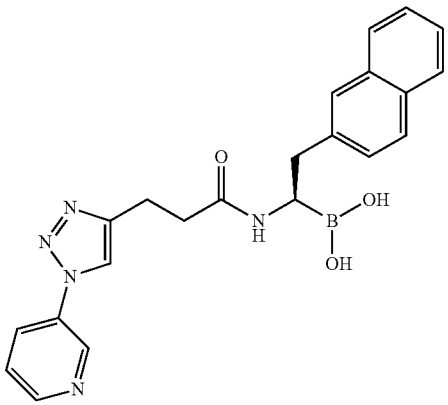 [SMILES: O=C(CCc1cn(-c2cccnc2)nn1)N[C@@H](Cc1ccc2ccccc2c1)B(O)O]

White solid. $^1$H NMR: (400 MHz, DMSO-d$_6$): δ 8.90 (s, 1H), 8.58-8.59 (m, 1H), 8.33 (s, 1H), 8.14 (d, J=8.04 Hz, 1H), 7.57-7.71 (m, 4H), 7.44 (s, 1H), 7.33-7.35 (m, 2H), 7.20 (d, J=8.24 Hz, 1H), 3.04-3.07 (m, 1H), 2.86-2.94 (m, 3H), 2.65-2.71 (m, 1H), 2.49-2.50 (m, 2H). MS (ESI+): 420.2 [M+Na—H$_2$O]. HPLC (Method A): Rt. 2.7 min, HPLC purity 95.9%

Example 100: (R)-(1-(3-(1-(4-methoxyphenyl)-1H-1,2,3-triazol-4-yl)propanamido)-2-(naphthalen-2-yl) ethyl)boronic acid

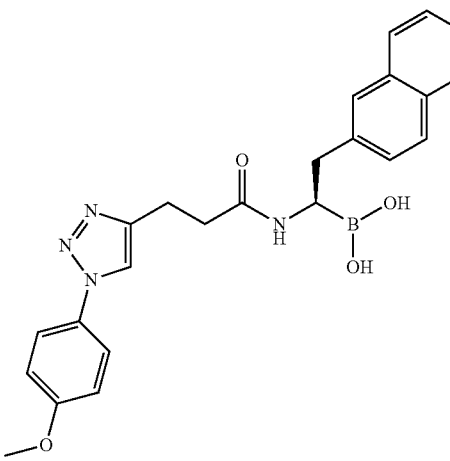

White solid. $^1$H NMR: (400 MHz, DMSO-d$_6$): δ 8.24 (s, 1H), 7.65-7.78 (m, 5H), 7.51 (s, 1H), 7.38-7.42 (m, 2H), 7.23-7.26 (m, 1H), 7.06-7.08 (m, 2H), 3.77 (s, 3H), 3.15-3.18 (m, 1H), 2.85-2.94 (m, 3H), 2.74-2.80 (m, 1H), 2.42-2.50 (m, 2H). MS (ESI+): 449.2 [M+Na—H$_2$O]. HPLC (Method A): Rt. 3.7 min, HPLC purity 90.2%

Example 102: (R)-(2-(1-methyl-1H-indazol-5-yl)-1-(3-(2-oxobenzo[d]thiazol-3(2H)-yl)propanamido)ethyl)boronic acid

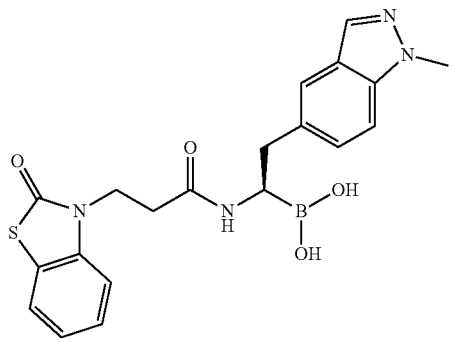 [SMILES: Cn1ncc2cc(C[C@H](NC(=O)CCn3c(=O)sc4ccccc43)B(O)O)ccc21]

White solid. ¹H NMR: (400 MHz, DMSO-d$_6$): δ 7.85 (s, 1H), 7.61 (d, J=8.68 Hz, 1H), 7.39 (d, J=8.64 Hz, 1H), 7.35-7.31 (m, 1H), 7.26 (d, J=7.56 Hz, 1H), 7.19-7.15 (m, 2H), 7.04 (dd, J=1.36, 8.66 Hz, 1H), 4.05 (t, J=7.00 Hz, 2H), 3.92 (s, 3H), 3.15-3.14 (m, 1H), 2.74 (t, J=5.36 Hz, 1H), 2.66 (t, J=5.28 Hz, 1H), 2.41 (t, J=6.92 Hz, 2H). MS (ESI+): 429.2 [M+Na—H$_2$O]. HPLC (Method A): Rt. 2.8 min, HPLC purity 98.0%

Example 103: (R)-(2-(1-methyl-1H-indazol-5-yl)-1-(3-(4-phenyl-1H-1,2,3-triazol-1-yl) propanamido)ethyl)boronic acid

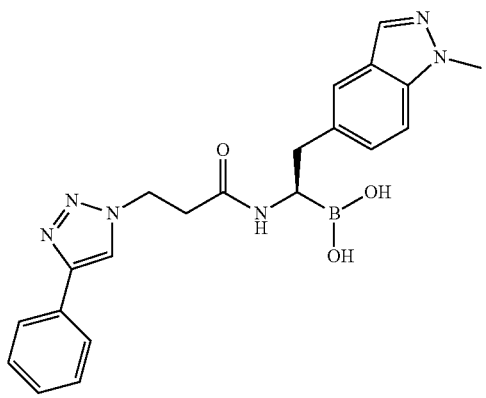 [SMILES: Cn1ncc2cc(C[C@H](NC(=O)CCn3cc(-c4ccccc4)nn3)B(O)O)ccc21]

White solid. ¹H NMR: (400 MHz, DMSO-d$_6$): δ 8.36 (s, 1H), 7.79 (d, J=8.40 Hz, 3H), 7.44-7.43 (m, 2H), 7.34-7.33 (m, 2H), 7.27 (s, 1H), 7.05 (dd, J=1.48, 8.66 Hz, 1H), 4.60-4.58 (m, 2H), 3.88 (s, 3H), 3.15 (t, J=5.64 Hz, 1H), 2.80 (t, J=5.36 Hz, 1H), 2.74-2.72 (m, 1H), 2.68 (t, J=6.52 Hz, 2H). MS (ESI+): 423.3 [M+Na—H$_2$O]. HPLC (Method A): Rt. 2.7 min, HPLC purity 95.0%

Example 104: (R)-(2-(benzo[b]thiophen-3-yl)-1-(3-(4-phenyl-1H-1,2,3-triazol-1-yl) propanamido)ethyl)boronic acid

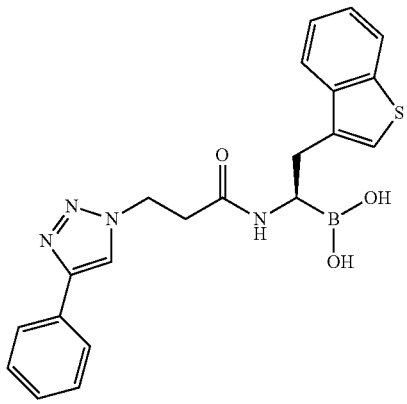 [SMILES: O=C(CCn1cc(-c2ccccc2)nn1)N[C@@H](Cc1csc2ccccc12)B(O)O]

White solid. ¹H NMR: (400 MHz, DMSO-d$_6$): δ 8.34 (s, 1H), 7.83-7.86 (m, 1H), 7.76-7.78 (m, 2H), 7.68-7.71 (m, 1H), 7.39-7.43 (m, 2H), 7.28-7.34 (m, 3H), 7.12 (s, 1H), 4.56 (t, J=6.68 Hz, 2H), 3.22-3.25 (m, 1H), 2.96-3.01 (m, 1H), 2.81-2.87 (m, 1H), 2.69 (t, J=6.56 Hz, 2H). MS (ESI+): 425.2 [M+Na—H$_2$O]. HPLC (Method A): Rt. 3.6 min, HPLC purity 94.8%

Example 105: (R)-(2-(benzo[b]thiophen-3-yl)-1-(3-(2-oxobenzo[d]thiazol-3(2H)-yl) propanamido)ethyl)boronic acid

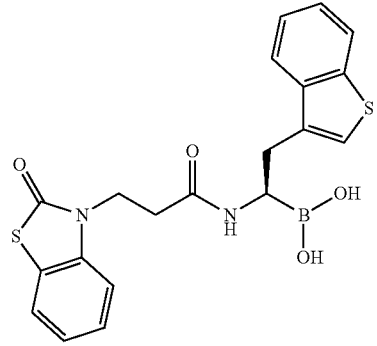 [SMILES: O=C(CCn1c(=O)sc2ccccc21)N[C@@H](Cc1csc2ccccc12)B(O)O]

White solid. ¹H NMR: (400 MHz, DMSO-d$_6$): δ 7.87-7.89 (m, 1H), 7.72-7.74 (m, 1H), 7.58 (d, J=7.20 Hz, 1H), 7.26-7.37 (m, 4H), 7.14-7.18 (m, 1H), 7.03 (s, 1H), 4.05-4.08 (m, 2H), 3.20-3.24 (m, 1H), 2.93-2.98 (m, 1H), 2.83-2.86 (m, 1H), 2.41-2.49 (m, 2H). MS (ESI+): 409.0 [M+H—H$_2$O]. HPLC (Method A): Rt. 3.8 min, HPLC purity 86.0%

Example 106: (R)-(1-(3-(1H-benzo[d]imidazol-1-yl) propanamido)-2-(benzo[b]thiophen-3-yl)ethyl)boronic acid

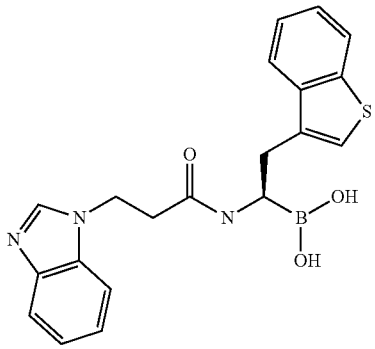 [SMILES: O=C(CCn1cnc2ccccc21)N[C@@H](Cc1csc2ccccc12)B(O)O]

White solid. ¹H NMR: (400 MHz, DMSO-d$_6$): δ 8.09 (s, 1H), 7.85-7.87 (m, 1H), 7.67-7.70 (m, 1H), 7.63 (d, J=7.48 Hz, 1H), 7.55 (d, J=7.56 Hz, 1H), 7.28-7.30 (m, 2H), 7.19-7.26 (m, 2H), 6.86 (s, 1H), 4.39-4.42 (m, 2H), 3.18-3.21 (m, 1H), 2.92-2.95 (m, 1H), 2.76-2.82 (m, 1H), 2.58-2.61 (m, 2H). MS (ESI+): 398.0 [M+Na—H$_2$O]. HPLC (Method A): Rt. 2.7 min, HPLC purity 96.0%

Example 107: (R)-(2-(benzo[d][1,3]dioxol-5-yl)-1-(3-(4-phenyl-1H-1,2,3-triazol-1-yl) propanamido) ethyl)boronic acid

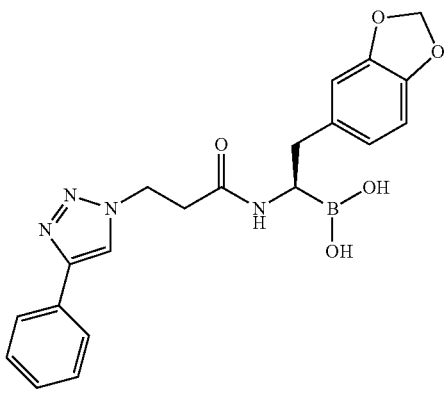 [SMILES: O=C(CCn1cc(-c2ccccc2)nn1)N[C@@H](Cc1ccc2c(c1)OCO2)B(O)O]

White solid. ¹H NMR: (400 MHz, DMSO-d$_6$): δ 8.25 (s, 1H), 7.72-7.74 (m, 2H), 7.38-7.42 (m, 2H), 7.29-7.33 (m, 1H), 6.45-6.48 (m, 2H), 6.25 (d, J=7.92 Hz, 1H), 5.73 (s, 2H), 4.59-4.61 (m, 2H), 2.74-2.84 (m, 3H), 2.49-2.56 (m, 1H), 2.26-2.32 (m, 1H). MS (ESI+): 413.0 [M+Na—H$_2$O]. HPLC (Method A): Rt. 3.1 min, HPLC purity 95.2%

Example 109: (R)-(2-(5-methoxybenzofuran-3-yl)-1-(3-(2-oxobenzo[d]thiazol-3(2H)-yl)propanamido) ethyl)boronic acid

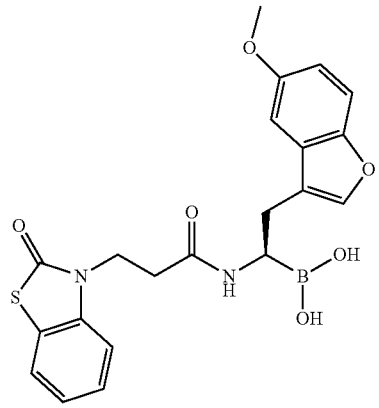 [SMILES: COc1ccc2occ(C[C@H](NC(=O)CCn3c(=O)sc4ccccc43)B(O)O)c2c1]

Pale brown solid. ¹H NMR: (400 MHz, DMSO-d$_6$): δ 7.58 (d, J=7.16 Hz, 1H), 7.34-7.39 (m, 2H), 7.31 (d, J=8.16 Hz, 1H), 7.27 (d, J=7.36 Hz, 1H), 7.13-7.17 (m, 1H), 7.07-7.08 (m, 1H), 6.83 (dd, J=2.56, 8.88 Hz, 1H), 4.06 (t, J=7.68 Hz, 2H), 3.74 (s, 3H), 3.17-3.20 (m, 1H), 2.73-2.74 (m, 1H), 2.64-2.68 (m, 1H), 2.42-2.46 (m, 2H). MS (ESI+): 423.0 [M+H—H$_2$O]. HPLC (Method A): Rt. 3.6 min, HPLC purity 92.6%

Example 92: (R)-(2-(benzofuran-3-yl)-1-(3-(piperazin-1-yl) propanamido)ethyl) boronic acid hydrochloride

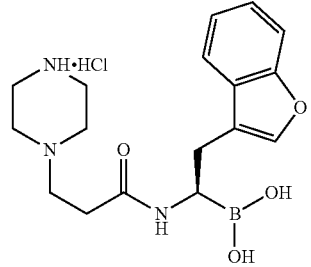

Step 1: (R)-(2-(benzofuran-3-yl)-1-(3-(4-(tert-butoxycarbonyl)piperazin-1-yl) propanamido)ethyl) boronic acid pinacol ester A cooled (−10° C.) solution of Intermediate 18 (300 mg, 0.66 mmol) in anhydrous N,N-dimethylformamide (10 ml) was treated with diisopropylethylamine (0.3 ml, 1.9 mmol) and 3-(4-(tert-butoxycarbonyl)piperazin-1-yl)propanoic acid (170 mg, 0.66 mmol) and TBTU (254 mg, 0.79 mmol). The reaction mixture was stirred at −10° C. for 3 h. The reaction mixture was concentrated under reduced pressure keeping an external bath temperature below 30° C., and then 25 ml ethyl acetate were added. The organic layer was washed with brine, dried over sodium sulfate and concentrated. The desired product (350 mg, 87%) was isolated by purification by chromatography on silica gel, eluting with 4% methanol in dichloromethane.

MS (ESI+): 580.4

Step 2: (R)-(2-(benzofuran-3-yl)-1-(3-(4-(tert-butoxycarbonyl)piperazin-1-yl) propanamido)ethyl) boronic acid A cooled (0° C.) solution of (R)-(2-(benzofuran-3-yl)-1-(3-(4-(tert-butoxycarbonyl) piperazin-1-yl) propanamido) ethyl)boronic acid pinacol ester (350 mg, 0.6 mmol) in methanol/pentane (1:1, 30 mL) was treated with 2-methylpropyl boronic acid (242 mg, 2.4 mmol) and an aqueous HCl solution (1.5 N, 0.7 mL) and the reaction mixture was stirred at room temperature for 15 h. The reaction mixture was then extracted with pentane thrice. The aqueous methanol layer was concentrated at temperature below 30° C. The residue was treated with ice and basified with an aqueous (2N) solution of NaOH and extracted with dichloromethane thrice (discarded). The aqueous layer was then acidified with an aqueous (1.5 N) HCl solution and extracted with dichloromethane thrice. The DCM layer was dried over sodium sulfate, filtered and concentrated. The desired product (85 mg, 31%) was isolated by purification by chromatography on silica gel, eluting with 30% methanol in dichloromethane.

MS (ESI+): 450.2 [M+Na—$H_2O$].

Step 3: (R)-(2-(benzofuran-3-yl)-1-(3-(piperazin-1-yl) propanamido)ethyl) boronic acid hydrochloride The compound (R)-(2-(benzofuran-3-yl)-1-(3-(4-(tert-butoxycarbonyl)piperazin-1-yl) propanamido)ethyl)boronic acid (0.085 g, 0.19 mmol) was taken in 1,4-dioxane (5 mL) and cooled to 10° C. To this was added 4 N HCl in dioxane (5 mL) and stirred at RT overnight. The reaction mixture was concentrated under reduced pressure and the residue was washed with diethyl ether to get solid. The solid was further lyophilized to obtain the title compound (47 mg, 64%) as a pale brown solid.

$^1$H NMR: (400 MHz, DMSO-$d_6$): δ 7.66 (s, 1H), 7.62 (d, J=7.24 Hz, 1H), 7.49 (d, J=8.12 Hz, 1H), 7.21-7.29 (m, 2H), 3.25-3.37 (m, 11H), 2.88-2.93 (m, 1H), 2.75-2.81 (m, 1H), 2.55-2.56 (m, 2H). MS (ESI+): 350.3 [M+Na—$H_2O$]. HPLC (Method A): Rt. 2.0 min, HPLC purity 93.5%

Example 83: (R)-(1-(2-(1H-imidazol-5-yl)acetamido)-2-(benzofuran-3-yl)ethyl) boronic acid hydrochloride

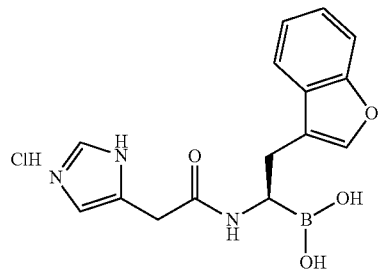 [SMILES: Cl ; O=C(Cc1cnc[nH]1)N[C@@H](Cc1coc2ccccc12)B(O)O]

Step 1: (R)-(1-(2-(1H-imidazol-5-yl)acetamido)-2-(benzofuran-3-yl)ethyl) boronic acid pinacol ester A cooled (−10° C.) solution of Intermediate 18 (170 mg, 0.37 mmol) in anhydrous N,N-dimethylformamide (20 ml) was treated with diisopropylethylamine (0.2 ml, 1.1 mmol) and 2-(1H)-imidazole-5-yl-acetic acid (47 mg, 0.37 mmol) and TBTU (142 mg, 0.44 mmol). The reaction mixture was stirred at −10° C. for 3 h. The reaction mixture was concentrated under reduced pressure keeping an external bath temperature below 30° C., and then 25 ml ethyl acetate were added. The organic layer was washed with brine, dried over sodium sulfate and concentrated. The desired product (110 mg, 66%) was isolated by purification by chromatography on silica gel, eluting with 7% methanol in dichloromethane.

MS (ESI+): 448.2

Step 2: (R)-(1-(2-(1H-imidazol-5-yl)acetamido)-2-(benzofuran-3-yl)ethyl) boronic acid hydrochloride A cooled (0° C.) solution of (R)-(1-(2-(1H-imidazol-5-yl)acetamido)-2-(benzofuran-3-yl)ethyl) boronic acid pinacol ester (110 mg, 0.24 mmol) in methanol/pentane (1:1, 20 mL) was treated with 2-methylpropyl boronic acid (96 mg, 0.96 mmol) and an aqueous HCl solution (1.5 N, 0.5 mL) and the reaction mixture was stirred at room temperature for 15 h. The reaction mixture was then extracted with pentane thrice. The aqueous methanol layer was concentrated at temperature below 30° C. To the residue was added water and extracted with dichloromethane thrice. The aqueous layer was lyophilized to obtain the title compound (25 mg, 32%) as a pale brown semi solid.

$^1$H NMR: (400 MHz, DMSO-$d_6$): δ 8.68 (s, 1H), 7.58 (t, J=7.60 Hz, 2H), 7.47 (d, J=8.08 Hz, 1H), 7.18-7.28 (m, 3H), 3.52 (s, 2H), 3.26-3.30 (m, 2H), 2.86-2.88 (m, 1H), 2.78-2.80 (m, 1H). MS (ESI+): 318.3 [M+Na—$H_2O$]. HPLC (Method A): Rt. 2.1 min, HPLC purity 95.2%

The following compound was synthesized using the same procedure followed for Example 83

Example 93: (R)-(2-(benzofuran-3-yl)-1-(3-(pyridin-4-yl)propanamido)ethyl)boronic acid hydrochloride

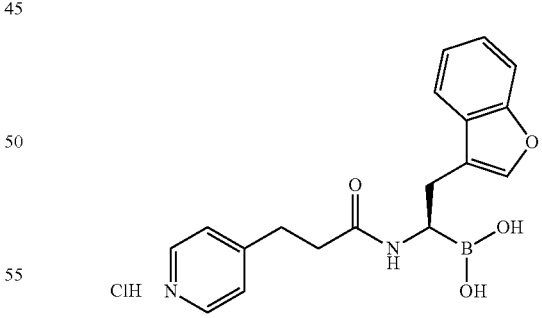

Pale brown semi solid. $^1$H NMR: (400 MHz, DMSO-$d_6$): δ 8.65 (d, J=6.56 Hz, 2H), 7.83 (d, J=6.48 Hz, 2H), 7.55-7.58 (m, 2H), 7.48 (d, J=7.96 Hz, 1H), 7.19-7.28 (m, 2H), 3.20-3.23 (m, 1H), 3.03 (t, J=7.16 Hz, 2H), 2.81-2.86 (m, 1H), 2.66-2.73 (m, 1H), 2.54-2.51 (m, 2H). MS (ESI+): 343.2 [M+Na—$H_2O$]. HPLC (Method A): Rt. 2.0 min, HPLC purity 96.1%

Example 101: (R)-(2-(1H-indol-3-yl)-1-(3-(2-oxobenzo[d]thiazol-3(2H)-yl propanamido)ethyl) boronic acid

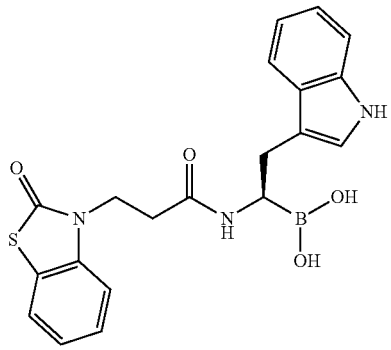 [SMILES: O=C(CCn1c(=O)sc2ccccc21)N[C@@H](Cc1c[nH]c2ccccc12)B(O)O]

Step 1: tert-butyl 3-((2R)-2-(3-(2-oxobenzo[d]thiazol-3(2H)-yl)propanamido)-2-(3a,5,5-trimethylhexahydro-4,6-methanobenzo[d][1,3,2]dioxaborol-2-yl)ethyl)-1H-indole-1-carboxylate A cooled (−10° C.) solution of [(1R)-1-amino-2-(1H-indol-3-yl)ethyl]boronic acid (+)-pinanediol ester trifluroacetate (500 mg, 0.90 mmol) in anhydrous N,N-dimethyl formamide (20 ml) was treated with diisopropylethylamine (0.5 ml, 2.7 mmol) and [3-(2-oxo-benzothiazol-3-yl) propionic acid] (190 mg, 0.9 mmol) and TBTU (346 mg, 1.1 mmol). The reaction mixture was stirred at −10° C. for 3 h. The reaction mixture was concentrated under reduced pressure keeping an external bath temperature below 30° C., and then 25 ml ethyl acetate were added. The organic layer was washed with brine, dried over sodium sulfate and concentrated. The desired product (280 mg, 48%) was isolated by purification by chromatography on silica gel, eluting with 30% ethylacetate in petroleum ether.
MS (ESI+): 644.2

Step 2: N-((1R)-2-(1H-indol-3-yl)-1-(3a,5,5-trimethylhexahydro-4,6-methanobenzo[d][1,3,2]dioxaborol-2-yl)ethyl)-3-(2-oxobenzo[d]thiazol-3(2H)-yl)propanamide hydrochloride The compound tert-butyl 3-((2R)-2-(3-(2-oxobenzo[d]thiazol-3(2H)-yl)propanamido)-2-(3a,5,5-trimethylhexahydro-4,6-methanobenzo[d][1,3,2]dioxaborol-2-yl)ethyl)-1H-indole-1-carboxylate (280 mg, 0.43 mmol) was taken in dichloromethane (10 mL) and cooled to 10° C. To this was added 4 N HCl in dioxane (10 mL) and stirred at RT overnight. The reaction mixture was concentrated under reduced pressure and the residue was washed with diethyl ether to obtain the desired product (200 mg, 85%).

Step 3: (R)-(2-(1H-indol-3-yl)-1-(3-(2-oxobenzo[d]thiazol-3(2H)-yl) propanamido)ethyl)boronic acid A cooled (0° C.) solution of N-((1R)-2-(1H-indol-3-yl)-1-(3a,5,5-trimethylhexahydro-4,6-methanobenzo[d][1,3,2]dioxaborol-2-yl)ethyl)-3-(2-oxobenzo[d]thiazol-3(2H)-yl)propanamide hydrochloride (200 mg, 0.36 mmol) in methanol/pentane (1:1, 20 mL) was treated with 2-methylpropyl boronic acid (145 mg, 1.4 mmol) and an aqueous HCl solution (1.5 N, 0.5 mL) and the reaction mixture was stirred at room temperature for 15 h. The reaction mixture was then extracted with pentane thrice. The aqueous methanol layer was concentrated at temperature below 30° C. The residue was treated with ice and basified with an aqueous (2N) solution of NaOH and extracted with dichloromethane thrice (discarded). The aqueous layer was then acidified with an aqueous (1.5 N) HCl solution and extracted with dichloromethane thrice. The DCM layer was dried over sodium sulfate, filtered and concentrated to give a solid residue, which was triturated with diethylether and lyophilized to obtain the title compound (13 mg, 15%) as an off-white solid.

$^1$H NMR: (400 MHz, DMSO-$d_6$): δ 7.59 (d, J=7.80 Hz, 1H), 7.42 (d, J=7.92 Hz, 1H), 7.26-7.34 (m, 3H), 7.17 (t, J=7.36 Hz, 1H), 7.01 (t, J=7.60 Hz, 1H), 6.88-6.93 (m, 2H), 4.05-4.09 (m, 2H), 3.17-3.21 (m, 1H), 2.80-2.85 (m, 1H), 2.70-2.75 (m, 1H), 2.41-2.44 (m, 2H).

MS (ESI+): 392.0 [M+H—H$_2$O]. HPLC (Method A): Rt. 3.2 min, HPLC purity 92.1%.

Example 110: ((1R)-2-(3-ethylphenyl)-1-(3-(2-oxothiazol-3(2H)-yl)-2-((4-phenyl-1H-1,2,3-triazol-1-yl)methyl)propanamido)ethyl)boronic acid

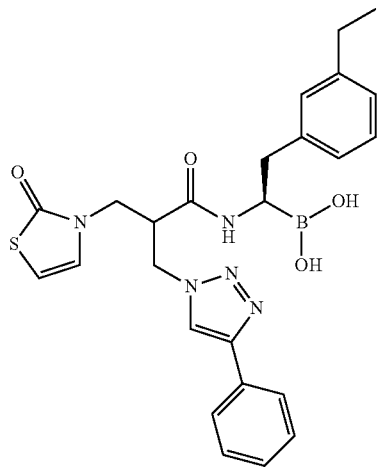 [SMILES: CCc1cccc(C[C@H](NC(=O)C(Cn2cc(-c3ccccc3)nn2)Cn2ccsc2=O)B(O)O)c1]

Step 1: Ethyl-2-(azidomethyl)acrylate

To a solution of ethyl-2-(bromomethyl)acrylate (5 g, 26.1 mmol) in DMSO (50 mL) was added sodium azide (2.5 g, 38.4 mmol) and the reaction mixture was stirred at RT for 2 h. The reaction was quenched with water and extracted with ethyl acetate. The organic layer was separated, dried over anhydrous sodium sulphate and concentrated. The crude (5.0 g) was taken to next step without further purification (Ethyl-2-(azidomethyl)acrylate was found to be unstable on standing for few hours).

Step 2: Ethyl-2-((4-phenyl-1H-1,2,3-triazol-1-yl)methyl)acrylate

To a solution of phenyl acetylene (3.0 g, 29.4 mmol) and Ethyl-2-(azidomethyl)acrylate (5.0 g, 32.3 mmol) in t-BuOH: H$_2$O (2:1) (50 mL) were added sodium ascorbate (0.87 g, 4.4 mmol) and CuSO4.5H$_2$O (0.36 g, 1.5 mmol). The reaction mixture was stirred at RT for 12 h. The reaction mixture was diluted with ethyl acetate and washed with water, brine solution. The organic layer was separated, dried over anhydrous sodium sulphate and concentrated. The solid obtained (3.0 g, 39%) was taken to next step without further purification.

$^1$H NMR: (400 MHz, DMSO-d6): δ 8.5 (s, 1H), 7.8 (d, J=8.2 Hz, 2H), 7.4 (t, J=7.7 Hz, 2H), 7.30-7.34 (m, 1H), 6.4 (s, 1H), 5.8 (s, 1H), 5.3 (s, 2H), 4.2 (q, J=7.0 Hz, 2H), 1.2 (t, J=7.0 Hz, 3H)

Step 3: Ethyl-3-(2-oxothiazol-3(2H)-yl)-2-((4-phenyl-1H-1,2,3-triazol-1-yl)methyl) propanoate To a solution of Ethyl-2-((4-phenyl-1H-1,2,3-triazol-1-yl)methyl)acrylate (3.0 g, 11.6 mmol) in acetonitrile (30 mL) was added thiazol-2(3H)-one (1.2 g, 11.6 mmol) and DBU (2.6 g, 17.4 mmol) at RT and the reaction mixture was stirred at RT for overnight. The reaction mixture was concentrated under reduced pressure and the residue was extracted with ethyl acetate and washed with water, brine solution. The organic layer was separated, dried over anhydrous sodium sulphate and concentrated. The crude compound was purified by column chromatography using ethyl acetate and petroleum ether as eluent to afford the title compound (1.2 g, 28%).

MS (ESI+): 359.2 [M+H]

Step 4: 3-(2-oxothiazol-3(2H)-yl)-2-((4-phenyl-1H-1,2,3-triazol-1-yl)methyl)propanoic acid To a solution of Ethyl-3-(2-oxothiazol-3(2H)-yl)-2-((4-phenyl-1H-1,2,3-triazol-1-yl)methyl) propanoate (1.2 g, 3.3 mmol) in THF:H$_2$O (20 mL) was added Lithium hydroxide monohydrate (0.41 g, 9.9 mmol) and the reaction mixture was stirred at RT overnight. The reaction mixture was evaporated. To the residue was added water and extracted with dichloromethane thrice (discarded). The aqueous layer was then just acidified and extracted with dichloromethane. The organic layer was then dried over anhydrous sodium sulphate and concentrated to get the title compound (200 mg, 18%).

MS (ESI+): 331.0 [M+H]

Step 5: ((1R)-2-(3-ethylphenyl)-1-(3-(2-oxothiazol-3 (2H)-yl)-2-((4-phenyl-1H-1,2,3-triazol-1-yl)methyl) propanamido)ethyl)boronic acid pinacol ester A cooled (−10° C.) solution of [(1R)-1-amino-2-(3-ethylphenyl)ethyl]boronic acid (+)-pinanediol ester trifluroacetate (200 mg, 0.45 mmol) in anhydrous N,N-dimethyl formamide (10 ml) was treated with diisopropylethylamine (0.2 ml, 1.3 mmol) and 3-(2-oxothiazol-3(2H)-yl)-2-((4-phenyl-1H-1,2,3-triazol-1-yl)methyl)propanoicacid (148 mg, 0.45 mmol) and TBTU (173 mg, 0.54 mmol). The reaction mixture was stirred at −10° C. for 3 h. The reaction mixture was concentrated under reduced pressure keeping an external bath temperature below 30° C., and then 25 ml ethyl acetate were added. The organic layer was washed with brine, dried over sodium sulfate and concentrated. The desired product (290 mg, 99%) was isolated by purification by chromatography on silica gel, eluting with 25% ethylacetate in petroleum ether.

MS (ESI+): 640.3

Step 6: ((1R)-2-(3-ethylphenyl)-1-(3-(2-oxothiazol-3 (2H)-yl)-2-((4-phenyl-1H-1,2,3-triazol-1-yl)methyl) propanamido)ethyl)boronic acid A cooled (0° C.) solution of ((1R)-2-(3-ethylphenyl)-1-(3-(2-oxothiazol-3(2H)-yl)-2-((4-phenyl-1H-1,2,3-triazol-1-yl)methyl)propanamido)ethyl)boronic acid pinacol ester (290 mg, 0.45 mmol) in methanol/pentane (1:1, 20 mL) was treated with 2-methylpropyl boronic acid (181 mg, 1.8 mmol) and an aqueous HCl solution (1.5 N, 0.5 mL) and the reaction mixture was stirred at room temperature for 15 h. The reaction mixture was then extracted with pentane thrice. The aqueous methanol layer was concentrated at temperature below 30° C. The residue was treated with ice and basified with an aqueous (2N) solution of NaOH and extracted with dichloromethane thrice (discarded). The aqueous layer was then acidified with an aqueous (1.5 N) HCl solution and extracted with dichloromethane thrice. The DCM layer was dried over sodium sulfate, filtered and concentrated to give a solid residue, which was triturated with diethylether and lyophilized to obtain the title compound (61 mg, 26%) as a pale pink solid.

$^1$H NMR: (400 MHz, DMSO-d6): δ 8.20 (d, J=8.56 Hz, 1H), 7.79-7.82 (m, 2H), 7.43 (t, J=7.76 Hz, 2H), 7.33-7.37 (m, 1H), 6.93-7.08 (m, 3H), 6.80-6.86 (m, 1H), 6.71-6.75 (m, 1H), 6.31-6.35 (m, 1H), 4.56-4.62 (m, 1H), 4.37-4.44 (m, 1H), 3.82-3.84 (m, 1H), 3.33-3.34 (m, 1H), 3.20-3.22 (m, 1H), 2.62-2.67 (m, 2H), 2.44-2.49 (m, 2H), 1.05-1.11 (m, 3H).

MS (ESI+): 488.3 [M+H—H$_2$O]. HPLC (Method A): Rt. 4.4 min, HPLC purity 91.0%

Example 111: Determination of LMP7 Activity

Measurement of LMP7 inhibition is performed in 384 well format based on fluorescence intensity assay.

Purified human immuno proteasome (0.5 nM) and serial diluted compounds in DMSO (range of concentrations from 10 μM to 38 pM) or controls (0.5% DMSO) are incubated for 30 minutes at 37° C. in assay buffer containing 50 mM Tris pH 7.4 and 0.03% SDS. The reaction is initiated by the addition of the fluorogenic peptide substrate, Suc-LLVY-AMC (Bachem I-1395), at a concentration of 40 μM. After 90 minutes of incubation at 37° C., fluorescence intensity is measured at $\lambda_{ex}$=350 nm and $\lambda_{em}$=450 nm with a fluorescence reader (BMG Pherastar reader or equivalent).

For examples 79, 80, 83, 84, 85, 87, 88, 89, 90, 91, 93, 94, 96, 97, 101 and 110 the measurement of LMP7 inhibition is performed in 384 well format based on fluorescence intensity assay.

Purified human immuno proteasome (0.25 nM) and serial diluted compounds in DMSO (range of concentrations from 10 μM to 38 pM) or controls (0.5% DMSO) are incubated for 30 minutes at 37° C. in assay buffer containing 50 mM Tris pH 7.4 and 0.03% SDS. The reaction is initiated by the addition of the fluorogenic peptide substrate, Suc-LLVY-AMC (Bachem I-1395), at a concentration of 40 μM. After 90 minutes of incubation at 37° C., fluorescence intensity is measured at $\lambda_{ex}$=350 nm and $\lambda_{em}$=450 nm with a fluorescence reader (BMG Pherastar reader or equivalent).

Example 112: Determination of Beta5 activity

Measurement of Beta5 inhibition is performed in 384 well format based on fluorescence intensity assay.

Purified human constitutive proteasome (1.0 nM) and serial diluted compounds in DMSO (range of concentrations from 10 μM to 38 pM) or controls (0.5% DMSO) are incubated for 30 minutes at 37° C. in assay buffer containing 50 mM Tris pH 7.4 and 0.03% SDS. The reaction is initiated by the addition of the fluorogenic peptide substrate, Suc-LLVY-AMC (Bachem 1-1395), at a concentration of 40 μM. After 90 minutes of incubation at 37° C., fluorescence intensity is measured at $\lambda_{ex}$=350 nm and $\lambda_{em}$=450 nm with a fluorescence reader (BMG Pherastar reader or equivalent).

The biological activity of the compounds is summarized in the following table:

| Ex | Formula | LMP7 IC50 (M) | Beta5 IC50 (M) | Selectivity LMP7 vs Beta5 |
|---|---|---|---|---|
| 1 | | *** | ** | ++ |
| 2 | | ** | * | nd |
| 3 | | *** | * | +++ |
| 4 | | *** | ** | +++ |
| 5 | | ** | * | nd |

-continued

| Ex | Formula | LMP7 IC50 (M) | Beta5 IC50 (M) | Selectivity LMP7 vs Beta5 |
|---|---|---|---|---|
| 6 | | *** | * | +++ |
| 7 | | *** | * | +++ |
| 8 | | *** | * | nd |
| 9 | | *** | ** | ++ |
| 10 | | ** | * | nd |
| 11 | | *** | * | +++ |

-continued

| Ex | Formula | LMP7 IC50 (M) | Beta5 IC50 (M) | Selectivity LMP7 vs Beta5 |
|---|---|---|---|---|
| 12 | | ** | * | nd |
| 13 | | *** | * | ++ |
| 14 | | *** | ** | +++ |
| 15 | | *** | * | +++ |

-continued

| Ex | Formula | LMP7 IC50 (M) | Beta5 IC50 (M) | Selectivity LMP7 vs Beta5 |
|---|---|---|---|---|
| 16 | | ** | * | nd |
| 17 | | *** | ** | ++ |
| 18 | | *** | ** | +++ |
| 19 | | *** | ** | ++ |
| 20 | | *** | ** | + |

-continued

| Ex | Formula | LMP7 IC50 (M) | Beta5 IC50 (M) | Selectivity LMP7 vs Beta5 |
|---|---|---|---|---|
| 21 | | *** | ** | ++ |
| 22 | | *** | ** | ++ |
| 23 | | *** | ** | ++ |
| 24 | | **** | *** | +++ |
| 25 | | *** | * | +++ |
| 26 | | *** | * | +++ |

-continued

| Ex | Formula | LMP7 IC50 (M) | Beta5 IC50 (M) | Selectivity LMP7 vs Beta5 |
|---|---|---|---|---|
| 27 | | **** | ** | +++ |
| 28 | | *** | ** | ++ |
| 29 | | **** | *** | ++ |
| 30 | | **** | *** | ++ |

-continued

| Ex | Formula | LMP7 IC50 (M) | Beta5 IC50 (M) | Selectivity LMP7 vs Beta5 |
|---|---|---|---|---|
| 31 | | **** | *** | ++ |
| 32 | | *** | *** | + |
| 33 | | *** | *** | + |
| 34 | | **** | *** | + |
| 35 | | **** | *** | + |

-continued

| Ex | Formula | LMP7 IC50 (M) | Beta5 IC50 (M) | Selectivity LMP7 vs Beta5 |
|---|---|---|---|---|
| 36 | | **** | ** | +++ |
| 37 | | *** | ** | ++ |
| 38 | | **** | *** | ++ |
| 39 | | *** | ** | +++ |

-continued

| Ex | Formula | LMP7 IC50 (M) | Beta5 IC50 (M) | Selectivity LMP7 vs Beta5 |
|---|---|---|---|---|
| 40 | | **** | *** | ++ |
| 41 | | **** | ** | +++ |
| 42 | | *** | ** | ++ |
| 43 | | *** | ** | ++ |
| 44 | | **** | *** | ++ |

-continued
| Ex | Formula | LMP7 IC50 (M) | Beta5 IC50 (M) | Selectivity LMP7 vs Beta5 |
|---|---|---|---|---|
| 45 | 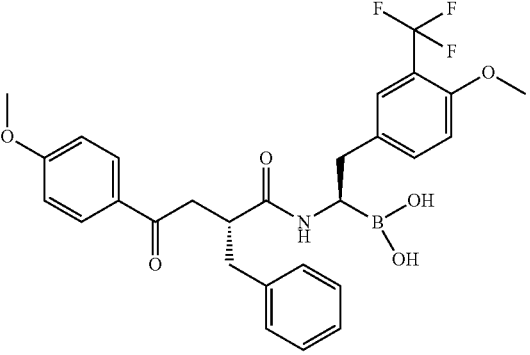 [SMILES: COc1ccc(C(=O)C[C@@H](Cc2ccccc2)C(=O)N[C@@H](Cc2ccc(OC)c(C(F)(F)F)c2)B(O)O)cc1] | ** |  | +++ |
| 46 | 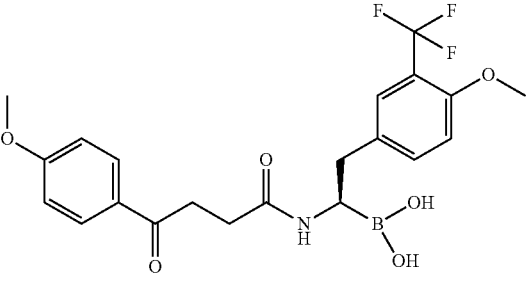 [SMILES: COc1ccc(C(=O)CCC(=O)N[C@@H](Cc2ccc(OC)c(C(F)(F)F)c2)B(O)O)cc1] | *** | * | nd |
| 47 | 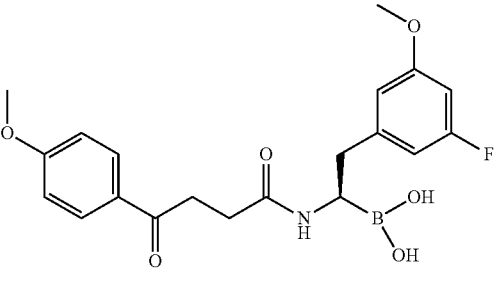 [SMILES: COc1ccc(C(=O)CCC(=O)N[C@@H](Cc2cc(F)cc(OC)c2)B(O)O)cc1] | *** | * | +++ |
| 48 | 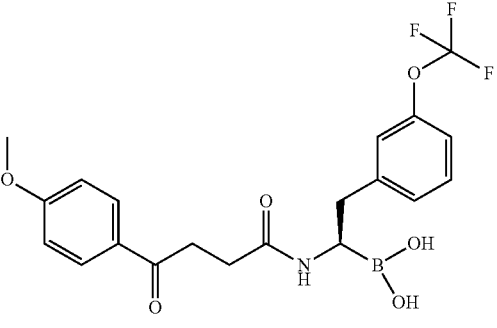 [SMILES: COc1ccc(C(=O)CCC(=O)N[C@@H](Cc2cccc(OC(F)(F)F)c2)B(O)O)cc1] | * |  | ++ |

-continued
| Ex | Formula | LMP7 IC50 (M) | Beta5 IC50 (M) | Selectivity LMP7 vs Beta5 |
|---|---|---|---|---|
| 49 | 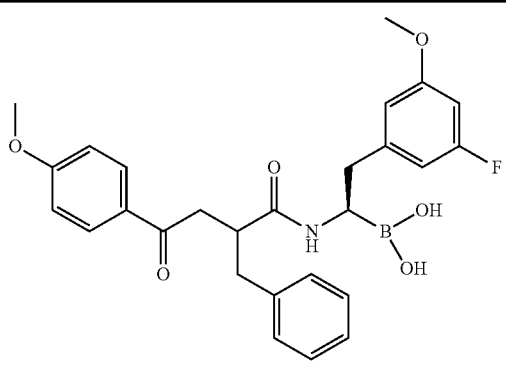 | ** | * | ++ |
| 50 | 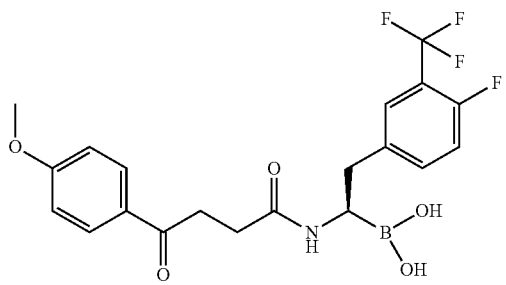 [SMILES: COc1ccc(C(=O)CCC(=O)N[C@@H](Cc2ccc(F)c(C(F)(F)F)c2)B(O)O)cc1] | *** | * | ++ |
| 51 | 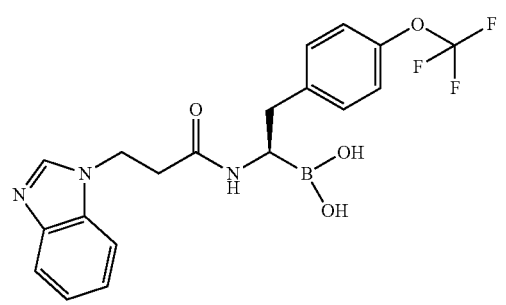 [SMILES: O=C(CCn1cnc2ccccc21)N[C@@H](Cc1ccc(OC(F)(F)F)cc1)B(O)O] | ** | * | + |
| 52 | 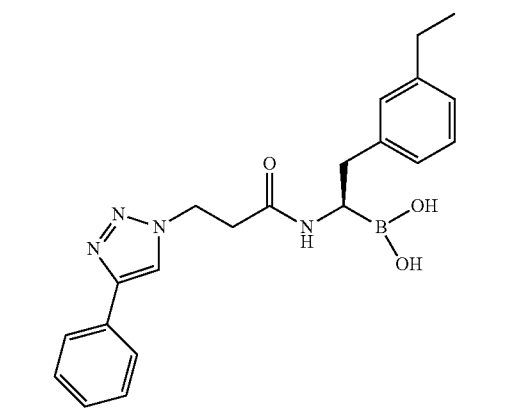 [SMILES: CCc1cccc(C[C@H](NC(=O)CCn2cc(-c3ccccc3)nn2)B(O)O)c1] | ** | * | +++ |

-continued

| Ex | Formula | LMP7 IC50 (M) | Beta5 IC50 (M) | Selectivity LMP7 vs Beta5 |
|---|---|---|---|---|
| 53 | | **** | *** | + |
| 54 | | **** | *** | ++ |
| 55 | | **** | *** | + |
| 56 | | *** | ** | ++ |

-continued
| Ex | Formula | LMP7 IC50 (M) | Beta5 IC50 (M) | Selectivity LMP7 vs Beta5 |
|---|---|---|---|---|
| 57 | 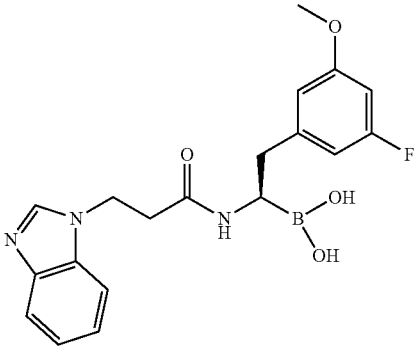 [SMILES: COc1cc(F)cc(C[C@H](NC(=O)CCn2cnc3ccccc32)B(O)O)c1] | ** | * | ++ |
| 58 | 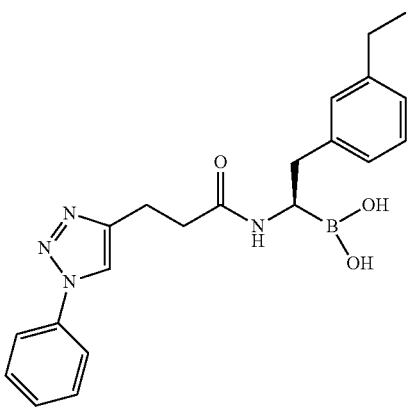 [SMILES: CCc1cccc(C[C@H](NC(=O)CCc2cn(-c3ccccc3)nn2)B(O)O)c1] | *** | * | +++ |
| 59 | 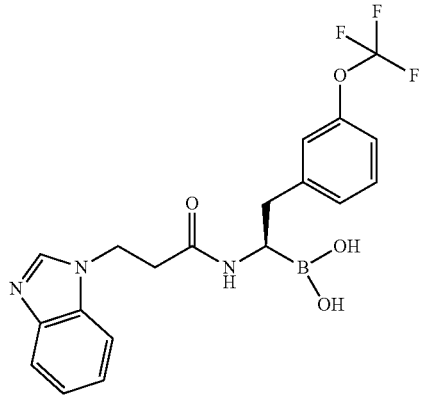 [SMILES: O=C(CCn1cnc2ccccc21)N[C@@H](Cc1cccc(OC(F)(F)F)c1)B(O)O] | ** | * | + |

-continued

| Ex | Formula | LMP7 IC50 (M) | Beta5 IC50 (M) | Selectivity LMP7 vs Beta5 |
|---|---|---|---|---|
| 60 | | *** | ** | ++ |
| 61 | | **** | ** | +++ |
| 62 | | **** | *** | ++ |
| 63 | | **** | **** | ++ |

-continued
| Ex | Formula | LMP7 IC50 (M) | Beta5 IC50 (M) | Selectivity LMP7 vs Beta5 |
|---|---|---|---|---|
| 64 | 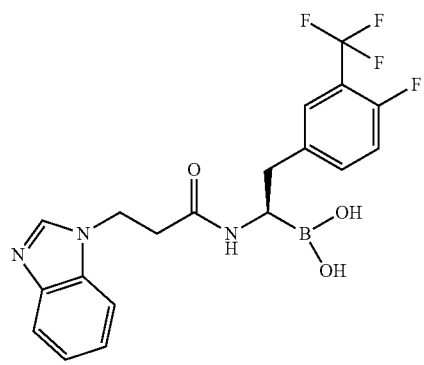 [SMILES: O=C(CCn1cnc2ccccc21)N[C@@H](Cc1ccc(F)c(C(F)(F)F)c1)B(O)O] | ** | * | ++ |
| 65 | 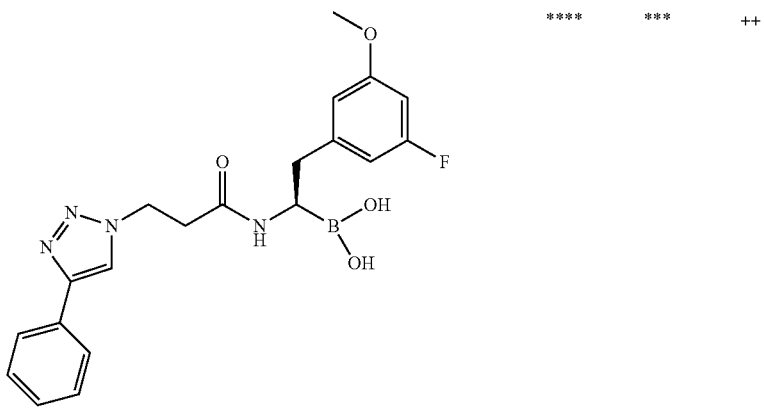 | ** | * | ++ |
| 66 | 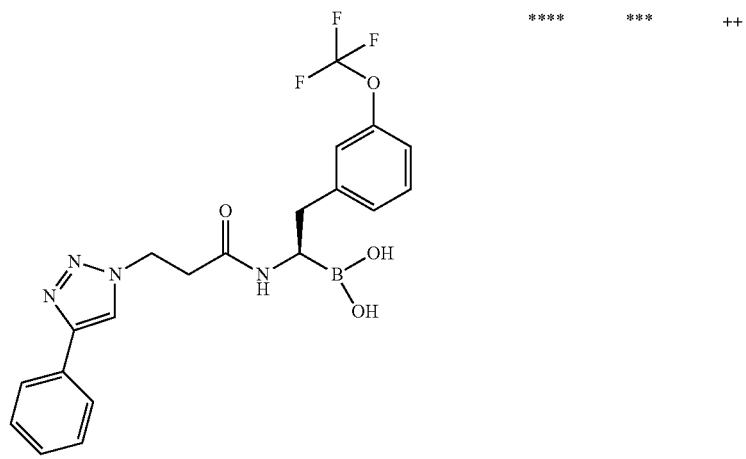 | ** | * | ++ |

-continued

| Ex | Formula | LMP7 IC50 (M) | Beta5 IC50 (M) | Selectivity LMP7 vs Beta5 |
|---|---|---|---|---|
| 67 | | **** | *** | ++ |
| 68 | | **** | ** | +++ |
| 69 | | *** | ** | + |

-continued
| Ex | Formula | LMP7 IC50 (M) | Beta5 IC50 (M) | Selectivity LMP7 vs Beta5 |
|---|---|---|---|---|
| 70 | 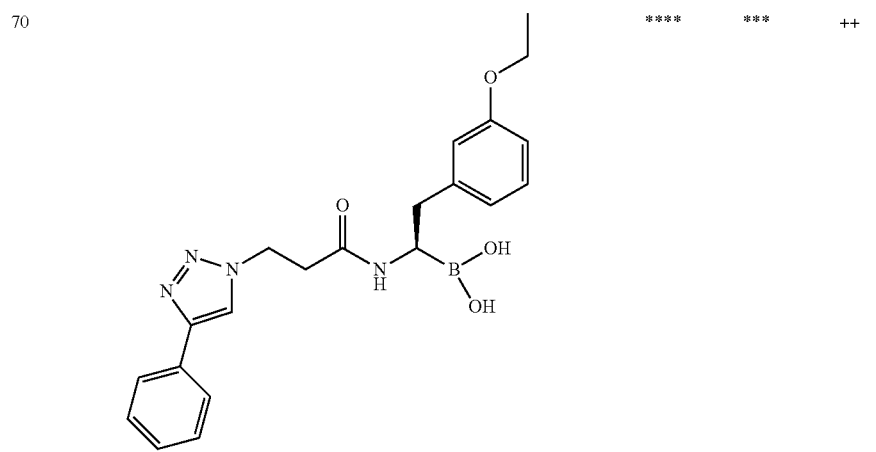 | ** | * | ++ |
| 71 | 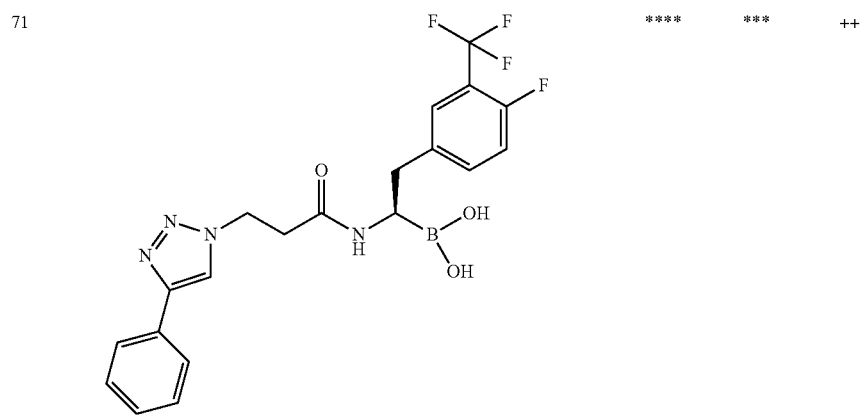 | ** | * | ++ |
| 72 | 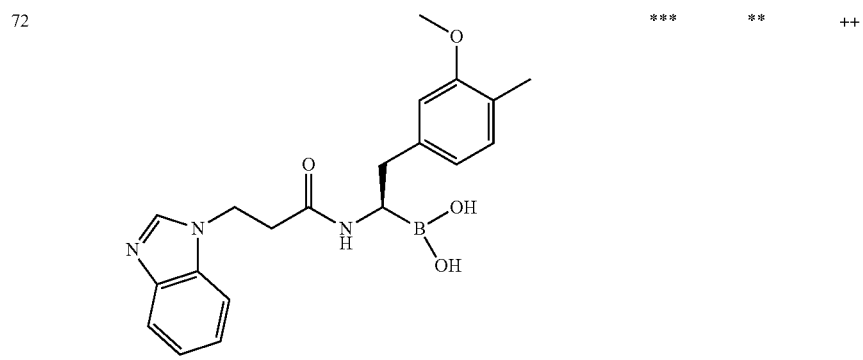 | * |  | ++ |

-continued
| Ex | Formula | LMP7 IC50 (M) | Beta5 IC50 (M) | Selectivity LMP7 vs Beta5 |
|---|---|---|---|---|
| 73 | 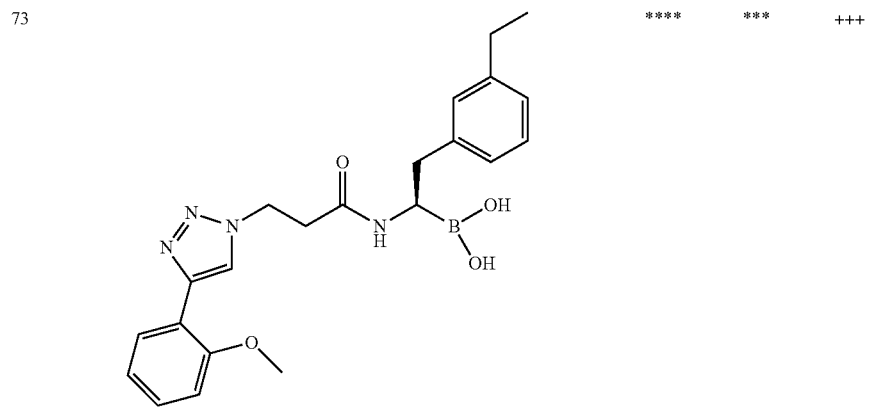 | ** | * | +++ |
| 74 | 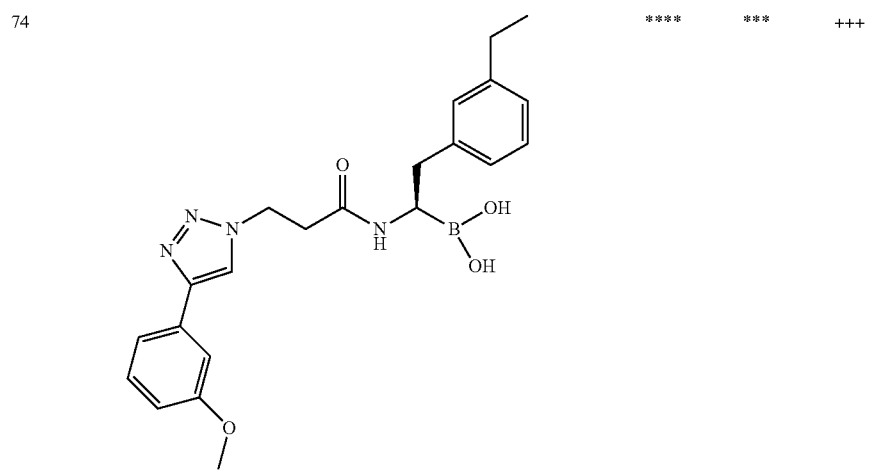 | ** | * | +++ |
| 75 | 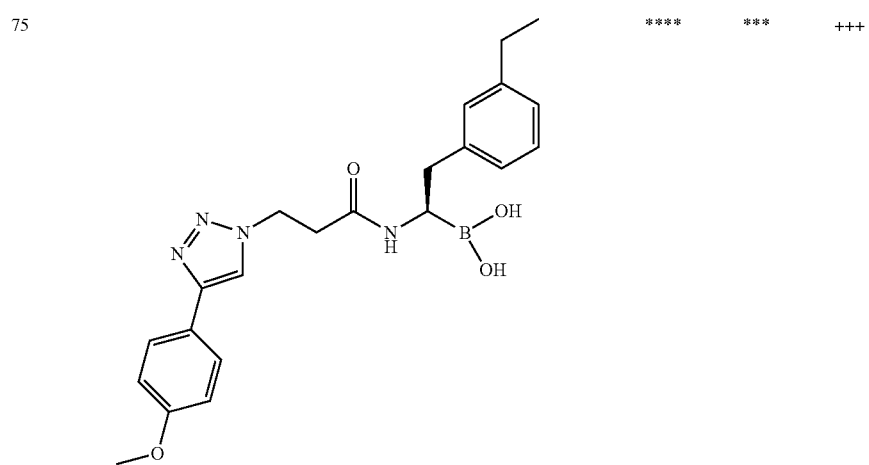 | ** | * | +++ |

-continued

| Ex | Formula | LMP7 IC50 (M) | Beta5 IC50 (M) | Selectivity LMP7 vs Beta5 |
|---|---|---|---|---|
| 76 | | **** | ** | +++ |
| 77 | | ** | | nd |
| 78 | | **** | ** | +++ |
| 79 | | **** | *** | +++ |
| 80 | | **** | **** | +++ |

-continued

| Ex | Formula | LMP7 IC50 (M) | Beta5 IC50 (M) | Selectivity LMP7 vs Beta5 |
|---|---|---|---|---|
| 81 | | **** | **** | ++ |
| 82 | | **** | **** | ++ |
| 83 | | **** | *** | ++ |
| 84 | | **** | **** | ++ |
| 85 | | **** | **** | +++ |

-continued

| Ex | Formula | LMP7 IC50 (M) | Beta5 IC50 (M) | Selectivity LMP7 vs Beta5 |
|---|---|---|---|---|
| 86 | | **** | *** | +++ |
| 87 | | **** | **** | ++ |
| 88 | | **** | **** | ++ |
| 89 | | **** | **** | ++ |

-continued
| Ex | Formula | LMP7 IC50 (M) | Beta5 IC50 (M) | Selectivity LMP7 vs Beta5 |
|---|---|---|---|---|
| 90 | 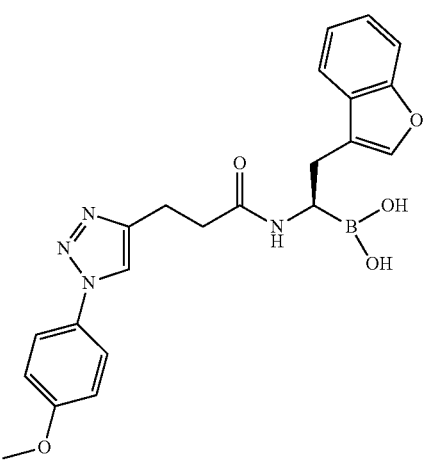 [SMILES: COc1ccc(-n2cc(CCC(=O)N[C@@H](Cc3coc4ccccc34)B(O)O)nn2)cc1] | ** | ** | +++ |
| 91 | 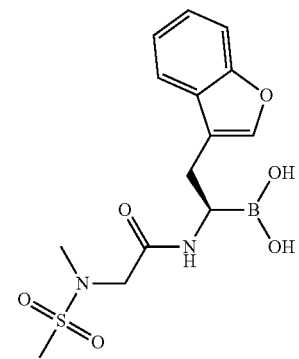 [SMILES: CN(CC(=O)N[C@@H](Cc1coc2ccccc12)B(O)O)S(C)(=O)=O] | ** | * | +++ |
| 92 | 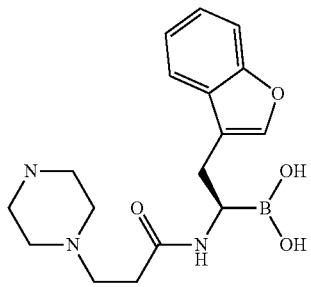 [SMILES: O=C(CCN1CCNCC1)N[C@@H](Cc1coc2ccccc12)B(O)O] | ** | * | +++ |
| 93 | 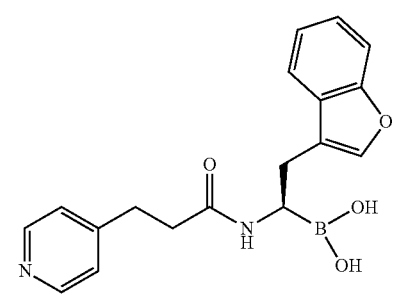 [SMILES: O=C(CCc1ccncc1)N[C@@H](Cc1coc2ccccc12)B(O)O] | ** | ** | ++ |

-continued
| Ex | Formula | LMP7 IC50 (M) | Beta5 IC50 (M) | Selectivity LMP7 vs Beta5 |
|---|---|---|---|---|
| 94 | 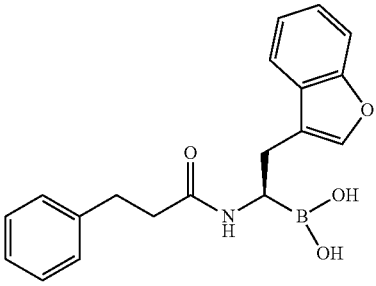 [SMILES: O=C(CCc1ccccc1)N[C@@H](Cc1coc2ccccc12)B(O)O] | ** | ** | +++ |
| 95 | 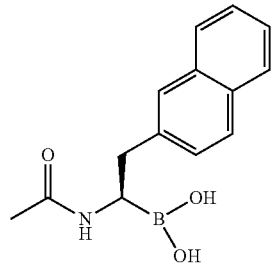 [SMILES: CC(=O)N[C@@H](Cc1ccc2ccccc2c1)B(O)O] | * |  | +++ |
| 96 | 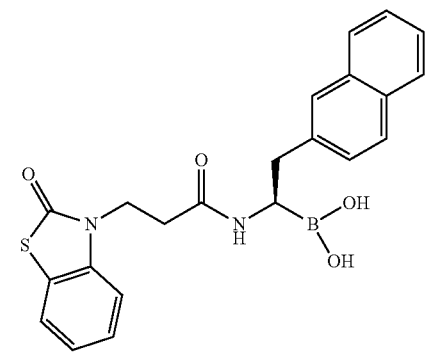 [SMILES: O=C(CCn1c(=O)sc2ccccc21)N[C@@H](Cc1ccc2ccccc2c1)B(O)O] | ** | ** | +++ |
| 97 | 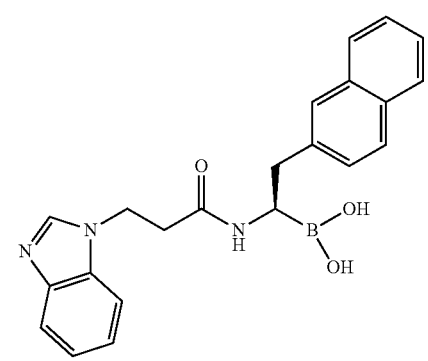 [SMILES: O=C(CCn1cnc2ccccc21)N[C@@H](Cc1ccc2ccccc2c1)B(O)O] | ** | ** | ++ |

-continued
| Ex | Formula | LMP7 IC50 (M) | Beta5 IC50 (M) | Selectivity LMP7 vs Beta5 |
|---|---|---|---|---|
| 98 | 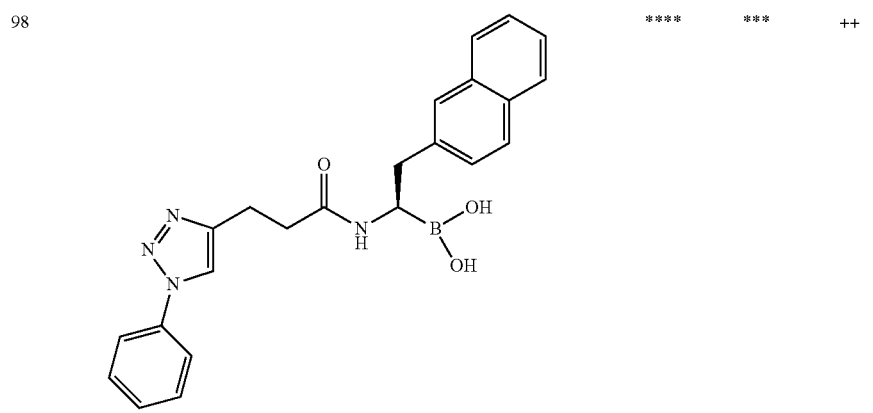 | ** | * | ++ |
| 99 | 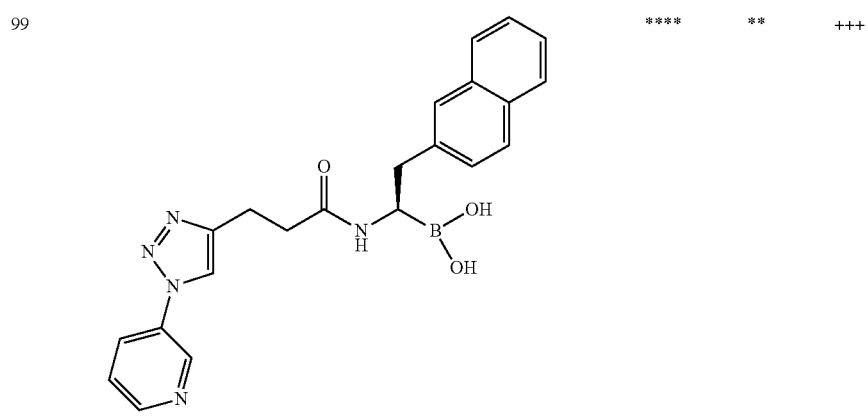 | ** |  | +++ |
| 100 | 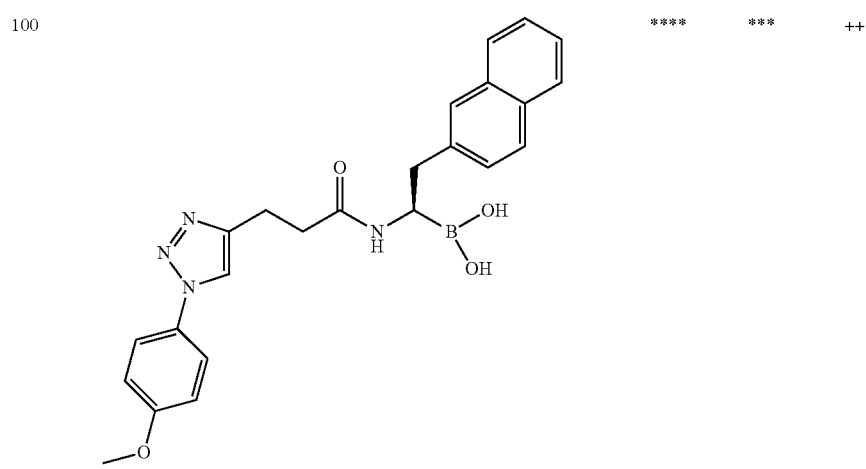 | ** | * | ++ |

| Ex | Formula | LMP7 IC50 (M) | Beta5 IC50 (M) | Selectivity LMP7 vs Beta5 |
|---|---|---|---|---|
| 101 | | **** | **** | +++ |
| 102 | | **** | **** | ++ |
| 103 | | **** | **** | ++ |
| 104 | | **** | **** | + |

-continued
| Ex | Formula | LMP7 IC50 (M) | Beta5 IC50 (M) | Selectivity LMP7 vs Beta5 |
|---|---|---|---|---|
| 105 | 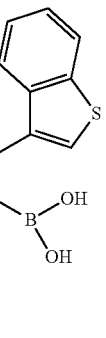 | ** | ** | ++ |
| 106 | 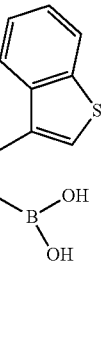 | ** | ** | ++ |
| 107 | 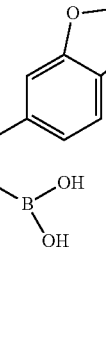 | ** | ** | ++ |
| 108 | 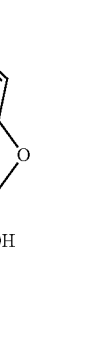 | * | * | + |

| Ex | Formula | LMP7 IC50 (M) | Beta5 IC50 (M) | Selectivity LMP7 vs Beta5 |
|---|---|---|---|---|
| 109 | | **** | *** | + |
| 110 | | **** | **** | ++ |

*: IC$_{50}$ > 5 μM,
**: 0.5 μM < IC$_{50}$ < 5 μM,
***: 0.05 μM < IC$_{50}$ < 0.5 μM,
****: IC$_{50}$ < 0.05 μM,
+: Selectivity < 10,
++: 10 < Selectivity < 30,
+++: Selectivity > 30,
n.d: not determined.

The invention claimed is:

1. A compound of Formula (I)

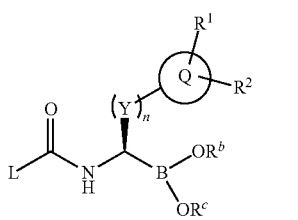

wherein $R^b$ and $R^c$ are each independently H or $C_1$-$C_6$-alkyl; or $R^b$ and $R^c$ together with the atoms to which each is attached, form a 5 or 6 membered-ring;

Q denotes Ar, Het or cycloalkyl;

$R^1$ and $R^2$ are each independently H, $OR^a$, Hal, or $C_1$-$C_6$-alkyl; wherein 1 to 5 H atoms may be independently substituted by OH or Hal;

Y denotes $CR^3R^4$;

$R^3$ and $R^4$ are each independently H or $C_1$-$C_6$-alkyl;

L denotes $L_1$, or $L_2$;

n is an integer selected from 1 to 3;

$L_1$ is

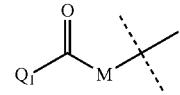

wherein $Q_1$ is Ar or Het, optionally substituted with 1 to 5 groups independently selected from ORa, Hal, phenyl, and C1-C6-alkyl, wherein 1 to 5 H atoms may be independently replaced by OH or Hal;

$L_2$ is

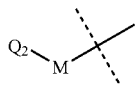

wherein $Q_2$ is a fused bicyclic system comprising 1 nitrogen atom and 1 to 3 additional groups independently selected from O, S, N, or CO, and wherein at least one of the rings is aromatic, wherein the fused bicyclic system is optionally substituted with 1 to 5 groups independently selected from $OR^a$, Hal, phenyl, and $C_1$-$C_6$-alkyl, wherein 1 to 5 H atoms may be independently replaced by OH or Hal;

or $Q_2$ is an unsaturated or aromatic 5 membered-ring system comprising 1 to 3 heteroatoms selected from N, O, S and CO, and optionally substituted with a phenyl ring or pyridine ring, wherein the phenyl ring and pyridine ring are optionally substituted with 1 to 4 groups independently selected from $OR^a$, Hal, phenyl, and $C_1$-$C_6$-alkyl, wherein 1 to 5 H atoms may be independently replaced by OH or Hal;

each M is independently a linear or branched alkylene having 1 to 5 carbon atoms wherein 1 or 2 H atoms may be replaced by $OR^a$ or a phenyl ring, which is optionally substituted with 1 to 5 groups independently selected from Hal, $OR^a$, and $C_1$-$C_6$-alkyl, each of which is optionally substituted with 1 to 5 groups independently selected from OH, and Hal; or each M is independently a cycloalkylene having 3 to 7 carbon atoms; or each M is independently a thiazolidinyl group;

each $R^a$ is independently H or $C_1$-$C_6$-alkyl wherein 1 to 5 H atom may be independently substituted by OH or Hal;

each Ar is independently a 6 membered-aromatic carbocyclic ring optionally fused with another carbocyclic saturated, unsaturated or aromatic ring having 5 to 8 carbon atoms;

Het denotes a 5- or 6-membered saturated, unsaturated or aromatic heterocyclic ring having 1 to 3 heteroatoms independently selected from N, N+O—, O, S, $SO$, and $SO_2$, and optionally fused with another saturated, unsaturated or aromatic ring having 5 to 8 atoms and optionally comprising 1 to 3 heteroatoms selected from N, O, and S;

Hal denotes Cl, Br, I of F;

and enantiomers, diastereoisomers, and pharmaceutically acceptable salts thereof.

2. The compound of claim 1 wherein L is selected from the following groups:

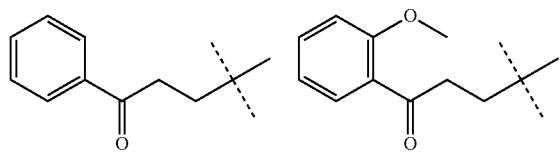

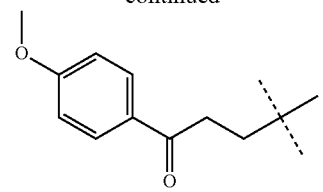

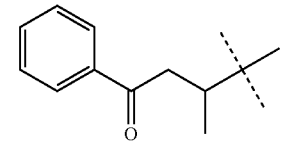

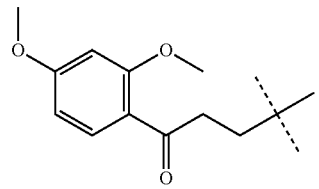
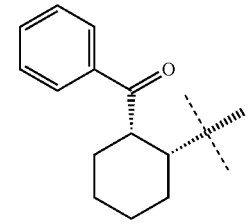

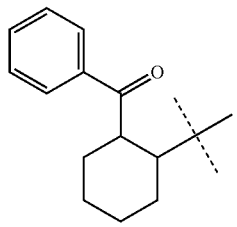
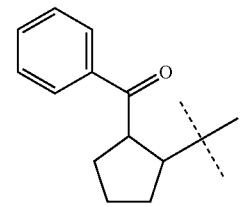

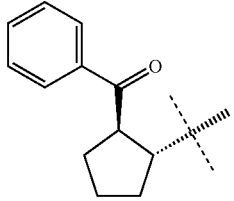
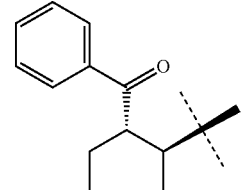

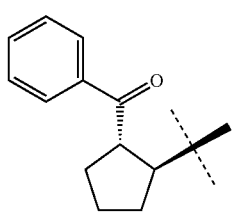
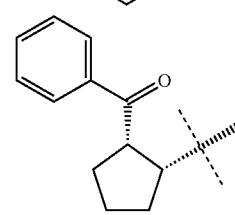

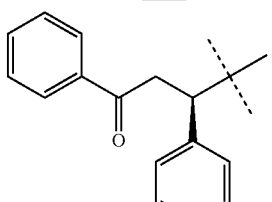
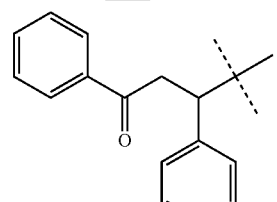

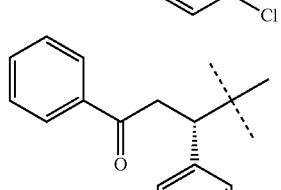
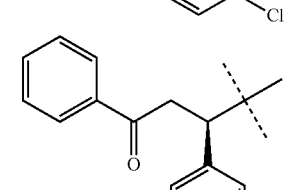

-continued
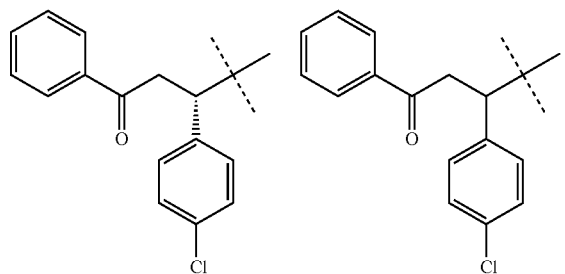
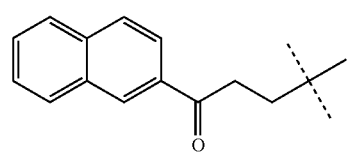
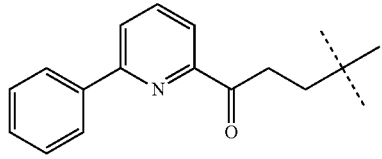
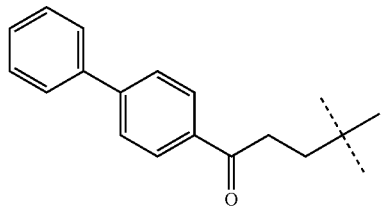
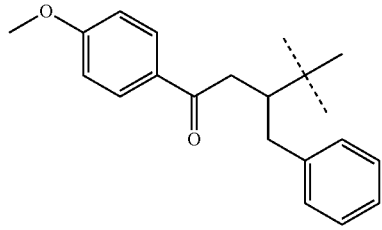
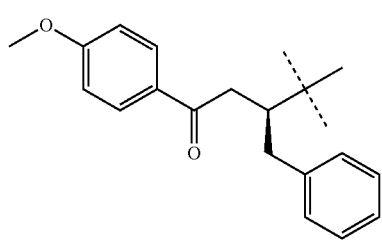
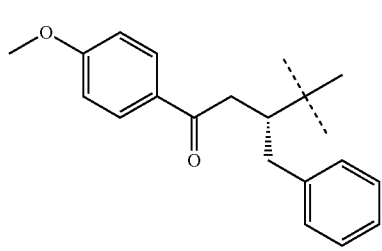
Or wherein L is selected from the following groups:
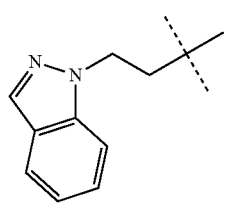
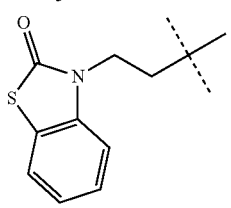
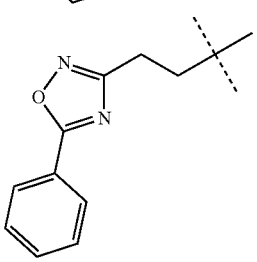
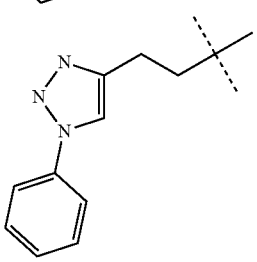
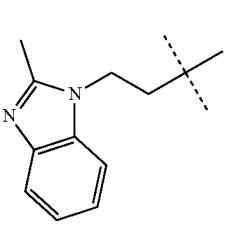
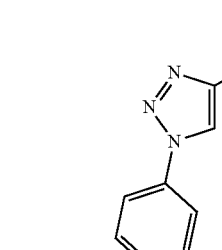
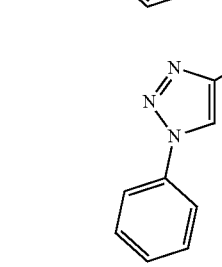

-continued
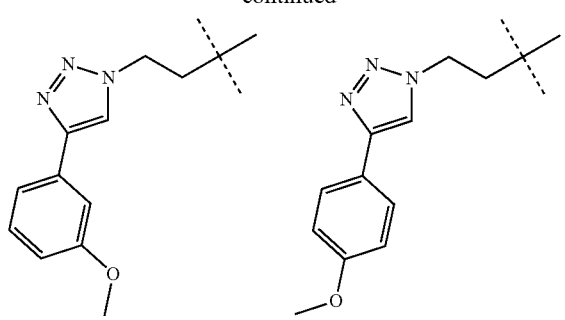
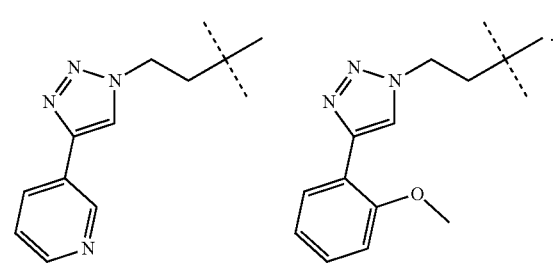
3. The compound of claim 1 wherein
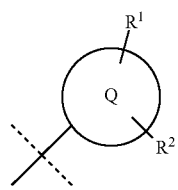
is selected from the following:
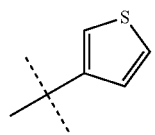 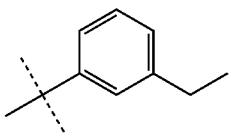
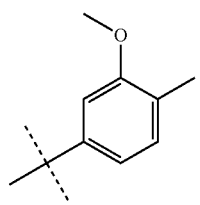 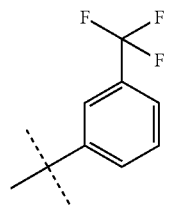
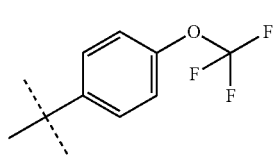 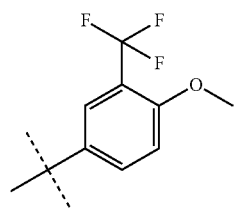
-continued
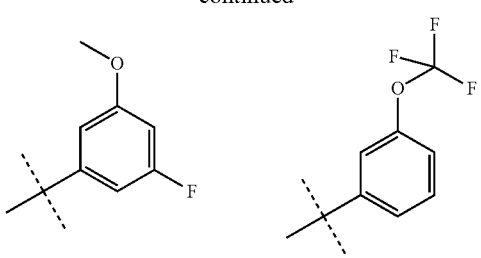
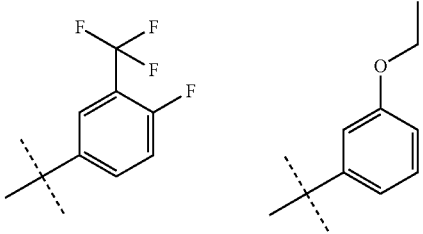
4. The compound of claim 1, selected from the following:
| Ex | Formula |
|---|---|
| 1 |  |
| 2 |  |
| 3 |  |

| Ex | Formula |
|---|---|
| 4 | 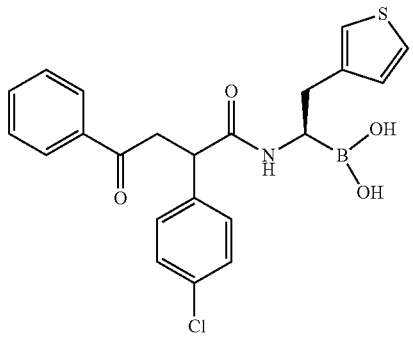 [SMILES: O=C(CC(C(=O)N[C@@H](Cc1ccsc1)B(O)O)c1ccc(Cl)cc1)c1ccccc1] |
| 5 | 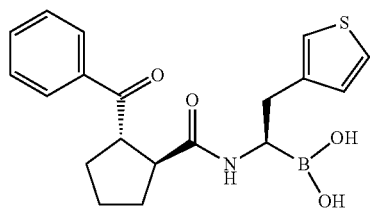 [SMILES: O=C(N[C@@H](Cc1ccsc1)B(O)O)[C@H]1CCC[C@@H]1C(=O)c1ccccc1] |
| 6 | 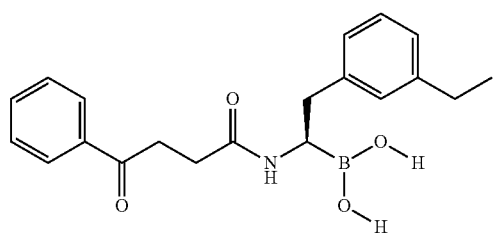 [SMILES: CCc1cccc(C[C@H](NC(=O)CCC(=O)c2ccccc2)B(O)O)c1] |
| 7 | 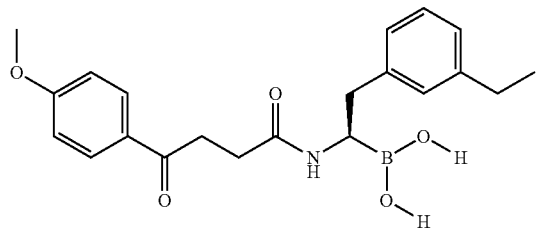 [SMILES: CCc1cccc(C[C@H](NC(=O)CCC(=O)c2ccc(OC)cc2)B(O)O)c1] |
| 8 | 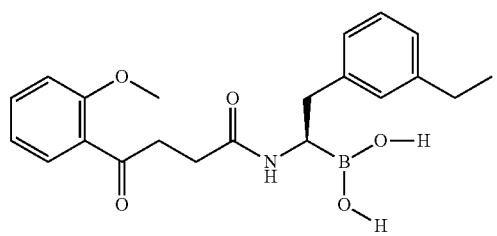 [SMILES: CCc1cccc(C[C@H](NC(=O)CCC(=O)c2ccccc2OC)B(O)O)c1] |
| 9 | 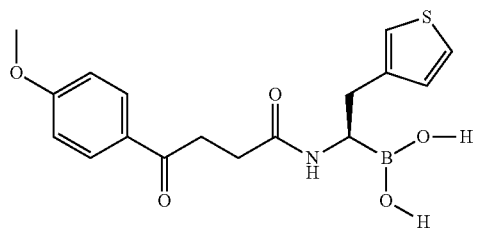 [SMILES: COc1ccc(C(=O)CCC(=O)N[C@@H](Cc2ccsc2)B(O)O)cc1] |
| Ex | Formula |
|---|---|
| 10 | 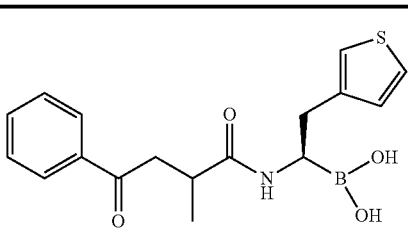 |
| 11 | 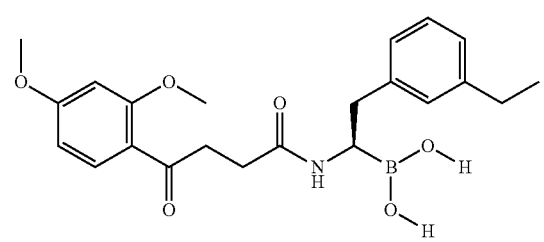 [SMILES: CCc1cccc(C[C@H](NC(=O)CCC(=O)c2ccc(OC)cc2OC)B(O)O)c1] |
| 12 | 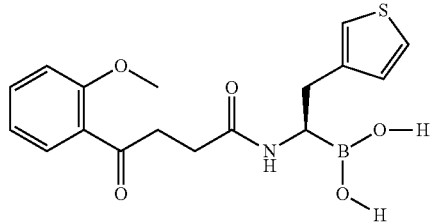 [SMILES: COc1ccccc1C(=O)CCC(=O)N[C@@H](Cc1ccsc1)B(O)O] |
| 13 | 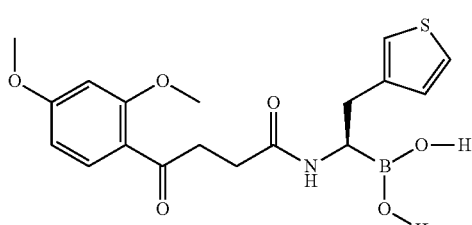 |
| 14 | 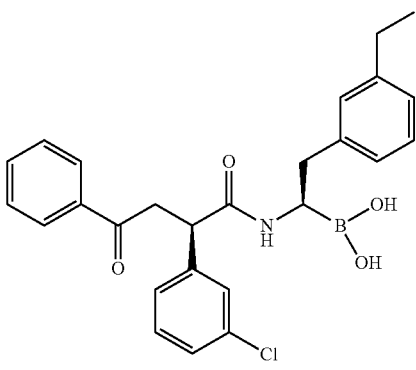 [SMILES: CCc1cccc(C[C@H](NC(=O)[C@H](CC(=O)c2ccccc2)c2cccc(Cl)c2)B(O)O)c1] |

| Ex | Formula |
|---|---|
| 15 | 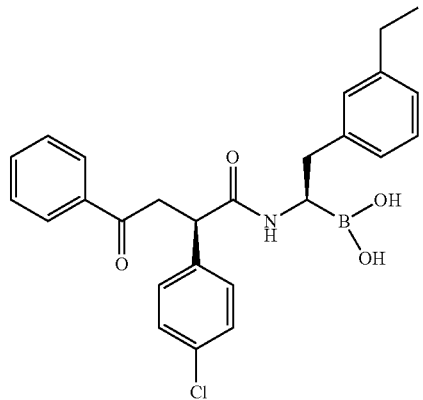 [SMILES: CCc1cccc(C[C@H](NC(=O)[C@H](CC(=O)c2ccccc2)c2ccc(Cl)cc2)B(O)O)c1] |
| 16 | 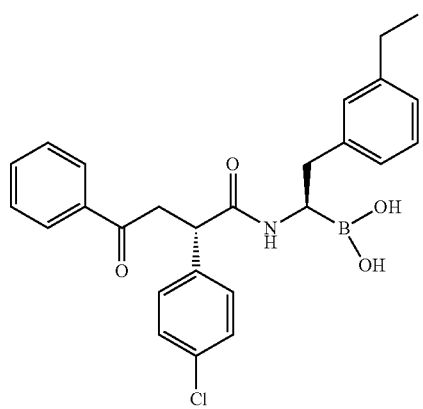 [SMILES: CCc1cccc(C[C@H](NC(=O)[C@@H](CC(=O)c2ccccc2)c2ccc(Cl)cc2)B(O)O)c1] |
| 17 | 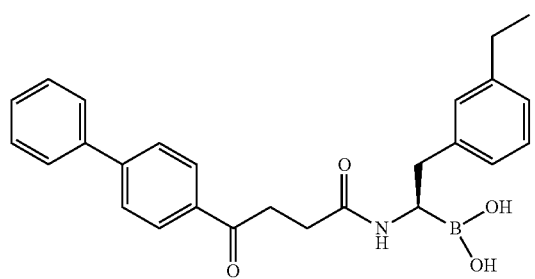 [SMILES: CCc1cccc(C[C@H](NC(=O)CCC(=O)c2ccc(-c3ccccc3)cc2)B(O)O)c1] |
| 18 | 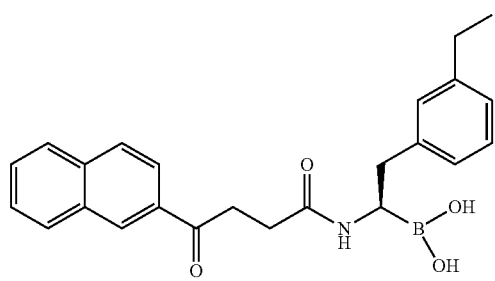 [SMILES: CCc1cccc(C[C@H](NC(=O)CCC(=O)c2ccc3ccccc3c2)B(O)O)c1] |
| 19 | 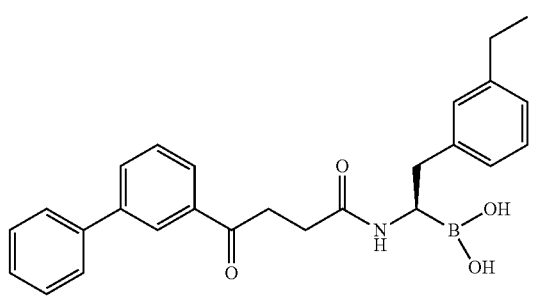 [SMILES: CCc1cccc(C[C@H](NC(=O)CCC(=O)c2cccc(-c3ccccc3)c2)B(O)O)c1] |
| 20 | 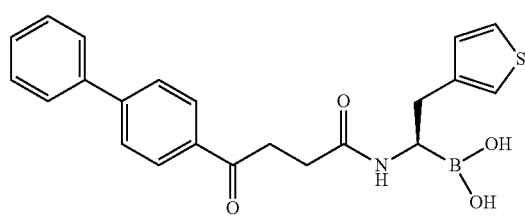 [SMILES: O=C(CCC(=O)c1ccc(-c2ccccc2)cc1)N[C@@H](Cc1ccsc1)B(O)O] |
| 21 | 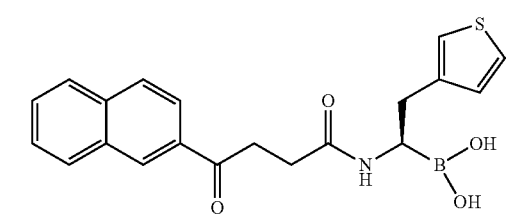 [SMILES: O=C(CCC(=O)c1ccc2ccccc2c1)N[C@@H](Cc1ccsc1)B(O)O] |
| 22 | 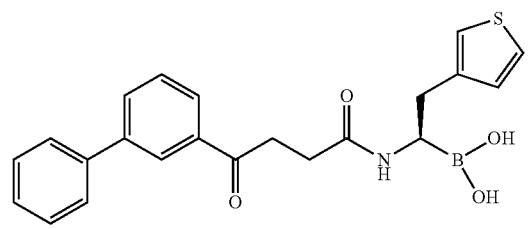 [SMILES: O=C(CCC(=O)c1cccc(-c2ccccc2)c1)N[C@@H](Cc1ccsc1)B(O)O] |
| 23 | 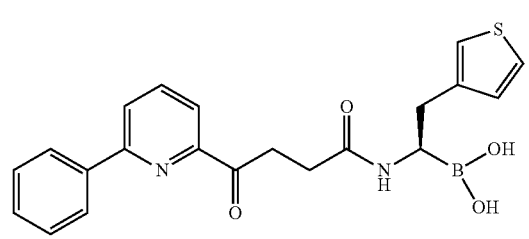 [SMILES: O=C(CCC(=O)c1cccc(-c2ccccc2)n1)N[C@@H](Cc1ccsc1)B(O)O] |
| 24 | 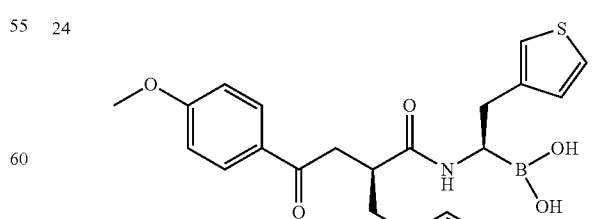 |

| Ex | Formula |
|---|---|
| 25 | |
| 26 | |
| 27 | |
| 28 | |
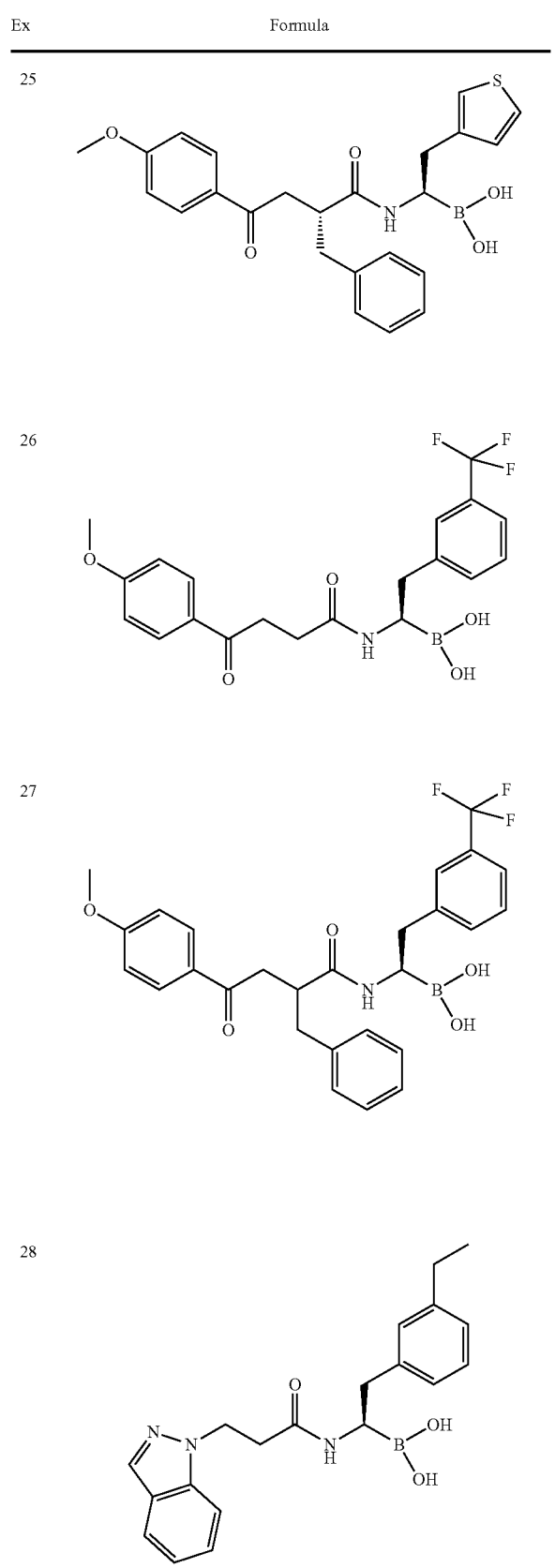
| Ex | Formula |
|---|---|
| 29 | |
| 30 | |
| 31 | |
| 32 | |
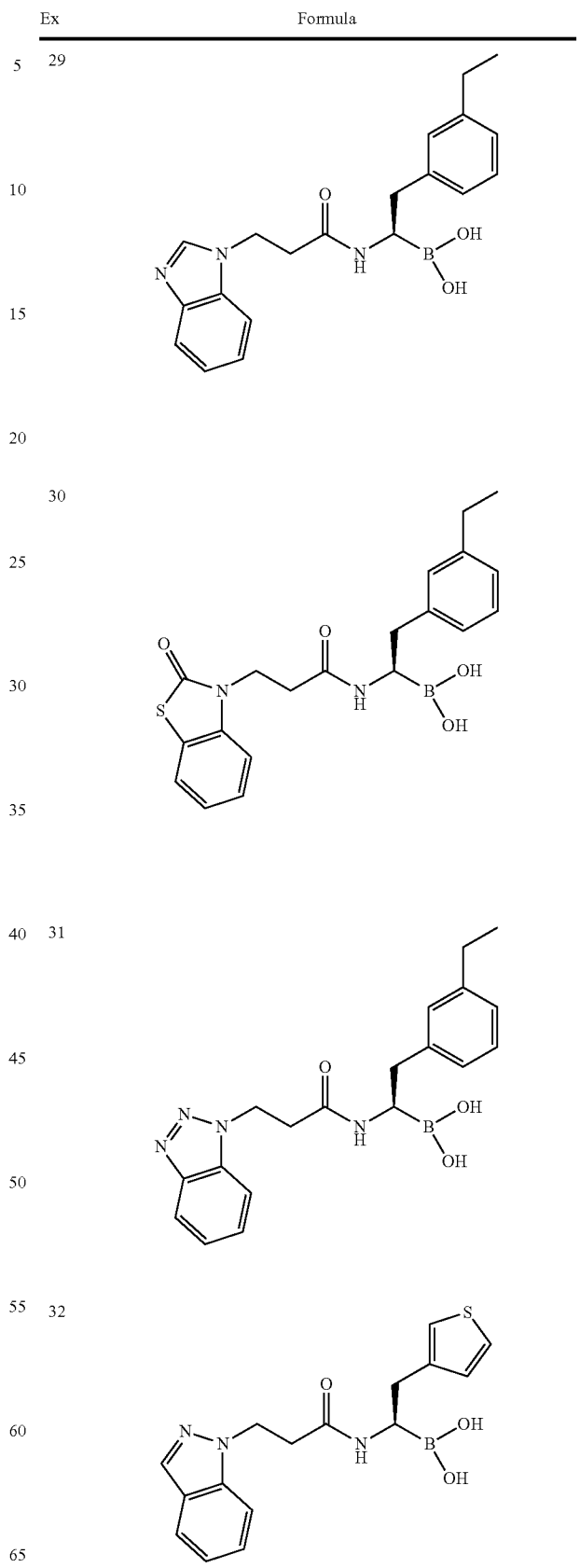

-continued
| Ex | Formula |
|---|---|
| 33 | 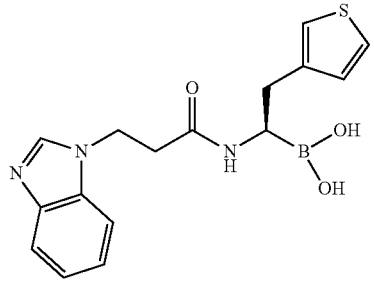 [SMILES: O=C(CCn1cnc2ccccc21)N[C@@H](Cc1ccsc1)B(O)O] |
| 34 | 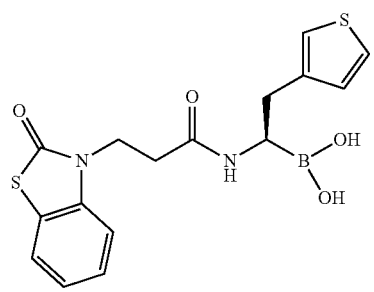 [SMILES: O=C(CCn1c(=O)sc2ccccc21)N[C@@H](Cc1ccsc1)B(O)O] |
| 35 | 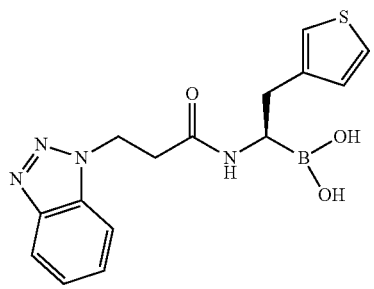 [SMILES: O=C(CCn1nnc2ccccc21)N[C@@H](Cc1ccsc1)B(O)O] |
| 36 | 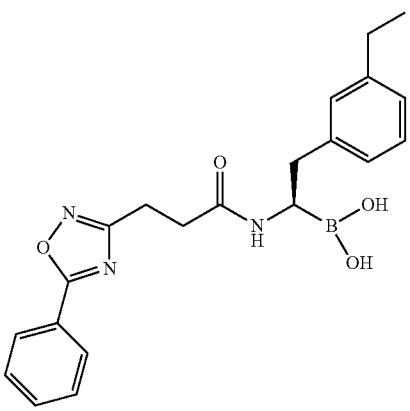 [SMILES: CCc1cccc(C[C@H](NC(=O)CCc2noc(-c3ccccc3)n2)B(O)O)c1] |
-continued
| Ex | Formula |
|---|---|
| 37 | 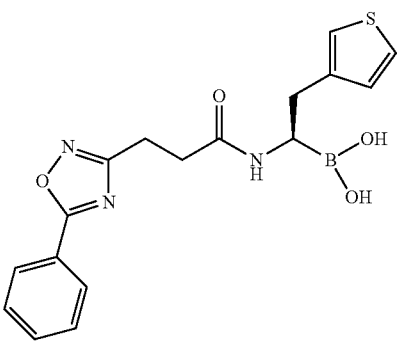 [SMILES: O=C(CCc1noc(-c2ccccc2)n1)N[C@@H](Cc1ccsc1)B(O)O] |
| 38 | 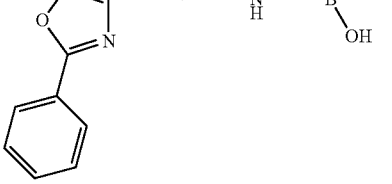 |
| 39 | 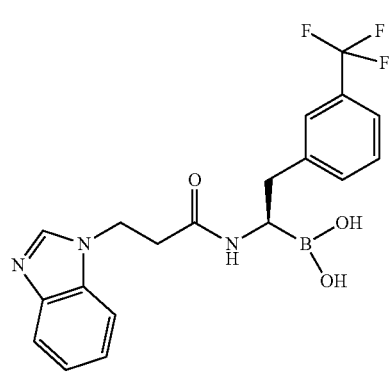 [SMILES: O=C(CCn1cnc2ccccc21)N[C@@H](Cc1cccc(C(F)(F)F)c1)B(O)O] |
| 40 | 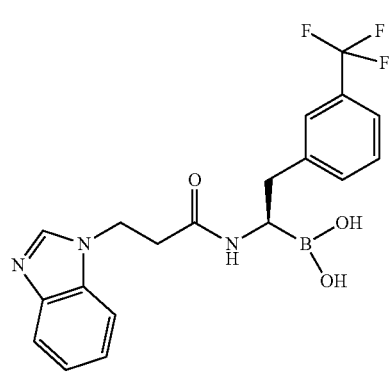 [SMILES: O=C(CCn1cnc2ccccc21)N[C@@H](Cc1cccc(C(F)(F)F)c1)B(O)O] |

195
-continued
| Ex | Formula |
|---|---|
| 41 | 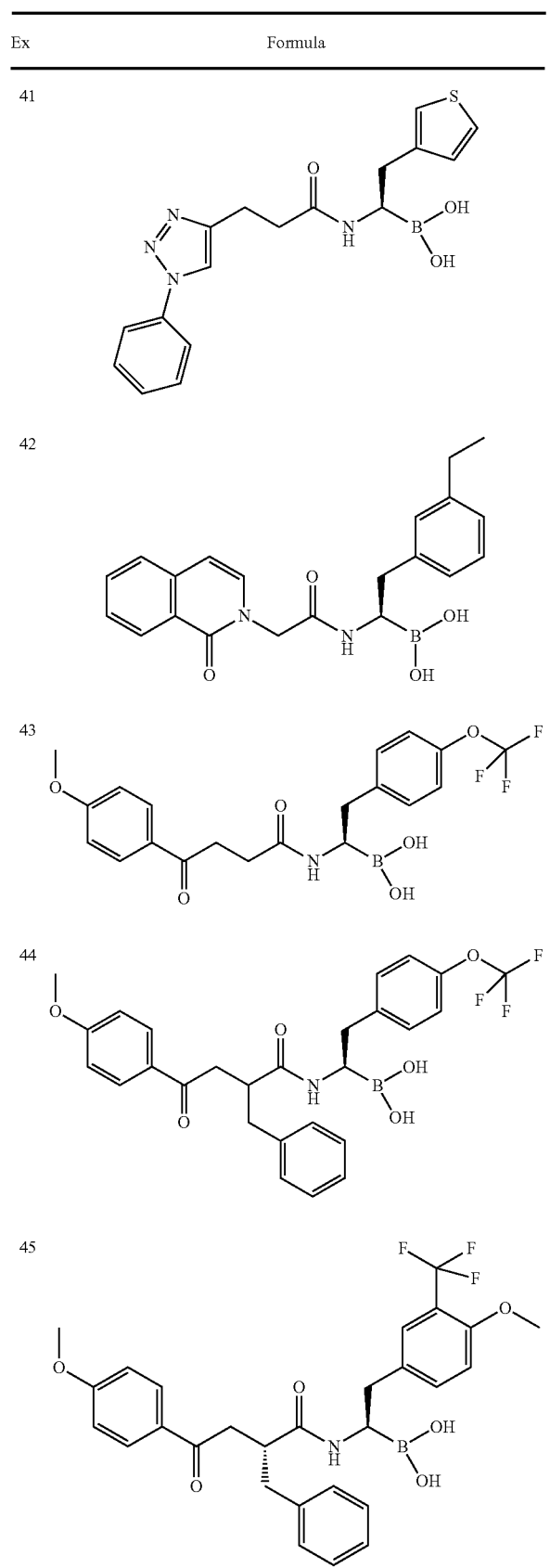 |
| 42 | |
| 43 | |
| 44 | |
| 45 | |
196
-continued
| Ex | Formula |
|---|---|
| 46 | 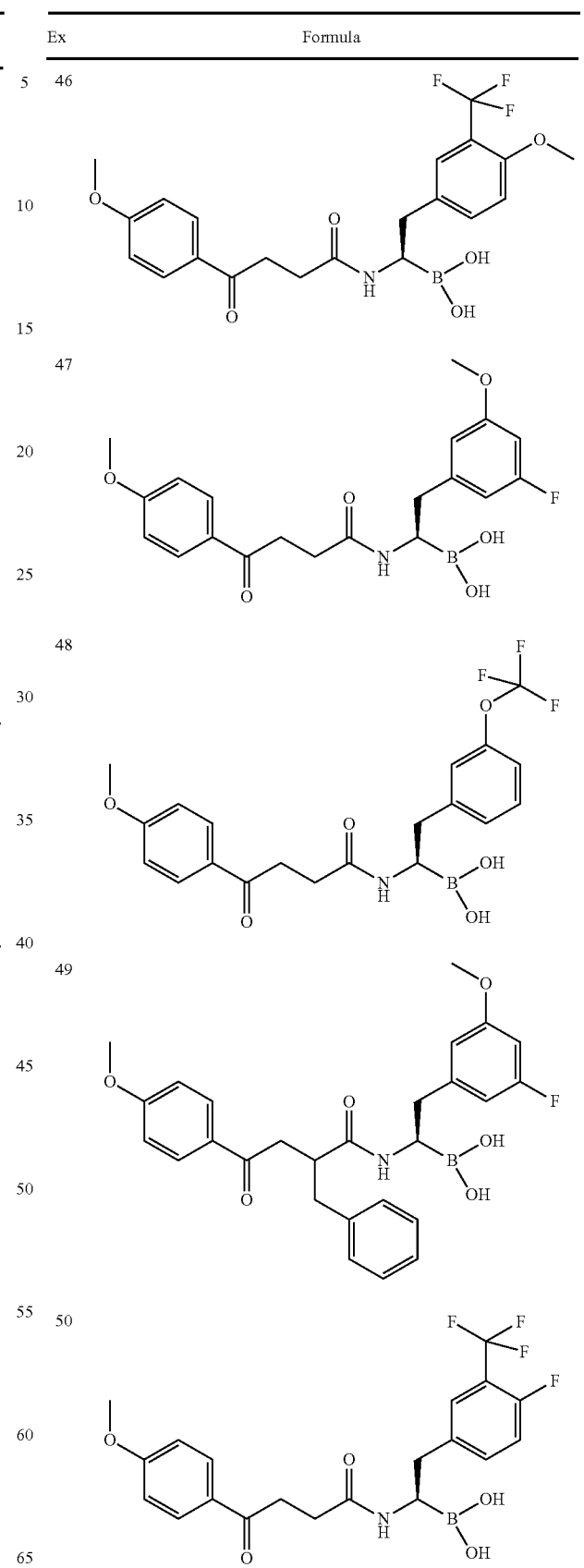 |
| 47 | |
| 48 | |
| 49 | |
| 50 | |

-continued
| Ex | Formula |
|---|---|
| 51 | 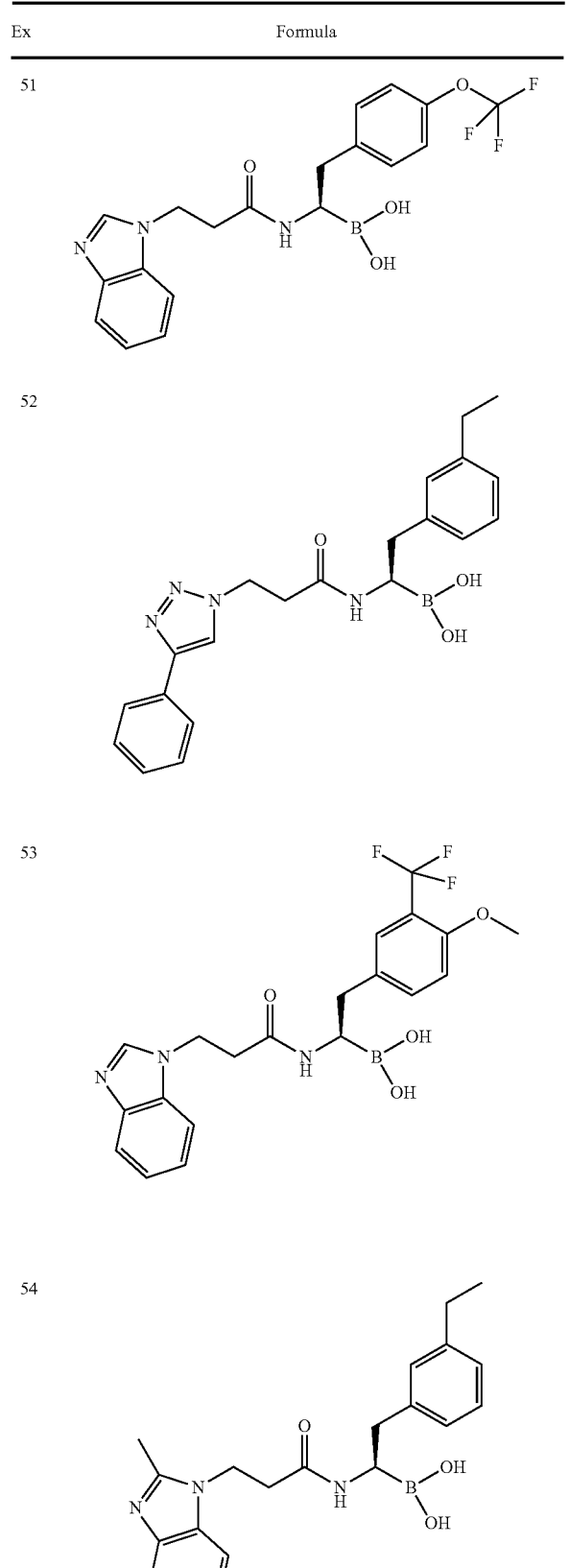 |
| 52 | |
| 53 | |
| 54 | |
-continued
| Ex | Formula |
|---|---|
| 55 | 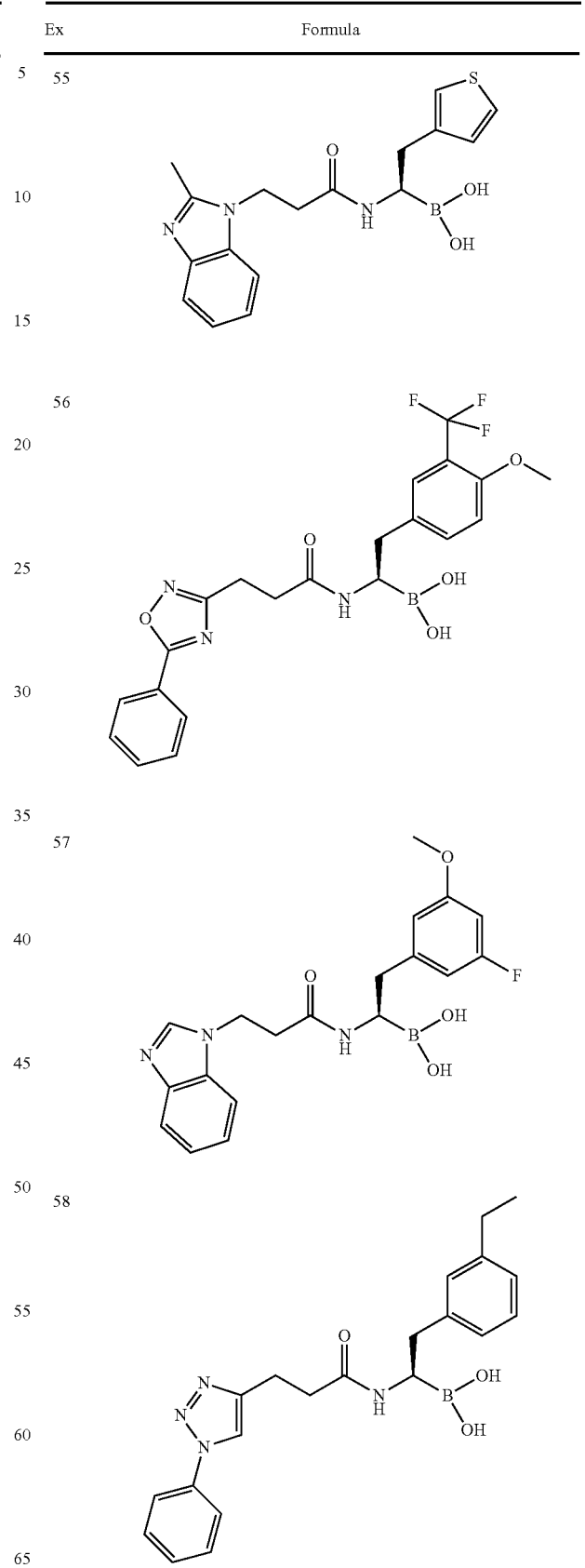 |
| 56 | |
| 57 | |
| 58 | |

| Ex | Formula |
|---|---|
| 59 | 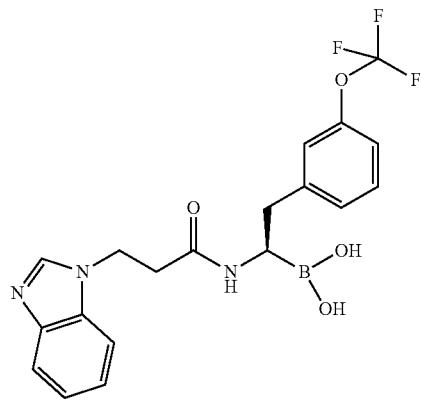 [SMILES: O=C(CCn1cnc2ccccc21)N[C@@H](Cc1cccc(OC(F)(F)F)c1)B(O)O] |
| 60 | 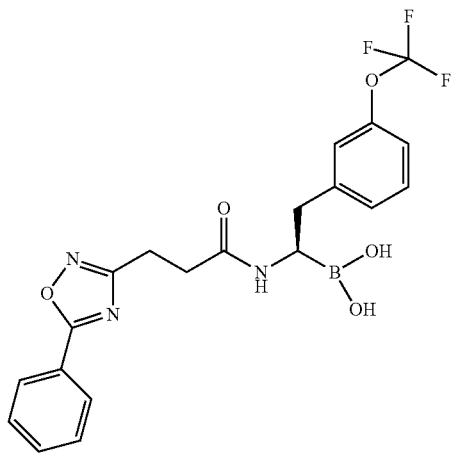 [SMILES: O=C(CCc1noc(-c2ccccc2)n1)N[C@@H](Cc1cccc(OC(F)(F)F)c1)B(O)O] |
| 61 | 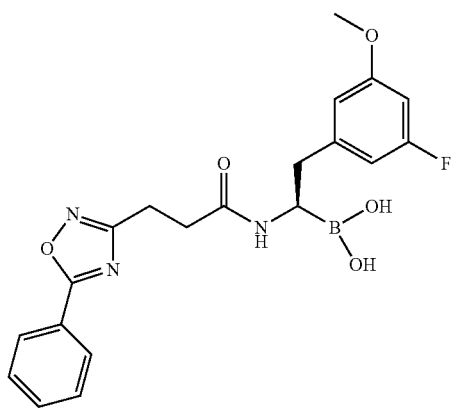 [SMILES: COc1cc(F)cc(C[C@H](NC(=O)CCc2noc(-c3ccccc3)n2)B(O)O)c1] |
| 62 | 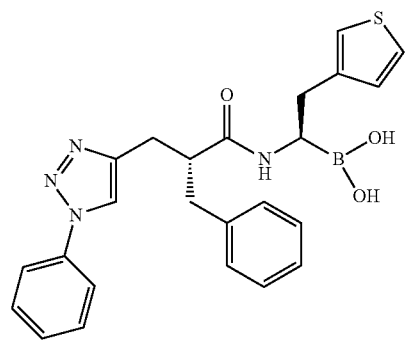 [SMILES: O=C(N[C@@H](Cc1ccsc1)B(O)O)[C@H](Cc1ccccc1)Cc1cn(-c2ccccc2)nn1] |
| Ex | Formula |
|---|---|
| 63 | 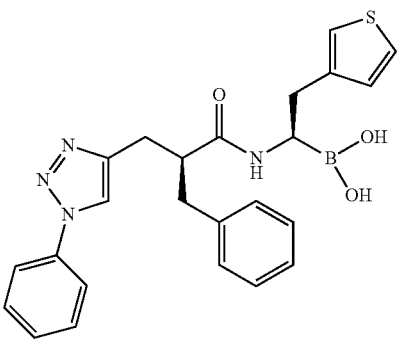 [SMILES: O=C(N[C@@H](Cc1ccsc1)B(O)O)[C@@H](Cc1ccccc1)Cc1cn(-c2ccccc2)nn1] |
| 64 | 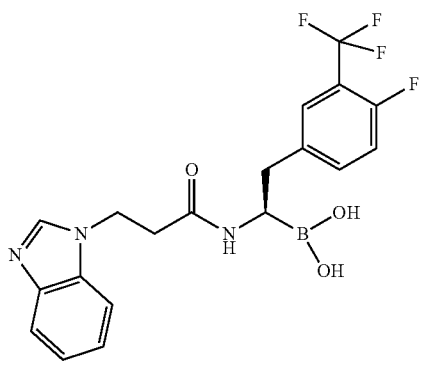 [SMILES: O=C(CCn1cnc2ccccc21)N[C@@H](Cc1ccc(F)c(C(F)(F)F)c1)B(O)O] |
| 65 | 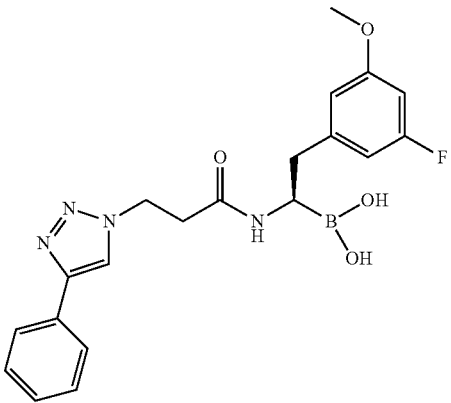 [SMILES: COc1cc(F)cc(C[C@H](NC(=O)CCn2cc(-c3ccccc3)nn2)B(O)O)c1] |
| 66 | 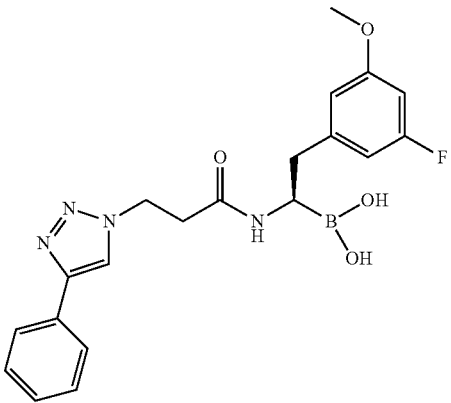 [SMILES: COc1cc(F)cc(C[C@H](NC(=O)CCn2cc(-c3ccccc3)nn2)B(O)O)c1] |

| Ex | Formula |
|---|---|
| 67 | 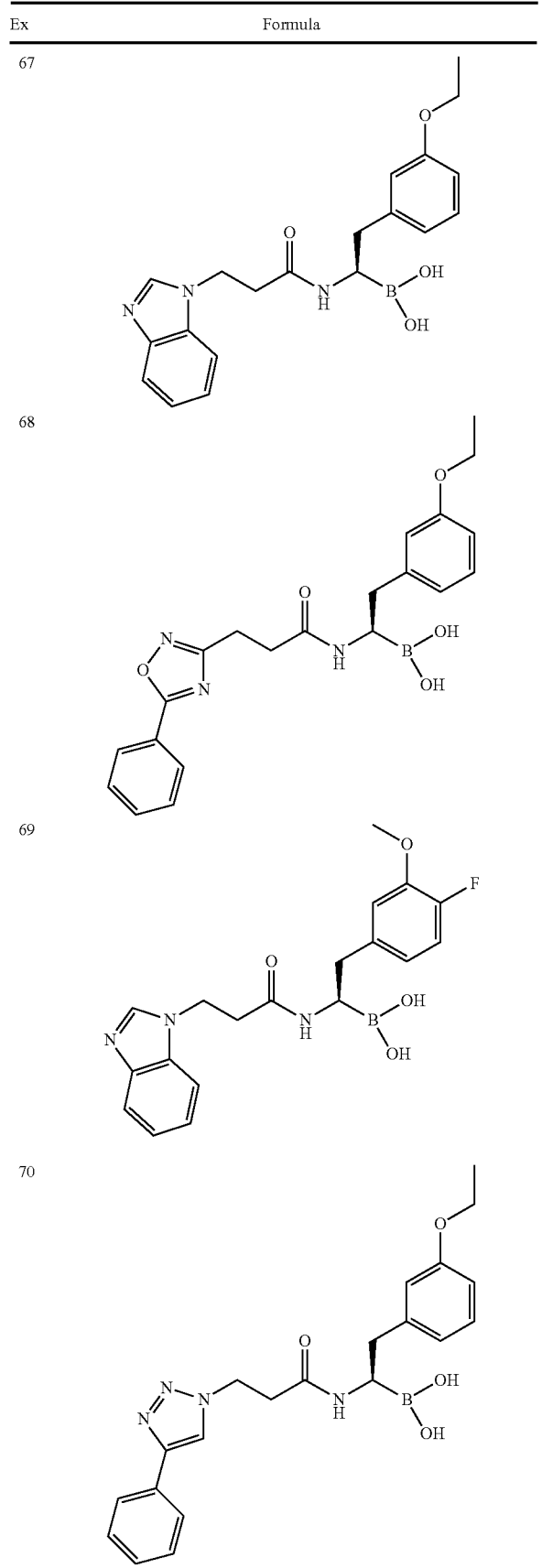 |
| 68 | |
| 69 | |
| 70 | |
| Ex | Formula |
|---|---|
| 71 | 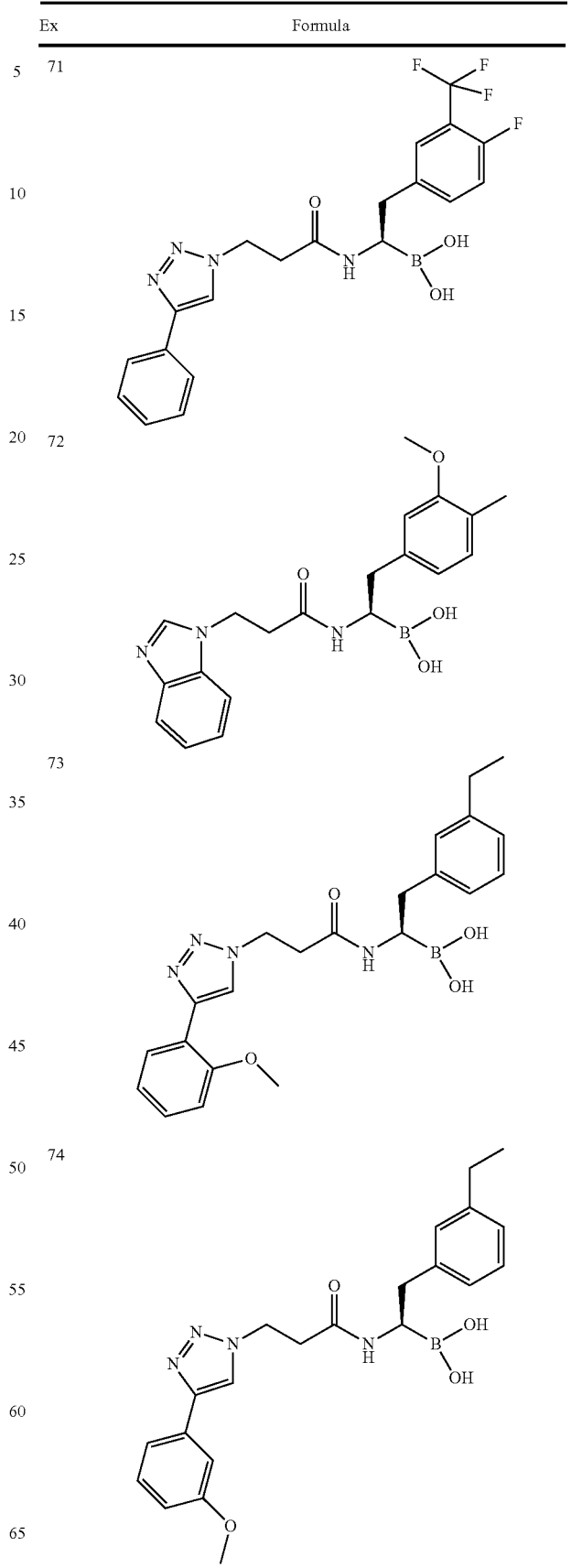 |
| 72 | |
| 73 | |
| 74 | |

-continued
| Ex | Formula |
|---|---|
| 75 | 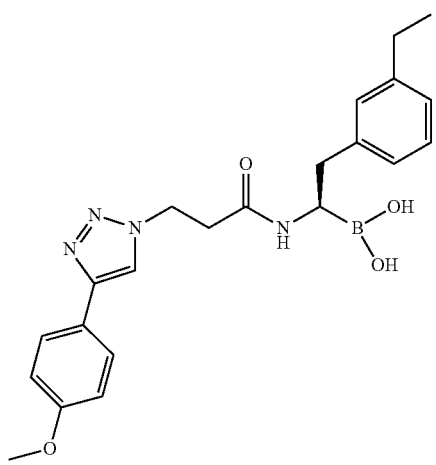 [SMILES: CCc1cccc(C[C@H](NC(=O)CCn2cc(-c3ccc(OC)cc3)nn2)B(O)O)c1] |
| 76 | 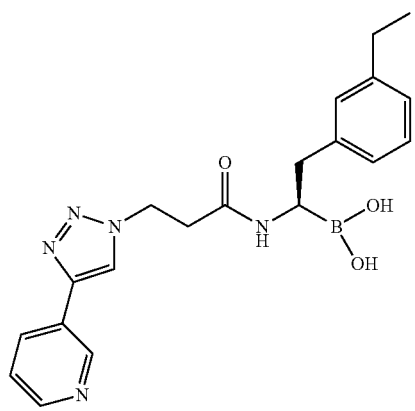 |
| 77 | 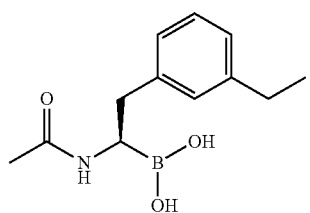 [SMILES: CCc1cccc(C[C@H](NC(C)=O)B(O)O)c1] |
| 78 | 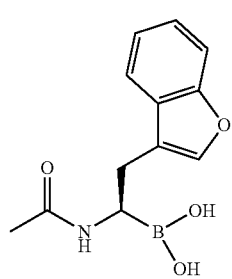 [SMILES: CC(=O)N[C@@H](Cc1coc2ccccc12)B(O)O] |
-continued
| Ex | Formula |
|---|---|
| 79 | 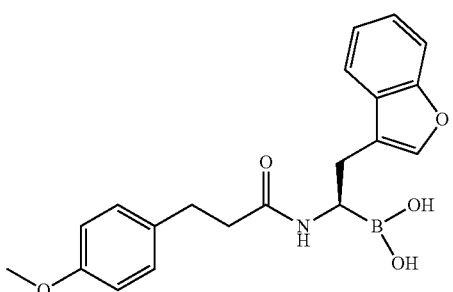 |
| 80 | 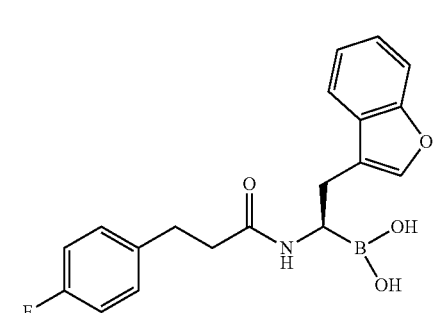 |
| 81 | 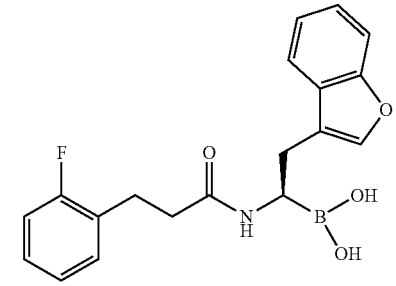 [SMILES: O=C(CCc1ccccc1F)N[C@@H](Cc1coc2ccccc12)B(O)O] |
| 82 | 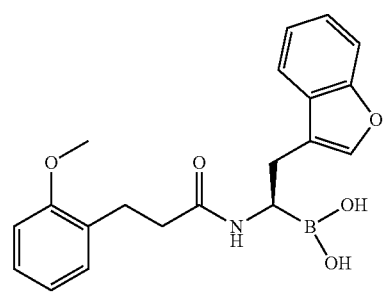 [SMILES: COc1ccccc1CCC(=O)N[C@@H](Cc1coc2ccccc12)B(O)O] |
| 83 | 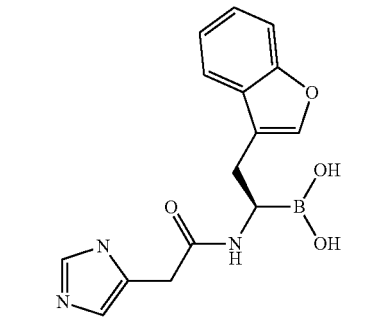 [SMILES: O=C(Cc1cnc[nH]1)N[C@@H](Cc1coc2ccccc12)B(O)O] |

-continued
| Ex | Formula |
|---|---|
| 84 | 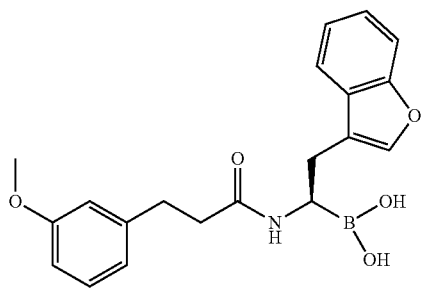 |
| 85 | 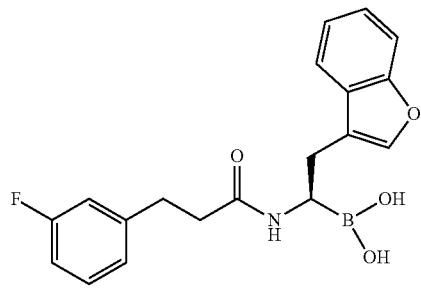 [SMILES: O=C(CCc1cccc(F)c1)N[C@@H](Cc1coc2ccccc12)B(O)O] |
| 86 | 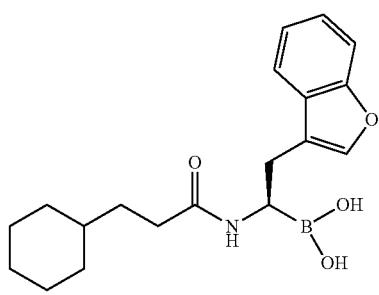 [SMILES: O=C(CCC1CCCCC1)N[C@@H](Cc1coc2ccccc12)B(O)O] |
| 87 | 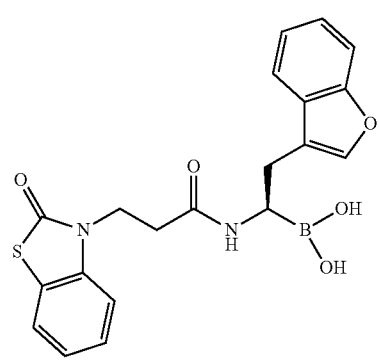 [SMILES: O=C(CCn1c(=O)sc2ccccc21)N[C@@H](Cc1coc2ccccc12)B(O)O] |
| 88 | 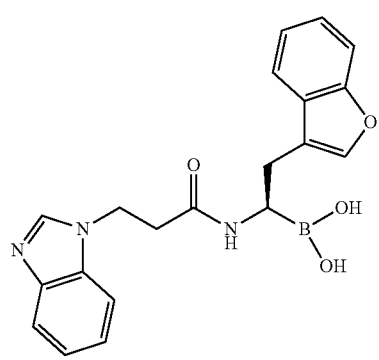 [SMILES: O=C(CCn1cnc2ccccc21)N[C@@H](Cc1coc2ccccc12)B(O)O] |
-continued
| Ex | Formula |
|---|---|
| 89 | 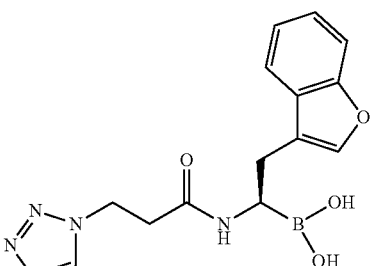 |
| 90 | 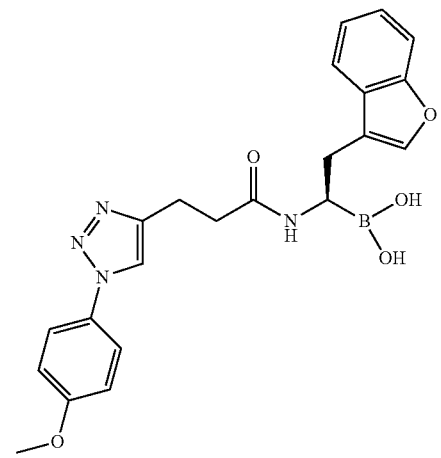 [SMILES: COc1ccc(-n2cc(CCC(=O)N[C@@H](Cc3coc4ccccc34)B(O)O)nn2)cc1] |
| 91 | 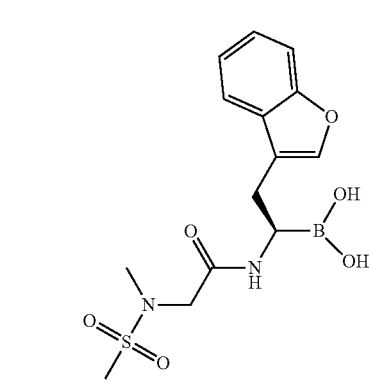 [SMILES: CN(CC(=O)N[C@@H](Cc1coc2ccccc12)B(O)O)S(C)(=O)=O] |
| 92 | 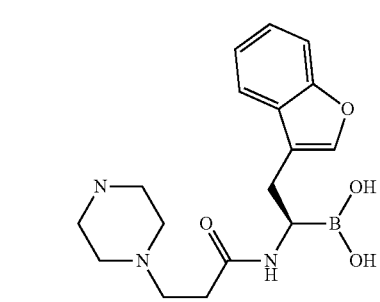 [SMILES: O=C(CCN1CCNCC1)N[C@@H](Cc1coc2ccccc12)B(O)O] |

| Ex | Formula |
|---|---|
| 93 | |
| 94 | |
| 95 | |
| 96 | |
| 97 | |
| 98 | |
| 99 | |
| 100 | |

| Ex | Formula |
|---|---|
| 101 | 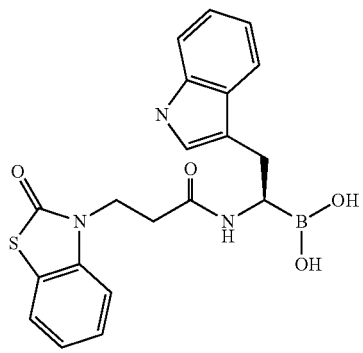 [SMILES: O=C(CCn1c(=O)sc2ccccc21)N[C@@H](Cc1c[nH]c2ccccc12)B(O)O] |
| 102 | 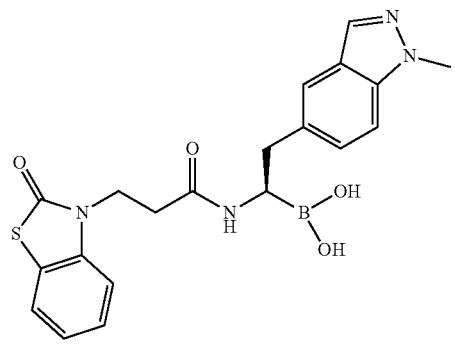 [SMILES: Cn1ncc2cc(C[C@H](NC(=O)CCn3c(=O)sc4ccccc43)B(O)O)ccc21] |
| 103 | 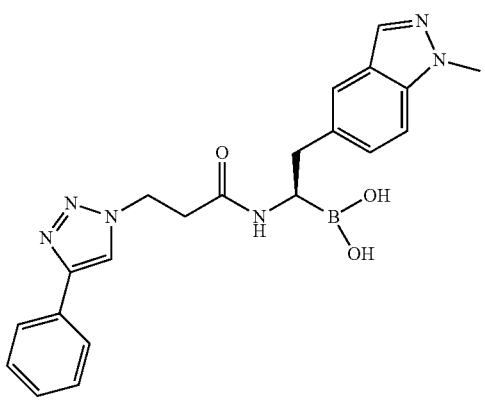 [SMILES: Cn1ncc2cc(C[C@H](NC(=O)CCn3cc(-c4ccccc4)nn3)B(O)O)ccc21] |
| 104 | 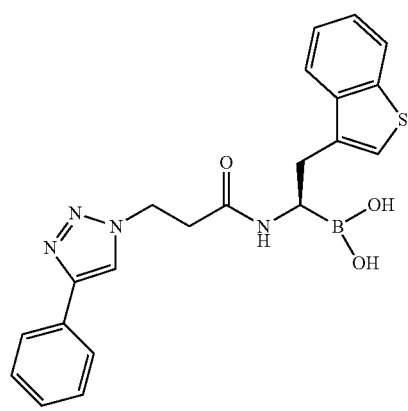 [SMILES: O=C(CCn1cc(-c2ccccc2)nn1)N[C@@H](Cc1csc2ccccc12)B(O)O] |
| 105 | 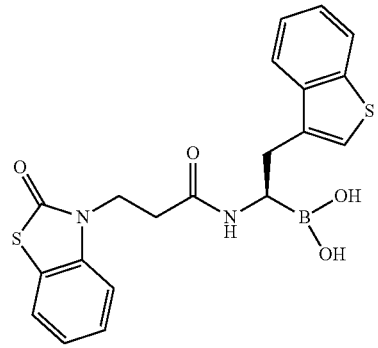 [SMILES: O=C(CCn1c(=O)sc2ccccc21)N[C@@H](Cc1csc2ccccc12)B(O)O] |
| 106 | 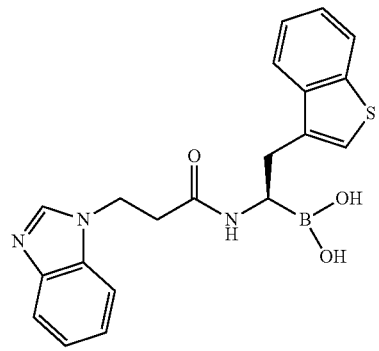 |
| 107 | 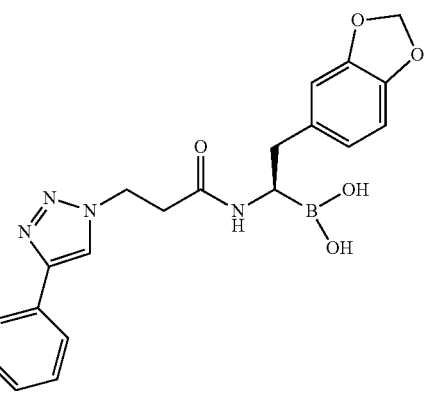 |
| 108 | 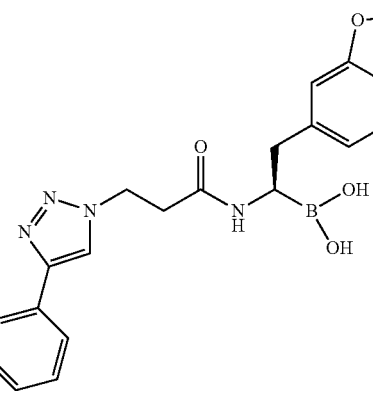 |

| Ex | Formula |
|---|---|
| 109 | 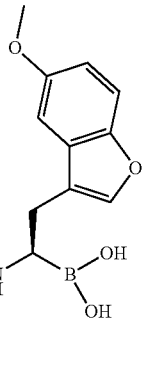 |
| 110 | 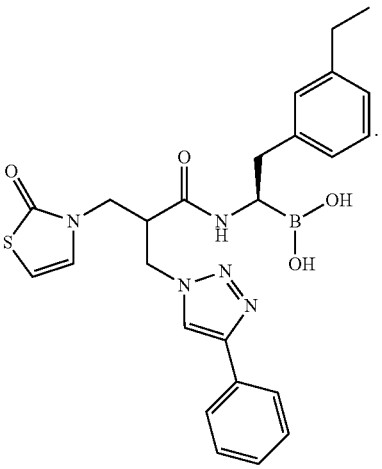 [SMILES: CCc1cccc(C[C@H](NC(=O)C(Cn2cc(-c3ccccc3)nn2)Cn2ccsc2=O)B(O)O)c1] |

5. A pharmaceutical composition comprising at least one compound of claim 1 and/or pharmaceutically acceptable salts, solvates and stereoisomers thereof, including mixtures thereof in all ratios, and optionally excipients and/or adjuvants.

6. A pharmaceutical composition comprising at least one compound of claim 1 and/or pharmaceutically usable salts, solvates and stereoisomers thereof, including mixtures thereof in all ratios, and at least one further active ingredient.

7. A kit consisting of separate packs of
   (a) an effective amount of a compound of claim 1 and/or pharmaceutically usable salts, solvates and stereoisomers thereof, including mixtures thereof in all ratios, and
   (b) an effective amount of a further medicament active ingredient.

8. A process for the synthesis of the compound of claim 1, comprising the step of reacting a compound of Formula (II)

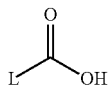

Wherein L is as defined in claim 1,
With a compound of Formula (III)

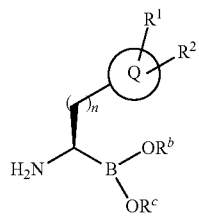

Wherein R1, R2, Q, Ra, Rb and n are as defined in claim 1.

9. The process according to claim 8 wherein the reaction between the compound of Formula (II) and the compound of Formula (III) is performed in the presence of a coupling agent selected from HATU, TBTU, polymer-supported 1-alkyl-2-chloropyridinium salt (polymer-supported Mukaiyama's reagent), 1-methyl-2-chloropyridinium iodide (Mukaiyama's reagent), and a carbodiimide.

10. The compound of claim 1, wherein Y is $CH_2$ or $C(CH_3)_2$.

11. The compound of claim 1, wherein $Q_1$ is phenyl, naphthyl or pyridine.

12. The compound of claim 1, wherein L is L1 and M is a cycloalkylene having 3 to 7 carbon atoms.

13. The compound of claim 12, wherein M is a 5- or 6-membered cycloalkylene.

14. The compound of claim 1, wherein L is L1 and M is a linear or branched alkylene having 1 to 5 carbon atoms wherein 1 or 2 H atoms are optionally substituted by $OR^a$ or a phenyl ring optionally substituted with 1 to 5 groups independently selected from Hal, $OR^a$, and $C_1$-$C_6$-alkyl optionally substituted with 1 to 5 groups independently selected from OH and Hal.

15. The compound of claim 1, wherein L is L2 and M is a linear or branched alkylene having 1 to 5 carbon atoms wherein 1 or 2 H atoms are optionally substituted by $OR^a$ or a phenyl ring optionally substituted with 1 to 5 groups independently selected from Hal, $OR^a$, and $C_1$-$C_6$-alkyl optionally substituted with 1 to 5 groups independently selected from OH and Hal.

16. The compound of claim 15, wherein M is a non-substituted linear alkylene having 1 to 5 carbon atoms.

* * * * *